(12) United States Patent
Tang et al.

(10) Patent No.: US 8,362,251 B2
(45) Date of Patent: Jan. 29, 2013

(54) PYRROLO [3,2-C] PYRIDINE-4-ONE 2-INDOLINONE PROTEIN KINASE INHIBITORS

(75) Inventors: Peng Cho Tang, Shanghai (CN); Yidong Su, Shanghai (CN); Lei Zhang, Shanghai (CN); Lu Xiao, Shanghai (CN)

(73) Assignee: Shanghai Hengrui Pharmaceutical Co., Ltd., Shanghai (CN)

( * ) Notice: Subject to any disclaimer, the term of this patent is extended or adjusted under 35 U.S.C. 154(b) by 0 days.

(21) Appl. No.: 13/196,386

(22) Filed: Aug. 2, 2011

(65) Prior Publication Data

US 2011/0301353 A1  Dec. 8, 2011

Related U.S. Application Data

(62) Division of application No. 12/223,180, filed as application No. PCT/CN2007/000256 on Jan. 24, 2007, now Pat. No. 8,012,966.

(30) Foreign Application Priority Data

| Jan. 27, 2006 | (CN) | 2006 1 0003229 |
| Mar. 15, 2006 | (CN) | 2006 1 0065001 |
| Aug. 30, 2006 | (CN) | 2006 1 0122000 |

(51) Int. Cl.
C07D 471/04 (2006.01)
(52) U.S. Cl. ...................................... 546/113
(58) Field of Classification Search .................. 546/113
See application file for complete search history.

(56) References Cited

U.S. PATENT DOCUMENTS

| 6,114,371 | A | 9/2000 | Tang et al. |
| 6,465,507 | B2 | 10/2002 | Tang et al. |
| 7,576,095 | B2 * | 8/2009 | Cheng ............................ 514/300 |
| 7,875,626 | B2 * | 1/2011 | Cheng ............................ 514/300 |
| 2003/0225127 | A1 | 12/2003 | Bender et al. |
| 2010/0160317 | A1 | 6/2010 | Tang et al. |

FOREIGN PATENT DOCUMENTS

| CN | 1311775 A | 9/2001 |
| WO | 9805335 A | 2/1998 |
| WO | 9961422 A | 12/1999 |
| WO | 0146196 A | 6/2001 |
| WO | 0194312 A | 12/2001 |
| WO | 02055517 A | 7/2002 |
| WO | 03027114 | * 4/2003 |
| WO | 03027114 A | 4/2003 |
| WO | 2007039740 | * 4/2007 |

OTHER PUBLICATIONS

Badger, A., et al., "Pharmacological profile of SB 203580, a selective inhibitor of cytokine suppressive ... function," 279(3), The Journal of Pharmacology 1453-1461, 1996.
Bolen, J., et al., "Leukocyte protein tyrosine kinases: potential targets for drug discovery," 15, Annual Review Immunology 371-404, 1997.
Bolen, J., et al., "Nonreceptor tyrosine protein kinases," 8 Oncogene 2025-2031, 1993.
Buchdunger, E., et al., "Selective inhibition of the platelet-derived growth factor signal transduction .. class," 92 Applied Biological Sciences 2258-2562, 1995.
Borthwick, A., et al., "Inhibition of glycogen synthase kinase-3 by insulin in cultured human . . . myoblasts," 210(3) Biochemical and Biophysical Communications 738-745, 1995.
Dvir, A., et al., "The inhibition of EGF-dependent proliferation of keratinocytes by tyrophostin tyrosine kinase blockers," 113(4) The Journal of Cell Biology 857-865, 1991.
Guillard, J., et al., "Synthesis of new melatonin analogues from Dimers of azaindole and indole by use of suzuki homocoupling," 60(4) Heterocycles 865-877, 2003.
Haijjar, D., et al., "Signal transduction in atherosclerosis: integration of cytokines and the eicosanoid network," 6 The FASEB Journal 2933-2941, 1992.
Huang, S., et al., "Duplication of the mutant RET allele in trisomy 10 or loss of the wild-type allele in multiple endocrine neoplasia," 60 Cancer Research 6223-6226, 2000.
Hunter, T., et al., "Cyclins and cancer II: cyclin D and CDK inhibitors come of age," 79 Cell 573-582, 1994.
Jackson, J., et al., "Pharmacological effects of SB 220025, a selective inhibitor of P38 mitogen-activated .. Inflammatory disease models," 284(2) Journal of Pharmacology 687-692, 1998.
Jiang, W., et al., "Hepatocyte growth factor/scatter factor, its molecular, cellular and clinical . . . in cancer," 29 Critical Reviews in Oncology/Hematology 209-248, 1999.
Littler, E., et al., "Human cytomegalovirus UL97 open reading frame encodes a protein that phosphorylates the antiviral nucleoside analogue ganciclovir," 358 Nature 160-162, 1992.

(Continued)

*Primary Examiner* — Niloofar Rahmani
(74) *Attorney, Agent, or Firm* — Rothwell, Figg, Ernst & Manbeck PC

(57) ABSTRACT

The present invention relates to pyrrolo[3,2-c]pyridine-4-one 2-indolinone compounds of Formula (I) and their pharmaceutically acceptable salts thereof, wherein $R_1$, R2, R3, R4, R5, R6, R7, R8 X, Y and --- have the meaning cited in the specification. Also disclosed are the pharmaceutical compositions containing the foregoing compounds, methods for the preparation and pharmaceutical use thereof, particularly as protein kinase inhibitors. Formula (I).

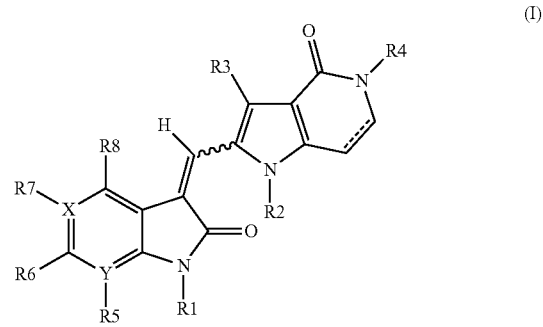

11 Claims, No Drawings

OTHER PUBLICATIONS

Karp, G., et al., "Preparation and alkylation of regioisomeric tetrahydrophthalimide-substituted indolin-2(3H)-ones," 31 Journal of Heterocyclic Chemistry 1513-1520, 1994.
MA, P., et al., "c-Met: structure, functions and potential for therapeutic inhibition," 22 Cancer and Metastasis 309-325, 2003.
MA, P., et al., "c-Met mutational analysis in small cell lung cancer: novel juxtamembrane domain mutations regulating cytoskeletal functions," 63 Cancer Research 6272-6281, 2003.
Mandelkow, E.-M., et al., "Glycogen synthase kinase-3 and the Alzheimer-like state of microtubule-associated protein tau," 314(3) FEBS 11885 315-321, 1992.
Maulik, G., et al., "Role of the hepatocyte growth factor receptor, c-Met, in oncogenesis and potential for .. inhibition," 13 Cytokine & Growth Factor Reviews 41-59, 2002.
Plowman, G., et al., "Receptor tyrosine kinases as targets for drug intervention," 7(6) Drug News & Perspectives 334-339, 1994.
Robinson, D., et al., "The protein tyrosine kinase family of the human genome," 19 Oncogene 5548-5557, 2000.
Salari, H., et al., "Erbstatin blocks platelet activating factor-induced protein-tyrosine phosphorylation, polyphosphoinositide . . . platelets," 263(1) FEBS 104-108, 1990.
Sengupta, A., et al., "Potentiation of GSK-3-catalyzed alzheimer-like phosphorylation of human tau by cdk5," 167 Molecular and Cellular Biochemistry 99-105, 1997.
Soledade, M., et al., "Concise syntheses of the cruciferous phytoalexins brassilexin, sinalexin, wasalexins . . . formylation," 70 Journal of Organic Chemistry 1828-1834, 2005.
Strawn, L., et al., "Flk-1 as a target for tumor growth inhibition," 56 Cancer Research 3540-3545, 1996.
Sun, L., et al., "Rational design of 4,5-disubstituted-5,7-dihydropyrrolo[2,3-d]pyrimidin-6-ones as a . . . kinases," 12 Bioorganic & Medicinal Chemistry Letters 2154-2157, 2002.
Tanaka, S., et al., "c-Cbl is downstream of c-Src in a signalling pathway necessary for bone resorption," 383 Nature 528-531, 1996.
Yashpal, K., et al., "Noxious thermal and chemical stimulation induce increases in 3H-phorbol 12,13-dibutyrate . . . kinase C," 15(5) Journal of Neuroscience 3263-3272, 1995.

* cited by examiner

PYRROLO [3,2-C] PYRIDINE-4-ONE 2-INDOLINONE PROTEIN KINASE INHIBITORS

CROSS-REFERENCE TO RELATED APPLICATIONS

This application is a division of U.S. patent application Ser. No. 12/233,180, filed on 24 Jul. 2008, now U.S. Pat. No. 8,012,966, which in turn is a national stage application under 35 U.S.C. §371 and claims priority, under 35 U.S.C. §§119, 120, 365, and 371, to each of International Patent Application No. PCT/CN2007/000256, filed on 24 Jan. 2007, published as WO 2007/085188 on 2 Aug. 2007; which in turn claims priority to Chinese Patent Application No. 200610003229.6, filed on 27 Jan. 2006; Chinese Patent Application No. 200610065001.X, filed on 15 Mar. 2006; and Chinese Patent Application No. 200610122000.4, filed on 30 Aug. 2006, the contents of each of which are incorporated herein in their entireties for all purposes.

FIELD OF THE INVENTION

This invention relates to a series of pyrrolofused six-membered heterocyclic compounds, especially novel 2-(2-oxoindoline-3-ylidene)methyl-6,7-dihydro-1H-Pyrrol[3,2-c]pyridine-4(5H)-one derivatives, methods for their preparation, pharmaceutical compositions containing them and therapeutic use thereof, particularly their pharmaceutical use as protein tyrosine kinase inhibitor.

BACKGROUND

Cellular signal transduction is a fundamental mechanism whereby extracellular stimuli are relayed to the interior of cells and subsequently regulate diverse cellular processes. These signals regulate a wide variety of physical responses in the cell including proliferation, differentiation, apoptosis and motility. The extracellular signals take the form of a diverse variety of soluble factors including growth factors as well as paracrine, autocrine and endocrine factors. By binding to specific transmembrane receptors, growth factor ligands communicate extracellular signals to the intracellular signalling pathways, thereby causing the individual cell to respond to extracellular signals. Many of these signal transduction processes utilize the reversible process of the phosphorylation of proteins involving specific protein kinases and phosphatases.

Protein kinases (PKs) are enzymes that catalyze the phosphorylation of hydroxy groups on tyrosine, serine and threonine residues of proteins, whereas protein phosphatases hydrolyze phosphate moieties from phosphorylated protein substrates. The converse functions of protein kinases and protein phosphatases balance and regulate the flow of signals in signal transduction processes. The phosphorylation state of a protein can affect its conformation, enzymatic activity, and cellular location, is modified through the reciprocal actions of protein kinases and protein phosphatases. Phosphorylation is an important regulatory mechanism in the signal transduction process and aberrations in the process result in abnormal cell differentiation, transformation and growth. For example, it has been discovered that a cell may become cancerous by virtue of the transformation of a portion of its DNA into an oncogene. Several such oncogenes encode proteins which are receptors for growth factors, for example tyrosine kinases. Tyrosine kinases may also be mutated to constitutively active forms that result in the transformation of a variety of human cells. Alternatively, the overexpression of normal tyrosine kinase enzymes may also result in abnodal cell proliferation.

There are two classes of Pks, the protein tyrosine kinases (PTKs) and the serine-threonine kinases (STKs). PTKs phosphorylate tyrosine residue on a protein. STKs phosphorylate serine or/and threonine on a protein. Tyrosine kinases can be of not only the receptor-type (having extracellular, transmembrane and intracellular domains) but the non-receptor type (being wholly intracellular). One of the prime aspects of PTK activity is their involvement with growth factor receptors which are cell-surface proteins. Growth factor receptors with PTK activity are known as receptor tyrosine kinases ("RTKs"). About 90 tyrosine kinases have been identified in the human genome, of which about 60 are of the receptor type and about 30 are of the non-receptor type. These can be categorized into 20 receptor tyrosine kinase sub-families according to the families of growth factors that they bind and into 10 non-receptor tyrosine kinase sub-families (Robinson et al, *Oncogene,* 2000, 19, 5548-5557). The classification includes the EGF family of receptor tyrosine kinases such as the EGF, TGFα, Neu and erbB receptors, the insulin family of receptor tyrosine kinases such as the insulin and IGF1 receptors and insulin-related receptor (IRR) and the Class III family of receptor tyrosine kinases such as the platelet-derived growth factor (PDGF) receptor tyrosine kinases, for example the PDGFα and PDGFβ receptors, the stem cell factor receptor tyrosine kinase SCF RTK (commonly known as c-Kit), the fms-related tyrosine kinase 3 (Flt3) receptor tyrosine kinase and the colony-stimulating factor 1 receptor (CSF-1R) tyrosine kinase, playing critical role in the control of cell growth and differentiation and are key mediators of cellular signals leading to the production of growth factors and cytokines (Schlessinger and Ullrich, *Neuron* 1992, 9, 383). A partial, non-limiting, list of such kinases includes Abl, ARaf, ATK, ATM, bcr-abl, Blk, BRaf, Brk, Btk, CDK1, CDK2, CDK3, CDK4, CDK5, CDK6, CDK7, CDK8, CDK9, CHK, AuroraA, AuroraB, AuroraC, cfms, c-fms, c-Kit, c-Met, cRaf1, CSF1R, CSK, c-Src, EGFR, ErbB2, ErbB3, ErbB4, ERK, ERK1, ERK2, Fak, fes, FGFR1, FGFR2, FGFR3, FGFR4, FGFR5, Fgr, FLK-4, Fps, Frk, Fyn, GSK, gsk3a, gsk3b, Hck, Chic, Axl, Pim-1, Plh-1, IGF-1R, IKK, IKK1, IKK2, IKK3, INS-R, Integrin-linked kinase, Jak, JAK1, JAK2, JAK3, JNK, JNK, Lck, Lyn, MEK, MEK1, MEK2, p38, PDGFR, PIK, PKB1, PKB2, PKB3, PKC, PKCa, PKCb, PKCd, PKCe, PKCg, PKC1, PKCm, PKCz, PLK1, Polo-like kinase, PYK2, tie$_1$, tie$_2$, TrkA, TrkB, TrkC, UL13, UL97, VEGF-R1, VEGF-R2, Yes and Zap70. Protein kinases have also been implicated as targets in central nervous system disorders such as Alzheimer's (Mandelkow, E. M. et al. *FEBS Lett.* 1992, 314, 315; Sengupta, A. et al. *Mol. Cell. Biochem.* 1997, 167, 99), pain sensation (Yashpal, K. *J. Neurosci.* 1995, 15, 3263-72), inflammatoy disorders such as arthritis (Badger, *J. Pharmn Exp. Ther.* 1996, 279, 1453), psoriasis (Dvir, et al, *J. Cell Biol.* 1991, 113, 857), bone diseases such as osteoporosis (Tanaka et al, *Nature,* 1996, 383, 528). cancer (Hunter and Pines, *Cell* 1994, 79, 573), atherosclerosis (Hajjar and Pomerantz, *FASEB J.* 1992, 6, 2933), thrombosis (Salari, *FEBS* 1990, 263, 104), metabolic disorders such as diabetes (Borthwick, A. C. et al. *Biochem. Biophys. Res. Commun.* 1995, 210, 738), blood vessel proliferative disorders such as angiogenesis (Strawn et al *Cancer Res.* 1996, 56, 3540; Jackson et al *J. Pharm. Exp. Ther.* 1998, 284, 687), restenosis (Buchdunger et al, *Proc, Nat. Acad. Sci USA* 1991, 92, 2258), autoimmune diseases and transplant rejection (Bolen and Brugge, *Ann. Rev. Immunol.* 1997, 15, 371) and infection diseases such as viral (Littler, E. Nature 1992, 358, 160), and fungal infections (Lum, R. T. PCT Int Appl., WO 9805335 A1 980212).

RTKs mediated signal transduction is initiated by extracellular interaction with a specific growth factor (ligand), followed by receptor dimerization, transient stimulation of the intrinsic protein tyrosine kinase activity and phosphorylation. Binding sites are thereby created for intracellular signal transduction molecules and lead to the formation of complexes with a spectrum of cytoplasmic signaling molecules that facilitate the appropriate cellular responses (e.g., cell division, metabolic homeostasis, and responses to the extracellular microenvironment).

With respect to receptor tyrosine kinases, it has been shown also that tyrosine phosphorylation sites function as high-affinity binding sites for SH2 (src homology) domains of signaling molecules. Several intracellular substrate proteins that associate with receptor tyrosine kinases have been identified. They may be divided into two principal groups: (1) substrates which have a catalytic domain; and (2) substrates which lack such domain but serve as adapters and associate with catalytically active molecules. The specificity of the interactions between receptors or proteins and SH2 domains of their substrates is determined by the amino acid residues immediately surrounding the phosphorylated tyrosine residue. Differences in the binding affinities between SH2 domains and the amino acid sequences surrounding the phosphotyrosine residues on particular receptors are consistent with the observed differences in their substrate phosphorylation profiles. These observations suggest that the function of each receptor tyrosine kinase is determined not only by its pattern of expression and ligand availability but also by the array of downstream signal transduction pathways that are activated by a particular receptor. Thus, phosphorylation provides an important regulatory step which determines the selectivity of signaling pathways recruited by specific growth factor receptors, as well as differentiation factor receptors. Aberrant expression or mutations in the protein tyrosine kinases have been shown to lead to either uncontrolled cell proliferation (e.g. malignant tumor growth) or to defects in key developmental processes.

It has been identified that such mutated and overexpressed forms of tyrosine kinases are present in a large proportion of common human cancers such as the leukaemia, breast cancer, prostate cancer, non-small cell lung cancer (NSCLC) including adenocarcinomas and squamous cell cancer of the lung, gastrointestinal cancer including colon, rectal and stomach cancer, bladder cancer, oesophageal cancer, ovarian cancer and pancreatic cancer. As further human tumour tissues are tested, it is expected that the widespread prevalence and relevance of tyrosine kinases will be further established. For example, it has been shown that EGFR tyrosine kinase is mutated and/or overexpressed in several human cancers including in tumours of the lung, head and neck, gastrointestinal tract, breast, oesophagus, ovary, uterus, bladder and thyroid.

One subfamily designated the "HER" or "Erb" RTKs, which include EGFR (epithelial growth factor receptor), HER2, HER3 and HER4. These RTKs consist of an extracellular glycosylated ligand binding domain, a transmembrane domain and an intracellular cytoplasm catalytic domain that can phosphorylate tyrosine residues on proteins. The enzymatic activity of receptor tyrosine kinases can be stimulated by either overexpression, or by ligand-mediated dimerization. The formation of homodimers as well as heterodimers has been demonstrated for the HER receptor family. An example of homodimerization is the dimerization of HER1 (EGF receptor) by one of the EGF family of ligands (which includes EGF, transforming growth factor alpha, betacellulin, heparin-binding EGF, and epiregulin). Heterodimerization among the four HER receptor kinases can be promoted by binding to members of the heregulin (also referred to neuregulin) family of ligands. Such heterodimerization as involving HER2 and HER3, or a HER3 and HER4 combination, results in a significant stimulation of the tyrosine kinase activity of the receptor dimers even though one of the receptors (HER3) is enzymatically inert. The kinase activity of HER2 has been shown to be activated also by virtue of overexpression of the receptor alone in a variety of cell types. Activation of receptor homodimers and heterodimers results in phosphorylation of tyrosine residues on the receptors and on other intracellular proteins. This is followed by the activation of intracellular signaling pathways such as those involving the microtubule associated protein kinase (MAP kinase) and the phosphatidylinositol3-kinase (PI3 kinase). Activation of these pathways has been shown to lead to cell proliferation and the inhibition of apoptosis. Inhibition of HER kinase signaling has been shown to inhibit cell proliferation and survival.

Another RTK subfamily, consists of insulin receptor (IR), insulin-like growth factor I receptor (IGF-1R) and insulin receptor related receptor (IRR). IR and IGF-1R interact with insulin, IGF-I and IGF-II to form a heterotetramer of two entirely extracellular glycosylated α subunits and two β subunits which cross the cell membrane and which contain the tyrosine kinase domain.

A third RTK subfamily is referred to as the platelet derived growth factor receptor ("PDGFR") group, which includes PDGFRα, PDGFRβ, CSFIR, c-Kit and c-fms. These receptors consist of glycosylated extracellular domains composed of variable numbers of immunoglobin-like loops and an intracellular domain wherein the tyrosine kinase domain is interrupted by unrelated amino acid sequences.

Platelet derived growth factor receptors such as PDGFRα and PDGFRβ are also transmembrance tyrosine kinase receptors. Upon binding of the ligand, they form either homodimers (PDGF-AA, PDGF-BB) or heterodimers (PDGF-AB). Follow is the receptor dimerizes, its tyrosine kinase is activated. This leads to downstream signaling and thus may support tumor growth. Mutations in this gene allow for receptor activation independent of ligand binding and appear to be driving forces in oncogenesis. Some tumors can be characterized by mutated PDGFR as a gene markers for therapy such as GIST. An expression of PDGF, the growth factor that activates PDGFR, was observed in a number of different tumor cell lines, inter alia in mamma, colon, ovarian, prostate carcinoma, sarcoma and glioblastomas cell lines. Among the tumors, brain tumors and prostate carcinoma (including adenocarcinomas and bone metastasis) have found special interest. Interesting data also exist regarding malign gliomes (anaplastic astrocytomas/glioblastomas).

C-Kit is a tyrosine kinase receptor which belongs to the PDGF receptor family and becomes activated upon binding of its ligand SCF (stem-cell factor). The expression pattern of c-Kit has been studied e.g. in a panel of different primary solid tumors. A strong expression of c-Kit could be found inter alia in sarcoma, gastrointestinal stromal tumors (GIST), seminoma and carcinoids [Weber et al., J. Clin. Oncol. 22(14S), 9642 (2004)]. GISTs are non-epithelial tumors, diagnostically separated from other common forms of bowel cancer. Many occur in the stomach, less in the small intestine and still less in the esophagus. Dissemination, to the liver, omentum and peritoneal cavity can be observed. GISTS probably arise from Interstitial Cajal Cells (ICC) which normally form part of the autonomic nervous system of the intestine and take part in the control of motility. Most (50 to 80%) of GISTS arise due to c-Kit gene mutation. In the gut, a staining positive for c-Kit/CD117 is likely to be a GIST. Mutations of c-Kit can make c-Kit function independent of activation by SCF, leading to a high cell division rate and possibly genomic instability. Also in mast cell tumors aberrations of c-Kit could be observed, as well as in mastocytosis and associated myeloproliferative syndrome and Urticaria Pigmentosa. An expression and/or aberrations of c-Kit can also be found in acute myeloicanemia (AML) and malign lymphomas. A c-Kit expression can also be demonstrated in small cell bronchial carcinoma, seminomas, dysgerminomas, testicular intraepithelial neoplasias, melanomas, mamma carcinomas, neuroblastomas, Ewing sarcoma, some soft part sarcomas as well as papillary/follicular thyroid carcinoma (see Schŭlte et al., innovartis March 2001). Inherited mutations of the RET (rearranged during transfection) proto-oncogene are e.g. known to be tumorigenic in patients with multiple endocrine neoplasia type 2-(MEN 2) which may lead to pheochromocytoma, medullary thyroid carcinoma and parathyroid hyperplasia/adenoma (see Huang et al., Cancer Res. 60, 6223-6 (2000)). In patients with MEN 2, germ-line mutations of RET and sometimes duplication of a mutant RET allele in trisomy 10 or loss of the wild type RET allele are commonly identified and believed to be activating, i.e. causing ligand-independent dimerization of the receptor.

Another group which, because of its similarity to the PDGFR subfamily, is sometimes subsumed into the later group is the fetus liver kinase ("Flk") receptor subfamily, This group is believed to be made up of kinase insert domain-receptor fetal liver kinase-1 (KDR/FLK-1, VEGFR2), Flk-1R, Flk-4 and Fms-like tyrosine kinase 1 (Flt-1), A further member of the tyrosine kinase growth factor receptor family is the fibroblast growth factor ("FGF") receptor subgroup. This group consists of four receptors, FGFR1-4, and seven ligands, FGF1-7. While not yet well defined, it appears that the receptors consist of a glycosylated extracellular domain containing a variable number of immunoglobin-like loops and an intracellular domain in which the tyrosine kinase sequence is interrupted by regions of unrelated amino acid sequences.

Still another member of the tyrosine kinase growth factor receptor family is the vascular endothelial growth factor ("VEGF") receptor subgroup, VEGF is a dimeric glycoprotein similar to PDGF but has different biological functions and target cell specificity in vivo, In particular, VEGFRs are known to be involved in the control of the onset of angiogenesis. As especially solid tumors depend on good blood supply, inhibition of VEGFRs and thus angiogenesis is under clinical investigation in the treatment of such tumors, showing promising-results. VEGF is also a major player in leukemias and lymphomas and highly expressed in a variety of solid malignant tumors, correlating well with malignant disease progression. Examples of tumor diseases with VEGFR-2 (KDR) expression are lung carcinomas, breast carcinomas, Non Hodgkin's lymphomas, ovarian carcinoma, pancreatic cancer, malignant pleural mesothelioma and melanoma. In addition to its angiogenic activity, the ligand of VEGFR, VEGF, may promote tumor growth by direct pro-survival effects in tumor cells. PDGF is also involved in angiogenesis, the process of forming new blood-vessels that is critical for continuing tumor growth. Normally, angiogenesis plays an important role in processes such as embryonic development, wound healing and several components of female reproductive function. However, undesirable or pathological angiogenesis has been associated with a number of disease states including diabetic retinopathy, psoriasis, cancer, rheumatoid arthritis, atheroma, Kaposi's sarcoma and Angiogenesis is stimulated via the promotion of the growth of endothelial cells. Several polypeptides with in vitro endothelial cell growth promoting activity have been identified including acidic and basic fibroblast growth factors (aFGF and bFGF) and vascular endothelial growth factor (VEGF). By virtue of the restricted expression of its receptors, the growth factor activity of VEGF, in contrast to that of aFGF and bFGF, is relatively specific towards endothelial cells. Recent evidence indicates that VEGF is an important stimulator of both normal and pathological angiogenesis and vascular permeability. This cytokine induces a vascular sprouting phenotype by inducing endothelial cell proliferation, protease expression and migration which subsequently leads to the formation of capillary tubes that promote the formation of the hyperpermeable, immature vascular network which is the characteristic of pathological angiogenesis. Accordingly, antagonism of the activity of VEGF is expected to be beneficial in the treatment of a number of disease states that are associated with angiogenesis and/or increased vascular permeability such as cancer, especially in inhibiting the development of tumors.

FLT3 is a member of the type III receptor tyrosine kinase (RTK) family. FLT3 (fins-like tyrosine kinase) is also known as FLk-2 (fetal liver kinase 2). Aberrant expression of the FLT3 gene has inter alia been documented in both adult and childhood leukemias including acute myeloid leukemia (AML), AML with trilineage myelodysplasia (AML/TMDS), acute lymphoblastic leukemia (ALL), and myelodysplastic syndrome (MDS), as well as MLL (mixed-lineage leukemia). Activating mutations of the FLT3 receptor have been found in about 35% of patients with acute myeloblastic leukemia (AML), and are associated with a poor prognosis. The most common mutation involves an in-frame duplication within the juxtamembrane domain, with an additional 5-10% of patients having a point mutation at asparagine 835. Both of these mutations are associated with constitutive activation of the tyrosine kinase activity of FLT3, and result in proliferation and viability signals in the absence of ligand. Patients expressing the mutant form of the receptor have been shown to have a decreased chance for cure. Thus, there is accumulating evidence for a role for hyperactivated (mutated) FLT3 kinase activity in human leukemias and myelodysplastic syndrome.

The hepatocyte growth factor (HGF) receptor (c-MET or HGFR) receptor tyrosine kinase (RTK) has been shown in many human cancers to be involved in oncogenesis, tumor progression with enhanced cell motility and invasion, as well as metastasis (see, e.g., Ma, P. C., Maulik, G., Christensen, J. & Salgia, R. (2003b). *Cancer Metastasis Rev,* 22, 309-25; Maulik, G., Shrikhande, A., Kijima, T., Ma, P. C., Morrison, P. T. & Salgia, R. (2002b). *Cytokine Growth Factor Rev,* 13, 41-59). c-MET (HGFR) can be activated through overexpression or mutations in various human cancers including small cell lung cancer (SCLC) (Ma, P. C., Kijima, T., Maulik, G., Fox, E. A., Sattler, M., Griffin, J. D., Johnson, B. E. & Salgia, R. (2003a). *Cancer Res,* 63, 6272-6281).

c-MET is a receptor tyrosine kinase that is encoded by the Met proto-oncogene and transduces the biological effects of hepatocyte growth factor (HGF), which is also referred to as scatter factor (SF). Jiang et al., *Crit. Rev. Oncol. Hematol.* 29: 209-248 (1999). c-MET and HGF are expressed in numerous tissues, although their expression is normally confined predominantly to cells of epithelial and mesenchymal origin, respectively. c-MET and HGF are required for normal mammalian development and have been shown to be important in cell migration, cell proliferation and survival, morphogenic differentiation, and organization of 3-dimensional tubular structures (e.g., renal tubular cells, gland formation, etc.). In addition to its effects on epithelial cells, HGF/SF has been reported to be an angiogenic factor, and c-MET signaling in endothelial cells can induce many of the cellular responses necessary for angiogenesis (proliferation, motility, invasion).

The c-MET receptor has been shown to be expressed in a number of human cancers. c-Met and its ligand, HGF, have also been shown to be co-expressed at elevated levels in a variety of human cancers (particularly sarcomas). However, because the receptor and ligand are usually expressed by different cell types, c-MET signaling is most commonly regulated by tumor-stroma (tumor-host) interactions. Furthermore, c-MET gene amplification, mutation, and rearrangement have been observed in a subset of human cancers. Families with germline mutations that activate c-MET kinase are prone to multiple kidney tumors as well as tumors in other tissues. Numerous studies have correlated the expression of c-MET and/or HGF/SF with the state of disease progression of different types of cancer (including lung, colon, breast, prostate, liver, pancreas, brain, kidney, ovaries, stomach, skin, and bone cancers). Furthermore, the overexpression of c-MET or HGF have been shown to correlate with poor prognosis and disease outcome in a number of major human cancers including lung, liver, gastric, and breast. c-MET has also been directly implicated in cancers without a successful treatment regimen such as pancreatic cancer, glioma, and hepatocellular carcinoma.

A more complete listing of the known RTK subfamilies is described in Plowman et al., *DN&P* 7(6): 334-339 (1994) which is incorporated by reference, including any drawings, as if fully set forth herein.

The non-receptor tyrosine kinases represent a collection of cellular enzymes which lack extracellular and transmembrane sequences. At present, over twenty-four individual non-receptor tyrosine kinases, comprising eleven subfamilies (Src, Frk, Btk, Csk, Abl, Zap70, Fes/Fps, Fak, Jak, Ack and LIMK) have been identified. At present, the Src subfamily of non-receptor tyrosine kinases are comprised of the largest number of PTKs and include Src, Yes, Fyn, Lyn, Lck, Blk, Hck, Fgr and Yrk. The Src subfamily of enzymes has been linked to oncogenesis. A more detailed discussion of non-receptor tyrosine kinases is provided in Bolen, 1993, Oncogen 8: 2025-2031, which is incorporated herein by reference.

The serine/threonine kinases, STKs, like the CTKs, are predominantly intracellular although there are a few receptor kinases of the STK type. STKs are the most common of the cytosolic kinases; i.e., kinases that perform their function in that part of the cytoplasm other than the cytoplasmic organelles and cytoskelton. The cytosol is the region within the cell where much of the cell's intermediary metabolic and biosynthetic activity occurs; e.g., it is in the cytosol that proteins are synthesized on ribosomes.

A further characteristic of hyperproliferative diseases such as cancer is damage to the cellular pathways that control progress through the cell cycle which, in normal eukaryotic cells, involves an ordered cascade of protein phosphorylation. As for signal transduction mechanisms, several families of protein kinases appear to play critical roles in the cell cycle cascade. The most widely studied of these cell cycle regulators is the cyclin dependent kinase family (the CDKs). Activity of specific CDKs at specific times is essential both to initiate and coordinate progress through the cell cycle. For example, the CDK4 protein appears to control entry into the cell cycle (the GO-GI-S transition) by phosphorylating the retinoblastoma gene product pRb which stimulates the release of the transcription factor E2F from pRb which, in turn, acts to increase the transcription of genes necessary for entry into S phase. The catalytic activity of CDK4 is stimulated by binding to a partner protein, Cyclin D. One of the first demonstrations of a direct link between cancer and the cell cycle was made with the observation that the Cyclin D1 gene was amplified and Cyclin D protein levels increased in many human tumours.

More recently, protein kinases that are structurally distinct from the CDK family have been identified which play critical roles in regulating the cell cycle and which also appear to be important in oncogenesis. They include the human homologues of the *Drosophila aurora* and *S. cerevisiae* Ipl 1 proteins. The three human homologues of these genes Aurora-A, Aurora-B and Aurora-C encode cell cycle regulated serine-threonine protein kinases that show a peak of expression and kinase activity through G2 and mitosis. Several observations implicate the involvement of human aurora proteins in cancer, especially Aurora-A and Aurora-B. Abrogation of Aurora-A expression and function by antisense oligonucleotide treatment of human tumour cell lines leads to cell cycle arrest and exerts an anti-proliferative effect. Additionally, small molecule inhibitors of Aurora-A and Aurora-B have been demonstrated to have an anti-proliferative effect in human tumor cells.

With regard to cancer, two of the major hypotheses advanced to explain the excessive cellular proliferation that drives tumor development relate to functions known to be PK regulated. That is, it has been suggested that malignant cell growth results from a breakdown in the mechanisms that control cell division and/or differentiation. It has been shown that the protein products of a number of proto-oncogenes are involved in the signal transduction pathways that regulate cell growth and differentiation. These protein products of proto-oncogenes include the extracellular growth factors, transmembrane growth factor PTK receptors (RTKs), cytoplasmic PTKs (CTKs) and cytosolic STKs, discussed above.

There is a need for small molecule compounds that may be readily synthesized and are potent inhibitors of one or more RTKs, CTKs or STKs that possess anti-tumor cell proliferative activity and as such are useful in treating or ameliorating RTKs, CTKs or STKs mediated, angiogenesis mediated or hyperproliferative disorder.

SUMMARY OF THE INVENTION

The present invention is directed to indolinone compounds of Formula (I) and methods for treating protein kinase related disorders and diseases. These compounds of Formula (I) are capable of modulating, regulating and/or inhibiting protein kinase signal transduction. Such compounds are useful for the treatment of diseases related to unregulated protein kinase transduction, including cell proliferative diseases such as cancer, angiogenesis, atherosclerosis restenosis, metabolic diseases such as diabetes, inflammatory diseases such as psoriasis, chronic obstructive pulmonary disease and arthritis, vascular proliferative disorders such as diabetic retinopathy, age-related macular degeneration and retinopathy of prematurity, autoimmune diseases and transplant rejection, central nervous system disorder such as Alzheimer's, pain sensation, bone diseases such as osteoporosis, infection disease such as viral and fungal infection.

Accordingly, in a first aspect, this invention provides a compound of Formula (I):

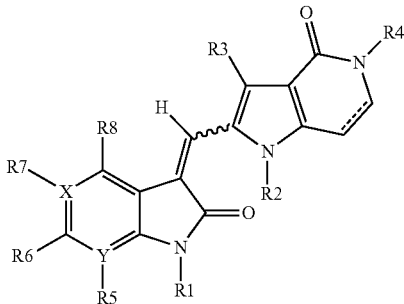

(I)

Wherein:
⋯⋯ is a single boud or double bond;
X and Y are each independently selected from C and N;
X and Y are N, wherein R5 and R7 are absent;
R1 and R2 are each independently selected from H, alkyl, cycloalkyl, heterocyclo alkyl, aryl, heteroaryl, alkoxyl, aryoxyl, —$COOR_9$, —$CONR_9R_{10}$, —$C(=S)NR_9R_{10}$, —$COR_9$, —$SOR_9$, —$SO_2R_9$, —$SO_2NR_9R_{10}$ and —$P(=O)(OR_9)(OR_{10})$;
R3 is selected from alkyl, trifluoromethyl, aryl and aralkyl, wherein said alkyl, aryl or aralkyl is substituted by one more halogen and hydrogen;
R4 is selected from alkyl, cycloalkyl, heterocyclo alkyl, aryl, heteroaryl, alkenyl, alkynyl, —$(CH_2)_n(OCH_2CH_2)_rR_{11}$, —$[CH_2CH(OH)]_rCH_2NR_9R_{10}$, and —$(CH_2)_nNR_9R_{10}$, wherein said alkyl, cycloalkyl, aryl, heteroaryl and heterocyclo alkyl are each optionally substituted by one more groups selected from the group consisting of aryl, hydroxyl, amino, amide group, aminocarbonyl, alkoxyl, aryoxyl, aminoalkyl, hydroxyalkyl, heterocyclo alkyl, carboxylic acid, carboxylic ester and —$NR_9R_{10}$;
X and Y are C, wherein R5, R6, R7, R8 are each independently selected from hydrogen, halo, haloalkoxyl, alkyl, cycloalkyl, heterocyclo alkyl, alkenyl, alkynyl, aryl, heteroaryl, hydroxyl, —$OR_9$, —$O[CH_2CH_2O]_rR_{11}$, —$SR_9$, —$NR_9R_{10}$, —$SOR_9$, —$SO_2R_9$, $NHSO_2R_9$, ⁻$SO_2NR_9R_{10}$, —$(CH_2)_5CO_2R_9$, —$(CH_2)_nCONR_9R_{10}$, —$C(=S)NR_9R_{10}$, —$COR_9$, ⁻$NR_9COR_{10}$, —$NHCO_2R_{10}$, —$OCO_2R_9$, —$OCO_2NR_9R_{10}$, —CN and —$NO_2$, wherein said aryl, heteroaryl, cycloalkyl, heterocyclo alkyl are each independently substituted by one more groups including alkyl, alkoxyl and halogen;
$R_9$ and $R_{10}$ are each independently selected from hydrogen, alkyl, cycloalkyl, aryl, heteroaryl and heterocyclo alkyl, wherein said alkyl, cycloalkyl, aryl, heteroaryl and heterocyclo alkyl are each substituted by one more group consisting of alkyl, aryl, hydroxyl, amino, amide group, aminocarbonyl, cyano, alkoxyl, aryoxyl, aminoalkyl, hydroxyalkyl, heterocyclo alkyl, carboxylic acid and carboxylic ester;
$R_9$ and $R_{10}$ may be taken together with the atom to which they are attached to form 4 to 8 membered ring, wherein the 5 to 8 membered rings may further optionally contain one to three heteroatoms selected from the group consisting of N, O, S, and the 4 to 8 membered rings so formed is optionally substituted by one more group consisting of alkyl, aryl, heteroaryl, haloalkyl, haloalkoxyl, hydroxyl, amino, amide group, cyano, alkoxyl, aryoxyl, aminoalkyl, hydroxyalkyl, heterocyclo alkyl, carboxylic acid, carboxylic ester, halogen and —$NR_9R_{10}$;

$R_{11}$ is hydrogen or alkyl;
n is 2-6; and
r is 1-6; or
pharmaceutically acceptable salts or stereoisomer thereof.
In another particular aspect of this embodiment, the compound has formula (Ia):

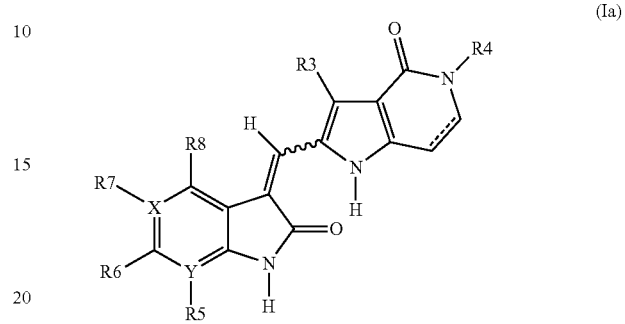

(Ia)

Wherein:
⋯⋯ is a single boud or double bond;
X and Y are selected from C or N;
X and Y are each independently N, wherein R5 and R7 are absent;
R3 is selected from alkyl, trifluoromethyl, aryl and aralkyl, wherein said alkyl, aryl and aralkyl are each independently substituted by one more halogen and hydrogen;
R4 is selected from alkyl, cycloalkyl, heterocyclo alkyl, aryl, heteroaryl, alkenyl, alkynyl, —$(CH_2)_n(OCH_2CH_2)_rR_{11}$, —$[CH_2CH(OH)]_rCH_2NR_9R_{10}$ and —$(CH_2)_nNR_9R_{10}$, wherein said alkyl, cycloalkyl, aryl, heteroaryl or heterocyclo alkyl is optionally independently substituted by one more groups selected from the group consisting of aryl, hydroxyl, amino, amide group, aminocarbonyl, alkoxyl, aryoxyl, aminoalkyl, hydroxyalkyl, heterocyclo alkyl, carboxylic acid, carboxylic ester and —$NR_9R_{10}$;
X and Y are each independently C, wherein R5, R6, R7 and R8 are each independently selected from hydrogen, halo, haloalkoxyl, alkyl, cycloalkyl, heterocyclo alkyl, alkenyl, alkynyl, heteroaryl, hydroxyl, —$OR_9$, —$O[CH_2CH_2O]_rR_{11}$, —$SR_9$, —$NR_9R_{10}$, —$SOR_9$, —$SO_2R_9$, —$NHSO_2R_9$, —$SO_2NR_9R_{10}$, —$(CH_2)_nCO_2R_9$, —$(CH_2)_nCONR_9R_{10}$, —$C(=S)NR_9R_{10}$, —$COR_s$, —$NR_9COR_{10}$, —$NHCO_2R_{10}$, —$OCO_2R_9$, $CO_2NR_9R_{10}$, —CN and —$NO_2$, wherein said aryl, heteroaryl, cycloalkyl, heterocyclo alkyl are independently substituted by one more groups including alkyl, alkoxyl and halogen;
$R_9$ and $R_{10}$ are each independently selected from hydrogen, alkyl, cycloalkyl, aryl, heteroaryl and heterocyclo alkyl, wherein said alkyl, cycloalkyl, aryl, heteroaryl and heterocyclo alkyl are each independently substituted by one more groups consisting of alkyl, aryl, hydroxyl, amino, amide group, aminocarbonyl, cyano, alkoxyl, aryoxyl, aminoalkyl, hydroxyalkyl, heterocyclo alkyl, carboxylic acid and carboxylic ester;
$R_9$ and $R_{10}$ may be taken together with the atom to which they are attached to form 4 to 8 membered ring, wherein the 5 to 8 membered rings may further optionally contain one to three heteroatoms selected from the group consisting of N, O, S, and the 4 to 8 membered rings so formed is optionally independently substituted by one more groups consisting of alkyl, aryl, heteroaryl, haloalkyl, haloalkoxyl, hydroxyl, amino, amide group, cyano, alkoxyl, aryoxyl, aminoalkyl, hydroxyalkyl, heterocyclo alkyl, carboxylic acid, carboxylic ester, halogen and —NR$_9$R$_{10}$;

R$_{11}$ is hydrogen or alkyl;

n is 2-6; and r is 1-6; or pharmaceutically acceptable salts or stereoisomer thereof.

In still another aspect, this invention is directed to compounds of formula (Ib)

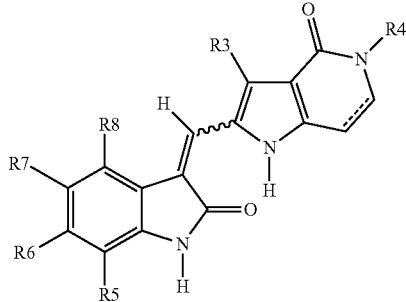

(Ib)

Wherein:

---- is a single bond or double bond;

R3 is selected from alkyl, trifluoromethyl, aryl and aralkyl, wherein said alkyl, aryl and aralkyl is substituted by one more halogen and hydrogen;

R4 is selected from alkyl, cycloalkyl, heterocyclo alkyl, aryl, heteroaryl, alkenyl, alkynyl, —(CH$_2$)$_n$(OCH$_2$CH$_2$)$_r$R$_{11}$, —[CH$_2$CH(OH)]$_r$CH$_2$NR$_9$R$_{10}$ and —(CH$_2$)$_n$NR$_9$R$_{10}$, wherein said alkyl, cycloalkyl, aryl, heteroaryl and heterocyclo alkyl are each optionally substituted by one more groups selected from the group consisting of aryl, hydroxyl, amino, amide group, aminocarbonyl, alkoxyl, aryoxyl, aminoalkyl, hydroxyalkyl, heterocyclo alkyl, carboxylic acid, carboxylic ester and —NR$_9$R$_{10}$;

X and Y are each independently C, wherein R5, R6, R7, R8 are each independently selected from hydrogen, halo, haloalkoxyl, alkyl, cycloalkyl, heterocyclo alkyl, alkenyl, alkynyl, aryl, heteroaryl, hydroxyl, —OR$_9$, —O[CH$_2$CH$_2$O]$_r$R$_{11}$, —SR$_9$, —NR$_9$R$_{10}$, —SOR$_9$, —SO$_2$R$_9$, NHSO$_2$R$_9$, —SO$_2$NR$_9$R$_{10}$, —(CH$_2$)$_n$CONR$_9$R$_{10}$, C(=S)NR$_9$R$_{10}$, —COR$_9$, —NR$_9$COR$_{10}$, —NHCO$_2$12$_{10}$, OCO$_2$R$_9$, —OCO$_2$NR$_9$R$_{10}$, —CN and —NO$_2$, wherein said aryl, heteroaryl, cycloalkyl and heterocyclo alkyl are each independently substituted by one more groups including alkyl, alkoxyl or halogen;

R$_9$ and R$_{10}$ are each independently selected from hydrogen, alkyl, cycloalkyl, aryl, heteroaryl and heterocyclo alkyl, wherein said alkyl, cycloalkyl, aryl, heteroaryl or heterocyclo alkyl are substituted by one more groups consisting of alkyl, aryl, hydroxyl, amino, amide group, aminocarbonyl, cyano, alkoxyl, aryoxyl, aminoalkyl, hydroxyalkyl, heterocyclo alkyl, carboxylic acid and carboxylic ester;

R$_9$ and R$_{10}$ may be taken together with the atom to which they are attached to form 4 to 8 membered ring, wherein the 5 to 8 membered rings may further optionally contain one to three heteroatoms selected from the group consisting of N, O, S, and the 4 to 8 membered rings so formed is optionally substituted by one more group consisting of alkyl, aryl, heteroaryl, haloalkyl, haloalkoxyl, hydroxyl, amino, amide group, cyano, alkoxyl, aryoxyl, aminoalkyl, hydroxyalkyl, heterocyclo alkyl, carboxylic acid, carboxylic ester, halogen and —NR$_9$R$_{10}$;

R$_{11}$ is hydrogen or alkyl;

n is 2-6; and r is 1-6; or pharmaceutically acceptable salts or stereoisomer thereof.

In another aspect, this invention is directed to compounds of formula (Ic)

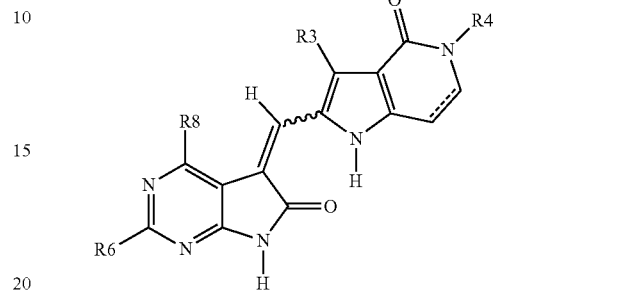

(Ic)

Wherein:

---- is a single bond or double bond;

R3 is selected from alkyl, trifluoromethyl, aryl and aralkyl, wherein said alkyl, aryl or aralkyl is substituted by one more halogen and hydrogen;

R4 is selected from alkyl, cycloalkyl, heterocyclo alkyl, aryl, heteroaryl, alkenyl, alkynyl, —(CH$_2$)$_n$(OCH$_2$CH$_2$)$_r$R$_{11}$, —[CH$_2$CH(OH)]$_r$CH$_2$NR$_9$R$_{10}$ and (CH$_2$)$_n$NR$_9$R$_{10}$, wherein said alkyl, cycloalkyl, aryl, heteroaryl and heterocyclo alkyl are each optionally substituted by one more groups selected from the group consisting of aryl, hydroxyl, amino, amide group, aminocarbonyl, alkoxyl, aryoxyl, aminoalkyl, hydroxyalkyl, heterocyclo alkyl, carboxylic acid, carboxylic ester and —NR$_9$R$_{10}$;

X and Y are C, wherein R5, R6, R7, R8 are each independently selected from hydrogen, halo, haloalkoxyl, alkyl, cycloalkyl, heterocyclo alkyl, alkenyl, alkynyl, aryl, heteroaryl, hydroxyl, —OR$_9$, —O[CH$_2$CH$_2$O]$_r$R$_{11}$, —SR$_9$, —NR$_9$R$_{10}$, —SOR$_9$, —SO$_2$R$_9$, —NHSO$_2$R$_9$, —SO$_2$NR$_9$R$_{10}$, (CH$_2$)$_n$CO$_2$R$_9$, —(CH$_2$)CONR$_9$R$_{10}$, —C(=S)NR$_9$R$_{10}$, —NR$_9$COR$_{10}$, —NHCO$_2$R$_{10}$, —OCO$_2$R$_9$, —OCO$_2$NR$_9$R$_{10}$, —CN and —NO$_2$, wherein said aryl, heteroaryl, cycloalkyl, heterocyclo alkyl are each independently substituted by one more groups including alkyl, alkoxyl or halogen;

R$_9$ and R$_{10}$ are each independently selected from hydrogen, alkyl, cycloalkyl, aryl, heteroaryl and heterocyclo alkyl, wherein said alkyl, cycloalkyl, aryl, heteroaryl and heterocyclo alkyl are each independently substituted by one more group consisting of alkyl, aryl, hydroxyl, amino, amide group, aminocarbonyl, cyano, alkoxyl, aryoxyl, aminoalkyl, hydroxyalkyl, heterocyclo alkyl, carboxylic acid and carboxylic ester;

R$_9$ and R$_{10}$ may be taken together with the atom to which they are attached to form 4 to 8 membered ring, wherein the 5 to 8 membered rings may further optionally contain one to three heteroatoms selected from the group consisting of N, O, S, and the 4 to 8 membered rings so formed is optionally substituted by one more group consisting of alkyl, aryl, heteroaryl, haloalkyl, haloalkoxyl, hydroxyl, amino, amide group, cyano, alkoxyl, aryoxyl, aminoalkyl, hydroxyalkyl, heterocyclo alkyl, carboxylic acid, carboxylic ester, halogen and —NR$_9$R$_{10}$;

R$_{11}$ is hydrogen or alkyl;

n is 2-6; and r is 1-6; or pharmaceutically acceptable salts or stereoisomer thereof.

In another aspect, this invention provides a compound selected from the group shown in Table I.

TABLE I

| Example No Aftermentioned | Structure | Name |
|---|---|---|
| 1 | 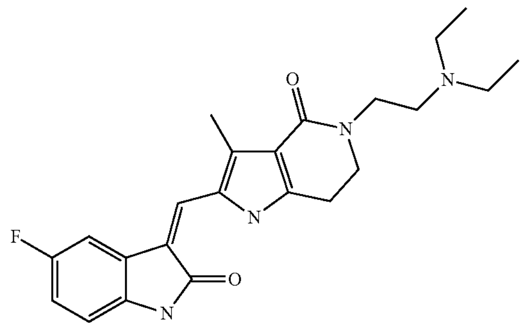 [SMILES: CCN(CC)CCN1CCc2[nH]c(/C=C3\C(=O)Nc4ccc(F)cc43)c(C)c2C1=O] | 5-(2-Diethylamino-ethyl)-2-(5-fluoro-2-oxo-1,2-dihydro-indol-3-ylidenemethyl)-3-methyl-1,5,6,7-tetrahydro-pyrrolo[3,2-c]pyridin-4-one |
| 2 | 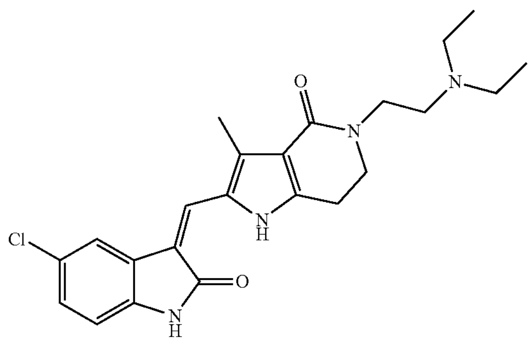 | 2-(5-Chloro-2-oxo-1,2-dihydro-indol-3-ylidenemethyl)-5-(2-diethylamino-ethyl)-3-methyl-1,5,6,7-tetrahydro-pyrrolo[3,2-c]pyridin-4-one |
| 3 | 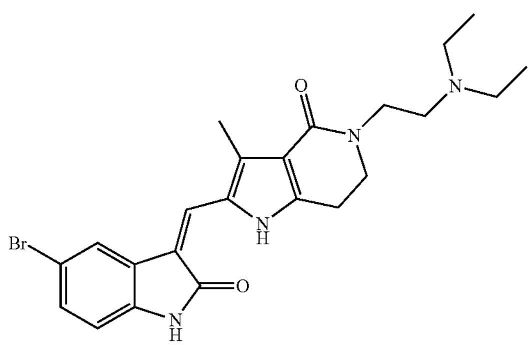 [SMILES: CCN(CC)CCN1CCc2[nH]c(/C=C3\C(=O)Nc4ccc(Cl)cc43)c(C)c2C1=O] | 2-(5-Bromo-2-oxo-1,2-dihydro-indol-3-ylidenemethyl)-5-(2-diethylamino-ethyl)-3-methyl-1,5,6,7-tetrahydro-pyrrolo[3,2-c]pyridin-4-one |
| 4 | 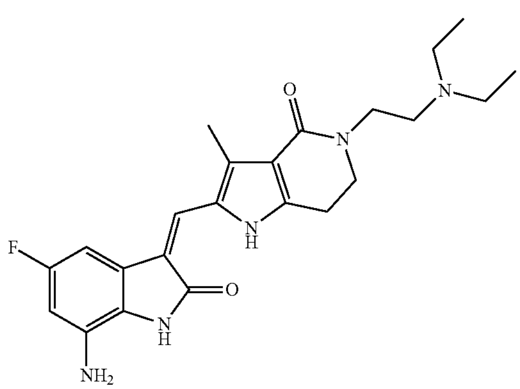 [SMILES: CCN(CC)CCN1CCc2[nH]c(/C=C3\C(=O)Nc4c(N)cc(F)cc43)c(C)c2C1=O] | 2-(7-Amino-5-fluoro-2-oxo-1,2-dihydro-indol-3-ylidenemethyl-1,5,6,7-tetrahydro-pyrrolo[3,2-c]pyridin-4-one |

TABLE I-continued

| Example No Aftermentioned | Structure | Name |
|---|---|---|
| 5 | 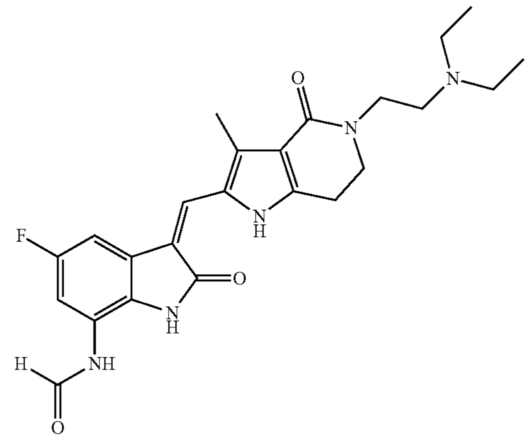 [SMILES: CCN(CC)CCN1CCc2[nH]c(/C=C3\C(=O)Nc4c(NC=O)cc(F)cc43)c(C)c2C1=O] | N-{3-[5-(2-Diethylamino-ethyl)-3-methyl-4-oxo-4,5,6,7-tetrahydro-1H-pyrrolo[3,2-c]pyridine-2-ylmethylene]-5-fluoro-2-oxo-2,3-dihydro-1H-indol-7-yl}-formamide |
| 6 | 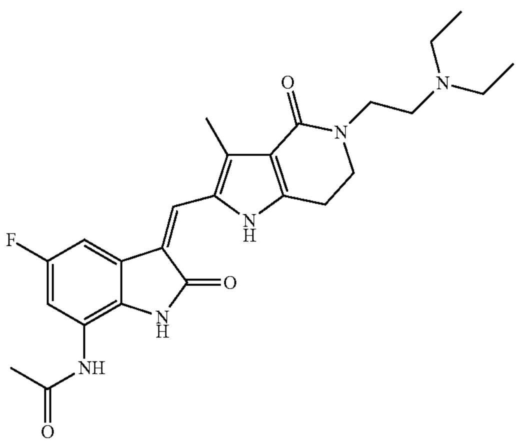 [SMILES: CCN(CC)CCN1CCc2[nH]c(/C=C3\C(=O)Nc4c(NC(C)=O)cc(F)cc43)c(C)c2C1=O] | N-{3-[5-(2-Diethylamino-ethyl)-3-methyl-4-oxo-4,5,6,7-tetrahydro-1H-pyrrolo[3,2-c]pyridine-2-ylmethylene]-5-fluoro-2-oxo-2,3-dihydro-1H-indol-7-yl}-acetamide |
| 7 | 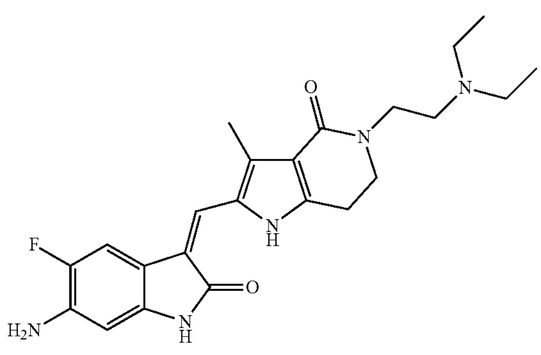 [SMILES: CCN(CC)CCN1CCc2[nH]c(/C=C3\C(=O)Nc4cc(N)c(F)cc43)c(C)c2C1=O] | 2-(6-Amino-5-fluoro-2-oxo-1,2-dihydro-indol-3-ylidenemethyl)-5-(2-diethylamino-ethyl)-3-methyl-1,5,6,7-tetrahydro-pyrrolo[3,2-c]pyridin-4-one |
| 8 | 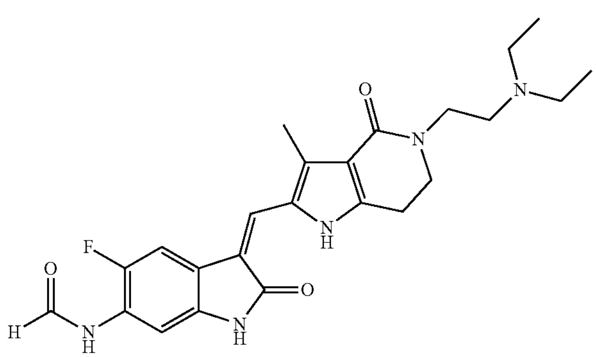 [SMILES: CCN(CC)CCN1CCc2[nH]c(/C=C3\C(=O)Nc4cc(NC=O)c(F)cc43)c(C)c2C1=O] | N-{3-[5-(2-Diethylamino-ethyl)-3-methyl-4-oxo-4,5,6,7-tetrahydro-1H-pyrrolo[3,2-c]pyridine-2-ylmethylene]-5-fluoro-2-oxo-2,3-dihydro-1H-indol-6-yl}-formamide |

TABLE I-continued

| Example No Aftermentioned | Structure | Name |
|---|---|---|
| 9 | 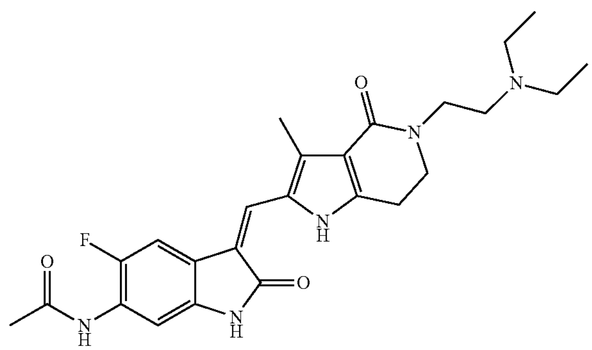 [SMILES: CCN(CC)CCN1CCc2[nH]c(/C=C3\C(=O)Nc4cc(NC(C)=O)c(F)cc43)c(C)c2C1=O] | N-{3-[5-(2-Diethylamino-ethyl)-3-methyl-4-oxo-4,5,6,7-tetrahydro-pyrrolo[3,2-c]pyridine-2-ylmethylene]-5-fluoro-2-oxo-2,3-dihydro-1H-indol-6-yl}-acetamide |
| 10 | 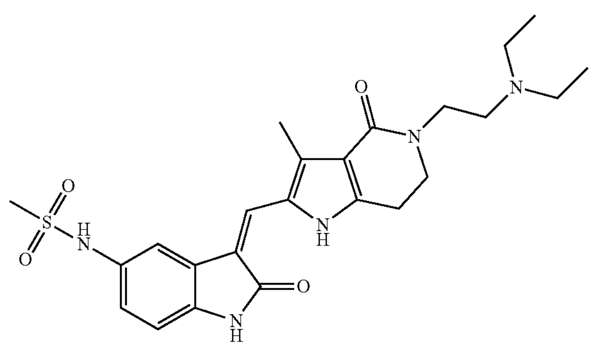 [SMILES: CCN(CC)CCN1CCc2[nH]c(/C=C3\C(=O)Nc4ccc(NS(C)(=O)=O)cc43)c(C)c2C1=O] | N-{3-[5-(2-Diethylamino-ethyl)-3-methyl-4-oxo-4,5,6,7-tetrahydro-1H-pyrrolo[3,2-c]pyridine-2-ylmethylene]-2-oxo-2,3-dihydro-1H-indol-5-yl}-methanesulfonamide |
| 11 | 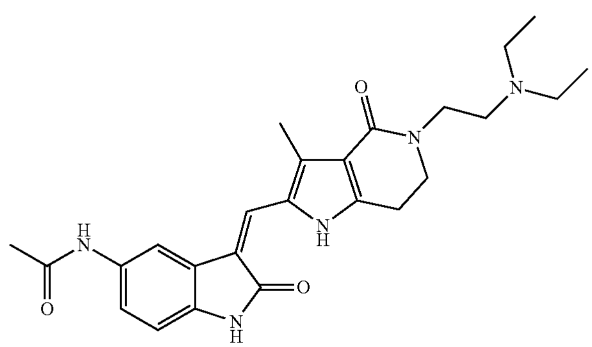 [SMILES: CCN(CC)CCN1CCc2[nH]c(/C=C3\C(=O)Nc4ccc(NC(C)=O)cc43)c(C)c2C1=O] | N-{3-[5-(2-Diethylamino-ethyl)-3-methyl-4-oxo-4,5,6,7-tetrahydro-1H-pyrrolo[3,2-c]pyridine-2-ylmethylene]-2-oxo-2,3-dihydro-1H-indol-5-yl}-acetamide |
| 12 | 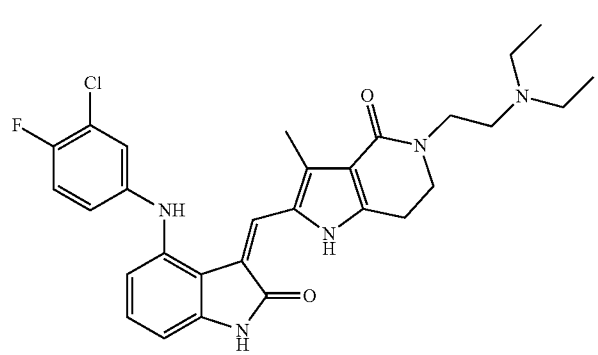 | 4-(3-Chloro-4-fluoro-phenylamino)-5-[5-(2-diethylamino-ethyl)-3-methyl-4-oxo-4,5,6,7-tetrahydro-1H-pyrrolo[3,2-c]pyridine-2-ylmethylene]-5,7-dihydro-pyrrolo[2,3-d]pyrimidin-6-one |

TABLE I-continued

| Example No Aftermentioned | Structure | Name |
|---|---|---|
| 13 | 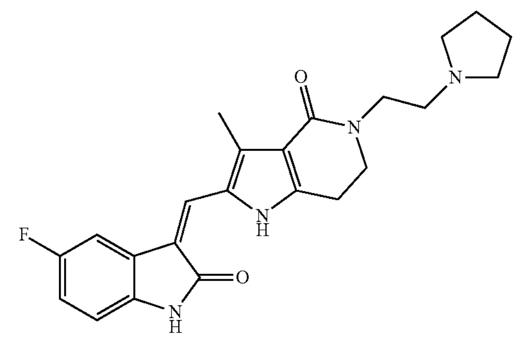 [SMILES: Cc1c(/C=C2\C(=O)Nc3ccc(F)cc32)[nH]c2c1C(=O)N(CCN1CCCC1)CC2] | 2-(5-Fluoro-2-oxo-1,2-dihydro-indol-3-ylidenemethyl)-3-methyl-5-(2-pyrrolidin-1-yl-ethyl)-1,5,6,7-tetrahydro-pyrrolo[3,2-c]pyridin-4-one |
| 14 | 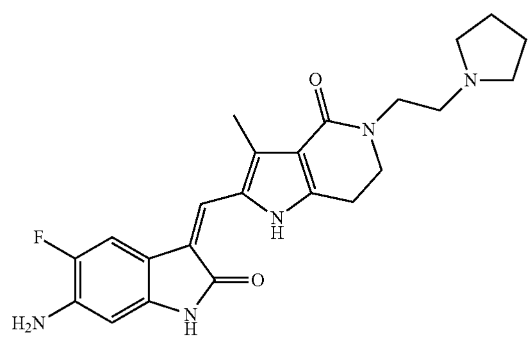 [SMILES: Cc1c(/C=C2\C(=O)Nc3cc(N)c(F)cc32)[nH]c2c1C(=O)N(CCN1CCCC1)CC2] | 2-(6-Amino-5-fluoro-2-oxo-1,2-dihydro-indol-3-ylidenemethyl)-3-methyl-5-(2-pyrrolidin-1-yl-ethyl)-1,5,6,7-tetrahydro-pyrrolo[3,2-c]pyridin-4-one |
| 15 | 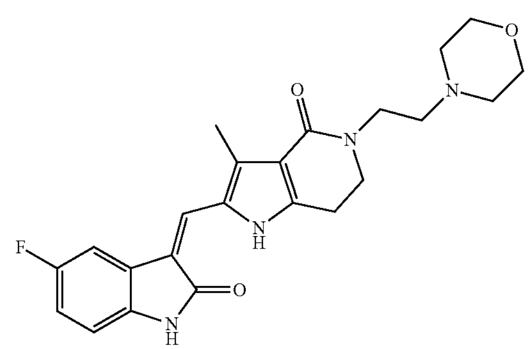 [SMILES: Cc1c(/C=C2\C(=O)Nc3ccc(F)cc32)[nH]c2c1C(=O)N(CCN1CCOCC1)CC2] | 2-(5-Fluoro-2-oxo-1,2-dihydro-indol-3-ylidenemethyl)-3-methyl-5-(2-morpholin-4-yl-ethyl)-1,5,6,7-tetrahydro-pyrrolo[3,2-c]pyridin-4-one |
| 16 | 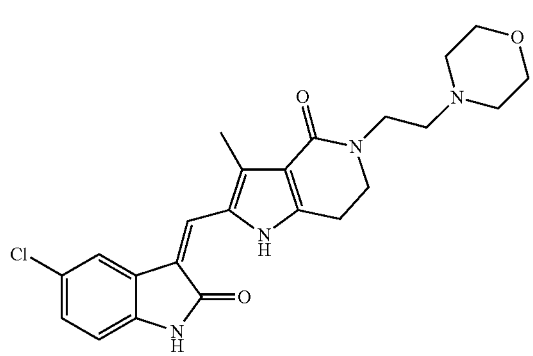 [SMILES: Cc1c(/C=C2\C(=O)Nc3ccc(Cl)cc32)[nH]c2c1C(=O)N(CCN1CCOCC1)CC2] | 2-(5-Chloro-2-oxo-1,2-dihydro-indol-3-ylidenemethyl)-3-methyl-5-(2-morpholin-4-yl-ethyl)-1,5,6,7-tetrahydro-pyrrolo[3,2-c]pyridin-4-one |

TABLE I-continued

| Example No Aftermentioned | Structure | Name |
|---|---|---|
| 17 | 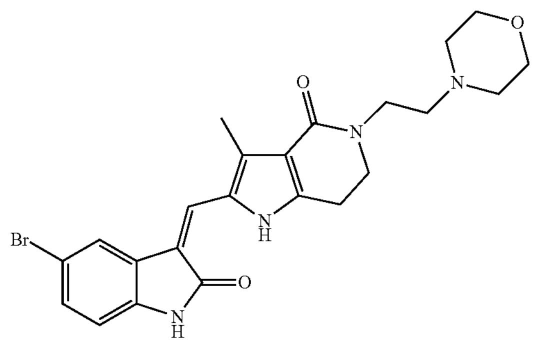 | 2-(5-Bromo-2-oxo-1,2-dihydro-indol-3-ylidenemethyl)-3-methyl-5-(2-mopholin-4-yl-ehtyl)-1,5,6,7-tetrahydro-pyrrolo[3,2-c]pyridin-4-one |
| 18 | 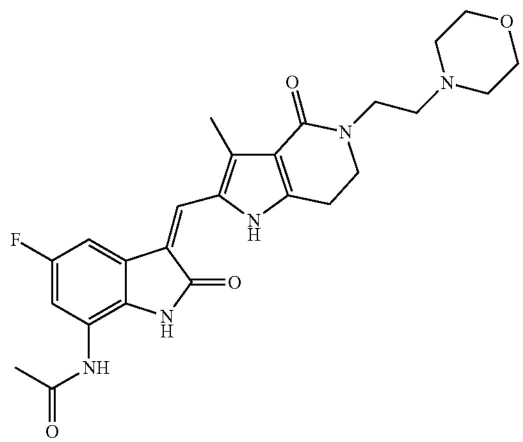 [SMILES: CC(=O)Nc1cc(F)cc2c1NC(=O)/C2=C\c1[nH]c2c(c1C)C(=O)N(CCN1CCOCC1)CC2] | N-{5-Fluoro-3-[3-methyl-5-(2-morpholin-4-yl-ethyl)-4-oxo-4,5,6,7-tetrahydro-1H-pyrrolo[3,2-c]pyridine-2-ylmethylene]-2-oxo-2,3-dihydro-1H-indol-7-yl}-acetamide |
| 19 | 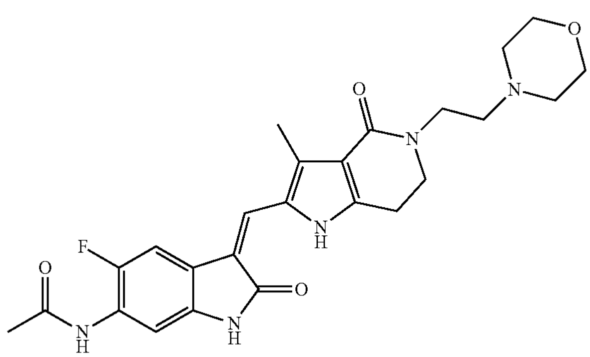 [SMILES: CC(=O)Nc1cc2c(cc1F)/C(=C/c1[nH]c3c(c1C)C(=O)N(CCN1CCOCC1)CC3)C(=O)N2] | N-{5-Fluoro-3-[3-methyl-5-(2-morpholin-4-yl-ethyl)-4-oxo-4,5,6,7-tetrahydro-1H-pyrrolo[3,2-c]pyridine-2-ylmethylene]-2-oxo-2,3-dihydro-1H-indol-6-yl}-acetamide |
| 20 | 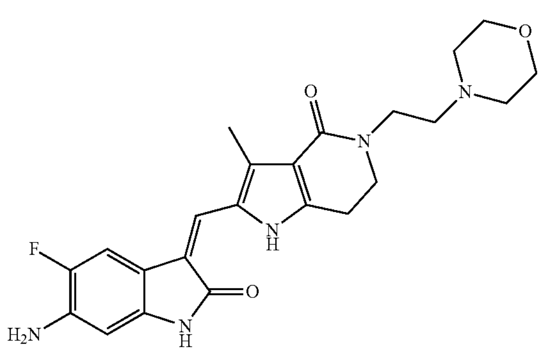 [SMILES: Cc1c(/C=C2\C(=O)Nc3cc(N)c(F)cc32)[nH]c2c1C(=O)N(CCN1CCOCC1)CC2] | 2-(6-Amino-5-fluoro-2-oxo-1,2-dihydro-indol-3-ylidenemethyl)-3-methyl-5-(2-morpholin-4-yl-ethyl)-1,5,6,7-tetrahydro-pyrrolo[3,2-c]pyridin-4-one |

TABLE I-continued

| Example No Aftermentioned | Structure | Name |
|---|---|---|
| 21 | 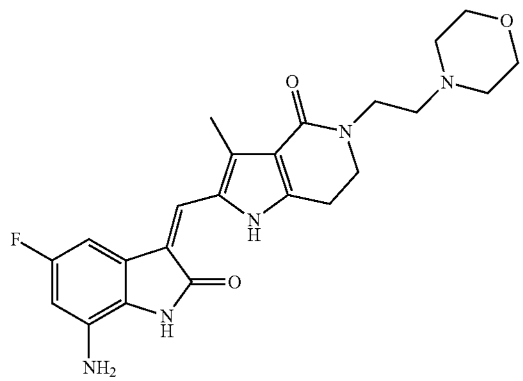 [SMILES: Cc1c(/C=C2\C(=O)Nc3c(N)cc(F)cc32)[nH]c2c1C(=O)N(CCN1CCOCC1)CC2] | 2-(7-Amino-5-fluoro-2-oxo-1,2-dihydro-indol-3-ylidenemethyl)-3-methyl-5-(2-morpholin-4-yl-ethyl)-1,5,6,7-tetrahydro-pyrrolo[3,2-c]pyridin-4-one |
| 22 | 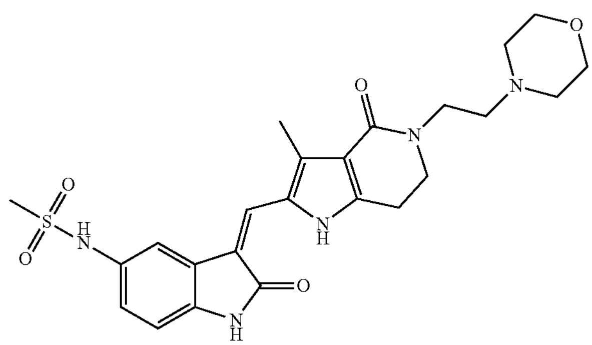 [SMILES: Cc1c(/C=C2\C(=O)Nc3ccc(NS(C)(=O)=O)cc32)[nH]c2c1C(=O)N(CCN1CCOCC1)CC2] | N-{3-[3-Methyl-5-(2-mopholin-4-yl-ethyl)-4-oxo-4,5,6,7-tetrahydro-1H-pyrrolo[3,2-c]pyridine-2-ylmethylene]-2-oxo-2,3-dihydro-1H-indol-5-yl}-methanesulfonamide |
| 23 | 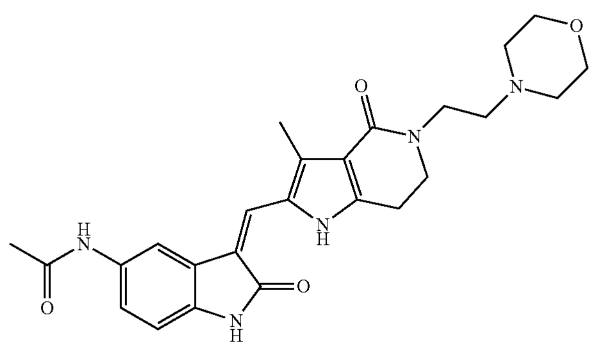 [SMILES: CC(=O)Nc1ccc2c(c1)/C(=C/c1[nH]c3c(c1C)C(=O)N(CCN1CCOCC1)CC3)C(=O)N2] | N-{3-[3-Methyl-5-(2-morpholin-4-yl-ethyl)-4-oxo-4,5,6,7-tetrahydro-1H-pyrrolo[3,2-c]pyridine-2-ylmethylene]-2-oxo-2,3-dihydro-1H-indol-5-yl}-acetamide |
| 24 | 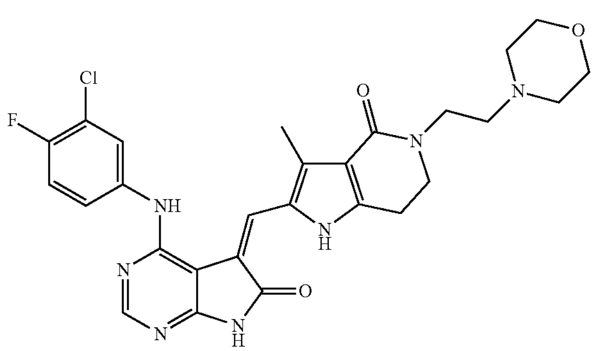 [SMILES: Cc1c(/C=C2\C(=O)Nc3ncnc(Nc4ccc(F)c(Cl)c4)c32)[nH]c2c1C(=O)N(CCN1CCOCC1)CC2] | 4-(3-Chloro-4-fluoro-phenylamino)-5-[3-methyl-5-(2-morpholin-4-yl-ethyl)-4-oxo-4,5,6,7-tetrahydro-1H-pyrrolo[3,2-c]pyridine-2-ylmethylene]-5,7-dihydro-pyrrolo[2,3-d]pyrimidin-6-one |

TABLE I-continued

| Example No Aftermentioned | Structure | Name |
|---|---|---|
| 25 | 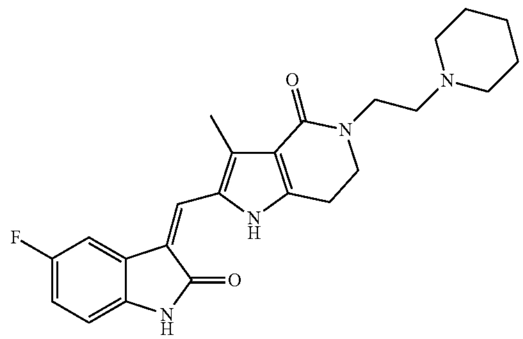 [SMILES: Cc1c(/C=C2\C(=O)Nc3ccc(F)cc32)[nH]c2c1C(=O)N(CCN1CCCCC1)CC2] | 2-(5-Fluoro-2-oxo-1,2-dihydro-indol-3-ylidenemethyl)-3-methyl-5-(2-piperidin-1-yl-ethyl)-1,5,6,7-tetrahydro-pyrrolo[3,2-c]pyridin-4-one |
| 26 | 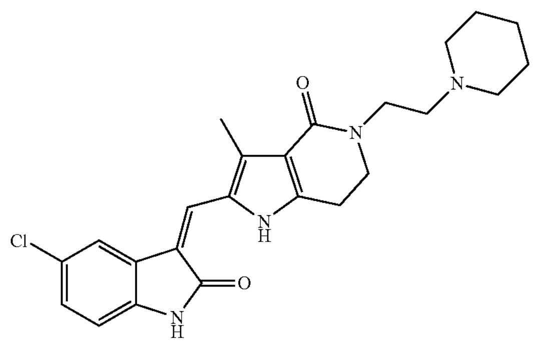 | 2-(5-Chloro-2-oxo-1,2-dihydro-indol-3-ylidenemethyl)-3-methyl-5-(2-piperidin-1-yl-ethyl)-1,5,6,7-tetrahydro-pyrrolo[3,2-c]pyridin-4-one |
| 27 | 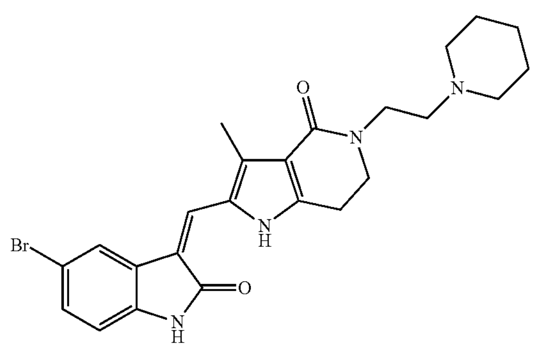 [SMILES: Cc1c(/C=C2\C(=O)Nc3ccc(Cl)cc32)[nH]c2c1C(=O)N(CCN1CCCCC1)CC2] | 2-(5-Bromo-2-oxo-1,2-dihydro-indol-3-ylidenemethyl)-3-methyl-5-(2-piperidin-1-yl-ethyl)-1,5,6,7-tetrahydro-pyrrolo[3,2-c]pyridin-4-one |
| 28 | 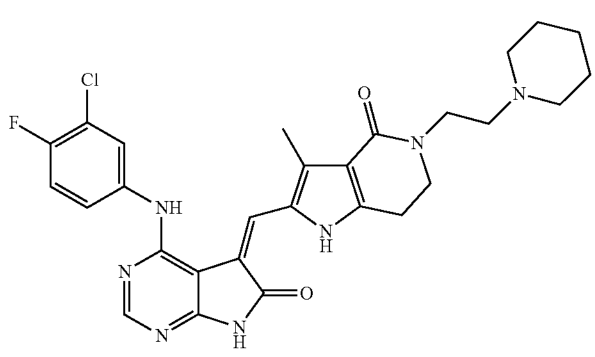 | 4-(3-Chloro-4-fluoro-phenylamino)-5-[3-methyl-4-oxo-5-(2-piperidin-1-yl-ethyl)-4,5,6,7-tetrahydro-1H-pyrrolo[3,2-c]pyridine-2-ylmethylene]-5,7-dihydro-pyrrolo[2,3-d] pyrimidin-6-one |

TABLE I-continued

| Example No Aftermentioned | Structure | Name |
|---|---|---|
| 29 | 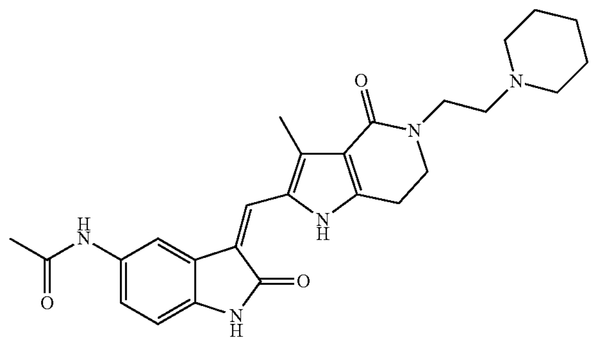 | N-{3-[3-Methyl-4-oxo-5-(2-piperidin-1-yl-ethyl)-4,5,6,7-tetrahydro-1H-pyrrolo[3,2-c]pyridine-2-ylmethylene]-2-oxo-2,3-dihydro-1H-indol-5-yl}-acetamide |
| 30 | 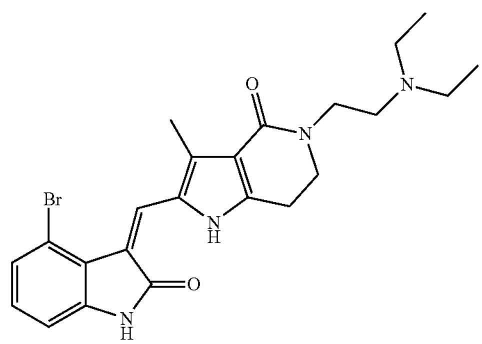 [SMILES: CCN(CC)CCN1CCc2[nH]c(/C=C3\C(=O)Nc4cccc(Br)c43)c(C)c2C1=O] | 2-(4-Bromo-2-oxo-1,2-dihydro-indol-3-ylidenemethyl)-5-(2-diethylamino-ehtyl)-3-methyl-1,5,6,7-tetrahydro-pyrrolo[3,2-c]pyridin-4-one |
| 31 | 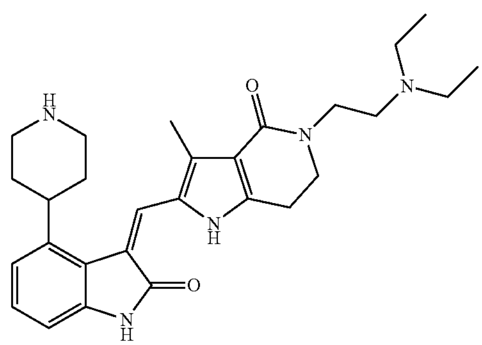 [SMILES: CCN(CC)CCN1CCc2[nH]c(/C=C3\C(=O)Nc4cccc(C5CCNCC5)c43)c(C)c2C1=O] | 5-(2-Diethylamino-ethyl)-3-methyl-2-(2-oxo-4-piperidin-4-yl-1,2-dihydro-indol-3-ylidenemethyl)-1,5,6,7-tetrahydro-pyrrolo[3,2-c]pyridin-4-one |
| 32 | 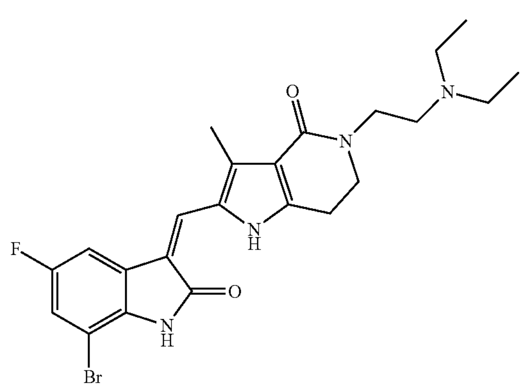 [SMILES: CCN(CC)CCN1CCc2[nH]c(/C=C3\C(=O)Nc4c(Br)cc(F)cc43)c(C)c2C1=O] | 2-(7-Bromo-5-fluoro-2-oxo-1,2-dihydro-indol-3-ylidenemethyl)-5-(2-diethylamino-ethyl)-3-methyl-1,5,6,7-tetrahydro-pyrrolo[3,2-c]pyridin-4-one |

TABLE I-continued

| Example No Aftermentioned | Structure | Name |
|---|---|---|
| 33 | 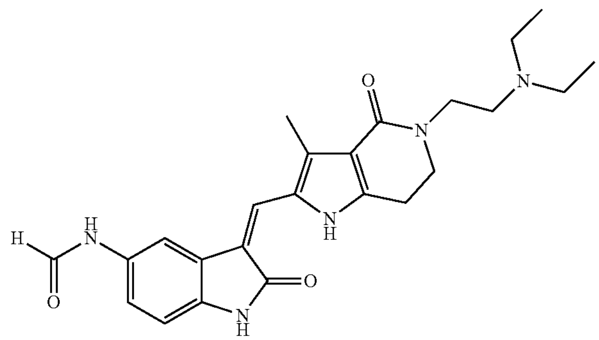 [SMILES: CCN(CC)CCN1CCc2[nH]c(/C=C3\C(=O)Nc4ccc(NC=O)cc43)c(C)c2C1=O] | N-{3-[5-(2-Diethylamino-ethyl)-3-methyl-4-oxo-4,5,6,7-tetrahydro-1H-pyrrolo[3,2-c]pyridine-2-ylmethylene]-2-oxo-2,3-dihydro-1H-indol-5-yl}-formamide |
| 34 | 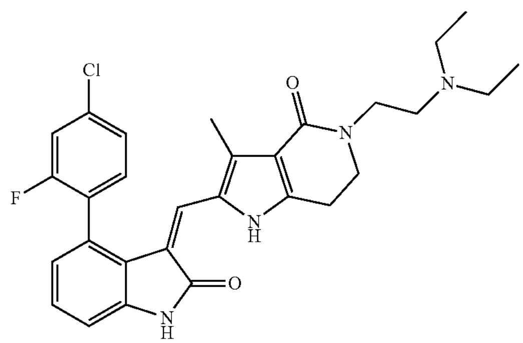 [SMILES: CCN(CC)CCN1CCc2[nH]c(/C=C3\C(=O)Nc4cccc(-c5ccc(Cl)cc5F)c43)c(C)c2C1=O] | 2-[4-(4-Chloro-2-fluoro-phenyl)-2-oxo-1,2-dihydro-indol-3-ylidenemethyl]-5-(2-diethylamino-ethyl)-3-methyl-1,5,6,7-tetrahydro-pyrrolo[3,2-c]pyridin-4-one |
| 35 | 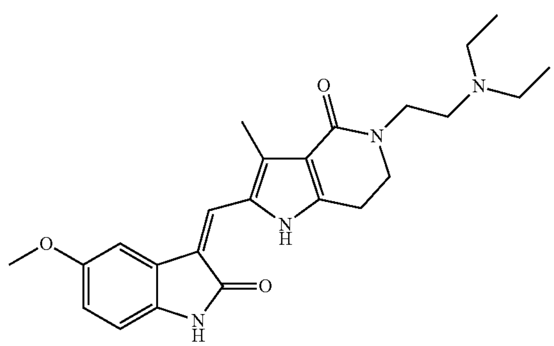 [SMILES: CCN(CC)CCN1CCc2[nH]c(/C=C3\C(=O)Nc4ccc(OC)cc43)c(C)c2C1=O] | 5-(2-Diethylamino-ethyl)-2-(5-methoxy-2-oxo-1,2-dihydro-indol-3-ylidenemethyl)-3-methyl-1,5,6,7-tetrahydro-pyrrolo[3,2-c]pyridin-4-one |
| 36 | 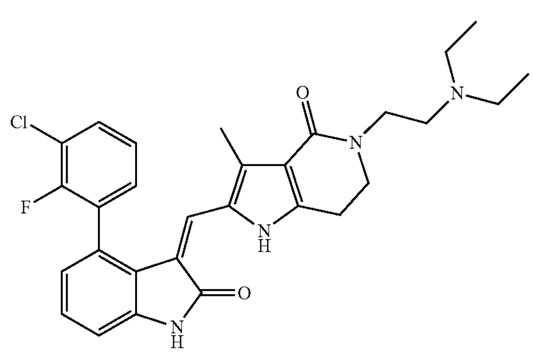 [SMILES: CCN(CC)CCN1CCc2[nH]c(/C=C3\C(=O)Nc4cccc(-c5cccc(Cl)c5F)c43)c(C)c2C1=O] | 2-[4-(3-Chloro-2-fluoro-phenyl)-2-oxo-1,2-dihydro-indol-3-ylidenemethyl]-5-(2-diethylamino-ethyl)-3-methyl-1,5,6,7-tetrahydro-pyrrolo[3,2-c]pyridin-4-one |

TABLE I-continued

| Example No Aftermentioned | Structure | Name |
|---|---|---|
| 37 | 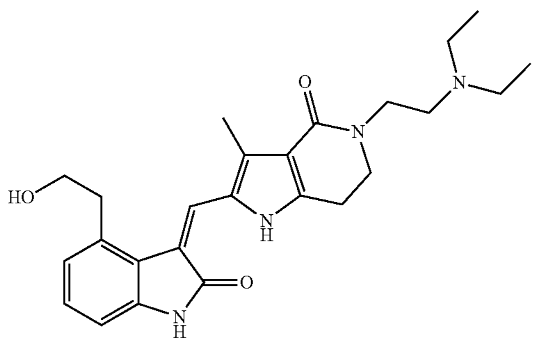 [SMILES: CCN(CC)CCN1CCc2[nH]c(/C=C3\C(=O)Nc4cccc(CCO)c43)c(C)c2C1=O] | 5-(2-Diethylamino-ethyl)-2-[4-(2-hydroxy-ethyl)-2-oxo-1,2-dihydro-indol-3-ylidenemethyl]-3-methyl-1,5,6,7-tetrahydro-pyrrolo[3,2-c]pyridin-4-one |
| 38 | 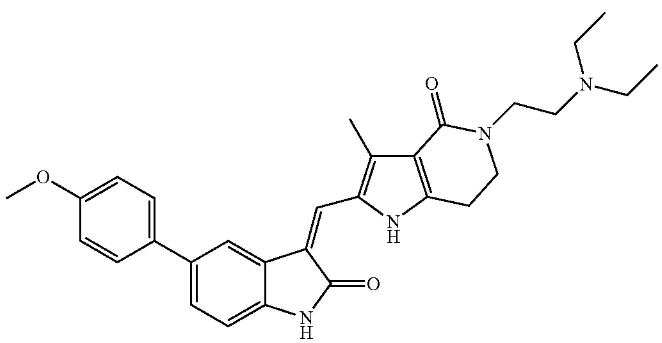 [SMILES: CCN(CC)CCN1CCc2[nH]c(/C=C3\C(=O)Nc4ccc(-c5ccc(OC)cc5)cc43)c(C)c2C1=O] | 5-(2-Diethylamino-ethyl)-2-[5-(4-methoxy-phenyl)-2-oxo-1,2-dihydro-indol-3-ylidenemethyl]-3-methyl-1,5,6,7-tetrahydro-pyrrolo[3,2-c]pyridin-4-one |
| 39 | 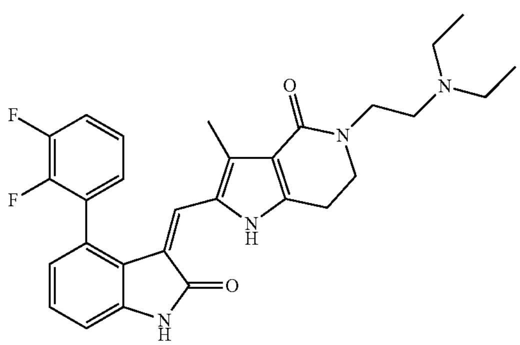 [SMILES: CCN(CC)CCN1CCc2[nH]c(/C=C3\C(=O)Nc4cccc(-c5cccc(F)c5F)c43)c(C)c2C1=O] | 5-(2-Diethylamino-ethyl)-2-[4-(2,3-difluoro-phenyl)-2-oxo-1,2-dihydro-indol-3-ylidenemethyl]-3-methyl-1,5,6,7-tetrahydro-pyrrolo[3,2-c]pyridin-4-one |
| 40 | 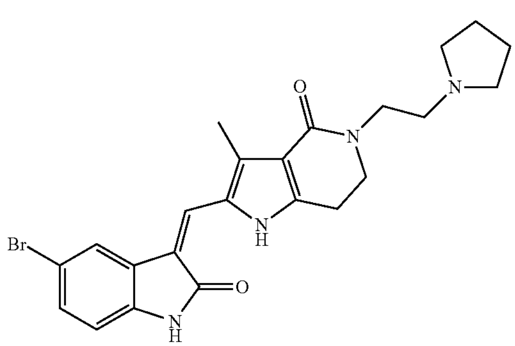 | 2-(5-Bromo-2-oxo-1,2-dihydro-indol-3-ylidenemethyl)-3-methyl-5-(2-pyrrolidin-1-yl-ethyl)-1,5,6,7-tetrahydro-pyrrolo[3,2-c]pyridin-4-one |

TABLE I-continued

| Example No Aftermentioned | Structure | Name |
|---|---|---|
| 41 | 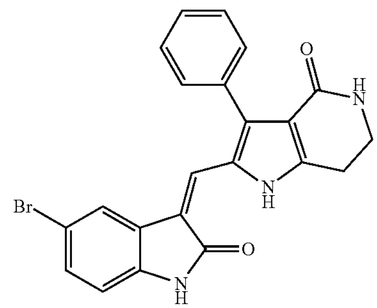 | 2-(5-Bromo-2-oxo-1,2-dihydro-indol-3-ylidenemethyl)-3-phenyl-1,5,6,7-tetrahydro-pyrrolo[3,2-c]pyridin-4-one |
| 42 | 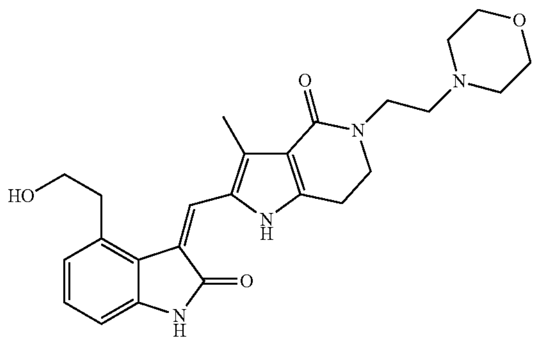 [SMILES: Cc1c(/C=C2\C(=O)Nc3cccc(CCO)c32)[nH]c2c1C(=O)N(CCN1CCOCC1)CC2] | 2-[4-(2-Hydroxy-ethyl)-2-oxo-1,2-dihydro-indol-3-ylidenemethyl]-3-methyl-5-(2-morpholin-4-yl-ethyl)-1,5,6,7-tetrahydro-pyrrolo[3,2-c]pyridin-4-one |
| 43 | 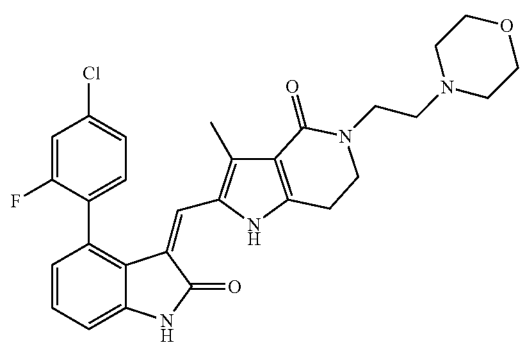 | 2-[4-(4-Chloro-2-fluoro-phenyl)-2-oxo-1,2-dihydro-inol-3-ylidenemethyl]-3-methyl-5-(2-morpholin-4-yl-ethyl)-1,5,6,7-tetrahydro-pyrrolo[3,2-c]pyridin-4-one |
| 44 | 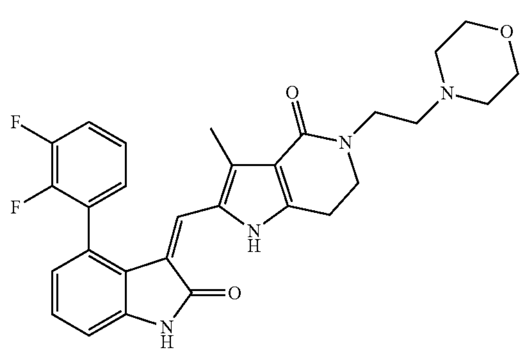 [SMILES: Cc1c(/C=C2\C(=O)Nc3cccc(-c4cccc(F)c4F)c32)[nH]c2c1C(=O)N(CCN1CCOCC1)CC2] | 2-[4-(2,3-Difluoro-phenyl)-2-oxo-1,2-dihydro-indol-3-ylidenemethyl]-3-methyl-5-(2-morpholin-4-yl-ethyl)-1,5,6,7-tetrahydro-pyrrolo[3,2-c]pyridin-4-one |

TABLE I-continued

| Example No Aftermentioned | Structure | Name |
|---|---|---|
| 45 | 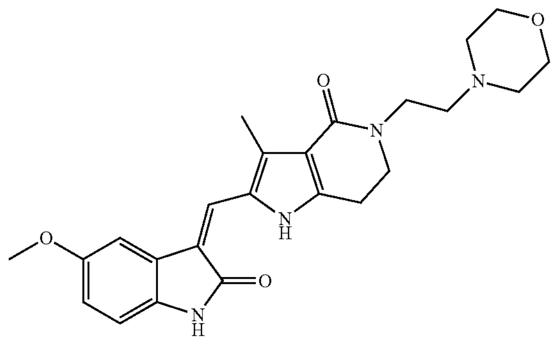 | 2-(5-Methoxy-2-oxo-1,2-dihydro-indol-3-ylidenemethyl)-3-methyl-5-(2-morpholin-4-yl-ethyl)-1,5,6,7-tetrahydro-pyrrolo[3,2-c]pyridin-4-one |
| 46 | 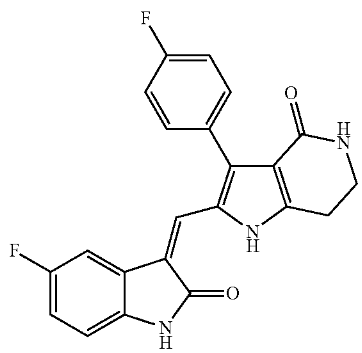 [SMILES: O=C1Nc2ccc(F)cc2/C1=C/c1[nH]c2c(c1-c1ccc(F)cc1)C(=O)NCC2] | 2-(5-Fluoro-2-oxo-1,2-dihydro-indol-3-ylidenemethyl)-3-(4-fluoro-phenyl)-1,5,6,7-tetrahydro-pyrrolo[3,2-c]pyridin-4-one |
| 47 | 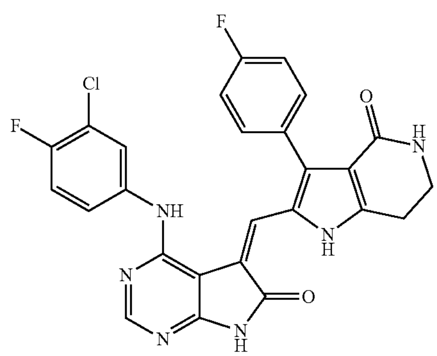 [SMILES: O=C1Nc2ncnc(Nc3ccc(F)c(Cl)c3)c2/C1=C/c1[nH]c2c(c1-c1ccc(F)cc1)C(=O)NCC2] | 4-(3-Chloro-4-fluoro-phenylamino)-5-[3-(4-fluoro-phenyl)-4-oxo-4,5,6,7-tetrahydro-1H-pyrrolo[3,2-c]pyridin-2-ylmethylene]-5,7-dihydro-pyrrolo[2,3-d]pyrimidin-6-one |
| 48 | 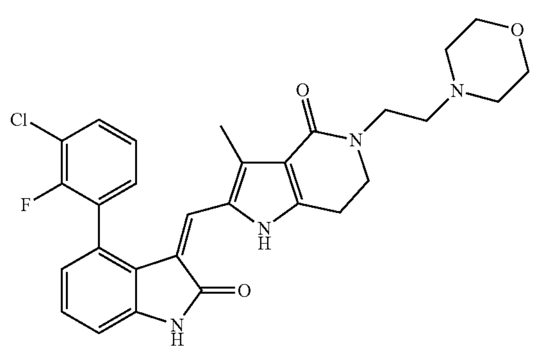 [SMILES: Cc1c(/C=C2\C(=O)Nc3cccc(-c4cccc(Cl)c4F)c32)[nH]c2c1C(=O)N(CCN1CCOCC1)CC2] | 2-[4-(3-Chloro-2-fluoro-phenyl)-2-oxo-1,2-dihydro-indol-3-ylidenemethyl]-3-methyl-5-(2-morpholin-4-yl-ethyl)-1,5,6,7-tetrahydro-pyrrolo[3,2-c]pyridin-4-one |

TABLE I-continued

| Example No Aftermentioned | Structure | Name |
|---|---|---|
| 49 | 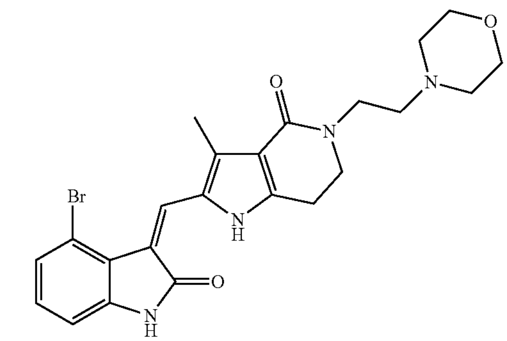 | 2-(4-Brorno-2-oxo-1,2-dihydro-indol-3-ylidenemethyl)-3-methyl-5-(2-morpholin-4-yl-ethyl)-1,5,6,7-tetrahydro-pyrrolo[3,2-c]pyridin-4-one |
| 50 | 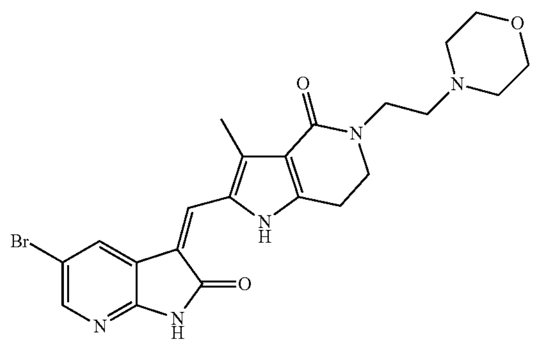 | 2-(5-Bromo-2-oxo-1,2-dihydro-pyrrolo-[2,3-b]pyridin-3-ylidenemethyl)-3-methyl-5-(2-morpholin-4-yl-ethyl)-1,5,6,7-tetrahydro-pyrrolo[3,2-c]pyridin-4-one |
| 51 | 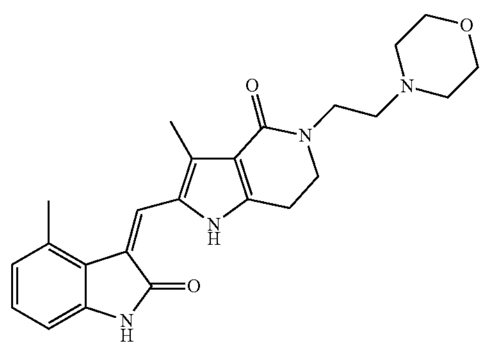 | 3-Methyl-2-(4-methyl-2-oxo-1,2-dihydro-indol-3-ylidenemethyl)-5-(2-morpholin-4-yl-ethyl)-1,5,6,7-tetrahydro-pyrrolo[3,2-c]pyridin-4-one |
| 52 | 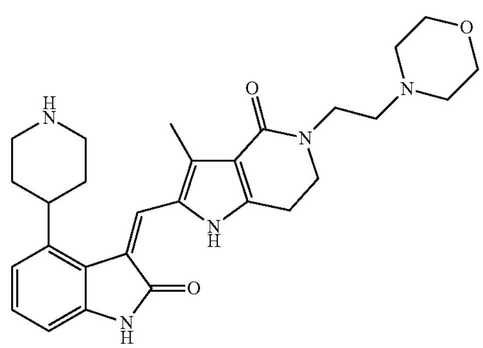 | 3-Methyl-5-(2-morpholin-4-yl-ethyl)-2-(2-oxo-4-piperidin-4-yl-1,2-dihydro-indol-3-ylidenemethyl)-1,5,6,7-tetrahydro-pyrrolo[3,2-c]pyridin-4-one |

TABLE I-continued

| Example No Aftermentioned | Structure | Name |
|---|---|---|
| 53 | 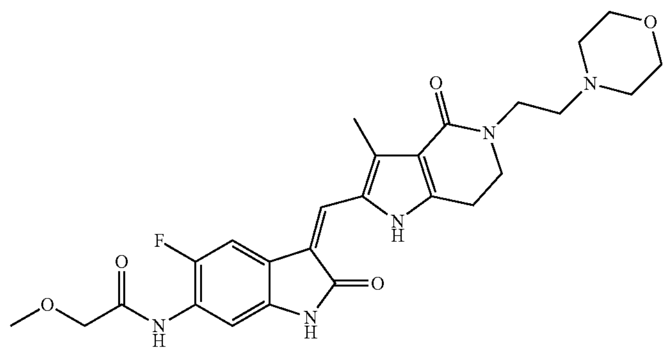 [SMILES: COCC(=O)Nc1cc2c(cc1F)/C(=C/c1[nH]c3c(c1C)C(=O)N(CCN1CCOCC1)CC3)C(=O)N2] | N-{5-Fluoro-3-[3-methyl-5-(2-morpholin-4-yl-ethyl)-4-oxo-4,5,6,7-tetrahydro-1H-pyrrolo[3,2-c]pyridin-2-ylmethylene]-2-oxo-2,3-dihydro-1H-indol-6-yl}-2-methoxy-acetamide |
| 54 | 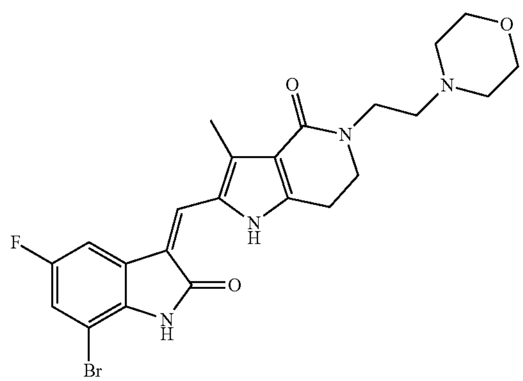 [SMILES: Cc1c(/C=C2\C(=O)Nc3c(Br)cc(F)cc32)[nH]c2c1C(=O)N(CCN1CCOCC1)CC2] | 2-(7-Bromo-5-fluoro-2-oxo-1,2-dihydro-indol-3-ylidenemethyl)-3-methyl-5-(2-morpholin-4-yl-ethyl)-1,5,6,7-tetrahydro-pyrrolo[3,2-c]pyridin-4-one |
| 55 | 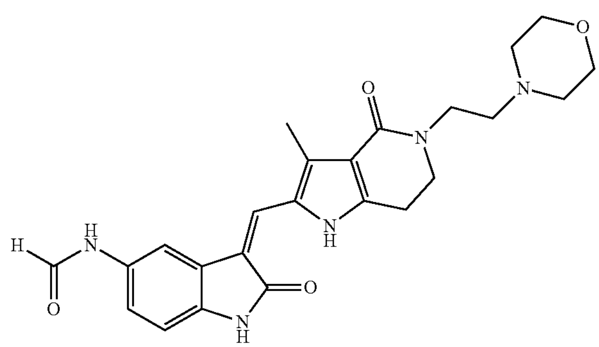 | N-{3-[3-Methyl-5-(2-morpholin-4-yl-ethyl)-4-oxo-4,5,6,7-tetrahydro-1H-pyrrolo[3,2-c]pyridin-2-ylmethylene]-2-oxo-2,3-dihydro-1H-indol-5-yl}-formamide |
| 56 | 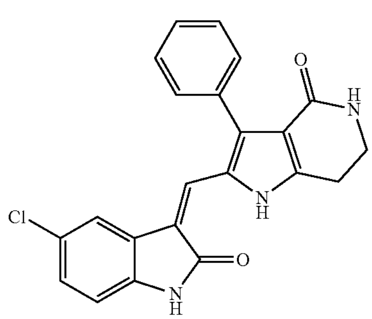 [SMILES: O=C1Nc2ccc(Cl)cc2/C1=C/c1[nH]c2c(c1-c1ccccc1)C(=O)NCC2] | 2-(5-Chloro-2-oxo-1,2-dihydro-indol-3-ylidenemethyl)-3-phenyl-1,5,6,7-tetrahydro-pyrrolo[3,2-c]pyridin-4-one |

TABLE I-continued

| Example No Aftermentioned | Structure | Name |
|---|---|---|
| 57 | 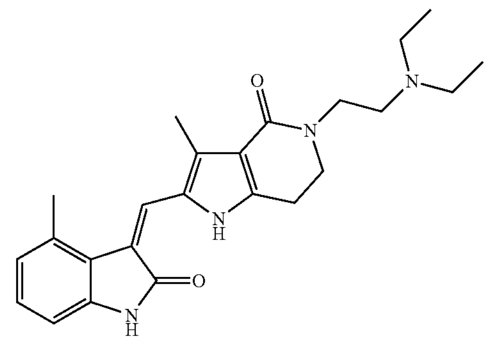 [SMILES: CCN(CC)CCN1CCc2[nH]c(/C=C3\C(=O)Nc4cccc(C)c43)c(C)c2C1=O] | 5-(2-Diethylamino-ethyl)-3-methyl-2-(4-methyl-2-oxo-1,2-dihydro-indol-3-ylidenemethyl)-1,5,6,7-tetrahydro-pyrrolo[3,2-c]pyridin-4-one |
| 58 | 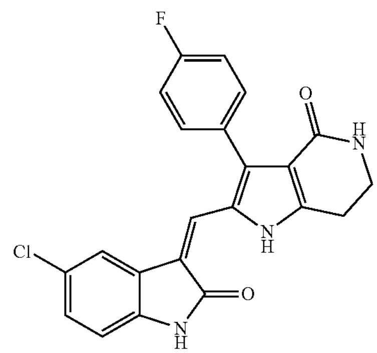 [SMILES: O=C1Nc2ccc(Cl)cc2/C1=C/c1[nH]c2c(c1-c1ccc(F)cc1)C(=O)NCC2] | 2-(5-Chloro-2-oxo-1,2-dihydro-indol-3-ylidenemethyl)-3-(4-fluoro-phenyl)-1,5,6,7-tetrahydro-pyrrolo[3,2-c]pyridin-4-one |
| 59 | 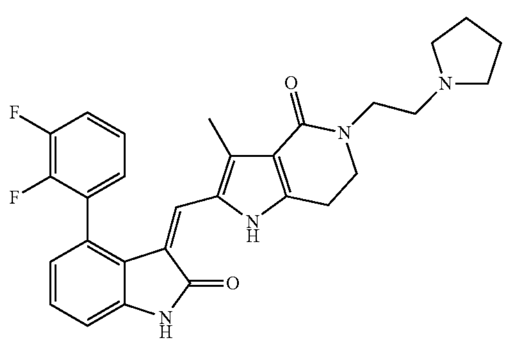 [SMILES: Cc1c(/C=C2\C(=O)Nc3cccc(-c4cccc(F)c4F)c32)[nH]c2c1C(=O)N(CCN1CCCC1)CC2] | 2-[4-(2,3-Difluoro-phenyl)-2-oxo-1,2-dihydro-indol-3-ylidenemethyl]-3-methyl-5-(2-pyrrolidin-1-yl-ethyl)-1,5,6,7-tetrahydro-pyrrolo[3,2-c]pyridin-4-one |
| 60 | 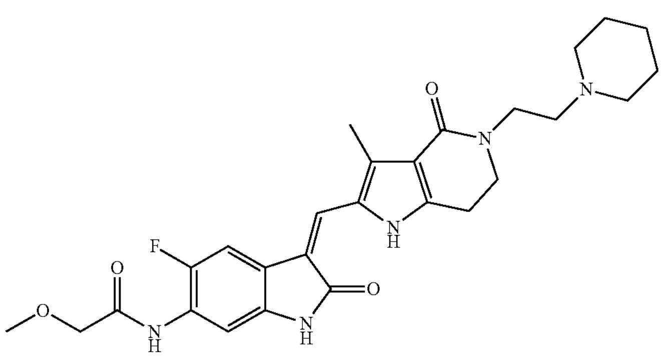 [SMILES: COCC(=O)Nc1cc2c(cc1F)/C(=C/c1[nH]c3c(c1C)C(=O)N(CCN1CCCCC1)CC3)C(=O)N2] | N-{5-Fluoro-3-[3-methyl-4-oxo-5-(2-piperidin-1-yl-ethyl)-4,5,6,7-tetrahydro-1H-pyrrolo[3,2-c]pyridin-2-ylmethylene]-2-oxo-2,3-dihydro-1H-indol-6-yl}-2-methoxy-acetamide |

TABLE I-continued

| Example No Aftermentioned | Structure | Name |
|---|---|---|
| 61 | 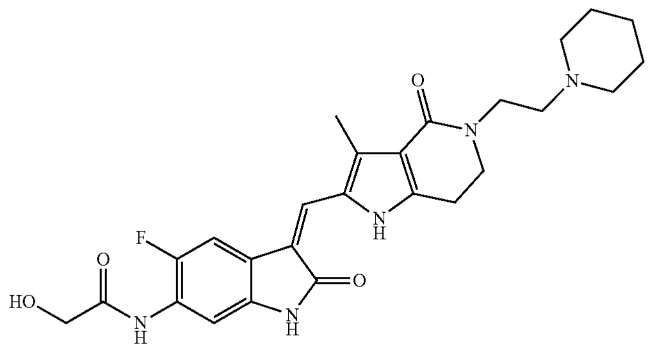 [SMILES: Cc1c(/C=C2\C(=O)Nc3cc(NC(=O)CO)c(F)cc32)[nH]c2c1C(=O)N(CCN1CCCCC1)CC2] | N-{5-Fluoro-3-[3-methyl-4-oxo-5-(2-piperidin-1-yl-ethyl)-4,5,6,7-tetrahydro-1H-pyrrolo[3,2-c]pyridin-2-ylmethylene]-2-oxo-2,3-dihydro-1H-indol-6-yl}-2-hydroxy-acetamide |
| 62 | 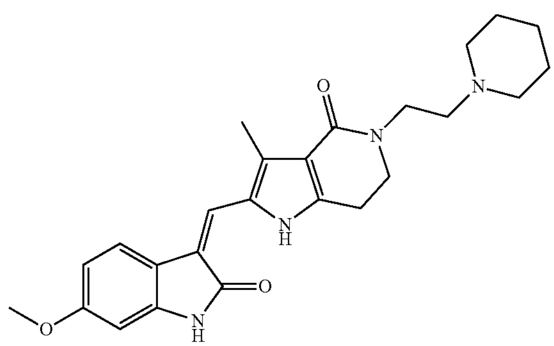 [SMILES: COc1ccc2c(c1)NC(=O)/C2=C\c1[nH]c2c(c1C)C(=O)N(CCN1CCCCC1)CC2] | 2-(6-Methoxy-2-oxo-1,2-dihydro-indol-3-ylidenemethyl)-3-methyl-5-(2-piperidin-1-yl-ethyl)-1,5,6,7-tetrahydro-pyrrolo[3,2-c]pyridin-4-one |
| 63 | 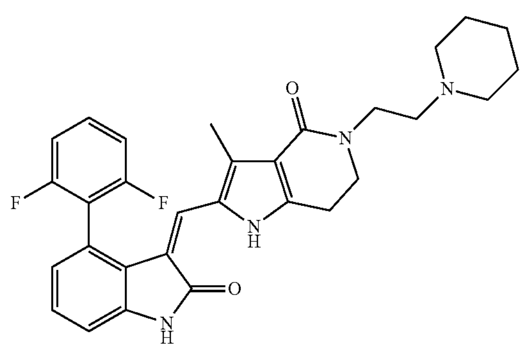 [SMILES: Cc1c(/C=C2\C(=O)Nc3cccc(-c4c(F)cccc4F)c32)[nH]c2c1C(=O)N(CCN1CCCCC1)CC2] | 2-[4-(2,6-Difluoro-phenyl)-2-oxo-1,2-dihydro-indol-3-ylidenemethyl]-3-methyl-5-(2-piperidin-1-yl-ethyl)-1,5,6,7-tetrahydro-pyrrolo[3,2-c]pyridin-4-one |
| 64 | 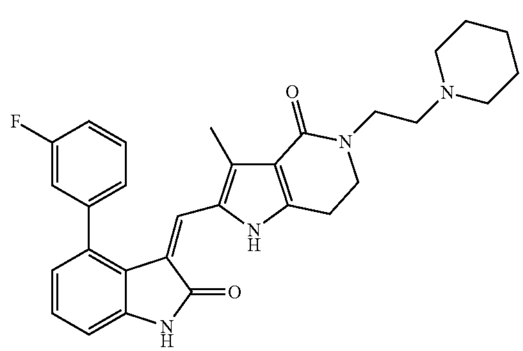 [SMILES: Cc1c(/C=C2\C(=O)Nc3cccc(-c4cccc(F)c4)c32)[nH]c2c1C(=O)N(CCN1CCCCC1)CC2] | 2-[4-(3-Fluoro-phenyl)-2-oxo-1,2-dihydro-indol-3-ylidenemethyl]-3-methyl-5-(2-piperidin-1-yl-ethyl)-1,5,6,7-tetrahydro-pyrrolo[3,2-c]pyridin-4-one |

TABLE I-continued

| Example No Aftermentioned | Structure | Name |
|---|---|---|
| 65 | 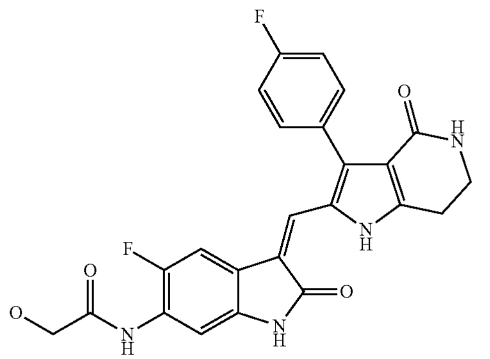 [SMILES: O=C(CO)Nc1cc2c(cc1F)/C(=C/c1[nH]c3c(c1-c1ccc(F)cc1)C(=O)NCC3)C(=O)N2] | N-{5-Fluoro-3-[3-(4-fluoro-phenyl)-4-oxo-4,5,6,7-tetrahydro-1H-pyrrolo[3,2-c]pyridin-2-ylmethylene]-2-oxo-2,3-dihydro-1H-indol-6-yl}-2-hydroxy-acetamide |
| 66 | 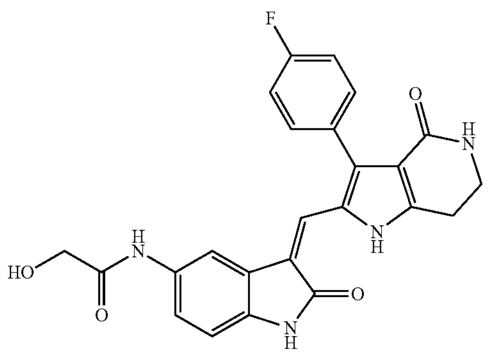 [SMILES: O=C(CO)Nc1ccc2c(c1)/C(=C/c1[nH]c3c(c1-c1ccc(F)cc1)C(=O)NCC3)C(=O)N2] | N-{3-[3-(4-Fluoro-phenyl)-4-oxo-4,5,6,7-tetrahydro-1H-pyrrolo[3,2-c]pyridin-2-yl methylene]-2-oxo-2,3-dihydro-1H-indol-5-yl}-2-hydroxy-acetamide |
| 67 | 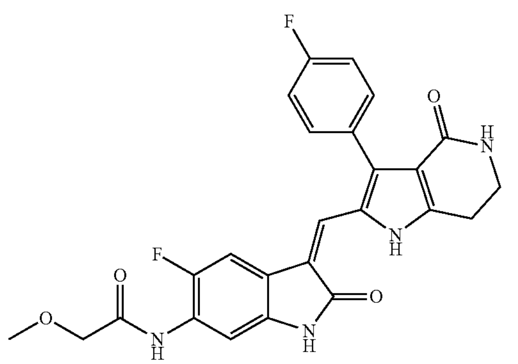 [SMILES: COCC(=O)Nc1cc2c(cc1F)/C(=C/c1[nH]c3c(c1-c1ccc(F)cc1)C(=O)NCC3)C(=O)N2] | N-{5-Fluoro-3-[3-(4-fluoro-phenyl)-4-oxo-4,5,6,7-tetrahydro-1H-pyrrolo[3,2-c]pyridin-2-ylmethylene]-2-oxo-2,3-dihydro-1H-indol-6-yl}-2-methoxy-acetamide |
| 68 | 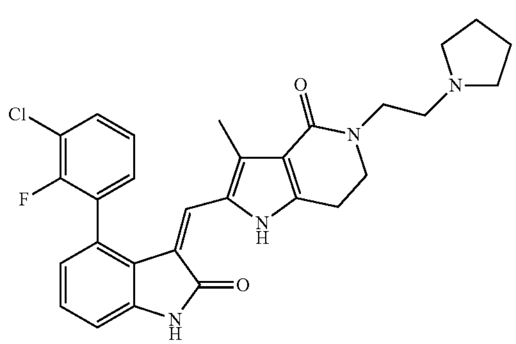 [SMILES: Cc1c(/C=C2\C(=O)Nc3cccc(-c4cccc(Cl)c4F)c32)[nH]c2c1C(=O)N(CCN1CCCC1)CC2] | 2-[4-(3-Chloro-2-fluoro-phenyl)-2-oxo-1,2-dihydro-indol-3-ylidenemethyl]-3-methyl-5-(2-pyrrolidin-1-yl-ethyl)-1,5,6,7-tetrahydro-pyrrolo[3,2-c]pyridin-4-one |

TABLE I-continued

| Example No Aftermentioned | Structure | Name |
|---|---|---|
| 69 | 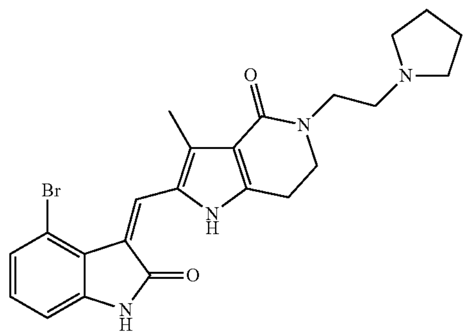 [SMILES: Cc1c(/C=C2\C(=O)Nc3cccc(Br)c32)[nH]c2c1C(=O)N(CCN1CCCC1)CC2] | 2-(4-Bromo-2-oxo-1,2-dihydro-indol-3-ylidenemethyl)-3-methyl-5-(2-pyrrolidin-1-yl-ethyl)-1,5,6,7-tetrahydro-pyrrolo[3,2-c]pyridin-4-one |
| 70 | 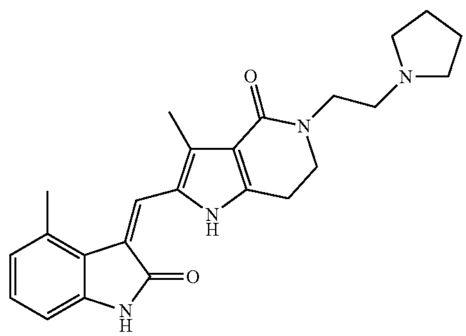 [SMILES: Cc1cccc2c1/C(=C/c1[nH]c3c(c1C)C(=O)N(CCN1CCCC1)CC3)C(=O)N2] | 3-Methyl-2-(4-methyl-2-oxo-1,2-dihydro-indol-3-ylidenemethyl)-5-(2-pyrrolidin-1-yl-ethyl)-1,5,6,7-tetrahydro-pyrrolo[3,2-c]pyridin-4-one |
| 71 | 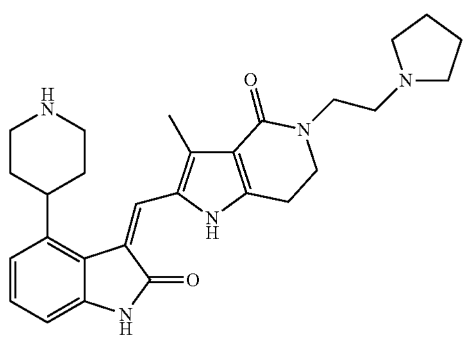 [SMILES: Cc1c(/C=C2\C(=O)Nc3cccc(C4CCNCC4)c32)[nH]c2c1C(=O)N(CCN1CCCC1)CC2] | 3-Methyl-2-(2-oxo-4-piperidin-4-yl-1,2-dihydro-indol-3-ylidenemethyl)-5-(2-pyrrolidin-1-yl-ethyl)-1,5,6,7-tetrahydro-pyrrolo[3,2-c]pyridin-4-one |
| 72 | 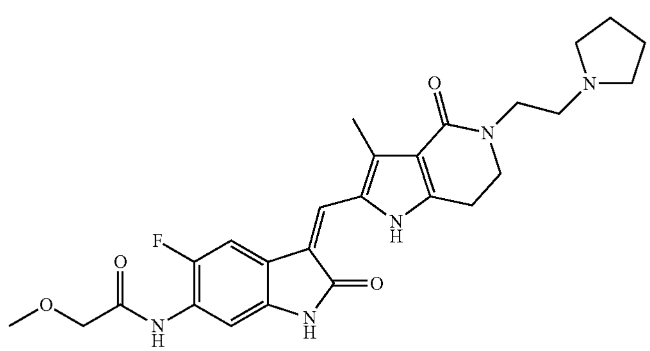 [SMILES: COCC(=O)Nc1cc2c(cc1F)/C(=C/c1[nH]c3c(c1C)C(=O)N(CCN1CCCC1)CC3)C(=O)N2] | N-{5-Fluoro-3-[3-methyl-4-oxo-5-(2-pyrrolidin-1-yl-ethyl)-4,5,6,7-tetrahydro-1H-pyrrolo[3,2-c]pyridin-2-ylmethylene]-2-oxo-2,3-dihydro-1H-indol-6-yl}-2-methoxy-acetamide |

TABLE I-continued

| Example No Aftermentioned | Structure | Name |
|---|---|---|
| 73 | 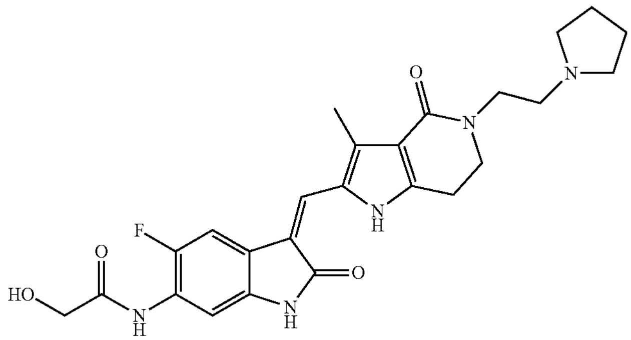 [SMILES: Cc1c(/C=C2\C(=O)Nc3cc(NC(=O)CO)c(F)cc32)[nH]c2c1C(=O)N(CCN1CCCC1)CC2] | N-{5-Fluoro-3-[3-methyl-4-oxo-5-(2-pyrrolidin-1-yl-ethyl)-4,5,6,7-tetrahydro-1H-pyrrolo[3,2-c]pyridin-2-ylmethylene]-2-oxo-2,3-dihydro-1H-indol-6-yl}-2-hydroxy-acetamide |
| 74 | 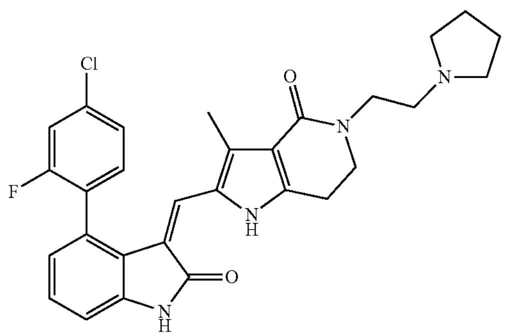 [SMILES: Cc1c(/C=C2\C(=O)Nc3cccc(-c4ccc(Cl)cc4F)c32)[nH]c2c1C(=O)N(CCN1CCCC1)CC2] | 2-[4-(4-Chloro-2-fluoro-phenyl)-2-oxo-1,2-dihydro-indol-3-ylidenemethyl]-3-methyl-5-(2-pyrrolidin-1-yl-ethyl)-1,5,6,7-tetrahydro-pyrrolo[3,2-c]pyridin-4-one |
| 75 | 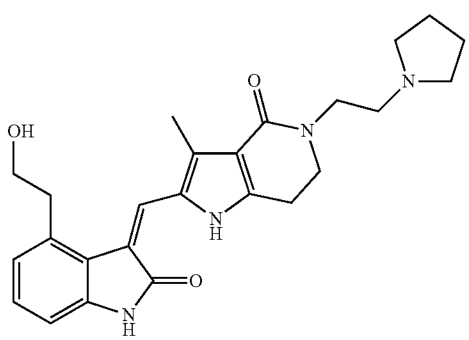 [SMILES: Cc1c(/C=C2\C(=O)Nc3cccc(CCO)c32)[nH]c2c1C(=O)N(CCN1CCCC1)CC2] | 2-[4-(2-Hydroxy-ethyl)-2-oxo-1,2-dihydro-indol-3-ylidenemethyl]-3-methyl-5-(2-pyrrolidin-1-yl-ethyl)-1,5,6,7-tetrahydro-pyrrolo[3,2-c]pyridin-4-one |
| 76 | 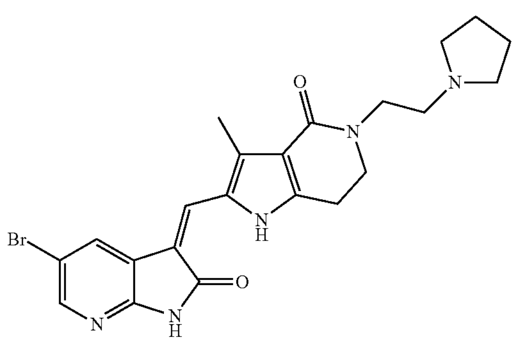 [SMILES: Cc1c(/C=C2\C(=O)Nc3ncc(Br)cc32)[nH]c2c1C(=O)N(CCN1CCCC1)CC2] | 2-(5-Bromo-2-oxo-1,2-dihydro-pyrrolo[2,3-b]pyridin-3-ylidenemethyl)-3-methyl-5-(2-pyrrolidin-1-yl-ethyl)-1,5,6,7-tetrahydro-pyrrolo[3,2-c]pyridin-4-one |

TABLE I-continued

| Example No Aftermentioned | Structure | Name |
|---|---|---|
| 77 | 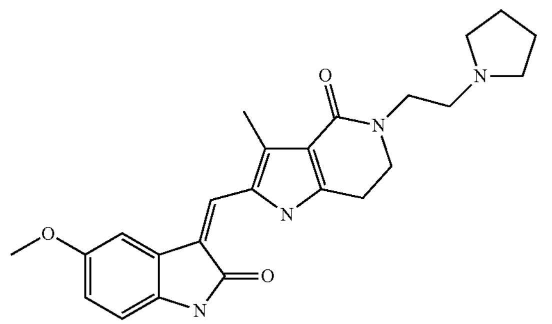 [SMILES: COc1ccc2c(c1)/C(=C/c1[nH]c3c(c1C)C(=O)N(CCN1CCCC1)CC3)C(=O)N2] | 2-(5-Methoxy-2-oxo-1,2-dihydro-indol-3-ylidenemethyl)-3-methyl-5-(2-pyrrolidin-1-yl-ethyl)-1,5,6,7-tetrahydro-pyrrolo[3,2-c]pyridin-4-one |
| 78 | 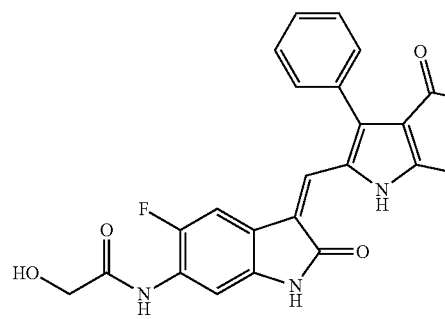 | N-[5-Fluoro-2-oxo-3-(4-oxo-3-phenyl-4,5,6,7-tetrahydro-1H-pyrrolo[3,2-c]pyridin-2-ylmethylene)-2,3-dihydro-1H-indol-6-yl]-2-hydroxy-acetamide |
| 79 | 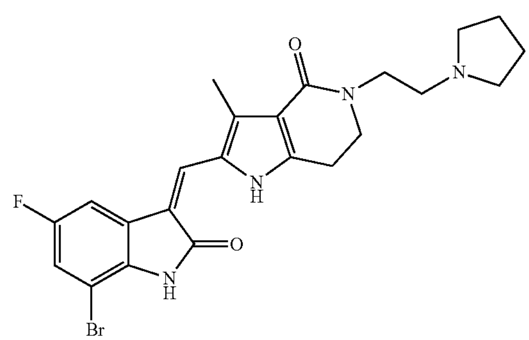 [SMILES: Cc1c(/C=C2\C(=O)Nc3c(Br)cc(F)cc32)[nH]c2c1C(=O)N(CCN1CCCC1)CC2] | 2-(7-Bromo-5-fluoro-2-oxo-1,2-dihydro-indol-3-ylidenemethyl)-3-methyl-5-(2-pyrrolidin-1-yl-ethyl)-1,5,6,7-tetrahydro-pyrrolo[3,2-c]pyridin-4-one |
| 80 | 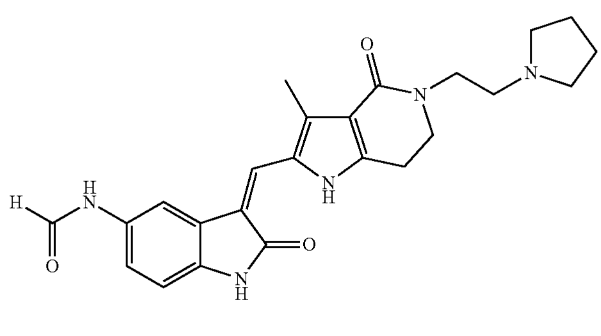 [SMILES: Cc1c(/C=C2\C(=O)Nc3ccc(NC=O)cc32)[nH]c2c1C(=O)N(CCN1CCCC1)CC2] | N-{3-[3-Methyl-4-oxo-5-(2-pyrrolidin-1-yl-ethyl)-4,5,6,7-tetrahydro-1H-pyrrolo[3,2-c]pyridin-2-ylmethylene]-2-oxo-2,3-dihydro-1H-indol-5-yl}-formamide |

TABLE I-continued

| Example No Aftermentioned | Structure | Name |
|---|---|---|
| 81 | 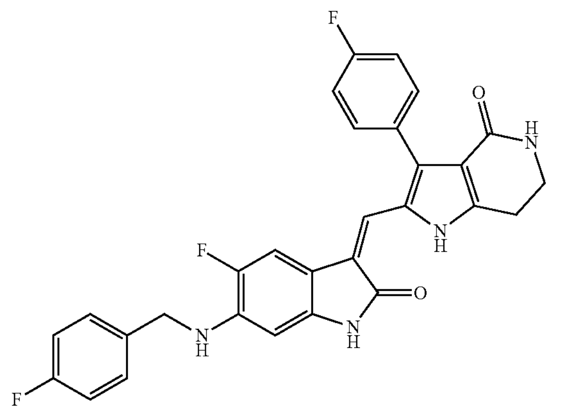 [SMILES: O=C1Nc2cc(NCc3ccc(F)cc3)c(F)cc2/C1=C/c1[nH]c2c(c1-c1ccc(F)cc1)C(=O)NCC2] | 2-[5-Fluoro-6-(4-fluoro-benzylamino)-2-oxo-1,2-dihydro-indol-3-ylidenemethyl]-3-(4-fluoro-phenyl)-1,5,6,7-tetrahydro-pyrrolo[3,2-c]pyridin-4-one |
| 82 | 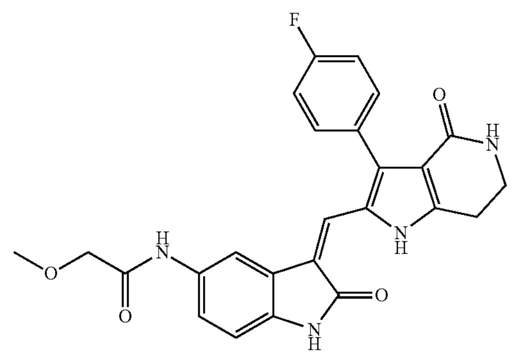 [SMILES: COCC(=O)Nc1ccc2c(c1)/C(=C/c1[nH]c3c(c1-c1ccc(F)cc1)C(=O)NCC3)C(=O)N2] | N-{3-[3-(4-Fluoro-phenyl)-4-oxo-4,5,6,7-tetrahydro-1H-pyrrolo[3,2-c]pyridin-2-yl methylene]-2-oxo-2,3-dihydro-1H-indol-5-yl}-2-methoxy-acetamide |
| 83 | 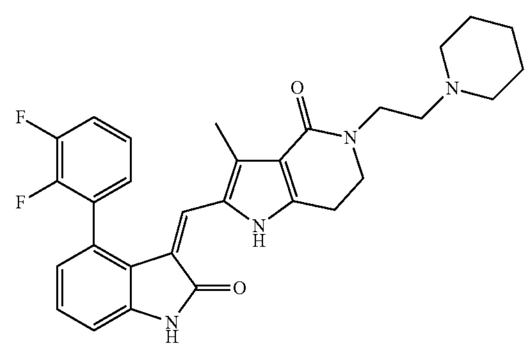 [SMILES: Cc1c(/C=C2\C(=O)Nc3cccc(-c4cccc(F)c4F)c32)[nH]c2c1C(=O)N(CCN1CCCCC1)CC2] | 2-[4-(2,3-Difluoro-phenyl)-2-oxo-1,2-dihydro-indol-3-ylidenemethyl]-3-methyl-5-(2-piperidin-1-yl-ethyl)-1,5,6,7-tetrahydro-pyrrolo[3,2-c]pyridin-4-one |
| 84 | 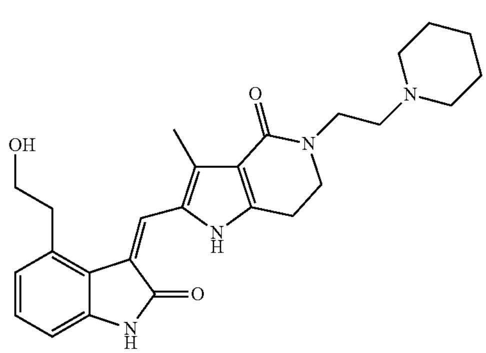 [SMILES: Cc1c(/C=C2\C(=O)Nc3cccc(CCO)c32)[nH]c2c1C(=O)N(CCN1CCCCC1)CC2] | 2-[4-(2-Hydroxy-ethyl)-2-oxo-1,2-dihydro-indol-3-ylidenemethyl]-3-methyl-5-(2-piperidin-1-yl-ethyl)-1,5,6,7-tetrahydro-pyrrolo[3,2-c]pyiidin-4-one |

TABLE I-continued

| Example No Aftermentioned | Structure | Name |
|---|---|---|
| 85 | 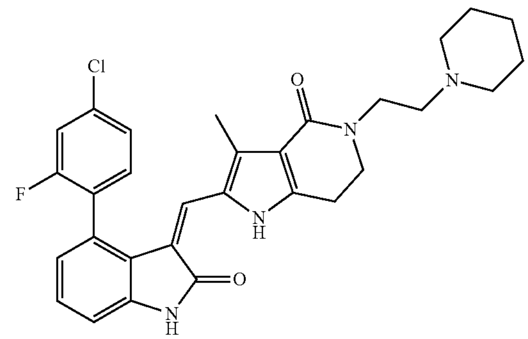 [SMILES: Cc1c(/C=C2\C(=O)Nc3cccc(-c4ccc(Cl)cc4F)c32)[nH]c2c1C(=O)N(CCN1CCCCC1)CC2] | 2-[4-(4-Chloro-2-fluoro-phenyl)-2-oxo-1,2-dihydro-indol-3-ylidenemethyl]-3-methyl-5-(2-piperidin-1-yl-ethyl)-1,5,6,7-tetrahydro-pyrrolo[3,2-c]pyridin-4-one |
| 86 | 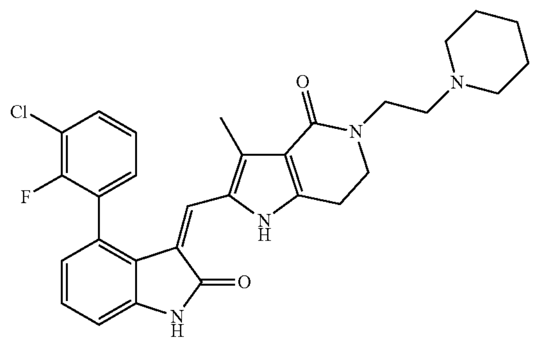 [SMILES: Cc1c(/C=C2\C(=O)Nc3cccc(-c4cccc(Cl)c4F)c32)[nH]c2c1C(=O)N(CCN1CCCCC1)CC2] | 2-[4-(3-Chloro-2-fluoro-phenyl)-2-oxo-1,2-dihydro-indol-3-ylidenemethyl]-3-methyl-5-(2-piperidin-1-yl-ethyl)-1,5,6,7-tetrahydro-pyrrolo[3,2-c]pyridin-4-one |
| 87 | 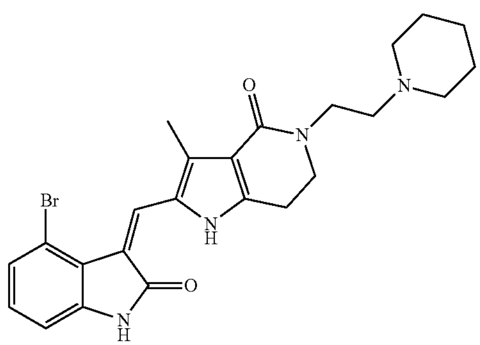 [SMILES: Cc1c(/C=C2\C(=O)Nc3cccc(Br)c32)[nH]c2c1C(=O)N(CCN1CCCCC1)CC2] | 2-(4-Bromo-2-oxo-1,2-dihydro-indol-3-ylidenemethyl)-3-methyl-5-(2-piperidin-1-yl-ethyl)-1,5,6,7-tetrahydro-pyrrolo[3,2-c]pyridin-4-one |
| 88 | 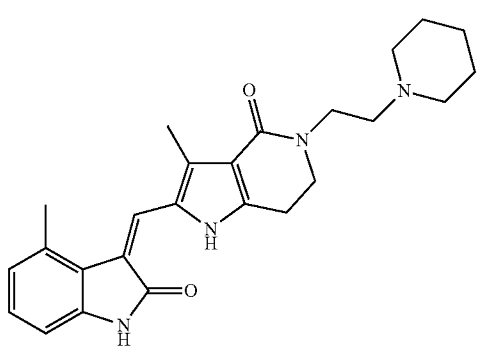 [SMILES: Cc1cccc2c1/C(=C/c1[nH]c3c(c1C)C(=O)N(CCN1CCCCC1)CC3)C(=O)N2] | 3-Methyl-2-(4-methyl-2-oxo-1,2-dihydro-indol-3-ylidenemethyl)-5-(2-piperidin-1-yl-ethyl)-1,5,6,7-tetrahydro-pyrrolo[3,2-c]pyridin-4-one |

TABLE I-continued

| Example No Aftermentioned | Structure | Name |
|---|---|---|
| 89 | 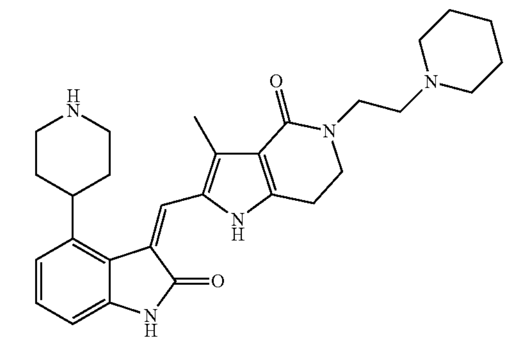 [SMILES: Cc1c(/C=C2\C(=O)Nc3cccc(C4CCNCC4)c32)[nH]c2c1C(=O)N(CCN1CCCCC1)CC2] | 3-Methyl-2-(2-oxo-4-piperidin-4-yl-1,2-dihydro-indol-3-ylidenemethyl)-5-(2-piperidin-1-yl-ethyl)-1,5,6,7-tetrahydro-pyrrolo[3,2-c]pyridin-4-one |
| 90 | 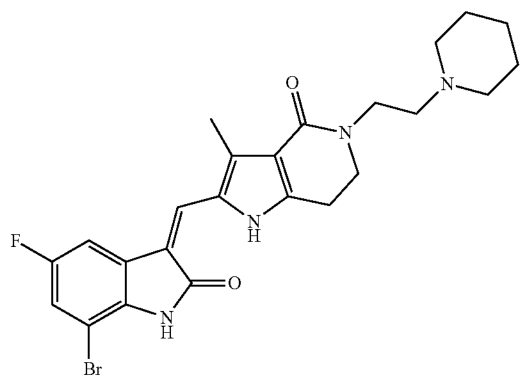 | 2-(7-Bromo-5-fluoro-2-oxo-1,2-dihydro-indol-3-ylidenemethyl)-3-methyl-5-(2-piperidin-1-yl-ethyl)-1,5,6,7-tetrahydro-pyrrolo[3,2-c]pyridin-4-one |
| 91 | 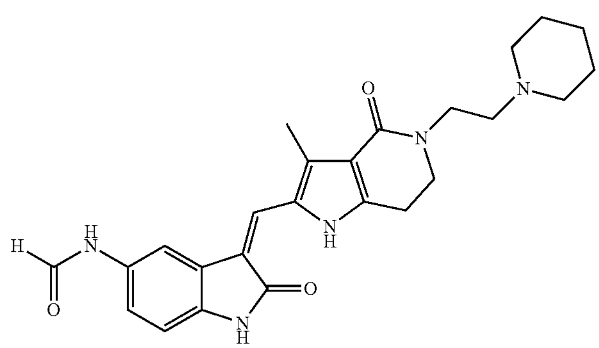 [SMILES: Cc1c(/C=C2\C(=O)Nc3ccc(NC=O)cc32)[nH]c2c1C(=O)N(CCN1CCCCC1)CC2] | N-{3-[3-Methyl-4-oxo-5-(2-piperidin-1-yl-ethyl)-4,5,6,7-tetrahydro-1H-pyrrolo[3,2-c]pyridin-2-ylmethylene]-2-oxo-2,3-dihydro-1H-indol-5-yl}-formamide |
| 92 | 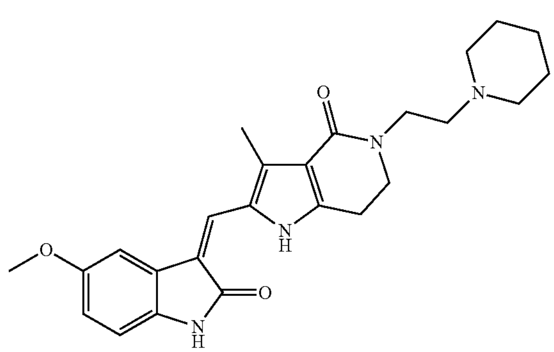 [SMILES: COc1ccc2c(c1)/C(=C/c1[nH]c3c(c1C)C(=O)N(CCN1CCCCC1)CC3)C(=O)N2] | 2-(5-Methoxy-2-oxo-1,2-dihydro-indol-3-ylidenemethyl)-3-methyl-5-(2-piperidin-1-yl-ethyl)-1,5,6,7-tetrahydro-pyrrolo[3,2-c]pyridin-4-one |

TABLE I-continued

| Example No Aftermentioned | Structure | Name |
|---|---|---|
| 93 | 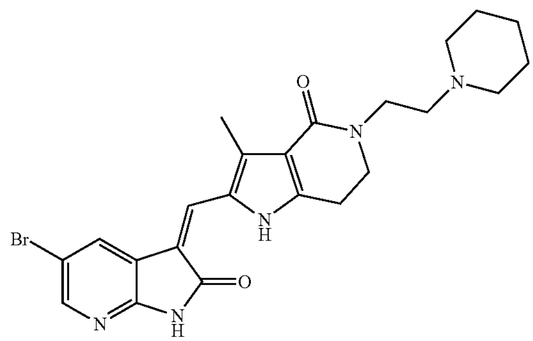 | 2-(5-Bromo-2-oxo-1,2-dihydro-pyrrolo[2,3-b]pyridin-3-ylidenemethyl)-3-methyl-5-(2-piperidin-1-yl-ethyl)-1,5,6,7-tetrahydro-pyrrolo[3,2-c]pyridin-4-one |
| 94 | 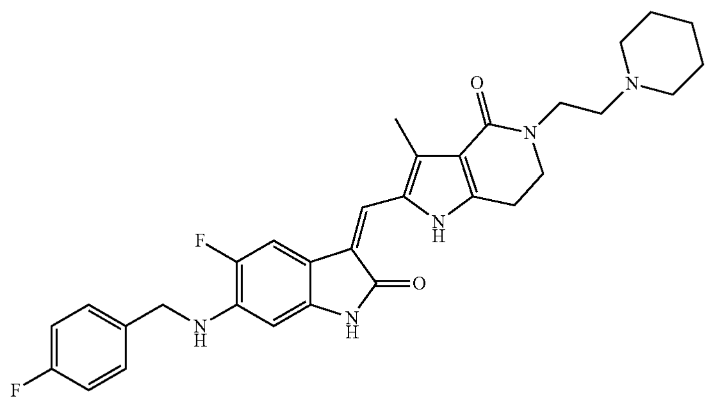 [SMILES: Cc1c(/C=C2\C(=O)Nc3cc(NCc4ccc(F)cc4)c(F)cc32)[nH]c2c1C(=O)N(CCN1CCCCC1)CC2] | 2-[5-Fluoro-6-(4-fluoro-benzylamino)-2-oxo-1,2-dihydro-indol-3-ylidenemethyl]-3-methyl-5-(2-piperidin-1-yl-ethyl)-1,5,6,7-tetrahydro-pyrrolo[3,2-c]pyridin-4-one |
| 95 | 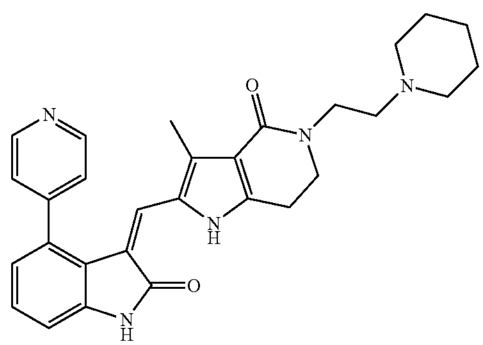 [SMILES: Cc1c(/C=C2\C(=O)Nc3cccc(-c4ccncc4)c32)[nH]c2c1C(=O)N(CCN1CCCCC1)CC2] | 3-Methyl-2-(2-oxo-4-pyridin-4-yl-1,2-dihydro-indol-3-ylidenemethyl)-5-(2-piperidin-1-yl-ethyl)-1,5,6,7-tetrahydro-pyrrolo[3,2-c]pyridin-4-one |
| 96 | 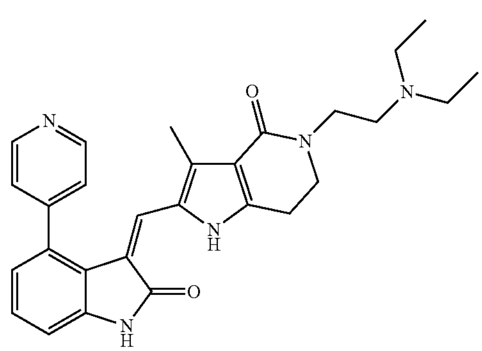 [SMILES: CCN(CC)CCN1CCc2[nH]c(/C=C3\C(=O)Nc4cccc(-c5ccncc5)c43)c(C)c2C1=O] | 5-(2-Diethylamino-ethyl)-3-methyl-2-(4-methyl-2-oxo-1,2-dihydro-indol-3-ylidenemethyl)-1,5,6,7-tetrahydro-pyrrolo[3,2-c]pyridin-4-one |

TABLE I-continued

| Example No Aftermentioned | Structure | Name |
|---|---|---|
| 97 | 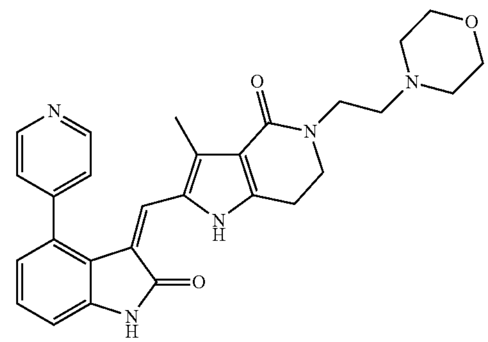 [SMILES: Cc1c(/C=C2\C(=O)Nc3cccc(-c4ccncc4)c32)[nH]c2c1C(=O)N(CCN1CCOCC1)CC2] | 3-Methyl-5-(2-morpholin-4-yl-ethyl)-2-(2-oxo-4-pyridin-4-yl-1,2-dihydro-indol-3-ylidenemethyl)-1,5,6,7-tetrahydro-pyrrolo[3,2-c]pyridin-4-one |
| 98 | 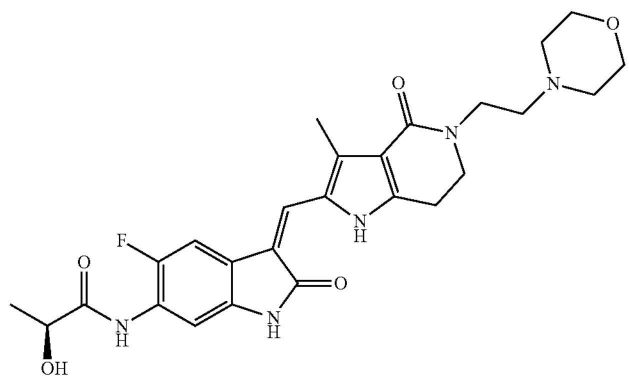 [SMILES: Cc1c(/C=C2\C(=O)Nc3cc(NC(=O)[C@H](C)O)c(F)cc32)[nH]c2c1C(=O)N(CCN1CCOCC1)CC2] | (S)-N-{5-Fluoro-3-[3-methyl-5-(2-morpholin-4-yl-ethyl)-4-oxo-4,5,6,7-tetrahydro-1H-pyrrolo[3,2-c]pyridin-2-ylmethylene]-2-oxo-2,3-dihydro-1H-indol-6-yl}-2-hydroxy-propionamide |
| 99 | 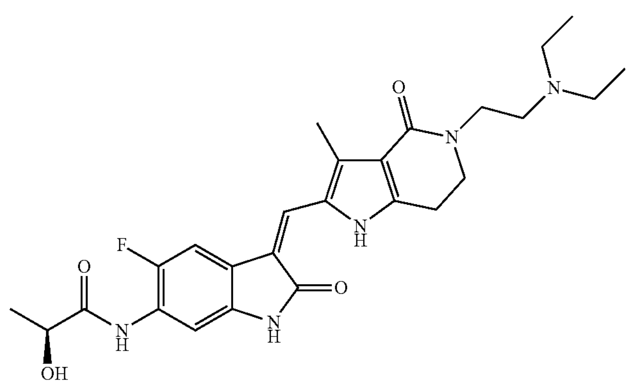 [SMILES: CCN(CC)CCN1CCc2[nH]c(/C=C3\C(=O)Nc4cc(NC(=O)[C@H](C)O)c(F)cc43)c(C)c2C1=O] | (S)-N-{3-[5-(2-Diethylamino-ethyl)-3-methyl-4-oxo-4,5,6,7-tetrahydro-1H-pyrrolo[3,2-c]pyridin-2-ylmethylene]-5-fluoro-2-oxo-2,3-dihydro-1H-indol-6-yl}-2-hydroxy-propionamide |
| 100 | 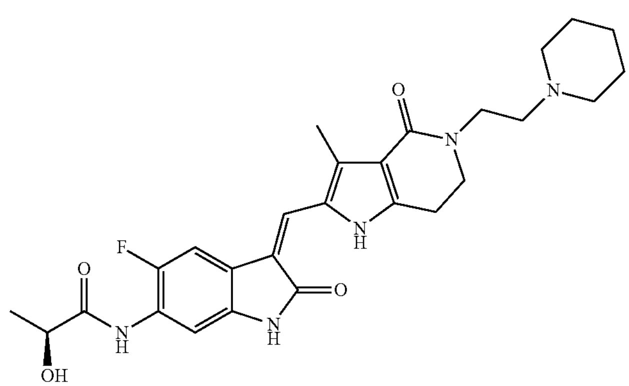 | (S)-N-{5-Fluoro-3-[3-methyl-4-oxo-5-(2-piperidin-1-yl-ethyl)-4,5,6,7-tetrahydro-1H-pyrrolo[3,2-c]pyridin-2-ylmethylene]-2-oxo-2,3-dihydro-1H-indol-6-yl}-2-hydroxy-propionamide |

TABLE I-continued

| Example No Aftermentioned | Structure | Name |
|---|---|---|
| 101 | 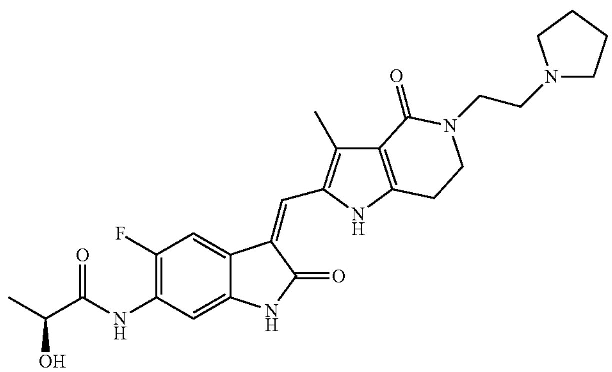 [SMILES: Cc1c(/C=C2\C(=O)Nc3cc(NC(=O)[C@H](C)O)c(F)cc32)[nH]c2c1C(=O)N(CCN1CCCC1)CC2] | (S)-N-{5-Fluoro-3-[3-methyl-4-oxo-5-(2-pyrrolidin-1-yl-ethyl)-4,5,6,7-tetrahydro-1H-pyrrolo[3,2-c]pyridin-2-ylmethylene]-2-oxo-2,3-dihydro-1H-indol-6-yl}-2-hydroxy-propionamide |
| 102 | 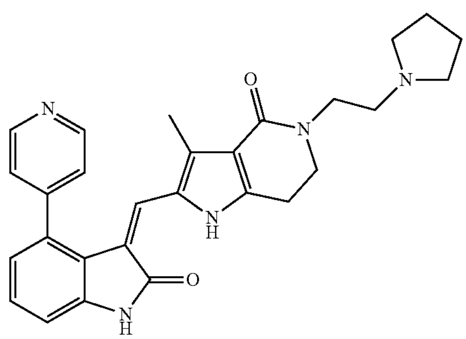 [SMILES: Cc1c(/C=C2\C(=O)Nc3cccc(-c4ccncc4)c32)[nH]c2c1C(=O)N(CCN1CCCC1)CC2] | 3-Methyl-2-(2-oxo-4-pyridin-4-yl-1,2-dihydro-indol-3-ylidenemethyl)-5-(2-pyrrolidin-1-yl-ethyl)-1,5,6,7-tetrahydro-pyrrolo[3,2-c]pyridin-4-one |
| 103 | 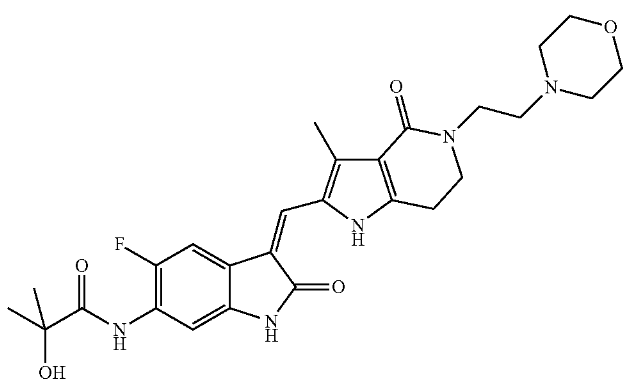 [SMILES: Cc1c(/C=C2\C(=O)Nc3cc(NC(=O)C(C)(C)O)c(F)cc32)[nH]c2c1C(=O)N(CCN1CCOCC1)CC2] | N-{5-Fluoro-3-[3-methyl-5-(2-morpholin-4-yl-ethyl)-4-oxo-4,5,6,7-tetrahydro-1H-pyrrolo[3,2-c]pyridin-2-ylmethylene]-2-oxo-2,3-dihydro-1H-indol-6-yl}-2-hydroxy-2-methyl-propionamide |
| 104 | 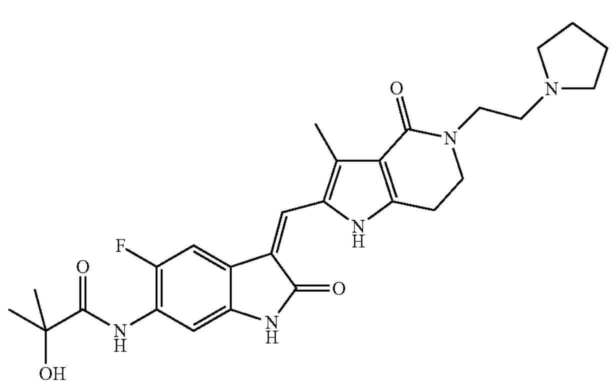 [SMILES: Cc1c(/C=C2\C(=O)Nc3cc(NC(=O)C(C)(C)O)c(F)cc32)[nH]c2c1C(=O)N(CCN1CCCC1)CC2] | N-{5-Fluoro-3-[3-methyl-4-oxo-5-(2-pyrrolidin-1-yl-ethyl)-4,5,6,7-tetrahydro-1H-pyrrolo[3,2-c]pyridin-2-ylmethylene]-2-oxo-2,3-dihydro-1H-indol-6-yl}-2-hydroxy-2-methyl-propionamide |

TABLE I-continued

| Example No Aftermentioned | Structure | Name |
|---|---|---|
| 105 | 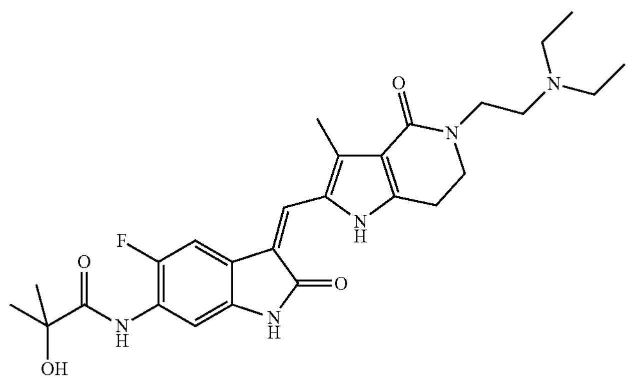 [SMILES: CCN(CC)CCN1CCc2[nH]c(/C=C3\C(=O)Nc4cc(NC(=O)C(C)(C)O)c(F)cc43)c(C)c2C1=O] | N-{3-[5-(2-Diethylamino-ethyl)-3-methyl-4-oxo-4,5,6,7-tetrahydro-1H-pyrrolo[3,2-c]pyridin-2-ylmethylene]-5-fluoro-2-oxo-2,3-dihydro-1H-indol-6-yl}-2-hydroxy-2-methyl-propionamide |
| 106 | 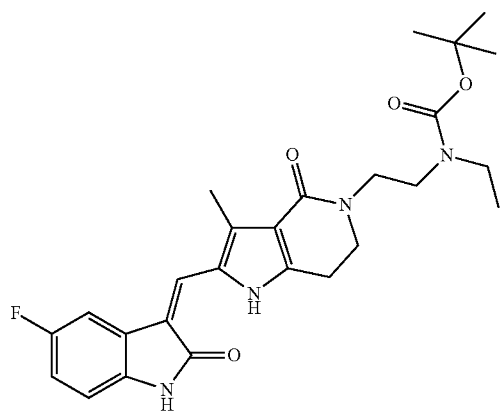 [SMILES: CCN(CCN1CCc2[nH]c(/C=C3\C(=O)Nc4ccc(F)cc43)c(C)c2C1=O)C(=O)OC(C)(C)C] | 5-(2-Ethylamino-ethyl)-2-(5-fluoro-2-oxo-1,2-dihydro-indol-3-ylidenemethyl)-3-methyl-1,5,6,7-tetrahydro-pyrrolo[3,2-c]pyridin-4-one |
| 107 | 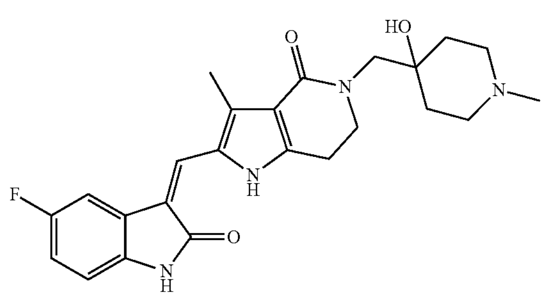 [SMILES: Cc1c(/C=C2\C(=O)Nc3ccc(F)cc32)[nH]c2c1C(=O)N(CC1(O)CCN(C)CC1)CC2] | 2-(5-Fluoro-2-oxo-1,2-dihydro-indol-3-ylidenemethyl)-5-(4-hydroxy-1-methyl-piperidin-4-ylmethyl)-3-methyl-1,5,6,7-tetrahydro-pyrrolo[3,2-c]pyridin-4-one |
| 108 | 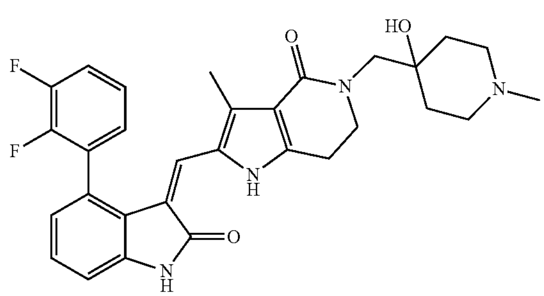 [SMILES: Cc1c(/C=C2\C(=O)Nc3cccc(-c4cccc(F)c4F)c32)[nH]c2c1C(=O)N(CC1(O)CCN(C)CC1)CC2] | 2-[4-(2,3-Difluoro-phenyl)-2-oxo-1,2-dihydro-indol-3-ylidenemethyl]-5-(4-hydroxy-1-methyl-piperidin-4-ylmethyl)-methyl-1,5,6,7-tetrahydro-pyrrolo[3,2-c]pyridin-4-one |

TABLE I-continued

| Example No Aftermentioned | Structure | Name |
|---|---|---|
| 109 | 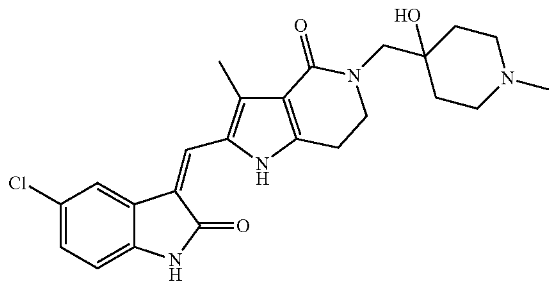 [SMILES: Cc1c(/C=C2\C(=O)Nc3ccc(Cl)cc32)[nH]c2c1C(=O)N(CC1(O)CCN(C)CC1)CC2] | 2-(5-Chloro-2-oxo-1,2-dihydro-indol-3-ylidenemethyl)-5-(4-hydroxy-1-methyl-piperidin-4-ylmethyl)-3-methyl-1,5,6,7-tetrahydro-pyrrolo[3,2-c]pyridin-4-one |
| 110 | 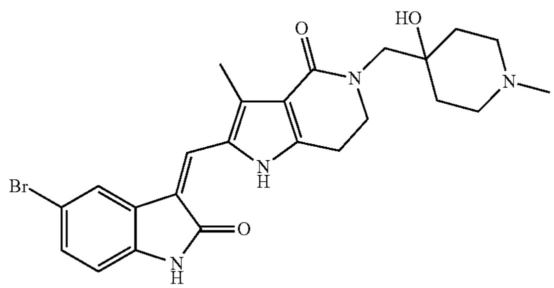 | 2-(5-Bromo-2-oxo-1,2-dihydro-indol-3-ylidenemethyl)-5-(4-hydroxy-1-methyl-piperidin-4-ylmethyl)-3-methyl-1,5,6,7-tetrahydro-pyrrolo[3,2-c]pyridin-4-one |
| 111 | 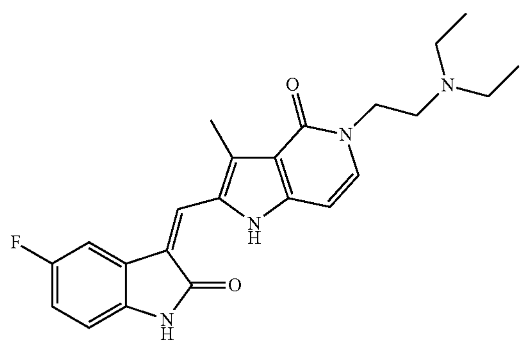 [SMILES: CCN(CC)CCn1ccc2[nH]c(/C=C3\C(=O)Nc4ccc(F)cc43)c(C)c2c1=O] | 5-(2-Diethylamino-ethyl)-2-(5-fluoro-2-oxo-1,2-dihydro-indol-3-ylidenemethyl)-3-methyl-1,5-dihydro-pyrrolo[3,2-c]pyridin-4-one |
| 112 | 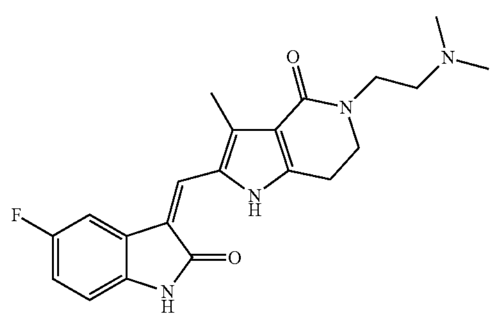 [SMILES: Cc1c(/C=C2\C(=O)Nc3ccc(F)cc32)[nH]c2c1C(=O)N(CCN(C)C)CC2] | 5-(2-Dimethylamino-ethyl)-2-(5-fluoro-2-oxo-1,2-dihydro-indol-3-ylidenemethyl)-3-methyl-1,5,6,7-tetrahydro-pyrrolo[3,2-c]pyridin-4-one |
| 113 | 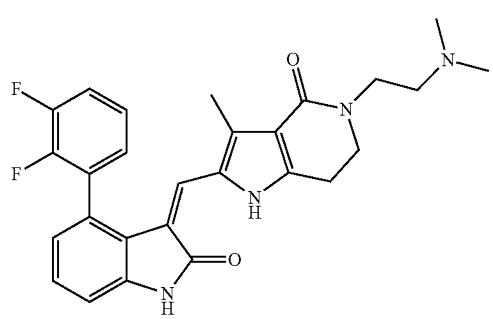 [SMILES: Cc1c(/C=C2\C(=O)Nc3cccc(-c4cccc(F)c4F)c32)[nH]c2c1C(=O)N(CCN(C)C)CC2] | 2-[4-(2,3-Difluoro-phenyl)-2-oxo-1,2-dihydro-indol-3-ylidenemethyl]-5-(2-dimethylamino-ethyl)-3-methyl-1,5,6,7-tetrahydro-pyrrolo[3,2-c]pyridin-4-one |

TABLE I-continued

| Example No Aftermentioned | Structure | Name |
|---|---|---|
| 114 | 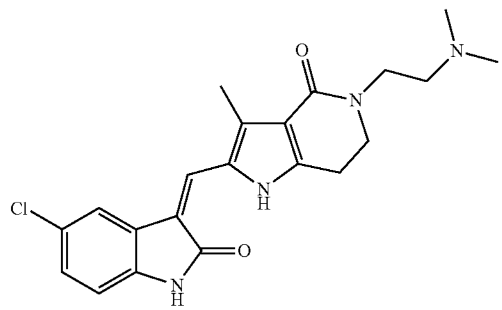 [SMILES: Cc1c(/C=C2\C(=O)Nc3ccc(Cl)cc32)[nH]c2c1C(=O)N(CCN(C)C)CC2] | 2-(5-Chloro-2-oxo-1,2-dihydro-indol-3-ylidenemethyl)-5-(2-dimethylamino-ethyl)-3-methyl-1,5,6,7-tetrahydro-pyrrolo[3,2-c]pyridin-4-one |
| 115 | 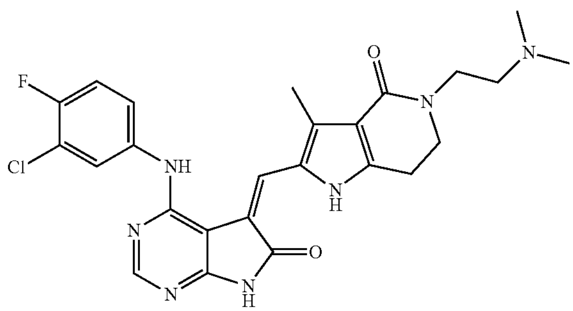 [SMILES: Cc1c(/C=C2\C(=O)Nc3ncnc(Nc4ccc(F)c(Cl)c4)c32)[nH]c2c1C(=O)N(CCN(C)C)CC2] | 4-(3-Chloro-4-fluoro-phenylamino)-5-[5-(2-dimethylamino-ethyl)-3-methyl-4-oxo-4,5,6,7-tetrahydro-1H-pyrrolo[3,2-c]pyridin-2-ylmethylene]-5,7-dihydro-pyrrolo[2,3-d]pyrimidin-6-one |
| 116 | 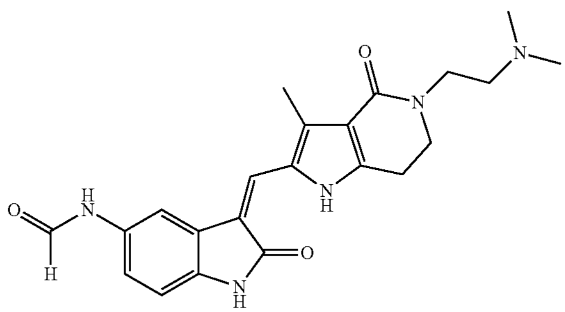 [SMILES: Cc1c(/C=C2\C(=O)Nc3ccc(NC=O)cc32)[nH]c2c1C(=O)N(CCN(C)C)CC2] | N-{3-[5-(2-Dimethylamino-ethyl)-3-methyl-4-oxo-4,5,6,7-tetrahydro-1H-pyrrolo[3,2-c]pyridin-2-ylmethylene]-2-oxo-2,3-dihydro-1H-indol-5-yl}-formamide |
| 117 | 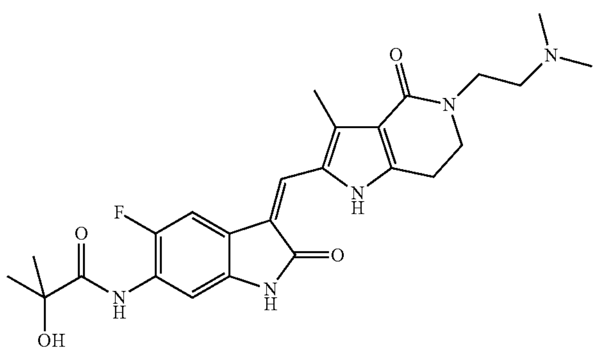 [SMILES: Cc1c(/C=C2\C(=O)Nc3cc(NC(=O)C(C)(C)O)c(F)cc32)[nH]c2c1C(=O)N(CCN(C)C)CC2] | N-{3-[5-(2-Dimethylamino-ethyl)-3-methyl-4-oxo-4,5,6,7-tetrahydro-1H-pyrrolo[3,2-c]pyridin-2-ylmethylene]-5-fluoro-2-oxo-2,3-dihydro-1H-indol-6-yl}-2-hydroxy-2-methyl-propionamide |
| 118 | 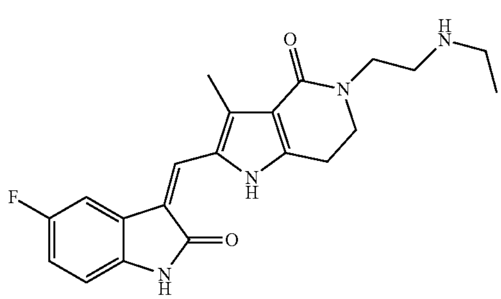 [SMILES: CCNCCN1CCc2[nH]c(/C=C3\C(=O)Nc4ccc(F)cc43)c(C)c2C1=O] | 5-(2-Ethylamino-ethyl)-2-(5-fluoro-2-oxo-1,2-dihydro-indol-3-ylidenemethyl)-3-methyl-1,5,6,7-tetrahydro-pyrrolo[3,2-c]pyridin-4-one |

TABLE I-continued

| Example No Aftermentioned | Structure | Name |
|---|---|---|
| 119 | 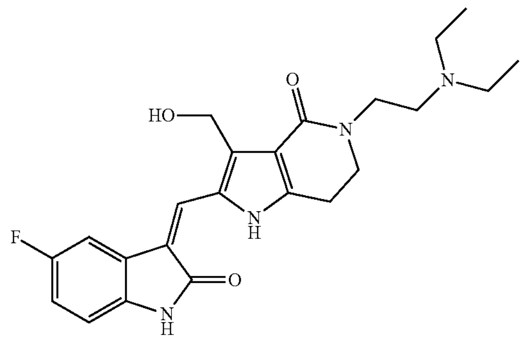 [SMILES: CCN(CC)CCN1CCc2[nH]c(/C=C3\C(=O)Nc4ccc(F)cc43)c(CO)c2C1=O] | 5-(2-Diethylamino-ethyl)-2-(5-fluoro-2-oxo-1,2-dihydro-indol-3-ylidenemethyl)-3-hydroxymethyl-1,5,6,7-tetrahydro-pyrrolo[3,2-c]pyridin-4-one |
| 120 | 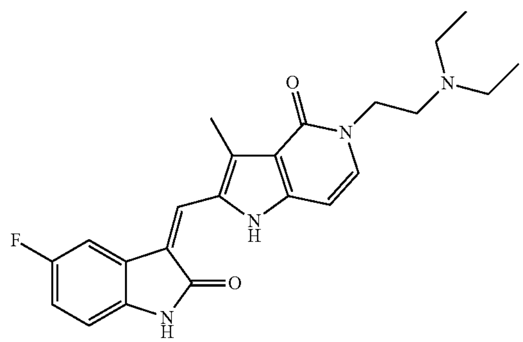 [SMILES: CCN(CC)CCn1ccc2[nH]c(/C=C3\C(=O)Nc4ccc(F)cc43)c(C)c2c1=O] | 5-(2-Diethylamino-ethyl)-2-(5-fluoro-2-oxo-1,2-dihydro-indol-3-ylidenemethyl)-3-methyl-1,5-dihydro-pyrrolo[3,2-c]pyridin-4-one |
| 121 | 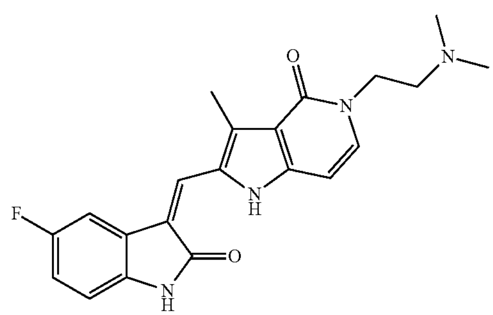 [SMILES: Cc1c(/C=C2\C(=O)Nc3ccc(F)cc32)[nH]c2ccn(CCN(C)C)c(=O)c12] | 5-(2-Dimethylamino-ethyl)-2-(5-fluoro-2-oxo-1,2-dihydro-indol-3-ylidenemethyl)-3-methyl-1,5-dihydro-pyrrolo[3,2-c]pyridin-4-one |
| 122 | 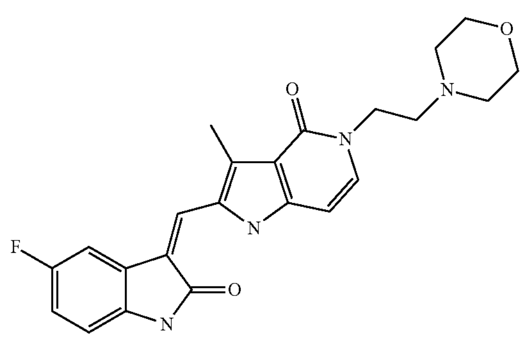 [SMILES: Cc1c(/C=C2\C(=O)Nc3ccc(F)cc32)[nH]c2ccn(CCN3CCOCC3)c(=O)c12] | 2-(5-Fluoro-2-oxo-1,2-dihydro-indol-3-ylidenemethyl)-3-methyl-5-(2-morpholin-4-yl-ethyl)-1,5-dihydro-pyrrolo[3,2-c]pyridin-4-one |

TABLE I-continued

| Example No Aftermentioned | Structure | Name |
|---|---|---|
| 123 | 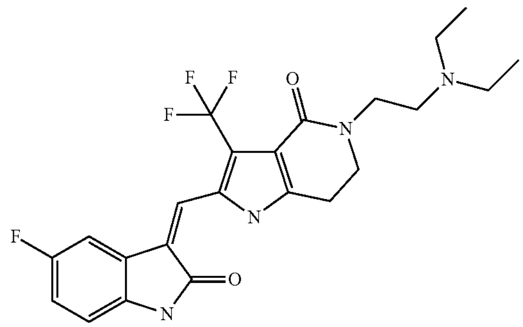 [SMILES: CCN(CC)CCN1CCc2[nH]c(/C=C3\C(=O)Nc4ccc(F)cc43)c(C(F)(F)F)c2C1=O] | 5-(2-Diethylamino-ethyl)-2-(5-fluoro-2-oxo-1,2-dihydro-indol-3-ylidenemethyl)-3-trifluoromethyl-1,5,6,7-tetrahydro-pyrrolo[3,2-c]pyridin-4-one |
| 124 | 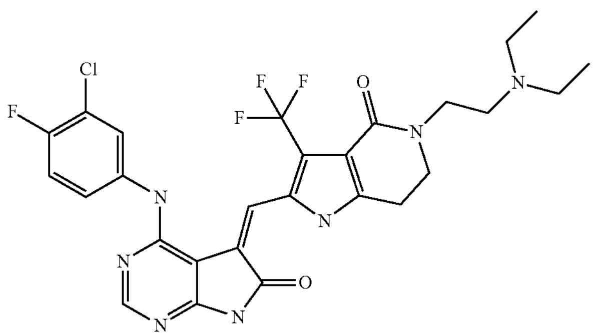 [SMILES: CCN(CC)CCN1CCc2[nH]c(/C=C3\C(=O)Nc4ncnc(Nc5ccc(F)c(Cl)c5)c43)c(C(F)(F)F)c2C1=O] | 4-(3-Chloro-4-fluoro-phenylamino)-5-[5-(2-diethylamino-ethyl)-4-oxo-3-trifluoromethyl-4,5,6,7-tetrahydro-1H-pyrrolo[3,2-c]pyridin-2-ylmethylene]-5,7-dihydro-pyrrolo[2,3-d]pyrimidin-6-one |
| 125 | 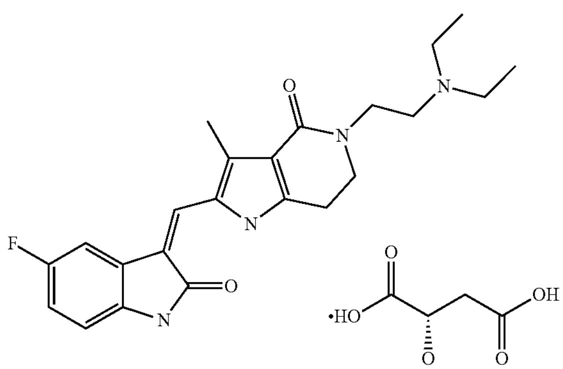 | 5-(2-Diethylamino-ethyl)-2-(5-fluoro-2-oxo-1,2-dihydro-indol-3-ylidenemethyl)-3-methyl-1,5,6,7-tetrahydro-pyrrolo[3,2-c]pyridin-4-one malate |
| 126 | 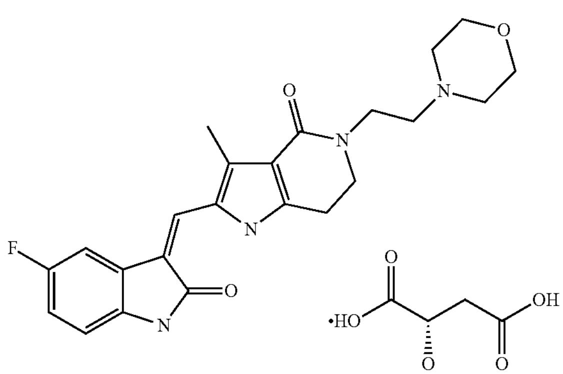 | 2-(5-Fluoro-2-oxo-1,2-dihydro-indol-3-ylidenemethyl)-3-methyl-5-(2-morpholin-4-yl-ethyl)-1,5,6,7-tetrahydro-pyrrolo[3,2-c]pyridin-4-one malate |

TABLE I-continued

| Example No Aftermentioned | Structure | Name |
|---|---|---|
| 127 | 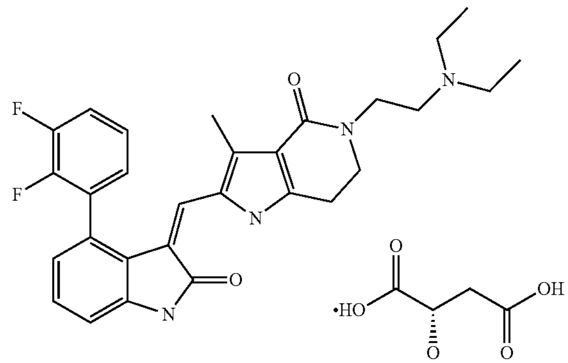 | 5-(2-Diethylamino-ethyl)-2-[4-(2,3-difluoro-phenyl)-2-oxo-1,2-dihydro-indol-3-ylidenemethyl]-3-methyl-1,5,6,7-tetrahydro-pyrrolo[3,2-c]pyridin-4-one malate |
| 128 | 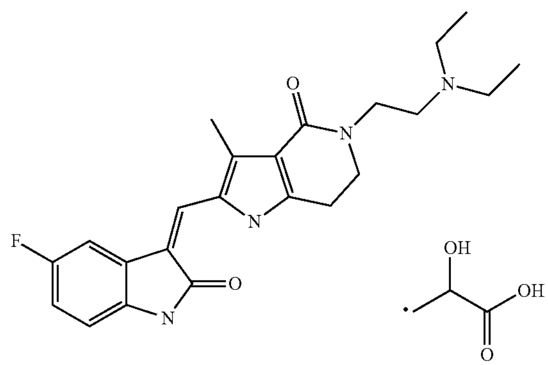 | 5-(2-Diethylamino-ethyl)-2-(5-fluoro-2-oxo-1,2-dihydro-indol-3-ylidenemethyl)-3-methyl-1,5,6,7-tetrahydro-pyrrolo[3,2-c]pyridin-4-one lactate |
| 129 | 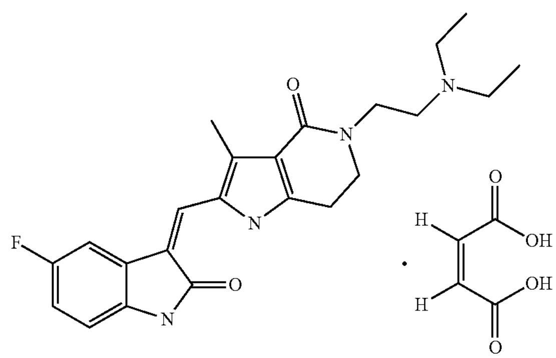 [SMILES: CCN(CC)CCN1CCc2[nH]c(/C=C3\C(=O)Nc4ccc(F)cc43)c(C)c2C1=O ; O=C(O)/C=C\C(=O)O] | 5-(2-Diethylamino-ethyl)-2-(5-fluoro-2-oxo-1,2-dihydro-indol-3-ylidenemethyl)-3-methyl-1,5,6,7-tetrahydro-pyrrolo[3,2-c]pyridin-4-one maleate |
| 130 | 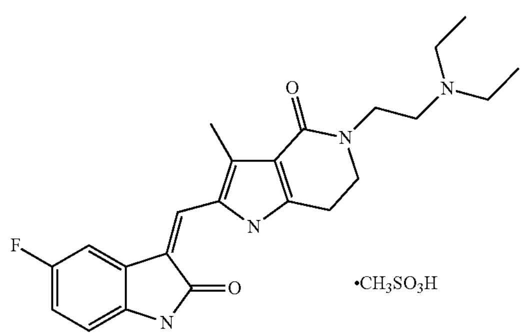 | 5-(2-Diethylamino-ethyl)-2-(5-fluoro-2-oxo-1,2-dihydro-indol-3-ylidenemethyl)-3-methyl-1,5,6,7-tetrahydro-pyrrolo[3,2-c]pyridin-4-one mesylate |

The compounds presented herein are exemplary only and are not be construed as limiting the scope of this invention in any manner. The chemical formulate referred to herein may exhibit eh phenomena of tautomerism and structural isomerism. For example, the compounds described herein may adopt an E or a Z configuration about the double bond connecting the 2-indolinone moiety to the pyrrole moiety or they may be a mixture of E and Z. This invention encompasses any tautomeric or structural isomeric form and mixtures thereof which possess the ability to modulate receptor tyrosine kinase, nonreceptor tyrosine kinase and/or a serine-threonine kinase activity and is not limited to any one tautomeric or structural isomeric form.

In addition, the pharmaceutically acceptable salts according to present invention are the those formed of present compound with the acids selected from the group of malic acid, lactic acid, maleic acid, hydrochloric acid, methanesulfonic acid, sulfuric acid, phosphoric acid, citric acid, acetic acid and trifluoroacetic acid.

In another aspect this invention provides a compound of formula (II) which is an intermediate in the synthesis of the present compound:

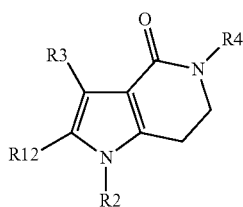

II

Wherein:
R2 is selected from H, alkyl, cycloalkyl, heterocyclo alkyl, aryl, heteroaryl, alkoxyl, aryoxyl, —COOR$_9$, —CONR$_9$R$_{10}$, —C(=S)NR$_9$R$_{10}$, —COR$_9$, —SOR$_9$, —SO$_2$R$_9$, —SO$_2$NR$_9$R$_{10}$ and —P(=O)(OR$_9$)(OR$_{10}$);

R3 is selected from alkyl, trifluoromethyl, aryl and aralkyl; wherein said alkyl, aryl or aralkyl is independently substituted by one more halogen and hydrogen;

R4 is selected from alkyl, cycloalkyl, heterocyclo alkyl, aryl, heteroaryl, heteroaryl, —(CH$_2$)$_n$(OCH$_2$CH$_2$)$_r$R$_{11}$, —[CH$_2$CH(OH)]$_r$CH$_2$NR$_9$R$_{10}$ and —(CH$_2$)$_n$NR$_9$R$_{10}$; wherein said alkyl, cylcoalkyl, aryl, heteroaryl amd heterocyclo alkyl optionally are each independently substituented by one more groups selected from the group consisting of aryl, hydroxyl, amino, amide group, aminocarbonyl, alkoxyl, aryoxyl, aminoalkyl, hydroxyalkyl, heterocyclo alkyl, carboxylic acid, carboxylic ester and —NR$_9$R$_{10}$;

R$_9$ and R$_{10}$ are each independently selected from hydrogen, alkyl, cycloalkyl, heteroaryl and heterocyclo alkyl, wherein said alkyl, cycloalkyl, aryl, heteroaryl and heterocyclo alkyl are each independently substituted by one more group consisting of alkyl, aryl, hydroxyl, amino, amide group, aminocarbonyl, cyano, alkoxyl, aryoxyl, aminoalkyl, hydroxyalkyl, heterocyclo alkyl, carboxylic acid and carboxylic ester;

R$_9$ and R$_{10}$ may be taken together with the atom to which they are attached to form 4 to 8 membered ring, wherein the 5 to 8 membered rings may further optionally contain one to three heteroatoms selected from the group consisting of N, O, S, and the 4 to 8 membered rings so formed is optionally substituted by one more group consisting of alkyl, aryl, heteroaryl, haloalkyl, haloalkoxyl, hydroxyl, amino, amide group, cyano, alkoxyl, aryoxyl, aminoalkyl, hydroxyalkyl, heterocyclo alkyl, carboxylic acid, carboxylic ester, halogen and —NR$_9$R$_{10}$;

R$_{11}$ is hydrogen or alkyl;
R$_{12}$ is hydrogen or aldehyde;
n is 2-6; and
r is 1-6; or
pharmaceutically acceptable salts or stereoisomer thereof.

In another aspect, this invention is directed to the manufacture process of present compound of formular (I): comprising reacting an oxindole with an aldehyde or a ketone in the presence of a base including piperidine or triethylamine in a solvent of 1-2 ml/mol 2-oxindole, and the mixture is then heated for from about 2 to about 12 hours, wherein the aldehyde has the following structure:

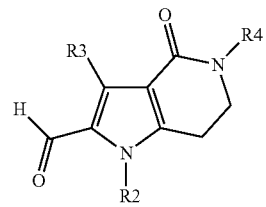

and the oxindole has the following structure:

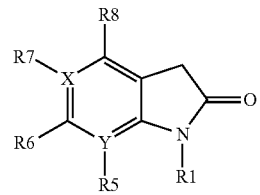

wherein, the definitions of R1, R2, R3, R4, R5, R6, R7 and R8 are the same with those defined correspondingly above.

In another aspect, this invention is directed to the manufacture process of manufacture process of intermediate formula (II), comprising:

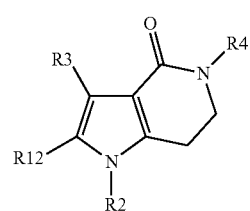

II pyrrole triester IIa is selectively hydrolyzed by a first base at a certain temperature to give pyrrole acid diester IIb; and

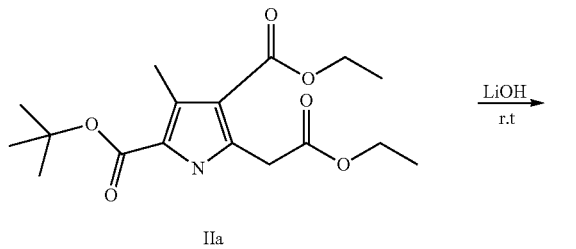

pyrrole amine ester IIc is heated with a second base in solvent to give the cyclized product of pyrrolofused lactam IId, the solvent is toluene or glycol;

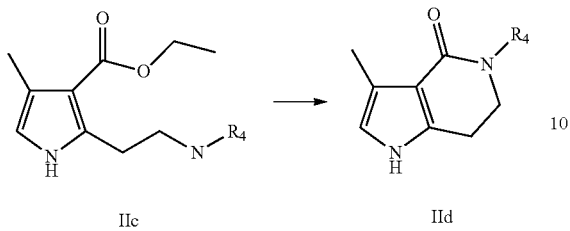

IIc  IId wherein, said first base is selected from aqueous lithium hydroxide, sodium hydroxide or potassium hydroxide; and said second base is selected from lithium hydroxide, triethylamine, t-BuOK or trimethyl aluminum; and the definitions of R2, R3, R4 and R12 are the same with those defined above; the temperature of selective hydrolyzation of Pyrrole triester IIa is 10° C.~50° C.

Furthermore, this invention is directed to the manufacture process of manufacture process of intermediate formula (II), comprising:

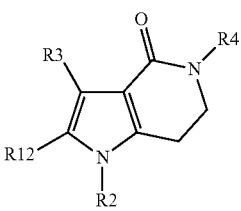

II pyrrole amine ester IIe is heated with a base in 95% ethanol to a reaction temperature to give the cyclized product of pyrrolo lactam IIf;

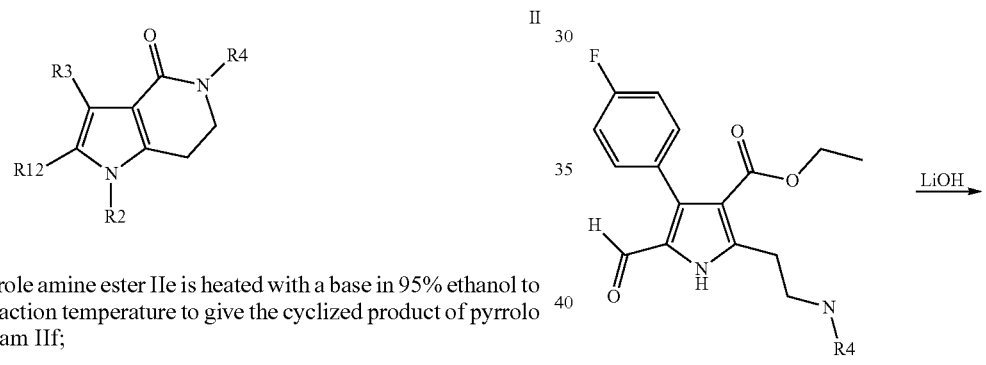

IIe

IIf wherein, said base is selected from lithium hydroxide or potassium carbonate; and the definition of R2, R3, R4 and R12 are the same with those defined in claim 8, and the reaction temperature is 35° C.~80° C.

Furthermore, this invention is directed to the manufacture process of manufacture process of intermediate formula (II), comprising:

II pyrrole amine ester IIg is heated with a base in 95% ethanol to a reaction temperature to give the cyclized product of pyrrolo lactam IIh;

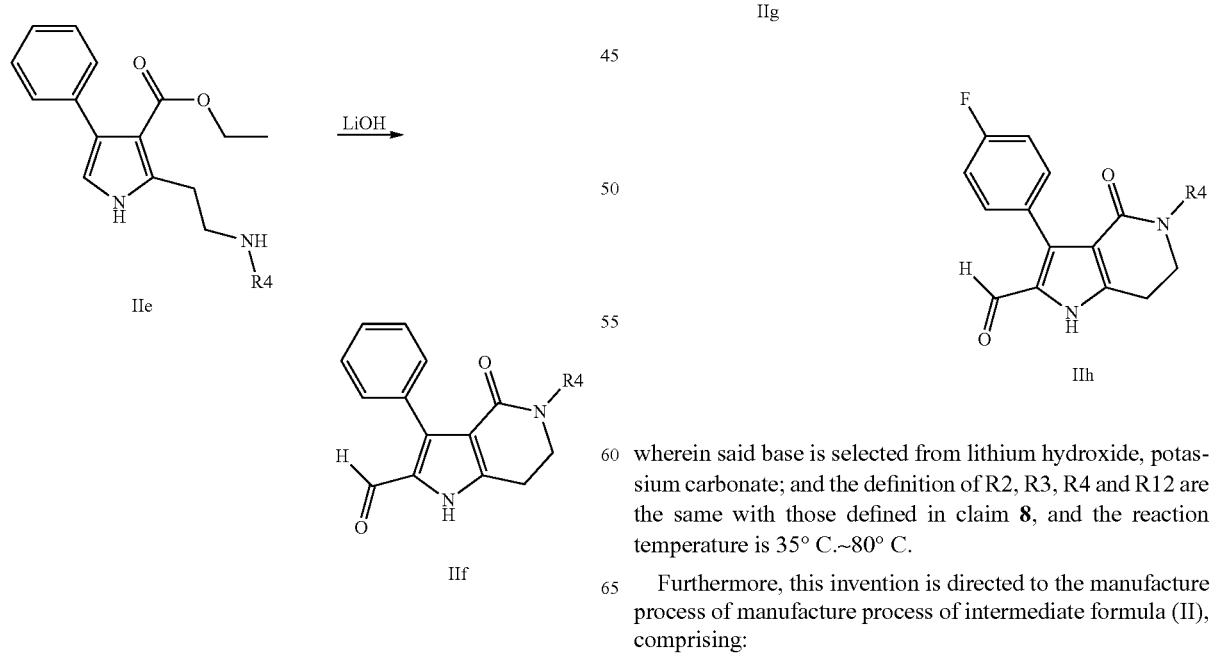

IIg

IIh wherein said base is selected from lithium hydroxide, potassium carbonate; and the definition of R2, R3, R4 and R12 are the same with those defined in claim 8, and the reaction temperature is 35° C.~80° C.

Furthermore, this invention is directed to the manufacture process of manufacture process of intermediate formula (II), comprising:

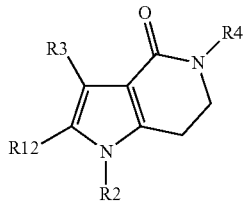

II the trifluoromethyl amine ester IIi and lactam keton IIj is reacted in acetic acid by knorr cyclization to afford trifluoromethyl pyrrolo lactam IIk

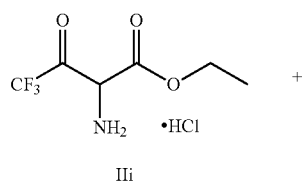

IIi

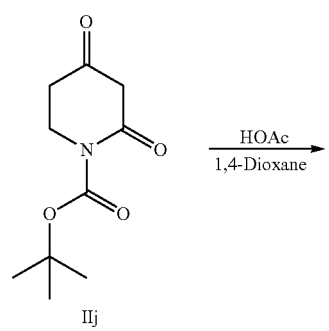

IIj $\xrightarrow{\text{HOAc}}{\text{1,4-Dioxane}}$

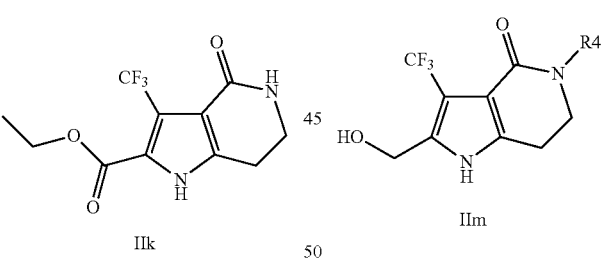

IIk trifluoromethyl pyrrolo lactam IIk is selectively alkylated by sodium hydride and R₄Br in dimethyl formamide to give compound IIL;

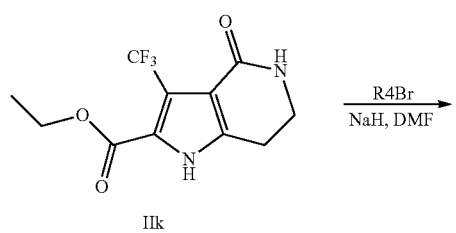

IIk $\xrightarrow{\text{R4Br}}{\text{NaH, DMF}}$

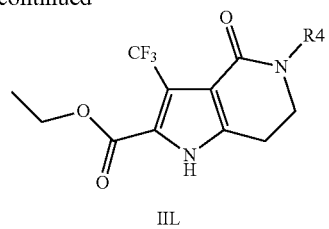

IIL the compound IIl is reacted with a reducing agent such as lithium aluminum hydride or DIBAL-H in tetrahydrofuran or dichloromethane at a certain temperature to obtain hydroxyl pyrrolo lactam IIm;

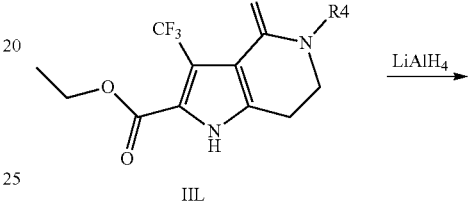

IIL $\xrightarrow{\text{LiAlH}_4}$

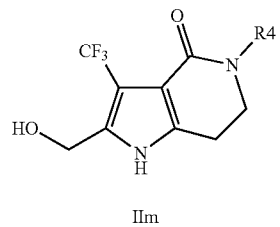

IIm hydroxyl pyrrolo lactam IIm is oxidated with 2-iodoxybenzoic acid as oxidant and paratoluenesulfonic acid in DMSO to give aldehyde pyrrolo lactam IIn;

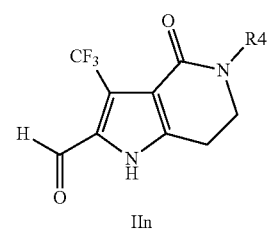

IIm $\xrightarrow{\text{IBX, TsOH}}{\text{DMSO}}$

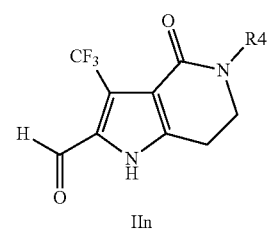

IIn the definitions of R2, R3, R4 and R12 are the same with those defined in claim 8, and the temperature of knorr cyclization is 100° C.~140° C., the certain temperature of reduction is −5° C.~25° C.

Another aspect of this invention is directed to a pharmaceutical composition comprising one or more compound(s) of Formula (I) or a pharmaceutically acceptable salt thereof and pharmaceutically acceptable carriers.

Another aspect of this invention is directed to a for treating a mammal from protein kinase related disorder that responds to modulation of one or more protein kinases comprising administering to the mammal a therapeutically effective amount of present compound of formula (I) or pharmaceutical composition thereof. Wherein the protein kinases is at least one selected from the group consisting of EGFR, HER-2, HER-3, HER-4, FGFR, Cdk, c-Met, c-Ret, PDGFR, VEGFR-2, Aurora, Raf, Flt3, c-Kit, Chk, Pim-1, Plk-1, Pyk-2, Src, Frk, Btk, Csk, Abl, Zap70, Fes/Fps, Fak, Jak, Ack, Yes, Fyn, Lyn, Lck, Blk, Hck, Fgr and Yrk, as well as aberrant forms thereof. Preferably, the protein kinases is at least one selected from the group consisting of HER-2, PDGFR, VEGFR-2, EGFR, c-Kit, c-Met, FGFR, Flt3, as well as aberrant forms thereof including mutant forms and allelic variants. Furthermore, said mammal is a human.

More preferably, the protein kinases related disorders are selected from the group consisting of leukemias, especially chronic myelogenous leukaemia, acute myeloid leukemia, acute myeloid leukemia, with trilineage myelodysplasia, acute lymphoblastic leukemia, myelodysplastic syndrome, mixed-lineage leukemia; different solid tumors including benign or especially malign types, preferably sarcoma, gastrointestinal stromal tumors, seminoma, carcinoids, mast cell tumors, lung carcinomas, bronchial carcinomas, seminomas, dysgerminomas, testicular intraepithelial neoplasias, melanomas, mamma carcinomas, neuroblastomas, papillary/follicular thyroid carcinoma, malign lymphomas, Non Hodgkin's lymphoma, multiple endocrine neoplasia type 2, pheochromocytoma, thyroid carcinoma, parathyroid hyperplasia/adenoma, mamma carcinoma, colon cancer, colorectal adenoma, ovarian cancer, breast cancer, prostate carcinoma, glioblastoma, brain tumors, prostate carcinoma including adenocarcinomas and bone metastatsis, malign gliomes, (anaplastic astrocytomas/glioblastomas, pancreatic cancer, malignant pleural mesothelioma, haemangioblastoma, haemangioma, carcinoma of the kidney, liver, adrenal gland, bladder, stomach including gastric tumors, rectum, vagina, cervix, endometrium, multiple myeloma, tumors of the neck and head, including neoplasias, especially of epithelial character, malignant nephrosclerosis; other hyperplasias or proliferative diseases, including mastocytosis, associated myeloproliferative syndrome, Urticaria Pigmentosa, an epidermal hyperproliferation, especially psoriasis; prostate hyperplasia; inflammatory diseases, especially rheumatoid or rheumatic inflammatory diseases, preferably arthritis, more preferably rheumatoid arthritis, other chronic inflammatory disorders, including chronic asthma, arterial or post-transplantational atherosclerosis, other diseases associated with deregulated angiogenesis including fibrosis, angiogenesis, smooth muscle proliferation in the blood vessels, including stenosis orrestenosis following angioplasty; retinopathies, macula degeneration other eye diseases, especially diabetic retinopathy or neovascular glaucoma; renal diseases including glomerulonephritis; diabetic nephropathy; inflammatory bowel disease, Crohn's disease, thrombotic microangiopathic syndromes; transplant rejections or glomerulopathy; fibrotic diseases including cirrhosis of the liver; mesangial cell-proliferative diseases and injuries of the nerve tissue; and/or from diseases that respond to the effect of said compound or pharmaceutically acceptable salts as immunosuppressants, as an aid in scar-free wound healing, and for treating age spots and contact dermatitis. Preferably, said protein kinase related disorder is cancer. Wherein said cancer is at least one selected from the group consisting of lung cancer, bone cancer, pancreatic cancer, skin cancer, cancer of the head or neck, cutaneous or intraocular melanoma, uterine cancer, ovarian cancer, rectal cancer, cancer of the anal region, stomach cancer, colon cancer, breast cancer, carcinoma of the fallopian tubes, carcinoma of the endometrium, carcinoma of the cervix, carcinoma of the vagina, carcinoma of the vulva, Hodgkin's Disease, cancer of the esophagus, cancer of the small intestine, cancer of the endocrine system, cancer of the thyroid gland, cancer of the parathyroid gland, cancer of the adrenal gland, sarcoma of soft tissue, cancer of the urethra, cancer of the penis, prostate cancer, chronic or acute leukemia, lymphocytic lymphomas, cancer of the bladder, cancer of the kidney or ureter, renal cell carcinoma, carcinoma of the renal pelvis, neoplasms of the central nervous system (CNS), primary CNS lymphoma, spinal axis tumors, brain stem glioma, pituitary adenoma, and combinations thereof. Preferably, said cancer is selected from gastrointestinal stromal tumors, renal cell carcinoma, breast cancer, colorectal cancer, non-small cell lung cancer, neuroendocrine tumors, thyroid cancer, small cell lung cancer, mastocytosis, glioma, sarcoma, acute myeloid leukemia, prostate cancer, lymphoma, and combinations thereof.

Furthermore, present method further comprises co-administering at least one anti-tumor agent selected from the group consisting of mitotic inhibitors, alkylating agents, anti-metabolites, intercalating antibiotics, growth factor inhibitors, cell cycle inhibitors, enzymes, topoisomerase inhibitors, biological response modifiers, antibodies, cytotoxics, anti-hormones, anti-androgens and mixtures thereof.

In still another aspect, this invention is directed to a method of modulation of a protein kinase comprising contacting said protein kinase with a compound of Formula (I) or a prodrug or a pharmaceutically acceptable salt of a compound of Formula (I). In a preferred embodiment, the protein kinase related disorder responds to modulation, especially inhibition, of one more protein kinases selected from the group consisting of receptor tyrosine kinases (RTKs), nonreceptor protein tyrosine kinases (CTKs) and serine/threonine protein kinases (STKs). In particular, using a compound of Formula (I) may be carried out in vitro or in vivo. In another preferred embodiment, the protein kinase related disorder responds to modulation, especially inhibition, of one more protein kinases selected consisting of EGFR, HER-2, HER-3, HER-4, FGFR, Cdk, c-Met, c-Ret, PDGFR, VEGFR-2, Aurora, Raf, Flt3, c-Kit, Chic, Pim-1, Plk-1, Pyk-2, Src, Frk, Btk, Csk, Abl, Zap70, Fes/Fps, Fak, Jak, Ack, Yes, Fyn, Lyn, Lck, Blk, Hck, Fgr and Yrk as well as aberrant forms thereof, such as mutant forms, and allelic In still another aspect, this invention relates to a method for treating a mammal from protein kinase related disorder that responds to modulation of one or more protein kinases comprising administering to the mammal a therapeutically effective amount of present compound of formula (I) or pharmaceutical composition thereof. In a preferred embodiment, the mammal is a human. In another preferred embodiment, the protein kinase related disorder responds to modulation, especially inhibition, of one or more protein kinases, especially at least one selected from the group consisting of PDGFR, VEGFR-2, EGFR, HER-2, c-Kit, c-Met, FGFR, Flt3, as well as aberrant forms thereof, such as mutant forms, or allelic variants.

In yet another aspect, the invention is directed to a method for treating a mammal from protein kinase related disorder that responds to modulation of one or more protein kinases comprising administering to the mammal a therapeutically effective amount of present compound of formula (I) or pharmaceutical composition thereof. Wherein the one or more protein kinases related disorders selected from the group consisting of leukemias, especially chronic myelogenous leukaemia, acute myeloid leukemia, acute myeloid leukemia, with trilineage myelodysplasia, acute lymphoblastic leukemia, myelodysplastic syndrome, mixed-lineage leukemia; different (especially primary, but also derived) solid tumors (including benign or especially malign types), preferably sarcoma, gastrointestinal stromal tumors, seminoma, carcinoids, mast cell tumors, lung carcinomas, bronchial carcinomas, seminomas, dysgerminomas, testicular intraepithelial neoplasias, melanomas, mamma carcinomas, neuroblastomas, papillary/follicular thyroid carcinoma, malign lymphomas, Non Hodgkin's lymphoma, multiple endocrine neoplasia type 2, pheochromocytoma, thyroid carcinoma, parathyroid hyperplasia/adenoma, mamma carcinoma, colon cancer, colorectal adenoma, ovarian cancer, breast cancer, prostate carcinoma, glioblastoma, brain tumors, prostate carcinoma (including adenocarcinomas and bone metastatsis), malign gliomes, (anaplastic astrocytomas/glioblastomas, pancreatic cancer, malignant pleural mesothelioma, haemangioblastoma, haemangioma, carcinoma of the kidney, liver, adrenal gland, bladder, stomach (especially gastric tumors), rectum, vagina, cervix, endometrium, multiple myeloma, tumors of the neck and head, including neoplasias, especially of epithelial character, malignant nephrosclerosis; other hyperplasias or proliferative diseases, especially mastocytosis, associated myeloproliferative syndrome, Urticaria Pigmentosa, an epidermal hyperproliferation, especially psoriasis; prostate hyperplasia; inflammatory diseases, especially rheumatoid or rheumatic inflammatory diseases, preferably arthritis, more preferably rheumatoid arthritis, other chronic inflammatory disorders, especially chronic asthma, arterial or post-transplantational atherosclerosis, other diseases associated with deregulated angiogenesis, especially fibrosis (preferably pulmonary, but also other types of fibrosis, especially renal fibrosis), angiogenesis, smooth muscle proliferation in the blood vessels, especially stenosis orrestenosis following angioplasty; retinopathies, macula degeneration other eye diseases, especially diabetic retinopathy or neovascular glaucoma; renal diseases, especially glomerulonephritis; diabetic nephropathy; inflammatory bowel disease, especially Crohn's disease, thrombotic microangiopathic syndromes; transplant rejections or glomerulopathy; fibrotic diseases, especially cirrhosis of the liver; mesangial cell-proliferative diseases and injuries of the nerve tissue; and/or from diseases that respond to the effect of said compound or pharmaceutically acceptable salts as immunosuppressants, as an aid in scar-free wound healing, and for treating age spots and contact dermatitis. In a preferred embodiment, the protein kinase related disorder is a cancer selected from the group consisting of lung cancer, bone cancer, pancreatic cancer, skin cancer, cancer of the head or neck, cutaneous or intraocular melanoma, uterine cancer, ovarian cancer, rectal cancer, small-cell lung cancer, squamous cell carcinoma, astrocytoma, Kaposi's sarcoma, glioblastoma, non small-cell lung cancer, cancer of the anal region, genitourinary cancer, gastrointestinal cancer, stomach cancer, colon cancer, breast cancer, carcinoma of the fallopian tubes, carcinoma of the endometrium, carcinoma of the cervix, carcinoma of the vagina, carcinoma of the vulva, Hodgkin's Disease, cancer of the esophagus, cancer of the small intestine, cancer of the endocrine system, cancer of the thyroid gland, cancer of the parathyroid gland, cancer of the adrenal gland, sarcoma of soft tissue, cancer of the urethra, cancer of the penis, prostate cancer, chronic or acute leukemia, lymphocytic lymphomas, cancer of the bladder, cancer of the kidney or ureter, renal cell carcinoma, carcinoma of the renal pelvis, neoplasms of the central nervous system (CNS), primary CNS lymphoma, spinal axis tumors, brain stem glioma, pituitary adenoma, and combinations thereof. In a further preferred embodiment, cancer is selected from the group of gastrointestinal stromal tumors, renal cell carcinoma, breast cancer, colorectal cancer, non-small cell lung cancer, neuroendocrine tumors, thyroid cancer, small cell lung cancer, mastocytosis, glioma, sarcoma, acute myeloid leukemia, prostate cancer, lymphoma, and combinations thereof.

In another aspect, this invention is directed to a method of treatment or in the manufacture of a medicament for the treatment to a mammal of the protein kinase related disorder selected from the group consisting of diabetes, an autoimmune disorder, a hyperproliferation disorder, restenosis, fibrosis, psoriasis, von Hippel-Lindau disease, osteoarthritis, rheumatoid arthritis, angiogenesis, an inflammatory disorder, an immunological disorder, a cardiovascular disorder and a central nervous disorder.

In another aspect, this invention is directed to a method of comprising co-administering a pharmaceutical composition comprising one or more compound(s) of Formula (I) or a pharmaceutically acceptable salt thereof and pharmaceutically acceptable excipients with at least one anti-tumor agent selected from the group consisting of mitotic inhibitors, alkylating agents, anti-metabolites, intercalating antibiotics, growth factor inhibitors, cell cycle inhibitors, enzymes, topoisomerase inhibitors, biological response modifiers, antibodies, cytotoxics, anti-hormones, anti-androgens and mixtures thereof.

It is also an aspect of this invention that a compound described herein, or its salts, might be combined with other chemotherapeutic agents for the treatment of the diseases and disorders discussed above. For instance, a compound or salt of this invention might be combined with alkylating agents such as fluorouracil (5-FU) alone or in further combination with leukovorin; or other alkylating agents such as, without limitation, other pyrimidine analogs such as UFT, capecitabine, gemcitabine and cytarabine, the alkyl sulfonates, e.g., busulfan (used in the treatment of chronic granulocytic leukemia), improsulfan and piposulfan; aziridines, e.g., benzodepa, carboquone, meturedepa and uredepa; ethyleneimines and methylmelamines, e.g., altretamine, triethylenemelamine, triethylenephosphoramide, triethylenethiophosphoramide and trimethylolmelamine; and the nitrogen mustards, e.g., chlorambucil (used in the treatment of chronic lymphocytic leukemia, primary macroglobulinemia and non-Hodgkin's lymphoma), cyclophosphamide (used in the treatment of Hodgkin's disease, multiple myeloma, neuroblastoma, breast cancer, ovarian cancer, lung cancer, Wilrn's tumor and rhabdomyosarcoma), estramustine, ifosfamide, novembrichin, prednimustine and uracil mustard (used in the treatment of primary thrombocytosis, non-Hodgkin's lymphoma, Hodgkin's disease and ovarian cancer); and triazines, e.g., dacarbazine (used in the treatment of soft tissue sarcoma). Likewise a compound or salt of this invention might be expected to have a beneficial effect in combination with other antimetabolite chemotherapeutic agents such as, without limitation, folic acid analogs, e.g. methotrexate (used in the treatment of acute lymphocytic leukemia, choriocarcinoma, mycosis fungiodes breast cancer, head and neck cancer and osteogenic sarcoma) and pteropterin; and the purine analogs such as mercaptopurine and thioguanine which find use in the treatment of acute granulocytic, acute lymphocytic and chronic granulocytic leukemias.

A compound or salt of this invention might also be expected to prove efficaciousin combination with natural product based chemotherapeutic agents such as, without limitation, the vinca alkaloids, e.g., vinblastin (used in the treatment of breast and testicular cancer), vincristine and vindesine; the epipodophylotoxins, e.g., etoposide and teniposide, both of which are useful in the treatment of testicular cancer and Kaposi's sarcoma; the antibiotic chemotherapeutic agents, e.g., daunorubicin, doxorubicin, epirubicin, mitomycin (used to treat stomach, cervix, colon, breast, bladder and pancreatic cancer), dactinomycin, temozolomide, plicamycin, bleomycin (used in the treatment of skin, esophagus and genitourinary tract cancer); and the enzymatic chemotherapeutic agents such as L-asparaginase. In addition to the above, a compound or salt of this invention might be expected to have a beneficial effect used in combination with the platinum coordination complexes (cisplatin, etc.); substituted ureas such as hydroxyurea; methylhydrazine derivatives, e.g.; procarbaiine; adrenocortical suppressants, e.g., mitotane, aminoglutethimide; and hormone and hormone antagonists such as the adrenocorticosteriods (e.g., prednisone), progestins (e.g., hydroxyprogesterone, caproate); estrogens (e.g., diethylstilbesterol); antiestrogens such as tamoxifen; androgens, e.g., testosterone propionate; and aromatase inhibitors (such as anastrozole.) Finally, the combination of a compound of this invention might be expected to be particularly effective in combination with mitoxantrone or paclitaxel for the treatment of solid tumor cancers or leukemias such as, without limitation, acute myelogenous (non-lymphocytic) leukemia. The above method can be carried out in combination with a chemotherapeutic agent selected from the group consisting of mitotic inhibitors, alkylating agents, antimetabolites, cell cycle inhibitors, enzymes, topoisomerase inhibitors, biological response modifiers, anti-hormones, antiangiogenic agents such as MMP-2, MMP-9 and COX-2 inhibitors, and anti-androgens.

In still another aspect, this invention is also directed to a method of identifying a chemical compound that modulates the catalytic activity of a protein kinase by contacting cells expressing said protein kinase with said compound and then monitoring said cells for an effect.

Another aspect of this invention is also directed to a compound or the pharmaceutically acceptable salts thereof according to this invention, wherein compounds of Formula (I) is the free base or acid addition salts, wherein the salts consist of malate, lactate, maleate, hydrochloride, mesylate, sulfate, phosphate, citrate, acetate, trifluoroacetate.

Another aspect of this invention is also directed to a use of present compound in the preparation of drugs for the treatment of protein kinase related disorder in a mammal that responds to modulation of one or more protein kinases. Wherein the drugs combine with other anti-tumor agent selected from the group consisting of mitotic inhibitors, alkylating agents, anti-metabolites, intercalating antibiotics, growth factor inhibitors, cell cycle inhibitors, enzymes, topoisomerase inhibitors, biological response modifiers, antibodies, cytotoxics, anti-hormones, anti-androgens and mixtures thereof to treat protein kinase related disorder.

Another aspect of this invention is also directed to a use of present composition in the preparation of medicament for the treatment of protein kinase related disorder in a mammal that responds to modulation of one or more protein kinases. Wherein said composition further comprises anti-tumor agent selected from the group consisting of mitotic inhibitors, alkylating agents, anti-metabolites, intercalating antibiotics, growth factor inhibitors, cell cycle inhibitors, enzymes, topoisomerase inhibitors, biological response modifiers, antibodies, cytotoxics, anti-hormones, anti-androgens and mixtures thereof for treating protein kinase related disorder.

DETAILED DESCRIPTION OF THE INVENTION

Definitions

Unless otherwise stated, the following terms used in the specification and claims have the meanings discussed below. Further, many of the groups define herein can be optionally substituted. The listing in this definitions section of typical substituents is exemplary and is not intended to limit the substituents defined elsewhere within this specification and claims.

The terms "indolinone", "2-indolinone" and "indolin-2-one" are used interchangeably herein to refer to a molecule having the chemical structure:

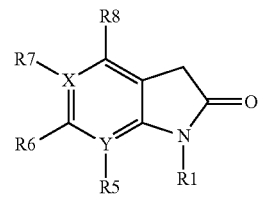

"Pyrrole" refers to a molecule having the chemical structure:

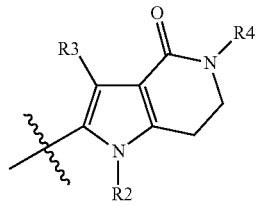

"Pyrrole-substituted 2-indolinone" and "3-pyrrolidinyl-2-indolinone" are used interchangeably herein to refer to a chemical compound having the general structure show in formula (I):

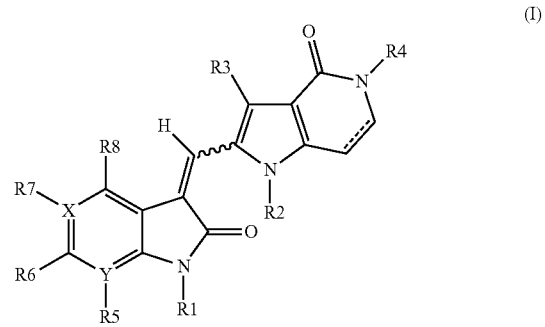

"Alkyl" refers to a saturated aliphatic hydrocarbon radical including straight chain and branched chain groups of 1 to 20 carbon atoms (whenever a numerical range; e.g. "1-20" is stated herein, it means that the group, in this case the alkyl group, may contain 1 carbon atom, 2 carbon atoms, 3 carbon atoms, etc, up to and including 20 carbon atoms). Alkyl groups containing from 1 to 4 carbon atoms are referred to as lower alkyl groups. When said lower alkyl groups lack substituents, they are referred to as unsubstituted lower alkyl groups. More preferably, an alkyl group is a medium size alkyl having 1 to 10 carbon atoms e.g., methyl, ethyl, propyl, 2-propyl, n-butyl, iso-butyl, tert-butyl, pentyl, and the like. Most preferably, it is a lower alkyl having 1 to 4 carbon atoms e.g., methyl, ethyl, propyl, 2-propyl, n-butyl, iso-butyl, or tert-butyl, and the like. The alkyl group may be substituted or unsubstituted. When substituted, the substituent group(s) is preferably one or more individually selected from halo, hydroxyl, —$OR_9$, —$O[CH_2CH_2O]_rR_{11}$, —$SR_9$, —$NR_9R_{10}$, —$SOR_9$, —$SO_2R_9$, —$NSO_2R_9$, —$SO_2NR_9R_{10}$, —$(CH_2)_nCO_2R_9$, —$(CH_2)_nCONR_9R_{10}$, —$C(=S)NR_9R_{10}$, —$COR_9$, —$NR_9COR_{10}$, —$NHCO_2R_{10}$, —$OCO_2R_9$, —$OCO_2NR_9R_{10}$, —CN, —$NO_2$, thiocarbonyl, perfluoroalkyl, O-carbamyl, N-carbamyl, O-thiocarbamyl, N-thiocarbarnyl, silyl, ammonium, haloalkoxyl, alkyl, cycloalkyl, heterocyclo, alkenyl, alkynyl, aryl, heteroaryl. When substituted, the substituent group(s) is preferably one or more, more preferably one to three, even more preferably one or two substituent(s) independently selected from the group consisting of halo, hydroxy, unsubstituted lower alkoxy, aryl optionally substituted with one or more groups, preferably one, two or three groups which are independently of each other halo, hydroxy, unsubstituted lower alkyl or unsubstituted lower alkoxy groups, aryloxy optionally substituted with one or more groups, preferably one, two or three groups which are independently of each other halo, hydroxy, unsubstituted lower alkyl or unsubstituted lower alkoxy groups, 6-member heteroaryl having from 1 to 3 nitrogen atoms in the ring, the carbons in the ring being optionally substituted with one or more groups, preferably one, two or three groups which are independently of each other halo, hydroxy, unsubstituted lower alkyl or unsubstituted lower alkoxy groups, 5-member heteroaryl having from 1 to 3 heteroatoms selected from the group consisting of nitrogen, oxygen and sulfur, the carbon and the nitrogen atoms in the group being optionally substituted with one or more groups, preferably one, two or three groups which are independently of each other halo, hydroxy, unsubstituted lower alkyl or unsubstituted lower alkoxy groups, 5- or 6-member heteroalicyclic group having from 1 to 3, heteroatoms selected from the group consisting of nitrogen, oxygen and sulfur, the carbon and nitrogen (if present) atoms in the group being optionally substituted with one or more groups, preferably one, two or three groups which are independently of each other halo, hydroxy, unsubstituted lower alkyl or unsubstituted lower alkoxy groups, mercapto, (unsubstituted lower alkyl) thio, arylthio optionally substituted with one or more groups, preferably one, two or three groups which are independently of each other halo, hydroxy, unsubstituted lower alkyl or unsubstituted lower alkoxy groups, cyano, acyl, thioacyl, O-carbamyl, N-carbamyl, O-thiocarbamyl, N-thiocarbamyl, C-amido, N-amido, nitro, N-sulfonamido, S-sulfonamido, R'S(O)—, R'S(O)$_2$—, C(O)OR', R'C(O)O—, and —NR'R", wherein R' and R" are independently selected from the group consisting of hydrogen, unsubstituted lower alkyl, trihalomethyl, unsubstituted ($C_3$-$C_6$)cycloalkyl, unsubstituted lower alkenyl, unsubstituted lower alkynyl and aryl optionally substituted with one or more, groups, preferably one, two or three groups which are independently of each other halo, hydroxy, unsubstituted lower alkyl or unsubstituted lower alkoxy groups.

Preferably, the alkyl group is substituted with one or two substituents independently selected from the group consisting of hydroxy, 5- or 6-member heteroalicyclic group having from 1 to 3 heteroatoms selected from the group consisting of nitrogen, oxygen and sulfur, the carbon and nitrogen (if present) atoms in the group being optionally substituted with one or more groups, preferably one, two or three groups which are independently of each other halo, hydroxy, unsubstituted lower alkyl or unsubstituted lower alkoxy groups, 5-member heteroaryl having from 1 to 3 heteroatoms selected from the group consisting of nitrogen, oxygen and sulfur, the carbon and the nitrogen atoms in the group being optionally substituted with one or more groups, preferably one, two or three groups which are independently of each other halo, hydroxy, unsubstituted lower alkyl or unsubstituted lower alkoxy groups, 6-member heteroaryl having, from 1 to 3 nitrogen atoms in the ring, the carbons in the ring being optionally substituted with one or more groups, preferably one, two or three groups which are independently of each other halo, hydroxy, unsubstituted lower alkyl or unsubstituted lower alkoxy groups, or —NR'R", wherein and R" are independently selected from the group consisting of hydrogen, unsubstituted lower alkyl. Even more preferably the alkyl group is substituted with one or two substituents which are independently of each other hydroxy, dimethylamino, ethylamino, diethylamino, dipropylamino, pyrrolidino, piperidino, morpholino, piperazino, 4-lower alkylpiperazino, phenyl, imidazolyl, pyridinyl, pyridazinyl, pyrimidinyl, oxazolyl, triazinyl, and the like.

"Alkenyl" refers to an aliphatic hydrocarbon having at least one carboncarbon double bond, including straight chain, branched chain or cyclic groups having at least one carbon-carbon double bond. Preferably, the alkenyl group has 2 to 20 carbon atoms (whenever a numerical range; e.g., "2-20", is stated herein, it means that the group, in this case the alkenyl group, may contain 2 carbon atoms, 3 carbon atoms, etc. up to and including 20 carbon atoms). More preferably, it is a medium size alkenyl having 2 to 10 carbon atoms. Most preferably, it is a lower alkenyl having 2 to 6 carbon atoms. The alkenyl group may be substituted or unsubstituted. When substituted, the substituent group(s) is preferably one or more individually selected from halo, —$OR_9$, —$O[CH_2CH_2O]_rR_{11}$, —$SR_9$, —$NR_9R_{10}$, —$SOR_9$, —$SO_2R_9$, —$NSO_2R_9$, —$SO_2NR_9R_{10}$, —$(CH_2)_nCO_2R_9$, —$(CH_2)_nCONR_9R_{10}$, —$C(=S)NR_9R_{10}$, —$COR_9$, —$NR_9COR_{10}$, —$NHCO_2R_{10}$, —$OCO_2R_9$, —$OCO_2NR_9R_{10}$, —CN, —$NO_2$, thiocarbonyl, perfluoroalkyl, O-carbamyl, N-carbamyl, O-thiocarbamyl, N-thiocarbamyl, silyl, ammonium, haloalkoxyl, alkyl, cycloalkyl, heterocyclo, alkenyl, alkynyl, aryl, heteroaryl.

"Alkynyl" refers to an aliphatic hydrocarbon having at least one carboncarbon triple bond, including straight chain, branched chain or cyclic groups having at least one carbon-carbon triple bond. Preferably, the alkenyl group has 2 to 20 carbon atoms (whenever a numerical range; e.g., "2-20", is stated herein, it means that the group, in this case the alkynyl group, may contain 2 carbon atoms, 3 carbon atoms, etc. up to and including 20 carbon atoms). More preferably, it is a medium size alkynyl having 2 to 10 carbon atoms. Most preferably, it is a lower alkynyl having 2 to 6 carbon atoms. The alkynyl group may be substituted or unsubstituted. When substituted, the substituent group(s) is preferably one or more individually selected from halo, —$OR_9$, —$[CH_2CH_2O]_rR_{11}$, —$SR_9$, —$NR_9R_{10}$, —$SOR_9$, —$SO_2R_9$, —$NSO_2R_9$, —$SO_2NR_9R_{10}$, —$(CH_2)_nCO_2R_9$, —$(CH_2)_nCONR_9R_{10}$, —$C(=S)NR_9R_{10}$, —$COR_9$, —$NR_9COR_{10}$, —$NHCO_2R_{10}$, —$OCO_2R_9$, —$OCO_2NR_9R_{10}$, —CN, —$NO_2$, thiocarbonyl, perfluoroalkyl, O-carbamyl, N-carbamyl, O-thiocarbamyl, N-thiocarbarnyl, silyl, ammonium, haloalkoxyl, alkyl, cycloalkyl, heterocyclo, alkenyl, alkynyl, aryl, heteroaryl.

"Aryl" refers to an all-carbon monocyclic or fused-ring polycyclic (i.e., rings which share adjacent pairs of carbon atoms) groups of 1 to 12 carbon atoms having a completely conjugated pi-electron system. Examples, without limitation, of aryl groups are phenyl, naphthalenyl and anthracenyl. The aryl group may be substituted or unsubstituted. When substituted, the substituted group(s) is preferably one or more, more preferably one, two or three, even more preferably one or two, independently selected from the group consisting of unsubstituted lower alkyl, trihaloalkyl, halo, hydroxy, unsubstituted lower alkoxy, mercapto, (unsubstituted lower alkyl)thio, cyano, acyl, thioacyl, O-carbamyl, N-carbamyl, O-thiocarbamyl, N-thiocarbamyl, C-amido, N-amido, nitro, N-sulfonamido, S-Sulfonamido, R'S(O)—, R'S(O)$_2$—, —C(O)OR', R'C(O)O—, and —NR'R", with R' and R" as defined above. Preferably, the aryl group is optionally substituted with one or two substituents independently selected from halo, unsubstituted lower alkyl, trihaloalkyl, hydroxy, mercapto, cyano, N-amido, mono or dialkylamino, carboxy, or N-sulfonamido.

"Cycloalkyl" refers to a 3 to 8 member all-carbon monocyclic ring, an all-carbon 5-member/6-member or 6-member/6-member fused bicyclic ring or a multicyclic fused ring (a "fused" ring system means that each ring in the system shares an adjacent pair of carbon atoms with each other ring in the system) group wherein one or more of the rings may contain one or more double bonds but none of the rings has a completely conjugated pi-electron system.

Examples, without limitation, of cycloalkyl groups are cyclopropane, cyclobutane, cyclopentane, cyclopentene, cyclohexane, cyclohexadiene, adamantane, cycloheptane, cycloheptatriene, and the like. A cycloalkyl group may be substituted or unsubstituted. When substituted, the substituent group(s) is preferably one or more individually selected from halo, hydroxyl, —OR$_9$, —O[CH$_2$CH$_2$O]$_r$R$_{11}$, —SR$_9$, —NR$_9$R$_{10}$, —SOR$_9$, —SO$_2$R$_9$, —NSO$_2$R$_9$, —SO$_2$NR$_9$R$_{10}$, —(CH$_2$)$_n$CO$_2$R$_9$, —(CH$_2$)$_n$CONR$_9$R$_{10}$, —C(=S)NR$_9$R$_{10}$, —COR$_9$, —NR$_9$COR$_{10}$, —NHCO$_2$R$_{10}$, —OCO$_2$R$_9$, —OCO$_2$NR$_9$R$_{10}$, —CN, —NO$_2$, thiocarbonyl, perfluoroalkyl, O-carbamyl, N-carbamyl, O-thiocarbamyl, N-thiocarbamyl, silyl, ammonium, haloalkoxyl, alkyl, cycloalkyl, heterocyclo, alkenyl, alkynyl, aryl, heteroaryl. When substituted, the substituent group(s) is preferably one or more, more preferably one or two substituents, independently selected from the group consisting of unsubstituted lower alkyl, trihaloalkyl, halo, hydroxy, unsubstituted lower alkoxy, aryl optionally substituted with one or more, preferably one or two groups independently of each other halo, hydroxy, unsubstituted lower alkyl or unsubstituted lower alkoxy groups, aryloxy optionally substituted with one or more, preferably one or two groups independently of each other halo, hydroxy, unsubstituted lower alkyl or unsubstituted lower alkoxy groups, 6-member heteroaryl having from 1 to 3 nitrogen atoms in the ring, the carbons in the ring being optionally substituted with one or more, preferably one or two groups independently of each other halo, hydroxy, unsubstituted lower alkyl or unsubstituted lower alkoxy groups, 5-member heteroaryl having from 1 to 3 heteroatoms selected from the group consisting of nitrogen, oxygen and sulfur, the carbon and nitrogen atoms of the group being optionally substituted with one or more, preferably one or two groups independently of each other halo, hydroxy, unsubstituted lower alkyl or unsubstituted lower alkoxy groups, 5- or 6-member heteroalicyclic group having from 1 to 3 heteroatoms selected from the group consisting of nitrogen, oxygen and sulfur, the carbon and nitrogen (if present) atoms in the group being optionally substituted with one or more, preferably one or two groups independently of each other halo, hydroxy, unsubstituted lower alkyl or unsubstituted lower alkoxy groups, mercapto, (unsubstituted lower alkyl) thio, arylthio optionally substituted with one or more, preferably one or two groups independently of each other halo, hydroxy, unsubstituted lower alkyl or unsubstituted lower alkoxy groups, cyano, acyl, thioacyl, O-carbamyl, N-carbamyl, O-thiocarbamyl, N-thiocarbamyl, C-amido, N-amido, nitro, N-sulfonamido, S-sulfonamido, R'S(O)—, R'S(O)$_2$—, —C(O)OR', R'C(O)O—, and —NR'R" are as defined above. Illustrative examples of cycloalkyl are derived from, but not limited to the following:

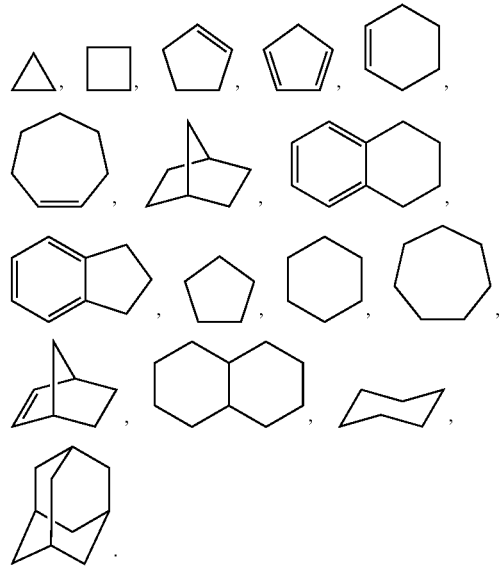

A "heterocyclic ring" or "heterocycle" group refers to a monocyclic or fused ring group having in the ring(s) one or more atoms selected from the group consisting of nitrogen, oxygen and sulfur. The rings may also have one or more double bonds. However, the rings may or may not have a completely conjugated pi-electron system. The heterocyclic ring may be substituted or unsubstituted. The heterocyci ring may contain one or more oxo groups. When substituted, the substituted group(s) is preferably one or more individually selected from halo, hydroxyl, —OR$_9$, —O[CH$_2$CH$_2$O]$_r$R$_{11}$, —SR$_9$, —NR$_9$R$_{10}$, —SOR$_9$, —SO$_2$R$_9$, —NSO$_2$R$_9$, —SO$_2$NR$_9$R$_{10}$, —(CH$_2$)$_n$CO$_2$R$_9$, —(CH$_2$)$_n$CONR$_9$R$_{10}$, —C(=S)NR$_9$R$_{10}$, —COR$_9$, —NR$_9$COR$_{10}$, —NHCO$_2$R$_{10}$, —OCO$_2$R$_9$, —OCO$_2$NR$_9$R$_{10}$, —CN, —NO$_2$, thiocarbonyl, perfluoroalkyl, O-carbamyl, N-carbamyl, O-thiocarbamyl, N-thiocarbarnyl, silyl, ammonium, haloalkoxyl, alkyl, cycloalkyl, heterocyclo, alkenyl, alkynyl, aryl, heteroaryl.

Examples of suitable saturated heteroalicyclic groups include, but are not limited to:

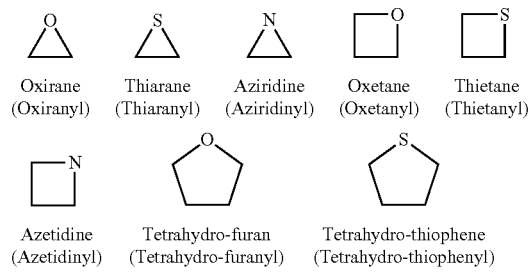

-continued

 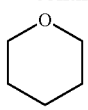 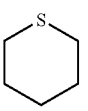

Pyrrolidine    Tetrahydro-pyran    Tetrahydro-thiopyran
(Pyrrolidinyl)    (Tetrahydro-pyranyl)    (Tetrahydro-thiopyranyl)

  

Piperidine    [1,4]Dioxane    [1,4]Oxathiane    Morpholine
(Piperidinyl)    (1,4]Dioxanyl)    ([1,4]Oxathianyl)    (Morpholinyl)

  

[1,4]Dithiane    Piperazine    Thiomorpholine
([1,4]Dithianyl)    (Piperazinyl)    (Thiomorpholinyl)

  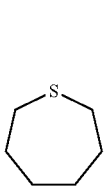

1-Methyl-piperidin-4-ol    Oxepane    Thiepane
(1-Methyl-piperidin-4-olyl)    (Oxepanyl)    (Thiepanyl)

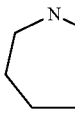 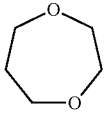 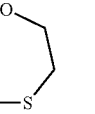

Azepane    [1,4]Dioxepane    [1,4]Oxathiepane
(Azepanyl)    ([1,4]Dioxepanyl)    ([1,4]Oxathiepanyl)

 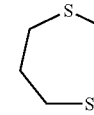 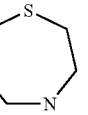

[1,4]Oxazepane    [1,4]Dithiepane    [1,4]Thiazepane
([1,4]Oxazepanyl)    ([1,4]Dithiepanyl)    ([1,4]Thiazepanyl)

[1,4]Diazepane
([1,4]Diazepanyl)

Examples of a suitable partially unsaturated heteroalicyclic groups include, but are not limited to:

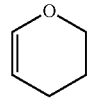 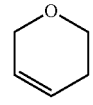

3,4-Dihydro-2H-pyran    3,6-Dihydro-2H-pyran
(3,4-Dihydro-2H-pyranyl)    (3,6-Dihydro-2H-pyranyl)

 

2H-Pyran    1,2,3,4-Tetrahydro-pyridine
(2H-Pyranyl)    (1,2,3,4-Tetrahydro-pyridinyl)

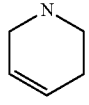

1,2,3,6-Tetrahydro-pyridine
(1,2,3,6-Tetrahydro-pyridinyl)

"Heteroaryl" refers to a monocyclic or fused ring (i.e., rings which share an adjacent pair of atoms) group of 5 to 12 ring atoms containing one, two, or three ring heteroatoms selected from N, O, or S, the remaining ring atoms being C, and, in addition, having a completely conjugated pi-electron system. Examples, without limitation, of unsubstituted heteroaryl groups are pyrrole, furan, thiophene, imidazole, oxazole, thiazole, pyrazole, pyridine, pyrimidine, quinoline, isoquinoline, purine and carbazole. The heteroaryl group may be substituted or unsubstituted. When substituted, the substituent group(s) is preferably one or more individually selected from halo, hydroxyl, —$OR_9$, —$O[CH_2CH_2O]_nR_{11}$, —$SR_9$, —$NR_9R_{10}$, —$SOR_9$, —$SO_2R_9$, —$NSO_2R_9$, —$SO_2NR_9R_{10}$, —$(CH_2)_nCO_2R_9$, —$(CH_2)_nCONR_9R_{10}$, —$C(=S)NR_9R_{10}$, —$COR_9$, —$NR_9COR_{10}$, —$NHCO_2R_{10}$, —$OCO_2R_9$, —$OCO_2NR_9R_{10}$, —CN, —$NO_2$, thiocarbonyl, perfluoroalkyl, O-carbamyl, N-carbamyl, O-thiocarbamyl, N-thiocarbamyl, silyl, ammonium, haloalkoxy, alkyl, cycloalkyl, heterocyclo, alkenyl, alkynyl, aryl, heteroaryl. When substituted, the substituted group(s) is preferably one or more, more preferably one, two, or three, even more preferably one or two, independently selected from the group consisting of unsubstituted lower alkyl, trihaloalkyl, halo, hydroxy, unsubstituted lower alkoxy, mercapto, (unsubstituted lower alkyl)thio, cyano, acyl, thioacyl, O-carbamyl, N-carbamyl, O-thiocarbamyl, N-thiocarbamyl, C-amido, N-amido, nitro, N-sulfonamido, S-sulfonamido, R'S(O)—, R'S(O)$_2$—, —C(O)OR', R'C(O)O—, and —NR'R", with R' and R" as defined above. Preferably, the heteroaryl group is optionally substituted with one or two substituents independently selected from halo, unsubstituted lower alkyl, trihaloalkyl, hydroxy, mercapto, cyano, N-amido, mono or dialkylamino, carboxy, or Nsulfonamido.

A pharmaceutically acceptable heteroaryl is one that is sufficiently stable to be attached to a compound of the invention, formulated into a pharmaceutical composition and subsequently administered to a patient in need thereof.

Examples of typical monocyclic heteroaryl groups include, but are not limited to:

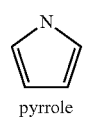  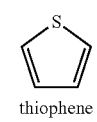 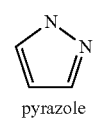

pyrrole    furan    thiophene    pyrazole
(pyrroleyl)    (furanyl)    (thiophenyl)    (pyrazolyl)

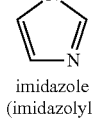 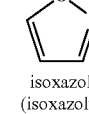 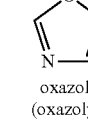 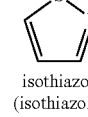

imidazole    isoxazole    oxazole    isothiazole
(imidazolyl)    (isoxazolyl)    (oxazolyl)    (isothiazolyl)

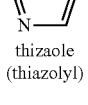 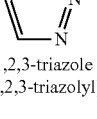 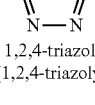 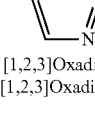

thizaole    1,2,3-triazole    1,2,4-triazole    [1,2,3]Oxadiazole
(thiazolyl)    (1,2,3-triazolyl)    (1,2,4-triazolyl)    ([1,2,3]Oxadiazolyl)

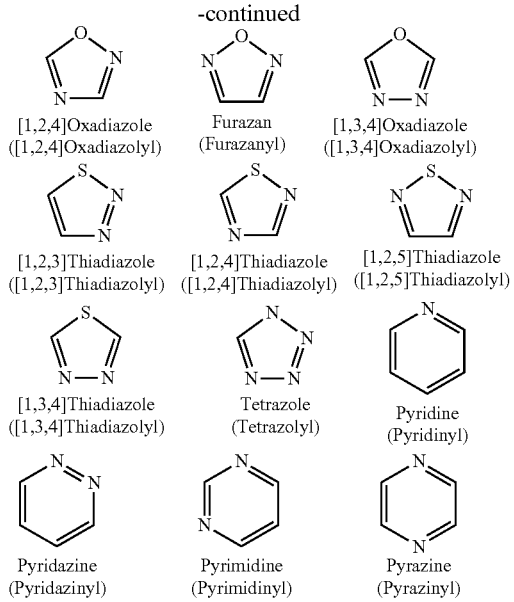
Examples of suitable fused ring heteroaryl groups include, but are not limited to:
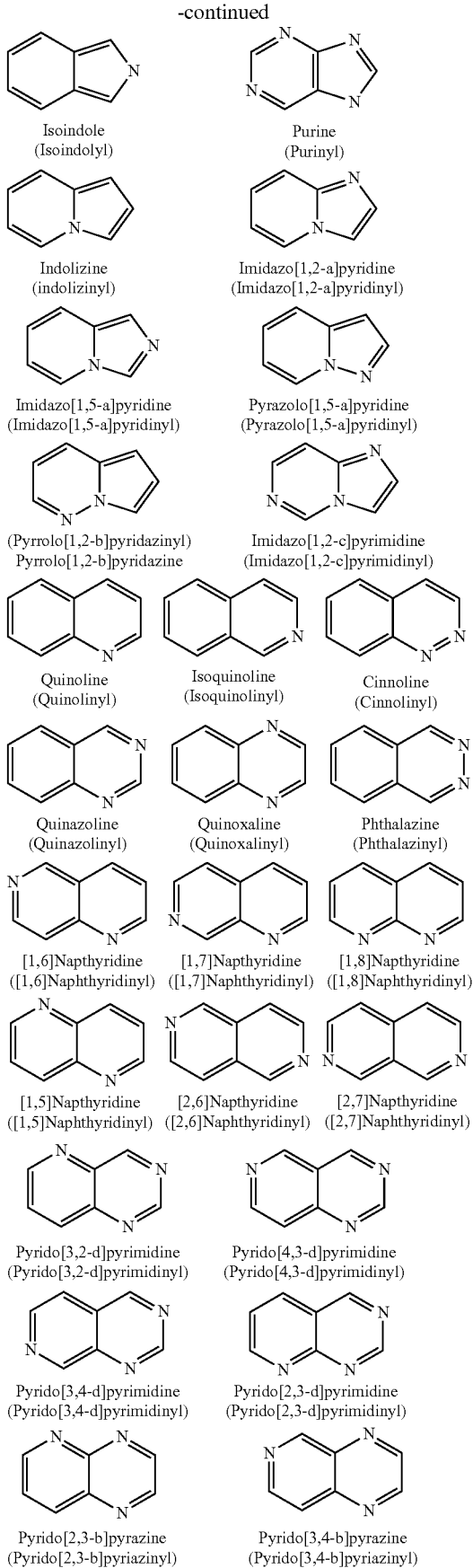

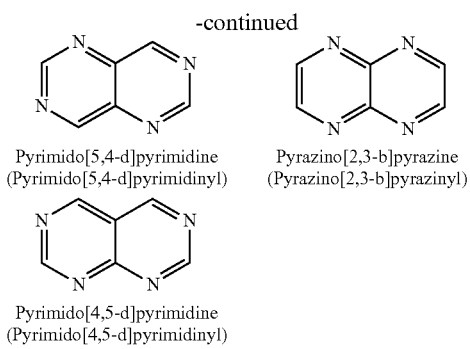

Pyrimido[5,4-d]pyrimidine
(Pyrimido[5,4-d]pyrimidinyl)

Pyrazino[2,3-b]pyrazine
(Pyrazino[2,3-b]pyrazinyl)

Pyrimido[4,5-d]pyrimidine
(Pyrimido[4,5-d]pyrimidinyl)

"Alkoxyl" refers to both an -0-(unsubstituted alkyl) and an -0-'(unsubstituted cycloalkyl) group. Representative examples include, but are not limited to, e.g., methoxy, ethoxy, propoxy, butoxy, cyclopropyloxy, cyclobutyloxy, cyclopentyloxy, cyclohexyloxy, and the like.

"Aryloxyl" refers to both an -0-aryl and an -0-heteroaryl group, as defined herein. Representative examples include, but are not limited to, phenoxy, pyridinyloxy, furanyloxy, thienyloxy, pyrimidinyloxy, pyrazinyloxy, and the like, and derivatives thereof.

"Halo" refers to fluoro, chloro, bromo, or iodo.

"Haloalkoxy" refers to a radical —OR where R is an haloalkyl as defined above. e.g., trifluoromethoxy, trichloroethoxy, 2,2-dichloropropoxy, and the like.

"Hydroxyalkyl" means a saturated straight or branched monovalent hydrocarbon radical of one to six carbon atoms substituted with one or two hydroxyl groups, provided that if two hydroxy groups are present they are not both on the same carbon atom. Representative examples include, but are not limited to, 2-hydroxyethyl, 2-hydroxypropyl, 3-hydroxypropyl, 1-(hydroxylmethyl)-2-methylpropyl, 2-hydroxybutyl, 3-hydroxybutyl, 4-hydroxybutyl, 2,3-dihydroxypropyl, 1-(hydroxymethyl)-2-hydroxyethyl, 2,3-dihydroxybutyl, 3,4-dihydroxybutyl and 2-(hydroxymethyl)-3-hydroxypropyl, preferably 2-hydroxyethyl, 2,3-dihydroxypropyl and 1-(hydroxymethyl)-2-hydroxyethyl.

"Aminoalkyl" means a saturated straight or branched monovalent hydrocarbon radical of one to six carbon atoms substituted with one or two —NH$_2$ e.g., 2-aminoethyl, 3-aminopropyl, 2-aminopropyl, 2-, 3-, or 4-aminobutyl, and the like.

"amine" refers to a chemical moiety of formula —NRaRb where R, and Rb are independently selected from the group consisting of hydrogen, saturated or unsaturated alkyl, and five-membered or six-membered aromatic or heteroaromatic ring, where the ring is optionally substituted with one, two or three substituents independently selected from the group consisting of alkyl, halogen, trihalomethyl, carboxylate, nitro, and ester moieties.

"aminocarbonyl" refers to a radical —C(O)R where R is an amine as defined above.

"carboxylic acid" or "carboxylate" refers to a chemical moiety with formula —(R)$_n$—COOH, where R is selected from the group consisting of saturated or unsaturated alkyl and five membered or six-membered aromatic or heteroaromatic ring and where n is 0 or 1.

"Acyl" refers to a —C(O)—R" group, where R" is selected from the group consisting of hydrogen, unsubstituted lower alkyl, trihalomethyl, unsubstituted cycloalkyl, aryl optionally substituted with one or more, preferably one, two, or three substituents selected from the group consisting of unsubstituted lower alkyl, trihalomethyl, unsubstituted lower alkoxy, halo and —NR"R" groups, heteroaryl (bonded through a ring carbon) optionally substituted with one or more, preferably one, two, or three substituents selected from the group consisting of unsubstituted lower alkyl, trihaloalkyl, unsubstituted lower alkoxy, halo and —NR'R" groups and heteroalicyclic (bonded through a ring carbon) optionally substituted with one or more, preferably one, two, or three substituents selected from the group consisting of unsubstituted lower alkyl, trihaloalkyl, unsubstituted lower alkoxy, halo and —NR'R" groups. Representative acy groups include, but are not limited to, acetyl, trifluoroacetyl, benzoyl, and the like.

"Aldehyde" refers to an acyl group in which R" is hydrogen.

"Thioacyl" refers to a —C(S)—R" group, with R" as defined herein.

"Ester" refers to a —C(O)OR" group with R" as defined herein except that R" cannot be hydrogen.

"Cyano" refers to a group.

"Hydroxy" refers to an —OH group.

As used herein, "PK" refers to receptor protein tyrosine kinase (RTKs), nonreceptor or "cellular" tyrosine kinase (CTKs) and serine-threonine kinases (STKs).

"Optional" or "optionally" means that the subsequently described event or circumstance may but need not occur, and that the description includes instances where the event or circumstance occurs and instances in which it does not. For example, "heterocycle group optionally substituted with an alkyl group" means that the alkyl may but need not be present, and the description includes situations where the heterocycle group is substituted with an alkyl group and situations where the heterocyclo group is not substituted with the alkyl group.

The term "method" refers to manners, means, techniques and procedures for accomplishing a given task including, but not limited to, those manners, means, techniques and procedures either known to, or readily developed from known manners, means, techniques and procedures by, practitioners of the chemical, pharmaceutical, biological, biochemical and medical arts.

"In vitro" refers to procedures performed in an artificial environment such as, e.g., without limitation, in a test tube or culture medium. The skilled artisan will understand that, for example, an isolated PK may be contacted with a modulator in an in vitro environment. Alternatively, an isolated cell may be contacted with a modulator in an in vitro environment.

As used herein, "in vivo" refers to procedures performed within a living organism such as, without limitation, a mouse, rat, rabbit, ungulate, bovine, equine, porcine, canine, feline, primate, or human.

As used herein, "PK related disorder," "PK driven disorder," and "abnormal PK activity" all refer to a condition characterized by inappropriate; i.e., under or, more commonly, over, PK catalytic activity, where the particular PK can be an RTK, a CTK or an STK. Inappropriate catalytic activity can arise as the result of either: (1) PK expression in cells which normally do not express PKs, (2) increased PK expression leading to unwanted cell'proliferation, differentiation and/or growth, or, (3) decreased PK expression leading to unwanted reductions in cell proliferation, differentiation and/or growth. Over-activity of a PK refers to either amplification of the gene encoding a particular PK or production of a level of PK activity which can correlate with a cell proliferation, differentiation and/or growth disorder (that is, as the level of the PK increases, the severity of one or more of the symptoms of the cellular disorder increases). Under-activity is, of course, the converse, wherein the severity of one or more symptoms of a cellular disorder increase as the level of the PK activity decreases.

As used herein, the terms "treat", "treating" and "treatment" refer to a method of alleviating or abrogating a PK mediated cellular disorder and/or its attendant symptoms. With regard particularly to cancer, these terms simply mean that the life expectancy of an individual affected with a cancer will be increased or that one or more of the symptoms of the disease will be reduced.

The term "organism" refers to any living entity comprised of at least one cell. A living organism can be as simple as, for example, a single eukaryotic cell or as complex as a mammal. In a preferred aspect, the organism is a mammal. In a particularly preferred aspect, the mammal is a human being.

The term "therapeutically effective amount" as used herein refers to that amount of the compound being administered which will relieve to some extent one or more of the symptoms of the disorder being treated. In reference to the treatment of cancer, a therapeutically effective amount refers to that amount which has the effect of (1) reducing the size of the tumor, (2) inhibiting (that is, slowing to some extent, preferably stopping) tumor metastasis, (3) inhibiting to some extent (that is, slowing to some extent, preferably stopping) tumor growth, and/or, (4) relieving to some extent (or, preferably, eliminating) one or more symptoms associated with the cancer.

A "pharmaceutical composition" refers to a mixture of one or more of the compounds described herein, or pharmaceutically acceptable salts or prodrugs thereof, with other chemical components, such as pharmaceutically acceptable excipients. The purpose of a pharmaceutical composition is to facilitate administration of a compound to an organism.

"Pharmaceutically acceptable excipient" refers to an inert substance added to a pharmaceutical composition to further facilitate administration of a compound. Examples, without limitation, of excipients include calcium carbonate, calcium phosphate, various sugars and types of starch, cellulose derivatives, gelatin, vegetable oils and polyethylene glycols.

"Pharmaceutically acceptable salt" refers to those salts, which retain the biological effectiveness and properties of the parent compound. Such salts include:
(1) acid addition salt which is obtained by reaction of the free base of the parent compound with inorganic acids such as hydrochloric acid, hydrobromic acid, nitric acid, phosphoric acid, sulfuric acid, and perhcloric acid and the like, or with organic acids such as acetic acid, oxalic acid, (D) or (1;) malic acid, maleic acid, methanesulfonic acid, ethanesulfonic acid, p-toluenesulfonic acid, salicylic acid, tartaric acid, citric acid, succinic acid or malonic acid and the like, preferably hydrochloric acid or (L)-malic acid; or
(2) salts formed when an acidic proton present in the parent compound either is replaced by a metal ion, e.g., an alkali metal ion, an alkaline earth ion, or an aluminum ion; or coordinates with an organic base such as ethanolamine, diethanolamine, triethanolamine, tromethamine, N-methylglucamine, and the like.

The compound of Formula (I) may also act as a prodrug. A "prodrug" refers to an agent, which is converted into the parent drug in vivo. Prodrugs are often useful because, in some situations, they may be easier to administer than the parent drug. They may, for instance, be bioavailable by oral administration whereas the parent drug is not. The prodrug may also have improved solubility in pharmaceutical compositions over the parent drug. An example, without limitation, of a prodrug would be a compound of the present invention, which is, administered as an ester (the "prodrug"), carbamate or urea.

Pharmaceutically acceptable salts include acid addition and base salts (including disalts). Suitable acid addition salts are formed from acids which form non-toxic salts. Examples include the acetate, aspartate, benzoate, besylate, bicarbonate/carbonate, bisulphate/sulfate, borate, camsylate, citrate, edisylate, esylate, formate, fumarate, gluceptate, gluconate, glucuronate, hexafluorophosphate, hibenzate, hydrochloride/chloride, hydrobromide/bromide, hydroiodide/iodide, isethionate, lactate, malate, maleate, malonate, mesylate, methylsulfate, naphthylate, 2-napsylate, nicotinate, nitrate, orotate, oxalate, palmitate, pamoate, phosphate/hydrogen phosphate/dihydrogen phosphate, saccharate, stearate, succinate, tartrate, tosylate and trifluoroacetate salts.

Suitable base salts are formed from bases which form non-toxic salts. Examples include the aluminum, arginine, benzathine, calcium, choline, diethylamine, diolamine, glycine, lysine, magnesium, meglumine, olamine, potassium, sodium, tromethamine and zinc salts.

For a review on suitable salts, see "Handbook of Pharmaceutical Salts: properties, Selection, and Use" by Stahl and Wermuth (Wiley-VCH, Weinheim, Germany, 2002), the disclosure of which is incorporated herein by reference in its entirety.

A pharmaceutically acceptable salt of the inventive compounds can be readily prepared by mixing together solutions of the compound and the desired acid or base, as appropriate. The salt may precipitate from solution and be collected by filtration or may be recovered by evaporation of the solvent. The degree of ionization in the salt may vary from completely ionized to almost non-ionized.

"Catalytic activity" refers to the rate of phosphorylation of tyrosine under the influence, direct or indirect, of RTKs and/or CTKs or the phosphorylation of serine and threonine under the influence, direct or indirect, of STKs.

"Monitoring" refers to observing or detecting the effect of contacting a compound with a cell expressing a particular PK. The observed or detected effect can be a change in cell phenotype, in the catalytic activity of a PK or a change in the interaction of a PK with a natural binding partner. Techniques for observing or detecting such effects are well known in the art.

The term "effect" refers to a change or an absence of a change in cell phenotype or cell proliferation. "Effect" can also describe a change or an absence of a change in the catalytic activity of the protein kinase. "Effect" can also describe a change or an absence of a change in an interaction between the protein kinase and a natural binding partner.

"Cell phenotype" refers to the outward appearance of a cell or tissue or the biological function of the cell or tissue. Examples, without limitation, of a cell phenotype are cell size, cell growth, cell proliferation, cell differentiation, cell survival, apoptosis, and nutrient uptake and use. Such phenotypic characteristics are measurable by techniques well-known in the art.

A "natural binding partner" refers to a polypeptide that binds to a particular PK in a cell. Natural binding partners can play a role in propagating a signal in a PK-mediated signal transduction process. A change in the interaction of the natural binding partner with the PK can manifest itself as an increased or decreased concentration of the PK/natural binding partner complex and, as a result, in an observable change in the ability of the PK to mediate signal transduction.

As used herein, "administer" or "administration" refers to the delivery of a compound or salt of the present invention or of a pharmaceutical composition containing a compound or salt of this invention to an organism for the purpose of prevention or treatment of a PK-related disorder.

The term "aberration," in conjunction with a signal transduction process, refers to a protein kinase that is over- or under-expressed in an organism, mutated such that its catalytic activity is lower or higher than wild-type protein kinase activity, mutated such that it can no longer interact with a natural binding partner, is no longer modified by another protein kinase or protein phosphatase, or no longer interacts with a natural binding partner.

The term "inhibit" refers to decreasing the cellular function of a protein kinase. The protein kinase function is preferably the interaction with a natural binding partner and most preferably catalytic activity.

Compounds of the invention containing one or more asymmetric carbon atoms can exist as two or more stereoisomers. Where a compound of the invention contains an alkenyl or alkenylene group, geometric cis/trans (or Z/E) isomers are possible. Where the compound contains, for example, a keto or oxime group or an aromatic moiety, tautomeric isomerism ('tautomerism') can occur. A single compound may exhibit more than one type of isomerism.

Included within the scope of the invention are all stereoisomers, geometric isomers and tautomeric forms of the inventive compounds, including compounds exhibiting more than one type of isomerism, and mixtures of one or more thereof. Also included are acid addition or base salts wherein the counterion is optically active, for example, D-lactate or L-lysine, or racemic, for example, DL-tartrate or DL-arginine.

Cis/trans isomers may be separated by conventional techniques well known to those skilled in the art, for example, chromatography and fractional crystallization.

Conventional techniques for the preparation/isolation of individual enantiomers include chiral synthesis from a suitable optically pure precursor or resolution of the racemate (or the racemate of a salt or derivative) using, for example, chiral high pressure liquid chromatography (HPLC).

Alternatively, the racemate (or a racemic precursor) may be reacted with a suitable optically active compound, for example, an alcohol, or, in the case where the compound contains an acidic or basic moiety, an acid or base such as tartaric acid or 1-phenylethylamine. The resulting diastereomeric mixture may be separated by chromatography and/or fractional crystallization and one or both of the diastereoisomers converted to the corresponding pure enantiomer(s) by means well known to one skilled in the art.

Chiral compounds of the invention (and chiral precursors thereof) may be obtained in enantiomerically-enriched form using chromatography, typically HPLC, on an asymmetric resin with a mobile phase consisting of a hydrocarbon, typically heptane or hexane, containing from 0 to 50% isopropanol, typically from 2 to 20%, and from 0 to 5% of an alkylamine, typically 0.1% diethylamine. Concentration of the eluate affords the enriched mixture.

Stereoisomeric conglomerates may be separated by conventional techniques known to those skilled in the art; see, for example, "Stereochemistry of Organic Compounds" by E L Eliel (Wiley, New York, 1994), the disclosure of which is incorporated herein by reference in its entirety.

Pharmaceutical Compositions and Use

A compound of the present invention or a physiologically acceptable salt thereof, can be administered as such to a human patient or can be administered in pharmaceutical compositions in which the foregoing materials are mixed with suitable carriers or excipient(s). Techniques for formulation and administration of drugs may be found in "Remington's Pharmacological Sciences," Mack Publishing Co., Easton, Pa., latest edition.

Routes of Administration

Suitable routes of administration may include, without limitation, oral, intraoral, rectal, transmucosal or intestinal administration or intramuscular, epicutaneous, parenteral, subcutaneous, transdermal, intramedullary, intrathecal, direct intraventricular, intravenous, intravitreal, intraperitoneal, intranasal, intramuscular, intradural, intrarespiratory, nasal inhalation or intraocular injections. The preferred routes of administration are oral and parenteral.

Alternatively, one may administer the compound in a local rather than systemic manner, for example, via injection of the compound directly into a solid tumor, often in a depot or sustained release formulation.

Furthermore, one may administer the drug in a targeted drug delivery system, for example, in a liposome coated with tumor-specific antibody. The liposomes will be targeted to and taken up selectively by the tumor.

Composition/Formulation

Pharmaceutical compositions of the present invention may be manufactured by processes well known in the art, e.g., by means of conventional mixing, dissolving, granulating, dragee-making, levigating, emulsifying, encapsulating, entrapping, lyophilizing processes or spray drying.

Pharmaceutical compositions for use in the methods of the present invention may be prepared by any methods of pharmacy, but all methods include the step of bringing in association the active ingredient with the carrier which constitutes one or more necessary ingredients. In particular, pharmaceutical compositions for use in accordance with the present invention may be formulated in conventional manner using one or more physiologically acceptable carriers comprising excipients and auxiliaries which facilitate processing of the active compounds into preparations which can be used pharmaceutically. Proper formulation is dependent upon the route of administration chosen.

Dosage forms include tablets, troches, dispersions, suspensions, solutions, capsules, patches, syrups, elixirs, gels, powders, magmas, lozenges, ointments, creams, pastes, plasters, lotions, discs, suppositories, nasal or oral sprays, aerosols and the like.

For injection, the compounds of the invention may be formulated in aqueous solutions, preferably in physiologically compatible buffers such buffers with or without a low concentration of surfactant or cosolvent, or physiological saline buffer. For transmucosal administration, penetrants appropriate to the barrier to be permeated are used in the formulation. Such penetrants are generally known in the art.

For oral administration, the compounds can be formulated by combining the active compounds with pharmaceutically acceptable carriers well known in the art. Such carriers enable the compounds of the invention to be formulated as tablets, pills, lozenges, dragees, capsules, liquids, gels, syrups, slurries, suspensions and the like, for oral ingestion by a patient. Pharmaceutical preparations for oral use can be made using a solid excipient, optionally grinding the resulting mixture, and processing the mixture of granules, after adding other suitable auxiliaries if desired, to obtain tablets or dragee cores. Useful excipients are, in particular, fillers such as sugars, including lactose, sucrose, mannitol, or sorbitol, cellulose preparations such as, for example, maize starch, wheat starch, rice starch and potato starch and other materials such as gelatin, gum tragacanth, methyl cellulose, hydroxypropylmethyl-cellulose, sodium carboxymethylcellulose, and/or polyvinyl-pyrrolidone (PVP). If desired, disintegrating agents may be added, such as cross-linked polyvinyl pyrrolidone, agar, or alginic acid. A salt such as sodium alginate may also be used.

Dragee cores are provided with suitable coatings. For this purpose, concentrated sugar solutions may be used which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses.

Pharmaceutical compositions which can be used orally include push-fit capsules made of gelatin, as well as soft, sealed capsules made of gelatin and a plasticizer, such as glycerol or sorbitol. The push-fit capsules can contain the active ingredients in admixture with a filler such as lactose, a binder such as starch, and/or a lubricant such as talc or magnesium stearate and, optionally, stabilizers. In soft-capsules, the active compounds may be dissolved or suspended in suitable liquids, such as fatty oils, liquid paraffin, liquid polyethylene glycols, cremophor, capmul, medium or long chain mono- di- or triglycerides. Stabilizers may be added in these formulations, also.

For administration by inhalation, the compounds for use according to the present invention are conveniently delivered in the form of an aerosol spray using a pressurized pack or a nebulizer and a suitable propellant, e.g., without limitation, dichlorodifluoromethane, trichlorofluoromethane, dichlorotetra-fluoroethane or carbon dioxide. In the case of a pressurized aerosol, the dosage unit may be controlled by providing a valve to deliver a metered amount. Capsules and cartridges of, for example, gelatin for use in an inhaler or insufflator may be formulated containing a powder mix of the compound and a suitable powder base such as lactose or starch.

The compounds may also be formulated for parenteral administration, e.g., by bolus injection or continuous infusion. Formulations for injection may be presented in unit dosage form, e.g., in ampoules or in multi-dose containers, with an added preservative. The compositions may take such forms as suspensions, solutions or emulsions in oily or aqueous vehicles, and may contain formulating materials such as suspending, stabilizing and/or dispersing agents.

Pharmaceutical compositions for parenteral administration include aqueous solutions of a water soluble form, such as, without limitation, a salt, of the active compound. Additionally, suspensions of the active compounds may be prepared in a lipophilic vehicle. Suitable lipophilic vehicles include fatty oils such as sesame oil, synthetic fatty acid esters such as ethyl oleate and triglycerides, or materials such as liposomes. Aqueous injection suspensions may contain substances which increase the viscosity of the suspension, such as sodium carboxymethyl cellulose, sorbitol, or dextran. Optionally, the suspension may also contain suitable stabilizers and/or agents that increase the solubility of the compounds to allow for the preparation of highly concentrated solutions.

Alternatively, the active ingredient may be in powder form for constitution with a suitable vehicle, e.g., sterile, pyrogen-free water, before use.

The compounds may also be formulated in rectal compositions such as suppositories or retention enemas, using, e.g., conventional suppository bases such as cocoa butter or other glycerides.

In addition to the formulations described previously, the compounds may also be formulated as depot preparations. Such long acting formulations may be administered by implantation (for example, subcutaneously or intramuscularly) or by intramuscular injection. A compound of this invention may be formulated for this route of administration with suitable polymeric or hydrophobic materials (for instance, in an emulsion with a pharmacologically acceptable oil), with ion exchange resins, or as a sparingly soluble derivative such as, without limitation, a sparingly soluble salt.

A non-limiting example of a pharmaceutical carrier for the hydrophobic compounds of the invention is a cosolvent system comprising benzyl alcohol, a nonpolar surfactant, a water-miscible organic polymer and an aqueous phase such as the VPD co-solvent system. VPD is a solution of 3% w/v benzyl alcohol, 8% w/v of the nonpolar surfactant Polysorbate 80, and 65% w/v polyethylene glycol 300, made up to volume in absolute ethanol. The VPD co-solvent system (VPD:D5W) consists of VPD diluted 1:1 with a 5% dextrose in water solution. This co-solvent system dissolves hydrophobic compounds well, and itself produces low toxicity upon systemic administration. Naturally, the proportions of such a co-solvent system may be varied considerably without destroying its solubility and toxicity characteristics. Furthermore, the identity of the co-solvent components may be varied: for example, other low-toxicity nonpolar surfactants may be used instead of Polysorbate 80, the fraction size of polyethylene glycol may be varied, other biocompatible polymers may replace polyethylene glycol, e.g., polyvinyl pyrrolidone, and other sugars or polysaccharides may substitute for dextrose.

Alternatively, other delivery systems for hydrophobic pharmaceutical compounds may be employed. Liposomes and emulsions are well known examples of delivery vehicles or carriers for hydrophobic drugs. In addition, certain organic solvents such as dimethylsulfoxide also may be employed, although often at the cost of greater toxicity.

Additionally, the compounds may be delivered using a sustained-release system, such as semipermeable matrices of solid hydrophobic polymers containing the therapeutic agent. Various sustained-release materials have been established and are well known by those skilled in the art. Sustained-release capsules may, depending on their chemical nature, release the compounds for a few weeks up to over 100 days. Depending on the chemical nature and the biological stability of the therapeutic reagent, additional strategies for protein stabilization may be employed.

The pharmaceutical compositions herein also may comprise suitable solid or gel phase carriers or excipients. Examples of such carriers or excipients include, but are not limited to, calcium carbonate, calcium phosphate, various sugars, starches, cellulose derivatives, gelatin, and polymers such as polyethylene glycols.

Many of the PK modulating compounds of the invention may be provided as physiologically acceptable salts wherein the claimed compound may form the negatively or the positively charged species. Examples of salts in which the compound forms the positively charged moiety include, without limitation, quaternary ammonium (defined elsewhere herein), salts such as the hydrochloride, sulfate, carbonate, lactate, tartrate, maleate, succinate wherein the nitrogen atom of the quaternary ammonium group is a nitrogen of the selected compound of this invention. which has reacted with the appropriate acid. Salts in which a compound of this invention forms the negatively charged species include, without limitation, the sodium, potassium, calcium and magnesium salts formed by the reaction of a carboxylic acid group in the compound with an appropriate base (e.g. sodium hydroxide (NaOH), potassium hydroxide (KOH), Calcium hydroxide (Ca(OH)2), etc.)

Dosage

The amount of the active compound administered will be dependent on the subject being treated, the severity of the disorder or condition, the rate of administration, the disposition of the compound and the discretion of the prescribing physician. However, an effective dosage is typically in the range of about 0.001 to about 100 mg per kg body weight per day, preferably about 0.01 to about 35 mg/kg/day, in single or divided doses. For a 70 kg human, this would amount to about 0.07 to about 7000 mg/day, preferably about 0.7 to about 2500 mg/day. In some instances, dosage levels below the lower limit of the aforesaid range may be more than adequate, while in other cases still larger doses may be used without causing any harmful side effect, with such larger doses typically divided into several smaller doses for administration throughout the day.

EXAMPLES

The following examples are given to enable those skilled in the art more clearly understand and to practice the present invention. They should not be considered as limiting the scope of the invention, but merely as being illustrative and reprentative thereof.

The compounds structure determination was confirmed by a Broker AVANCE-400 spectrophotometer and FINNIGAN LCQ Ad (ESI) machine. Chemical shifts were given in ppm ($10^{-6}$). The solvent was deuterated-dimethyl sulfoxide (DMSO-d6) with tetramethylsilane (TMS) as internal standard.

Preparation Examples

Example 1

5-(2-Diethylamino-ethyl)-2-(5-fluoro-2-oxo-1,2-dihydro-indol-3-ylidenemethyl)-3-methyl-1,5,6,7-tetrahydro-pyrrolo[3,2-c]pyridin-4-one

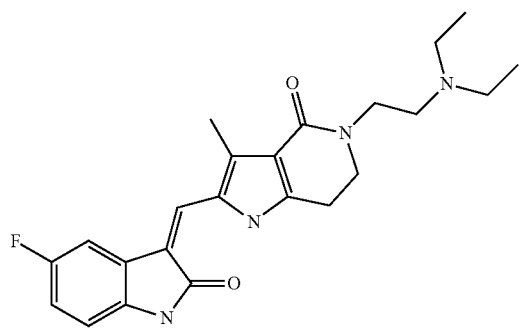 [SMILES: CCN(CC)CCN1CCc2[nH]c(/C=C3\C(=O)Nc4ccc(F)cc43)c(C)c2C1=O]

A stirred solution of 3-oxo-butyric acid tert-butyl ester (32 g, 0.2 mol) in glacial acetic acid was added dropwise with an aqueous solution of sodium nitrite (13.8 g, 0.2 mol sodium nitrite in 20 ml of water) while maintaining the temperature at 0~5° C. Upon completion of the addition, the reaction mixture was stirred in an ice-water bath for 1 hour and at room temperature for another 3 hours. The solution of 2-hydroxyimino-3-oxo-butyric acid tert-butyl ester was obtained which was used as such. A mixture of 3-oxo-glutaric acid diethyl ester (40 g, 0.2 mol) in 90 ml of glacial acetic acid was added with the above solution of 2-hydroxyimino-3-oxo-butyric acid tert-butyl ester and zinc dust (26 g, 0.4 mol) alternatively at a rate to maintain the reaction temperature below 65° C. Upon completion of the addition, the mixture was stirred at 75° C. for 2 hours, added with cold water (100 ml), and the mixture was stirred at room temperature for 1 hour. The zinc dust was removed by filtration and the filtrate was extracted with ethyl acetate (100 ml×3). The combined organic extracts were washed with water (100 ml×3), saturated sodium bicarbonate solution (100 ml×4), and brine (100 ml), dried over anhydrous sodium sulfate, filtered filtered and concentrated under reduced pressure to give 5-ethoxycarbonylmethyl-3-methyl-1H-pyrrole-2,4-dicarboxylic acid 2-tert-butyl ester 4-ethyl ester (60 g, 88.5%) as a yellow oil.

MS m/z (ESI): 340[M+1]

A solution of 5-ethoxycarbonylmethyl-3-methyl-1H-pyrrole-2,4-dicarboxylic acid 2-tert-butyl ester 4-ethyl ester (30 g, 88.5 mmol) in tetrahydrofuran (268 ml), and methanol (134 ml) was added with aqueous lithium hydroxide solution (0.465 mol lithium hydroxide in 197 ml of water). Upon completion of the addition, the mixture was stirred for 1.5 hours at room temperature. The resulting mixture was concentrated under reduced pressure. The residue was added with water (200 ml) and extracted with ethyl ether. The water phase was adjusted to pH 1~3 with 20% hydrochloric acid solution. The resulting solid was filtered, washed with ethyl ether, and dried in vacuo to give 5-carboxymethyl-3-methyl-1H-pyrrole-2,4-dicarboxylic acid 2-tert-butyl ester 4-ethyl ester (20 g, 72.3%) as a yellow solid.

A solution of 5-carboxymethyl-3-methyl-1H-pyrrole-2,4-dicarboxylic acid 2-tert-butyl ester 4-ethyl ester (6.3 g, 20 mmol) in 600 ml of dichloromethane and trifluoroacetic acid (120 ml, 1.55 mol) was heated to reflux under a nitrogen atmosphere for 2.5 hours. The reaction mixture was stirred in the dry ice-ethanol bath and added with aqueous sodium hydroxide solution (1.55 mol sodium hydroxide in 100 ml of water) while maintaining the temperature at −30° C. Upon completion of the addition, the mixture was extracted with dichloromethane (100 ml×7). The combined organic extracts were washed with brine (100 ml), dried over anhydrous sodium sulfate, filtered and concentrated under reduced pressure to give 2-carboxymethyl-4-methyl-1H-pyrrole-3-carboxylic acid ethyl ester (3.6 g, 85.7%) as a white solid.

A stirred solution of 2-carboxymethyl-4-methyl-1H-pyrrole-3-carboxylic acid ethyl ester (2.11 g, 10 mmol) in N,N-dimethylformamide (5 ml) and dichloromethane (50 ml) was added with N1,N1-diethylethane-1,2-diamine (1.23 g, 11 mmol), N-ethyl-N'-(dimethylaminopropyl)-carbodiimide hydrochloride (5 g, 26 mmol) and 1-hydroxybenzotriazol (1.5 g, 11 mmol) in an ice-water bath. Upon completion of the addition, the mixture was stirred at room temperature overnight, added with cold water (50 ml), extracted with dichloromethane (50 ml×3). The combined organic extracts were washed with saturated sodium bicarbonate (50 ml), water (50 ml), brine (50 ml), dried over anhydrous sodium sulfate, filtered and concentrated under reduced pressure to give 2-[(2-diethylamino-ethylcarbamoyl)-methyl]-4-methyl-1H-pyrrole-3, carboxylic acid ethyl ester (28.1 g, 90.9%) as a colorless oil.

A stirred solution of 2-[(2-diethylamino-ethylcarbamoyl)-methyl]-4-methyl-1H-pyrrole-3-carboxylic acid ethyl ester (310 mg, 1 mmol) in anhydrous tetrahydrofuran (2 ml) was added dropwise slowly with 1M borane-tetrahydrofuran complex in tetrahydrofuran (3 ml, 3 mmol) under an argon atmosphere. Upon completion of the addition, the mixture was stirred at room temperature for 1 hour and heated to reflux for another 5 hours. The reaction mixture was added with cold water (5 ml) and 1N hydrochloric acid (2 ml) dropwise, the mixture was stirred for 5 minutes, adjusted to pH 10 with 10% aqueous sodium hydroxide solution and extracted with ethyl acetate (10 ml×5). The combined organic extracts were washed with brine (15 ml), dried with anhydrous sodium sulfate, filtered and concentrated under reduced pressure to give 2-[2-(2-diethylamino-ethylamino)-ethyl]-4-methyl-1H-pyrrole-3-carboxylic acid ethyl ester (300 mg) as a brown oil which was used as such.

A stirred solution of 2-[2-(2-diethylamino-ethylamino)-ethyl]-4-methyl-1H-pyrrole-3-carboxylic acid ethyl ester (295 mg, 1 mmol) in 5 ml of toluene was added dropwise slowly with 2 M trimethyl aluminum in toluene (1 ml, 2 mmol) under an argon atmosphere. The mixture was stirred for 1 hour at room temperature and heated to reflux for another 4 hours. The reaction mixture was cooled down to 0° C., added with 1N hydrochloric acid (3 ml) and cold water (10 ml), and stirred for 5 minutes. The mixture was adjusted to pH 12 with 10% aqueous sodium hydroxide solution and extracted with dichloromethane (30 ml×4). The combined organic extracts were filtered through a pad of Celite. The filtrate was dried with anhydrous sodium sulfate, filtered and concentrated under reduced pressure to give 5-(2-diethylamino-ethyl)-3-methyl-1,5,6,7-tetrahydro-pyrrolo[3,2-e]pyridine-4-one (242 mg, 97%) as a brown oil.

A stirred solution of N,N-dimethylformamide (2 ml) was added slowly with 104 µl of phosphorus oxychloride under an argon atmosphere while maintaining the temperature at 0° C. Upon completion of the addition, the mixture was stirred for 15 minutes at room temperature, and cooled down to 0~5° C. in an ice-water bath. A mixture of 5-(2-diethylamino-ethyl)-3-methyl-1,5,6,7-tetrahydro-pyrrolo[3,2-e]pyridin-4-one (249 mg, 1 mmol) in 2 ml of N,N-dimethylformamide was added dropwise to the above solution. Upon completion of the addition, the mixture was stirred for 2 hours at 0° C., added with cold water (15 ml), stirred for 5 minutes. The resulting mixture was adjusted to pH 12 with 10% aqueous sodium hydroxide solution and extracted with dichloromethane (15 ml×6). The combined organic extracts were washed with brine (15 ml), dried with anhydrous sodium sulfate, filtered and concentrated under reduced pressure. The residue was purified by silica gel column chromatography with triethylamine: methanol:dichloromethane (1:20:500) as eluents to give 5-(2-diethylamino-ethyl)-3-methyl-4-oxo-4,5,6,7-tetrahydro-1H-pyrrolo[3,2-c]pyridine-2-carbaldehyde (105 mg, 38%) as a pink oil which was used as such.

A stirred solution of 5-(2-diethylamino-ethyl)-3-methyl-4-oxo-4,5,6,7-tetrahydro-1H-pyrrolo[3,2-e]pyridine-2-carbaldehyde (74 mg, 0.237 mmol), 5-fluoro-1,3-dihydro-indol-2-one (40 mg, 0.267 mmol, commercially available from Aldrich) in 0.66 ml of ethanol was added dropwise with anhydrous piperidine (0.1 ml). The mixture was stirred at room temperature overnight. The resulting solid was filtered under reduced pressure, washed with anhydrous ethanol (1 ml×3), purified by silica gel column chromatography with triethylamine:methanol:dichloromethane (1:20:500) as eluents to give 5-(2-diethylamino-ethyl)-2-(5-fluoro-2-oxo-1,2-dihydro-indol-3-ylidenemethyl)-3-methyl-1,5,6,7-tetrahydro-pyrrolo[3,2-c]pyridin-4-one (60 mg, 54.8%) as a yellow solid MS m/z (ESI): 411.4[M+1]

$^1$H NMR (400 MHz, DMSO-d6) 7.76 (d, 1H, ArH), 7.74 (s, 1H, CH), 6.95 (td, 1H, ArH), 6.85~6.88 (m, 1H, ArH), 3.62 (t, 2H, CH$_2$), 3.48 (t, 2H, CH$_2$), 3.45 (t, 2H, CH$_2$), 2.99 (t, 2H, CH$_2$), 2.53 (s, 3H, —CH$_3$), 2.49 (q, 4H, 2×-NCH$_2$), 0.97 (t, 6H, 2×-NCH$_2$CH$_3$).

Example 2

2-(5-Chloro-2-oxo-1,2-dihydro-indol-3-ylidenemethyl)-5-(2-diethylamino-ethyl)-3-methyl-1,5,6,7-tetrahydro-pyrrolo[3,2-c]pyridin-4-one

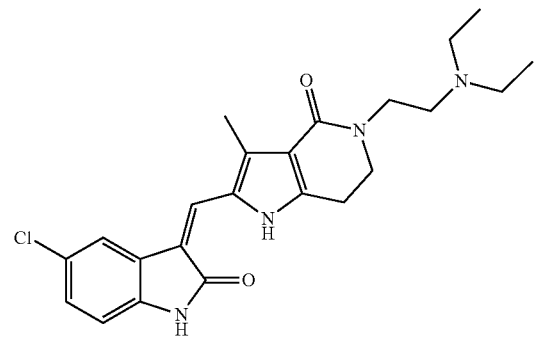

The title compound was prepared under the same conditions as described in Example 1 with 5-(2-diethylamino-ethyl)-3-methyl-4-oxo-4,5,6,7-tetrahydro-1H-pyrrolo[3,2-c]pyridine-2-carbaldehyde and 5-chloro-1,3-dihydro-indole-2-one (commercially available from Aldrich) as starting materials to give 2-(5-chloro-2-oxo-1,2-dihydro-indol-3-ylidenemethyl)-5-2-diethylamino-ethyl)-3-methyl-1,5,6,7-tetrahydro-pyrrolo[3,2-c]pyridin-4-one (55 mg, 91.7%) as a yellow solid.

MS m/z (ESI): 427[M+1]

$^1$H NMR (400 MHz, DMSO-d6) 7.97 (d, 1H, ArH), 7.78 (s, 1H, CH), 7.16 (dd, 1H, ArH), 6.89 (d, 1H, ArH), 3.61 (t, 2H, CH$_2$), 3.45 (t, 2H, CH$_2$), 3.42 (t, 2H, CH$_2$), 3.00 (t, 2H, CH$_2$), 2.54 (s, 3H, —CH$_3$), 2.51 (q, 4H, 2×NCH$_2$), 0.97 (t, 6H, 2×NCH$_2$CH$_3$)

Example 3

2-(5-Bromo-2-oxo-1,2-dihydro-indol-3-ylidenemethyl)-5-(2-diethylamino-ethyl)-3-methyl-1,5,6,7-tetrahydro-pyrrolo[3,2-c]pyridin-4-one

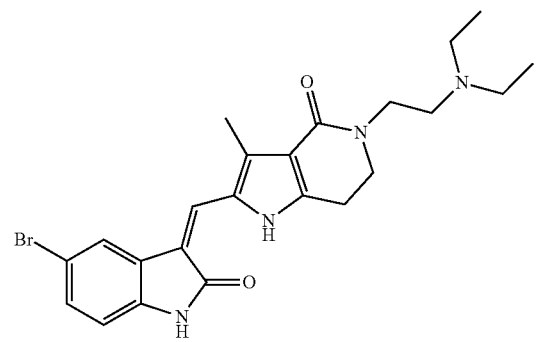 [SMILES: CCN(CC)CCN1CCc2[nH]c(/C=C3\C(=O)Nc4ccc(Cl)cc43)c(C)c2C1=O]

The title compound was prepared under the same conditions as described in Example 1 with 5-(2-diethylamino-ethyl)-3-methyl-4-oxo-4,5,6,7-tetrahydro-1H-pyrrolo[3,2-c]pyridine-2-carbaldehyde and 5-bromo-1,3-dihydro-indole-2-one (commercially available from Aldrich) as starting materials to give 2-(5-bromo-2-oxo-1,2-dihydro-indol-3-ylidenemethyl)-5-2-diethylamino-ethyl)-3-methyl-1,5,6,7-tetrahydro-pyrrolo[3,2-c]pyridin-4-one (56 mg, 98.7%) as a brown solid.

MS m/z (ESI): 472[M+1]

¹H NMR (400 MHz, DMSO-d6) 8.09 (d, 1H, ArH), 7.78 (s, 1H, CH), 7.28 (dd, 1H, ArH), 6.85 (d, 1H, ArH), 3.62 (t, 2H, CH₂), 3.48 (t, 2H, CH₂), 3.43 (t, 2H, CH₂), 3.00 (t, 2H, CH₂), 2.54 (s, 3H, —CH₃), 2.50 (q, 4H, 2×-NCH₂), 0.97 (t, 6H, 2×-NCH₂CH₃)

Example 4

2-(7-Amino-5-fluoro-2-oxo-1,2-dihydro-indol-3-ylidenemethyl-1,5,6,7-tetrahydro-pyrrolo[3,2-c]pyridin-4-one

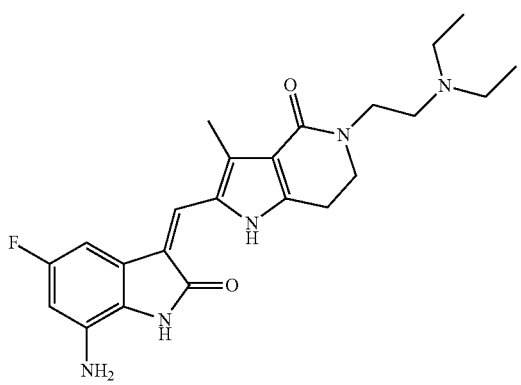 [SMILES: CCN(CC)CCN1CCc2[nH]c(/C=C3\C(=O)Nc4c(N)cc(F)cc43)c(C)c2C1=O]

5-Fluoro-1,3-dihydro-indol-2-one (5.0 g, 33 mmol) was added with 98% sulfuric acid (17.6 ml) and 65%-68% nitric acid (2.1 ml) in an ice-water bath with salt at −5° C. Upon the completion of the addition, the mixture was stirred for 1 hour at room temperature and added with ice-water until precipitate was formed. The solid was filtered and washed with water (50 ml×3) and recrystallized from acetic acid and water to give 7-amino-5-fluoro-1,3-dihydro-indol-2-one (4.0 g, 62.5%) as an orange solid.

MS m/z (ESI): 196[M+1]

The title compound was prepared under the same conditions as described in Example 1 with 5-(2-diethylamino-ethyl)-3-methyl-4-oxo-4,5,6,7-tetrahydro-1H-pyrrolo[3,2-c]pyridine-2-carbaldehyde and 5-fluoro-7-amino-1,3-dihydro-indol-2-one to give 2-(7-amino-5-fluoro-2-oxo-1,2-dihydro-indol-3-ylidenemethyl-1,5,6,7-tetrahydro-pyrrolo[3,2-c]pyridin-4-one (49 mg, 64.1%) as an orange solid.

MS m/z (ESI): 426[M+1]

¹H NMR (400 MHz, DMSO-d6) 7.57 (s, 1H, —CH), 6.96 (d, 1H, —ArH), 6.30 (d, 1H, —ArH), 3.61 (t, 2H, —CH₂), 3.35 (t, 2H, —CH₂), 3.17 (t, 2H, —CH₂), 2.98 (t, 2H, —CH₂), 2.54 (s, 3H, —CH₃), 2.50 (q, 4H, 2×-NCH₂), 0.97 (t, 6H, 2×-NCH₂CH₃)

Example 5

N-{3-[5-(2-Diethylamino-ethyl)-3-methyl-4-oxo-4,5,6,7-tetrahydro-1H-pyrrolo[3,2-c]pyridine-2-ylmethylene]-5-fluoro-2-oxo-2,3-dihydro-1H-indol-7-yl}-formamide

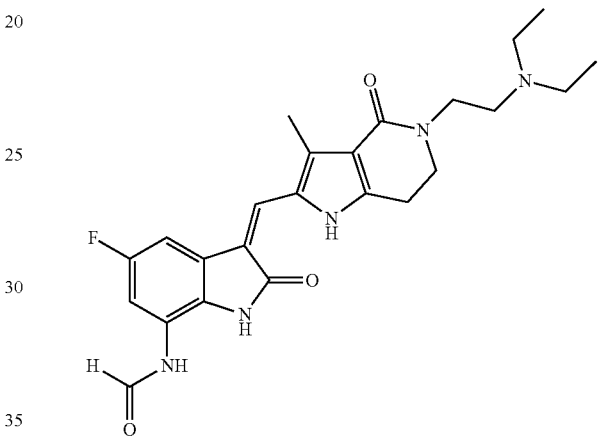

A solution of acetic anhydride (0.8 ml) and formic acid (0.6 ml) was stirred for 1 hour at room temperature, and added with 7-amino-5-fluoro-1,3-dihydro-indol-2-one (2.0 g, 12 mmol) obtained from Example 4 in 30 ml of tetrahydrofuran and piperidine (0.02 ml). The resulting mixture was stirred for 3 hours at room temperature until a precipitate was formed. The solid was filtered and recrystallized from methanol to give N-(5-fluoro-2-oxo-2,3-dihydro-1H-indol-7-yl)-formamide (700 mg, 30.4%) as a white solid.

MS m/z (ESI): 195[M+1]

The title compound was prepared under the same conditions as described in Example 1 with 5-(2-diethylamino-ethyl)-3-methyl-4-oxo-4,5,6,7-tetrahydro-1H-pyrrolo[3,2-c]pyridine-2-carbaldehyde and N-(5-fluoro-2-oxo-2,3-dihydro-1H-indol-7-yl)-formamide to give N-{3-[5-(2-diethylamino-ethyl)-3-methyl-4-oxo-4,5,6,7-tetrahydro-1H-pyrrolo[3,2-c]pyridine-2-ylmethylene]-5-fluoro-2-oxo-2,3-dihydro-1H-indol-7-yl}-formamide (36 mg, 40.5%) as a red solid.

MS m/z (ESI): 454[M+1]

¹H NMR (400 MHz, DMSO-d6), 9.798 (s, 1H, —NH), 8.328 (s, 1H, —CHO), 7.772 (s, 1H, —CH), 7.452~7.424 (d, 1H, —ArH), 3.637~3.603 (t, 2H, —CH₂), 3.450 (t, 2H, CH₂), 3.024~2.991 (t, 2H, —CH₂), 0.983~0.949 (t, 6H, 2×CH₃)

Example 6

N-{3-[5-(2-Diethylamino-ethyl)-3-methyl-4-oxo-4,5,6,7-tetrahydro-1H-pyrrolo[3,2-c]pyridine-2-ylmethylene]-5-fluoro-2-oxo-2,3-dihydro-1H-indol-7-yl}-acetamide

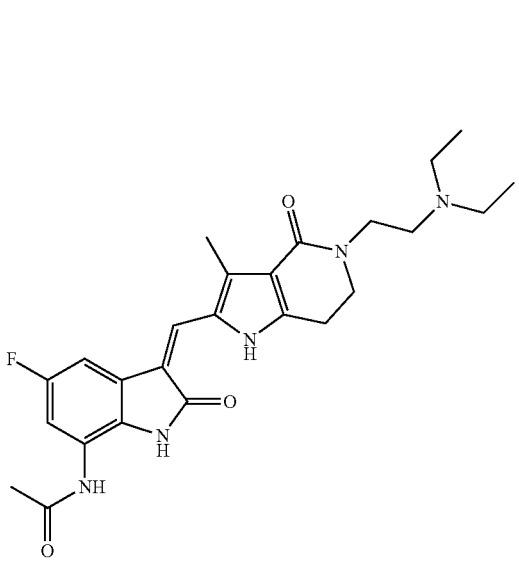 [SMILES: CCN(CC)CCN1CCc2[nH]c(/C=C3\C(=O)Nc4c(NC(C)=O)cc(F)cc43)c(C)c2C1=O]

A stirred solution of 7-amino-5-fluoro-1,3-dihydro-indol-2-one (1.0 g, 6 mmol) obtained from Example 4 in 30 ml of tetrahydrofuran was added with tirethylamine (1.3 ml, 9 mmol). The solution was cooled down to 0° C. in an ice-water bath and added with acetyl chloride (1.3 ml, 9 mmol) dropwise. The resulting mixture was heated to reflux for 1.5 hours and cooled until precipitate was formed. The solid was filtered, washed with water (50 ml×3) and dried in vacuo to give N-(5-fluoro-2-oxo-2,3-dihydro-1H-indol-7-yl)-acetamide (1.2 g, 96%) as a white solid.

The title compound was prepared under the same conditions as described in Example 1 with 5-(2-diethylamino-ethyl)-3-methyl-4-oxo-4,5,6,7-tetrahydro-1H-pyrrolo[3,2-c]pyridine-2-carbaldehyde and N-(5-fluoro-2-oxo-2,3-dihydro-1H-indol-7-yl)-acetamide which was prepared by the acetylation of 7-amino-5-fluoro-1,3-dihydro-indole-2-one (prepared according to U.S. Pat. No. 6,114,371, US1997-810659) as starting materials to give N-{3-[5-(2-diethylamino-ethyl)-3-methyl-4-oxo-4,5,6,7-tetrahydro-1H-pyrrolo[3,2-c]pyridine-2-ylmethylene]-5-fluoro dihydro-1H-indol-7-yl}-acetamide (36 mg, 30.8%) as a yellow solid.

MS m/z (ESI): 468 [M+1]

$^1$H NMR (400 MHz, DMSO-d6) 7.74 (s, 1H, —CH), 7.58 (d, 1H, —ArH), 7.39 (d, 1H, —ArH), 3.63 (t, 2H, —CH$_2$), 3.38 (t, 2H, —CH$_2$), 3.01 (t, 2H, —CH$_2$), 2.96 (t, 2H, —CH$_2$), 2.65 (q, 4H, 2×-NCH$_2$), 2.54 (s, 3H, —CH$_3$), 2.11 (s, 3H, —NHCOCH$_3$), 1.02 (t, 6H, 2×-NCH$_2$CH$_3$)

Example 7

2-(6-Amino-5-fluoro-2-oxo-1,2-dihydro-indol-3-ylidenemethyl)-5-(2-diethylamino-ethyl)-3-methyl-1,5,6,7-tetrahydro-pyrrolo[3,2-c]pyridin-4-one

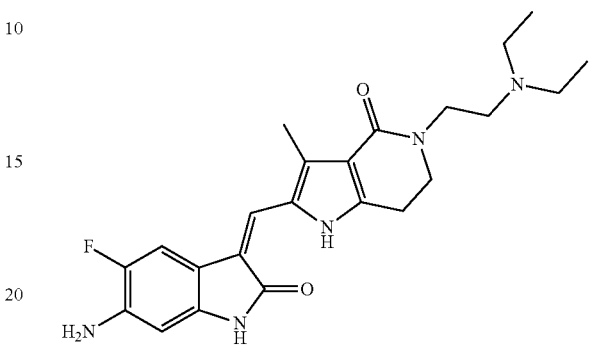

The title compound was prepared under the same conditions as described in Example 1 with 5-(2-diethylamino-ethyl)-3-methyl-4-oxo-4,5,6,7-tetrahydro-1H-pyrrolo[3,2-c]pyridine-2-carbaldehyde and 5-fluoro-6-amino-1,3-dihydro-indol-2-one (prepared according to *J. Heterocylic Chem.*, 31, 1513, 1994) as starting materials to give 2-(6-amino-5-fluoro-2-oxo-1,2-dihydro-indol-3-ylidenemethyl)-5-(2-diethylamino-ethyl)-3-methyl-1,5,6,7-tetrahydro-pyrrolo[3,2-c]pyridin-4-one (42 mg, 61.8%) as a red solid.

MS m/z (ESI) 426[M+1]

$^1$H NMR (400 MHz, DMSO-d6) 7.52 (d, 1H, —ArH), 7.36 (s, 1H, —CH), 6.36 (d, 1H, —ArH), 5.30 (br s, 1H, —NH$_2$), 3.61 (t, 2H, —CH$_2$), 3.32 (t, 2H, —CH$_2$), 3.17 (t, 2H, —CH$_2$), 2.96 (t, 2H, —CH$_2$), 2.45 (s, 3H, —CH$_3$), 2.64 (q, 4H, 2×-NCH$_2$), 1.01 (t, 6H, 2×-NCH$_2$ CH$_3$)

Example 8

N-{3-[5-(2-Diethylamino-ethyl)-3-methyl-4-oxo-4,5,6,7-tetrahydro-1H-pyrrolo[3,2-c]pyridine-2-ylmethylene]-5-fluoro-2-oxo-2,3-dihydro-1H-indol-6-yl}-formamide

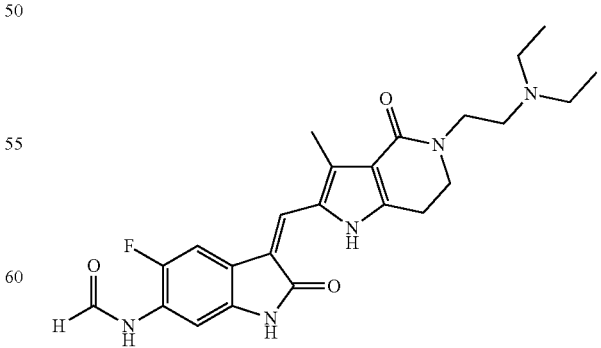

A solution of acetic anhydride (1.6 ml) and formic acid (1.2 ml) was stirred for 1 hour at room temperature, and added with 6-amino-5-fluoro-1,3-dihydro-indol-2-one (4.0 g, 24 mmol) obtained from Example 7 in 60 ml of tetrahydrofuran and piperidine (0.04 ml). Upon the completion of the addition, the mixture was stirred for 3 hours at room temperature until a precipitate was formed. The solid was filtered and recrystallized from methanol to give N-(5-fluoro-2-oxo-2,3-dihydro-1H-indol-7-yl)-formamide (4.6 g, 99%) as a white solid.

MS m/z (ESI): 195[M+1]

The title compound was prepared under the same conditions as described in Example 1 with 5-(2-diethylamino-ethyl)-3-methyl-4-oxo-4,5,6,7-tetrahydro-1H-pyrrolo[3,2-c]pyridine-2-carbaldehyde and N-(5-fluoro-2-oxo-2,3-dihydro-1H-indol-6-yl)-formamide as starting materials to give N-{3-[5-(2-diethylamino-ethyl)-3-methyl-4-oxo-4,5,6,7-tetrahydro-1H-pyrrolo[3,2-c]pyridine-2-ylmethylene]-5-fluoro-2-oxo-2,3-dihydro-1H-indol-6-yl}-formamide (51 mg, 69.4%) as a red solid.

MS m/z (ESI): 454[M+1]

Example 9

N-{3-[5-(2-Diethylamino-ethyl)-3-methyl-4-oxo-4,5,6,7-tetrahydro-pyrrolo[3,2-c]pyridine-2-ylmethylene]-5-fluoro-2-oxo-2,3-dihydro-1H-indol-6-yl}-acetamide

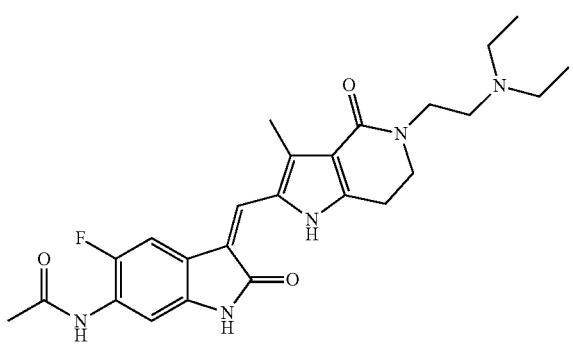 [SMILES: CCN(CC)CCN1CCc2[nH]c(/C=C3\C(=O)Nc4cc(NC(C)=O)c(F)cc43)c(C)c2C1=O]

A stirred solution of 6-amino-5-fluoro-1,3-dihydro-indol-2-one (1.0 g, 6 mmol) obtained from Example 7 in 30 ml of tetrahydrofuran was added with tirethylamine (1.3 ml, 9 mmol). The solution was cooled down to 0° C. in an ice-water bath and added with acetyl chloride (1.3 ml, 9 mmol) dropwise. Upon the completion of the addition, the resulting mixture was heated to reflux for 1.5 hours and cooled until precipitate was formed. The solid was filtered, washed with water (50 ml×3) and dried in vacuo to give N-(5-fluoro-2-oxo-2,3-dihydro-1H-indol-6-yl)-acetamide (1.25 g, 99%) as a white solid.

MS m/z (ESI): 209[M+1]

The title compound was prepared under the same conditions as described in Example 1 with 5-(2-diethylamino-ethyl)-3-methyl-4-oxo-4,5,6,7-tetrahydro-1H-pyrrolo[3,2-c]pyridine-2-carbaldehyde and N-(5-fluoro-2-oxo-2,3-dihydro-1H-indol-6-yl)-acetamide as starting materials to give N-{3-[5-(2-diethylamino-ethyl)-3-methyl-4-oxo-4,5,6,7-tetrahydro-pyrrolo[3,2-c]pyridine-2-ylmethylene]-5-fluoro-2-oxo-2,3-dihydro-1H-indol-6-yl}-acetamide (38 mg, 32%) as a light yellow solid.

MS m/z (ESI): 468[M+1]

$^1$H NMR (400 MHz, DMSO-d6) 7.80 (d, 1H, —ArH), 7.64 (s, 1H, —CH), 7.59 (d, 1H, —ArH), 3.66 (t, 2H, —CH$_2$), 3.38 (t, 2H, —CH$_2$), 3.01 (t, 2H, —CH$_2$), 2.96 (t, 2H, —CH$_2$), 2.52 (s, 3H, —CH$_3$), 2.50 (q, 4H, 2×-NCH$_2$), 2.10 (s, 3H, —NHCOCH$_3$), 1.20 (t, 6H, 2×-NCH$_2$CH$_3$)

Example 10

N-{3-[5-(2-Diethylamino-ethyl)-3-methyl-4-oxo-4,5,6,7-tetrahydro-1H-pyrrolo[3,2-c]pyridine-2-ylmethylene]-2-oxo-2,3-dihydro-1H-indol-5-yl}-methanesulfonamide

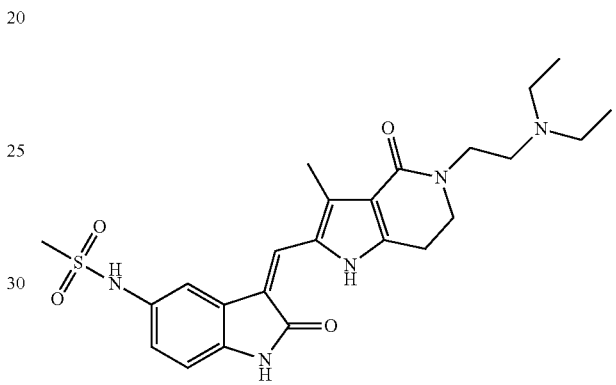

A stirred solution of 5-amino-1,3-dihydro-indol-2-one (2 g, 13.5 mmol, prepared according to U.S. Pat. No. 6,114,371) in 30 ml of dichloromethane was added with tirethylamine (1.9 ml). The solution was cooled down to −30° C. in an acetone-dry ice bath and added with methanesulfonyl chloride (1 ml, 13.5 mmol) dropwise. Upon the completion of the addition, the resulting mixture was heated at 45° C. for 1 hour until precipitate was formed. The solid was filtered, washed with water (50 ml×3) and dried in vacuo to give N-(2-oxo-2,3-dihydro-1H-indol-5-yl)-methanesulfonamide (2.7 g, 90%) as a white solid.

MS m/z (ESI): 225 [M−1]

The title compound was prepared under the same conditions as described in Example 1 with 5-(2-diethylamino-ethyl)-3-methyl-4-oxo-4,5,6,7-tetrahydro-1H-pyrrolo[3,2-c]pyridine-2-carbaldehyde and 5-methanesulfonamino-1,3-dihydro-indol-2-one as starting materials to give N-{3-[5-(2-diethylamino-ethyl)-3-methyl-4-oxo-4,5,6,7-tetrahydro-1H-pyrrolo[3,2-c]pyridine-2-ylmethylene]-2-oxo-2,3-dihydro-1H-indol-5-yl}-methanesulfonamide (56 mg, 64%) as a light yellow solid.

MS ink (ESI): 486[M+1]

$^1$H NMR (400 MHz, DMSO-d6) 7.60 (s, 1H, —CH), 7.02 (d, 1H, —ArH), 6.87 (d, 1H, —ArH), 6.78 (d, 1H, —ArH), 3.62 (t, 2H, —CH$_2$), 3.46 (t, 2H, —CH$_2$), 3.33 (t, 2H, —CH$_2$), 3.00 (t, 2H, —CH$_2$), 2.95 (s, 3H, —SO$_2$CH$_3$), 2.55 (s, 3H, —CH$_3$), 2.50 (q, 4H, 2×-NCH$_2$), 0.99 (t, 6H, 2×-NCH$_2$CH$_3$)

Example 11

N-{3-[5-(2-Diethylamino-ethyl)-3-methyl-4-oxo-4,5,6,7-tetrahydro-1H-pyrrolo[3,2-c]pyridine-2-ylmethylene]-2-oxo-2,3-dihydro-1H-indol-5-yl}-acetamide

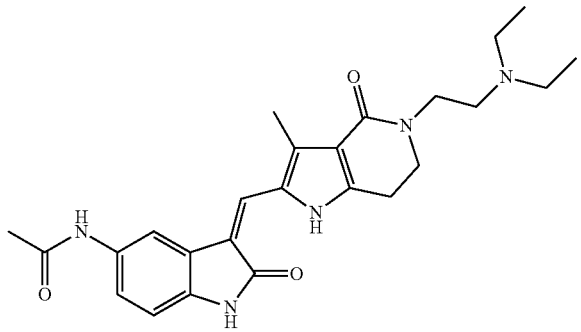 [SMILES: CCN(CC)CCN1CCc2[nH]c(/C=C3\C(=O)Nc4ccc(NC(C)=O)cc43)c(C)c2C1=O]

The title compound was prepared under the same conditions as described in Example 1 with 5-(2-diethylamino-ethyl)-3-methyl-4-oxo-4,5,6,7-tetrahydro-1H-pyrrolo[3,2-c]pyridine-2-carbaldehyde and 5-acetamino-1,3-dihydro-indol-2-one as starting materials to give N-{3-[5-(2-diethylamino-ethyl)-3-methyl-4-oxo-4,5,6,7-tetrahydro-1H-pyrrolo[3,2-c]pyridine-2-ylmethylene]-2-oxo-2,3-dihydro-1H-indol-5-yl}-acetamide (52 mg, 57.9%) as a light yellow solid.

MS m/z (ESI): 450[M+1]

$^1$H NMR (400 MHz, DMSO-d6) 7.84 (s, 1H, —CH), 7.49 (s, 1H, —ArH), 7.28 (d, 1H, —ArH), 6.83 (d, 1H, —ArH), 3.63 (t, 2H, —CH$_2$), 3.47 (t, 2H, —CH$_2$), 3.37 (t, 2H, —CH$_2$), 3.00 (t, 2H, —CH$_2$), 2.59 (q, 4H, 2×-NCH$_2$), 2.51 (s, 3H, —CH$_3$), 2.03 (s, 3H, —CH$_3$), 1.00 (t, 6H, 2×-NCH$_2$CH$_3$)

Example 12

4-(3-Chloro-4-fluoro-phenylamino)-5-[5-(2-diethylamino-ethyl)-3-methyl-4-oxo-4,5,6,7-tetrahydro-1H-pyrrolo[3,2-c]pyridine-2-ylmethylene]-5,7-dihydro-pyrrolo[2,3-d]pyrimidin-6-one

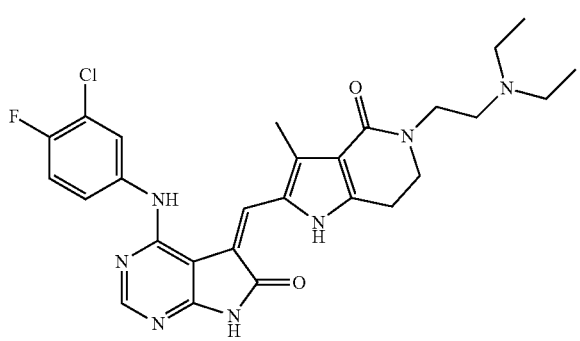 [SMILES: CCN(CC)CCN1CCc2[nH]c(/C=C3\C(=O)Nc4ncnc(Nc5ccc(F)c(Cl)c5)c43)c(C)c2C1=O]

A stirred solution of 5-amino-1,3-dihydro-indol-2-one (3.5 g, 23.6 mmol, prepared according to U.S. Pat. No. 6,114,371) in 20 ml of tetrahydrofuran was added with tirethylamine (1.3 ml, 9 mmol). The solution was cooled down to −30° C. in an acetone-dry ice bath and added with acetyl chloride (1.3 ml, 9 mmol) dropwise. Upon the completion of the addition, the resulting mixture was stirred for 20 minutes at room temperature and added with ethyl acetate (20 ml) until precipitate was formed. The solid was filtered, washed with water (50 ml×3) and dried in vacuo to give N-(2-oxo-2,3-dihydro-1H-indol-5-yl)-acetamide (4 g, 88.9%) as a white solid.

MS m/z (ESI): 191[M+1].

The title compound was prepared under the same conditions as described in Example 1 with 5-(2-diethylamino-ethyl)-3-methyl-4-oxo-4,5,6,7-tetrahydro-1H-pyrrolo[3,2-c]pyridine-2-carbaldehyde and 4-(3-chloro-4-fluoro-phenylamino)-5,7-dihydro-pyrrolo[2,3-d]-pyrimidin-6-one as starting materials to give 4-(3-chloro-4-fluoro-phenylamino)-5-[5-(2-diethylamino-ethyl)-3-methyl-4-oxo-4,5,6,7-tetrahydro-1H-pyrrolo[3,2-c]pyridine-2-ylmethylene]-5,7-dihydro-pyrrolo[2,3-d]pyrimidin-6-one (53 mg, 39.4%) as a yellow solid.

MS m/z (ESI): 539[M+1]

$^1$H NMR (400 MHz, DMSO-d6) 8.31 (s, 1H, —CH), 7.69 (dd, 1H, —ArH), 7.36~7.39 (m, 3H, 2×-ArH, —CH), 3.61 (t, 2H, —CH$_2$), 3.44 (t, 2H, —CH$_2$), 3.01 (t, 2H, —CH$_2$), 2.83 (t, 2H, —CH$_2$), 2.51 (q, 4H, 2×-NCH$_2$), 2.37 (s, 3H, —CH$_3$), 0.96 (t, 6H, 2×-NCH$_2$CH$_3$)

Example 13

2-(5-Fluoro-2-oxo-1,2-dihydro-indol-3-ylidenemethyl)-3-methyl-5-(2-pyrrolidin-1-yl-ethyl)-1,5,6,7-tetrahydro-pyrrolo[3,2-c]pyridin-4-one

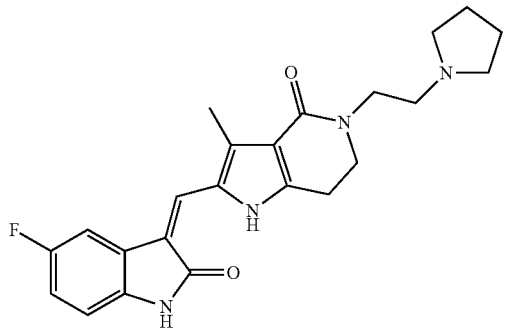 [SMILES: Cc1c(/C=C2\C(=O)Nc3ccc(F)cc32)[nH]c2c1C(=O)N(CCN1CCCC1)CC2]

A stirred solution of 2-carboxymethyl-4-methyl-1H-pyrrole-3-carboxylic acid ethyl ester (1.27 g, 6 mmol) in N,N-dimethylformamide (3 ml) and dichloromethane (30 ml) was added with 2-pyrrolidine-1-yl-ethamine (0.83 ml, 6.6 mmol), N-ethyl-N'-(dimethylaminopropyl)-carbodiimide hydrochloride (3 g, 12 mmol) and 1-hydroxybenzotriazol (0.9 g, 6 mmol) in the ice/water-bath. Upon completion of the addition, the reaction mixture was stirred at room temperature overnight, then added with cold water (20 ml), extracted with dichloromethane (50 ml×3). The combined organic extracts were washed with saturated sodium bicarbonate solution (50 ml), water (50 ml), brine (50 ml), dried with anhydrous sodium sulfate, filtered and concentrated under reduced pressure to give 4-methyl-2-[(2-pyrrolidin-1-yl-ethylcarbamoyl)-methyl]-1H-pyrrole-3-carboxylic acid ethyl ester (1.898 g, 100%) as a brown oil which was used as such.

MS m/z (ESI) 308[M+1]

A stirred solution of 4-methyl-2-[(2-pyrrolidin-1-yl-ethylcarbamoyl)-methyl]-1H-pyrrole-3-carboxylic acid ethyl ester (1.843 g, 6 mmol) in 12 ml of anhydrous tetrahydrofuran was added dropwise slowly with borane-tetrahydrofuran in tetrahydrofuran (18 ml, 18 mmol) under an argon atmosphere. Upon completion of the addition, the mixture was stirred for 1 hour at room temperature and heated to reflux for another 5 hours. The reaction mixture was added with cold water (5 ml) and 1N hydrochloric acid (20 ml) dropwise. The mixture was stirred for another 5 minutes, adjusted to pH 10 with 10% aqueous sodium hydroxide solution and extracted with ethyl acetate (20 ml×3). The combined organic extracts were washed with brine (15 ml), dried with anhydrous sodium sulfate, filtered and concentrated under reduced pressure to give 4-methyl-2-[2-(2-pyrrolidin-1-yl-ethylamino)-ethyl]-1H-pyrrole-3-carboxylic acid ethyl ester (1.441 g) as a brown oil which was used as such.

A stirred solution of 4-methyl-2-[2-(2-pyrrolidin-1-yl-ethylamino)-ethyl]-1H-pyrrole-3-carboxylic acid ethyl ester (1.441 g, 4.92 mmol) in 22.5 ml of toluene was added dropwise slowly with 2M trimethyl aluminum in toluene (5.1 ml, 10.2 mmol) under an argon atmosphere. The mixture was stirred for 1 hour at room temperature and heated to reflux for another 4 hours. The reaction mixture was cooled down to 0° C., added with 1N hydrochloric acid (20 ml) dropwise and cold water (20 ml), and stirred for 5 minutes. The mixture was adjusted to pH12 with 10% aqueous sodium hydroxide solution and extracted with dichloromethane (40 ml×3). The combined organic extracts were filtered through a pad of Celite. The filtrate was dried with anhydrous sodium sulfate, filtered and concentrated under reduced pressure to give 3-methyl-5-(2-pyrrolidin-1-yl-ethyl)-1,5,6,7-tetrahydro-pyrrolo[3,2-c]pyridin-4-one (719 mg, 59.2%) as a brown oil which was used as such.

N,N-dimethylformamide (1.5 ml) was added slowly with phosphorus oxychloride (115 μl, 3.2 mmol) under an argon atmosphere while maintaining the temperature at 0° C. Upon completion of the addition, the mixture was stirred for 15 minutes at room temperature, and cooled down to 0~5° C. in an ice-water bath. A mixture of 3-methyl-5-(2-pyrrolidin-1-yl-ethyl)-1,5,6,7-tetrahydro-pyrrolo[3,2-c]pyridin-4-one (719 mg, 2.91 mmol) in 3 ml of N,N-dimethylformamide was added dropwise to the above solution. Upon completion of the addition, the mixture was stirred for 2 hours at 0° C., added with cold water (20 ml) and stirred for another 5 minutes. The resulting mixture was adjusted to pH 12 with 10% aqueous sodium hydroxide solution and extracted with dichloromethane (30 ml×3). The combined organic extracts were washed with brine (15 ml), dried with anhydrous sodium sulfate, filtered and concentrated under reduced pressure. The residue was purified by silica gel column chromatography with triethylamine: methanol:dichloromethane (1:20:500) as eluents to give 3-methyl-4-oxo-5-(2-pyrrolidin-1-yl-ethyl)-4,5,6,7-tetrahydro-1H-pyrrolo[3,2-c]pyridine-2-carbaldehyde (411 mg, 51.37%) as a brown oil which was used as such.

A stirred solution of 3-methyl-4-oxo-5-(2-pyrrolidin-1-yl-ethyl)-4,5,6,7-tetrahydro-1H-pyrrolo[3,2-c]pyridine-2-carbaldehyde (81 mg, 0.79 mmol), 5-fluoro-1,3-dihydro-indol-2-one (44 mg, 0.79 mmol) in 0.48 ml of ethanol was added dropwise with anhydrous piperidine (0.06 ml). The mixture was stirred at room temperature overnight. The precipitate was filtered under reduced pressure, washed with anhydrous ethanol (0.2 ml×5) and purified by silica gel column chromatography with triethylamine:methanol:dichloromethane (1:20:500) as eluents to give 2-(5-fluoro-2-oxo-1,2-dihydro-indol-3-ylidenemethyl)-3-methyl-5-(2-pyrrolidin-1-yl-ethyl)-1,5,6,7-tetrahydro-pyrrolo[3,2-c]pyridin-4-one (24 mg, 7.4%) as a brown solid MS m/z (ESI): 409[M+1]

¹H NMR (400 MHz, DMSO-d6) 7.80 (s, 1H, —ArH), 7.76 (s, 1H, —CH), 6.95 (td, 1H, —ArH), 6.84~6.87 (m, 1H, —ArH), 3.62 (t, 2H, —CH₂), 3.52 (t, 2H, —CH₂), 3.01 (t, 2H, —CH₂), 2.60 (t, 2H, —CH₂), 2.55 (s, 3H, CH₃), 2.51 (q, 4H, 2×-NCH₂), 1.67~1.70 (m, 4H, 2×-CH₂)

Example 14

2-(6-Amino-5-fluoro-2-oxo-1,2-dihydro-indol-3-ylidenemethyl)-3-methyl-5-(2-pyrrolidin-1-yl-ethyl)-1,5,6,7-tetrahydro-pyrrolo[3,2-c]pyridin-4-one

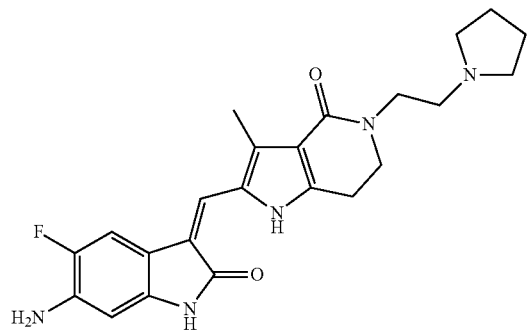 [SMILES: Cc1c(/C=C2\C(=O)Nc3cc(N)c(F)cc32)[nH]c2c1C(=O)N(CCN1CCCC1)CC2]

The title compound was prepared under the same conditions as described in Example 13 with 3-methyl-4-oxo-5-(2-pyrrolidin-1-yl-ethyl)-4,5,6,7-tetrahydro-1H-pyrrolo[3,2-c]pyridine-2-carbaldehyde and 5-fluoro-6-amino-1,3-dihydro-indol-2-one as starting materials to give 2-(6-amino-5-fluoro-2-oxo-1,2-dihydro-indol-3-ylidenemethyl)-3-methyl-5-(2-pyrrolidin-1-yl-ethyl)-1,5,6,7-tetrahydro-pyrrolo[3,2-c]pyridin-4-one (22 mg, 54%) as a red solid.

MS m/z (ESI): 424[M+1]

¹H NMR (400 MHz, DMSO-d6) 7.53 (d, 1H, —ArH), 7.35 (s, 1H, —CH), 6.35 (d, 1H, —ArH), 5.30 (br s, 1H, —NH₂), 3.60 (t, 2H, —CH₂), 3.51 (t, 2H, —CH₂), 2.96 (t, 2H, —CH₂), 2.60 (t, 2H, —CH₂), 2.51 (s, 3H, —CH₃), 2.47 (q, 4H, 2×-NCH₂), 1.64~1.69 (m, 4H, 2×-CH₂)

Example 15

2-(5-Fluoro-2-oxo-1,2-dihydro-indol-3-ylidenemethyl)-3-methyl-5-(2-morpholin-4-yl-ethyl)-1,5,6,7-tetrahydro-pyrrolo[3,2-c]pyridin-4-one

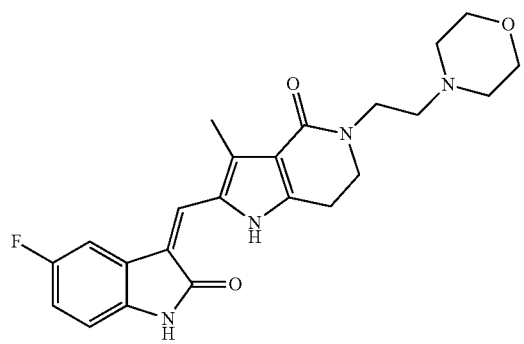 [SMILES: Cc1c(/C=C2\C(=O)Nc3ccc(F)cc32)[nH]c2c1C(=O)N(CCN1CCOCC1)CC2]

A stirred solution of 2-carboxymethyl-4-methyl-1H-pyrrole-3-carboxylic acid ethyl ester (2.67 g, 12.67 mmol) in N,N-dimethylformamide (7 ml) and dichloromethane (65 ml) was added with 2-morpholin-4-yl-ethamine (1.81 g, 13.9 mmol), N-ethyl-N'-(dimethylaminopropyl)-carbodiimide hydrochloride (4.84 g, 25.34 mmol) and 1-hydroxybenzotriazol (1.71 g, 12.67 mmol) in an ice/water-bath. Upon completion of the addition, the reaction mixture was stirred at room temperature overnight, added with cold water (50 ml) and extracted with dichloromethane (50 ml×3). The combined organic extracts were washed with saturated sodium bicarbonate (50 ml), water (50 ml), brine (50 ml), dried with anhydrous sodium sulfate, filtered and concentrated under reduced pressure to give 4-methyl-2-[(2-morpholin-4-yl-ethylcarbamoyl)-methyl]-1H-pyrrole-3-carboxylic acid ethyl ester (3.48 g, 85%) as a brown oil which was used as such.

A stirred solution of 4-methyl-2-[(2-morpholin-4-yl-ethylcarbamoyl)-methyl]-1H-pyrrole-3-carboxylic acid ethyl ester (3.48 g, 10.8 mmol) in anhydrous tetrahydrofuran (20 ml) was added dropwise slowly with 1M borane-tetrahydrofuran complex in tetrahydrofuran (32.4 ml, 32.4 mmol) under an argon atmosphere. Upon Completion of the addition, the mixture was stirred for 1 hour at room temperature and heated to reflux for another 5 hours. The resulting mixture was added with cold water (5 ml) and 1N hydrochloric acid (15 ml) dropwise, adjusted to pH 10 with 10% aqueous sodium hydroxide solution and extracted with ethyl acetate (10 ml×5). The combined organic extracts were washed with brine (15 ml), dried with anhydrous sodium sulfate, filtered and concentrated under reduced pressure to give 4-methyl-2-[2-(2-morpholin-4-yl-ethylamino)-ethyl]-1H-pyrrole-3-carboxylic acid ethyl ester (3.08 g) as a red oil which was used as such.

A stirred solution of 4-methyl-2-[2-(2-morpholin-4-yl-ethylamino)-ethyl]-1H-pyrrole-3-carboxylic acid ethyl ester (3.08 g, 10 mmol) in 50 ml of toluene was added dropwise slowly with 2M trimethyl aluminum in toluene (10 ml, 20 mmol) under an argon atmosphere. The mixture was stirred for 1 hour at room temperature and heated to reflux for another 4 hours. The reaction mixture was cooled down to 0° C. in ice/water bath, added with 1N hydrochloric acid (30 ml) and cold water (50 ml), and stirred for 5 minutes. The mixture was adjusted to pH12 with 10% aqueous sodium hydroxide solution and extracted with dichloromethane (40 ml×3). The combined organic extracts were washed with brine (15 ml), filtered through a pad of Celite. The filtrate was dried with anhydrous sodium sulfate, filtered and concentrated, under reduced pressure to give 3-methyl-5-(2-morpholin-4-yl-ethyl)-1,5,6,7-tetrahydro-Pyrrolo[3,2-c]pyridin-4-one (2.31 g) as a red oil which was used as such.

N,N-dimethylformamide (1.68 ml) was added dropwise slowly with phosphorus oxychloride (0.9 ml, 9.65 mmol) under an argon atmosphere while maintaining the temperature at 0° C. Upon completion of the addition, the mixture was stirred for 15 minutes at room temperature and cooled down to 0~5° C. in an ice-water bath. A mixture of 3-methyl-5-(2-morpholin-4-yl-ethyl)-1,5,6,7-tetrahydro-pyrrolo[3,2-c]pyridin-4-one (2.31 g, 8.77 mmol) in 10.5 ml of N,N-dimethylformamide was added dropwise to the above solution. Upon completion of the addition, the mixture was stirred for 2 hours at 0° C., added with cold water (5 ml) and stirred for 5 minutes. The resulting mixture was adjusted to pH 12 with 10% aqueous sodium hydroxide solution and extracted with dichloromethane (15 ml×6). The combined organic extracts were washed with brine (15 ml), dried with anhydrous sodium sulfate, filtered and concentrated under reduced pressure. The residue was purified by silica gel column chromatography with dichloromethane:methanol (10:1) as eluents to give 3-methyl-5-(2-morpholin-4-yl-ethyl)-4-oxo-4,5,6,7-tetrahydro-1H-pyrrolo[3,2-c]pyridine-2-carbaldehyde (550 mg, 17.5%) as a red oil.

MS m/z (ESI): 292[M+1]

$^1$H NMR(CHCl$_3$-d6, 400 MHz) 9.598 (s, 1H, —CHO), 3.730~3.614 (m, 8H, 2×-OCH$_2$—; 2×-CONCH$_2$), 3.000~2.966 (t, 2H, —CH$_2$), 2.628 (s, 3H, —CH$_3$), 2.603~2.569 (t, 2H, —NCH$_2$), 2.540~2.531 (m, 4H, 2×-NCH$_2$)

A stirred solution of 3-methyl-5-(2-morpholin-4-yl-ethyl)-4-oxo-4,5,6,7-tetrahydro-1H-pyrrolo[3,2-c]pyridine-2-carbaldehyde (52 mg, 0.15 mmol), 5-fluoro-1,3-dihydro-indol-2-one (25 mg, 0.4 mmol) in 0.4 ml of ethanol was added dropwise with anhydrous piperidine (0.04 ml). The mixture was stirred at room temperature overnight. The precipitate was filtered under reduced pressure. The resulting solid was washed with anhydrous ethanol (0.2 ml×5), purified by silica gel column chromatography with dichloromethane:methanol (10:1) as eluents to give 2-(5-fluoro-2-oxo-1,2-dihydro-indol-3-ylidenemethyl)-3-methyl-5-(2-morpholin-4-yl-ethyl)-1,5,6,7-tetrahydro-pyrrolo[3,2-c]pyridin-4-one (30 mg, 38%) as a yellow solid.

MS m/z (ESI): 425[M+1]

$^1$HNMR (400 MHz, DMSO-d6) 7.767~7.761 (d, 1H, —ArH), 7.742~7.734 (d, 1H, —CH=C), 6.974~6.928 (dd, 1H, —ArH), 6.885~6.853 (dd, 1H, —ArH), 3.633~3.474 (m, 8H, 2×-OCH$_2$; 2×-CONCH$_2$), 3.021~2.987 (t, 2H, —CH$_2$), 2.530 (s, 3H, —CH$_3$), 2.465~2.428 (t, 2H, —NCH$_2$), 2.338~2.319 (m, 4H, 2×-NCH$_2$)

Example 16

2-(5-Chloro-2-oxo-1,2-dihydro-indol-3-ylidenemethyl)-3-methyl-5-(2-morpholin-4-yl-ethyl)-1,5,6,7-tetrahydro-pyrrolo[3,2-c]pyridin-4-one

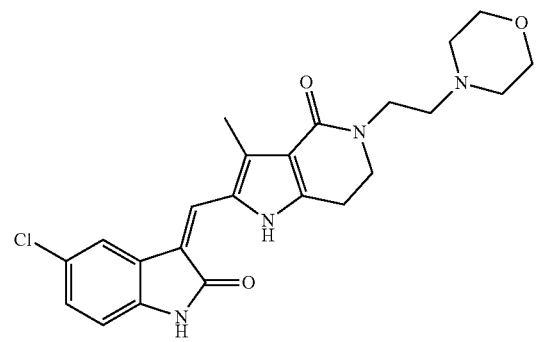

The title compound was prepared under the same conditions as described in Example 15 with 3-methyl-5-(2-morpholin-4-yl-ethyl)-4-oxo-4,5,6,7-tetrahydro-1H-pyrrolo[3,2-c]pyridine-2-carbaldehyde and 5-chloro-1,3-dihydro-indol-2-one as starting materials to give 2-(5-chloro-2-oxo-1,2-dihydro-indol-3-ylidenemethyl)-3-methyl-5-(2-morpholin-4-yl-ethyl)-1,5,6,7-tetrahydro-pyrrolo[3,2-c]pyridin-4-one (31 mg, 38.8%) as a yellow solid.

MS m/z (ESI): 441[M+1]

$^1$HNMR (400 MHz, DMSO-d6) 7.975~7.971 (d, 1H, —ArH), 7.790~7.783 (d, 1H, —CH=C), 7.173~7.148 (dd, 1H, —ArH), 6.907~6.886 (dd, 1H, —ArH), 3.632~3.507 (m, 8H, 2×-OCH₂; 2×-CONCH₂), 3.023~2.989 (t, 2H, —CH₂), 2.538 (s, 3H, —CH₃), 2.473 (t, 2H, —NCH₂), 2.436 (m, 4H, 2×-NCH₂)

Example 17

2-(5-Bromo-2-oxo-1,2-dihydro-indol-3-ylidenemethyl)-3-methyl-5-(2-mopholin-4-yl-ethyl)-1,5,6,7-tetrahydro-pyrrolo[3,2-c]pyridin-4-one

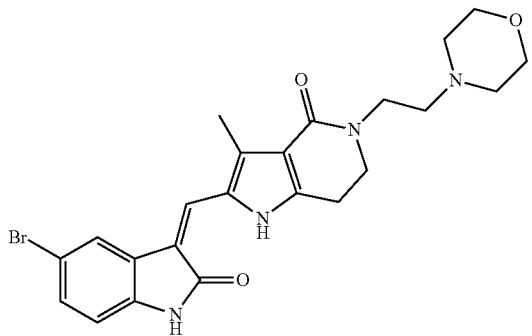 [SMILES: Cc1c(/C=C2\C(=O)Nc3ccc(Cl)cc32)[nH]c2c1C(=O)N(CCN1CCOCC1)CC2]

The title compound was prepared under the same conditions as described in Example 15 with 3-methyl-5-(2-morpholin-4-yl-ethyl)-4-oxo-4,5,6,7-tetrahydro-1H-pyrrolo[3,2-c]pyridine-2-carbaldehyde and 5-bromo-6-amino-1,3-dihydro-indol-2-one as starting materials to give 2-(5-bromo-2-oxo-1,2-dihydro-indol-3-ylidenemethyl)-3-methyl-5-(2-mopholin-4-yl-ethyl)-1,5,6,7-tetrahydro-pyrrolo[3,2-c]pyridin-4-one (35 mg, 39.8%) as a red solid.

MS m/z (ESI): 486[M+1]

¹HNMR (400 MHz, DMSO-d6). 8.101 (s, 1H, —ArH), 7.795~7.787 (d, 1H, —CH=C), 7.301~7.276 (dd, 1H, —ArH), 6863~6.843 (dd, 1H, —ArH), 3.632~3.506 (m, 8H, 2×-OCH₂; 2×-CONCH₂), 3.023~2.990 (t, 2H, —CH₂), 2.540 (s, 3H, —CH₃), 2.468 (t, 2H, —NCH₂), 2.430 (m, 4H, 2×-NCH₂)

Example 18

N-{5-Fluoro-3-[3-methyl-5-(2-morpholin-4-yl-ethyl)-4-oxo-4,5,6,7-tetrahydro-1H-pyrrolo[3,2-c]pyridine-2-ylmethylene]-2-oxo-2,3-dihydro-1H-indol-7-yl}-acetamide

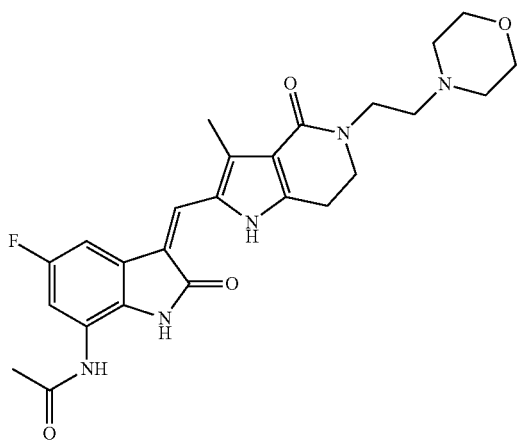 [SMILES: CC(=O)Nc1cc(F)cc2c1NC(=O)/C2=C\c1[nH]c2c(c1C)C(=O)N(CCN1CCOCC1)CC2]

The title compound was prepared under the same conditions as described in Example 15 with 3-methyl-5-(2-morpholin-4-yl-ethyl)-4-oxo-4,5,6,7-tetrahydro-1H-pyrrolo[3,2-c]pyridine-2-carbaldehyde and N-(5-fluoro-2-oxo-2,3-dihydro-1H-indol-7-yl)-acetamide as starting materials to give N-{5-fluoro-3-[3-methyl-5-(2-morpholin-4-yl-ethyl)-4-oxo-4,5,6,7-tetrahydro-1H-pyrrolo[3,2-c]pyridine-2-ylmethylene]-2-oxo-2,3-dihydro-1H-indol-7-yl}-acetamide (33 mg, 37%) as an orange solid.

MS m/z (ESI): 482[M+1]

¹HNMR (400 MHz, DMSO-d6) 7.740 (s, 1H, —CH=C), 7.587~7.571 (d, 1H, —ArH), 7.391~7.368 (d, 1H, —ArH), 3.635~3.512 (m, 8H, 2×-OCH₂; 2×-CONCH₂), 3.036~3.002 (t, 2H, —CH₂), 2.535 (s, 3H, —CH₃), 2.466~2.450 (t, 2H, —NCH₂), 2.428 (m, 4H, 2×-NCH₂), 2.090 (s, 3H, —CH₃CO)

Example 19

N-{5-Fluoro-3-[3-methyl-5-(2-morpholin-4-yl-ethyl)-4-oxo-4,5,6,7-tetrahydro-1H-pyrrolo[3,2-c]pyridine-2-ylmethylene]-2-oxo-2,3-dihydro-1H-indol-6-yl}-acetamide

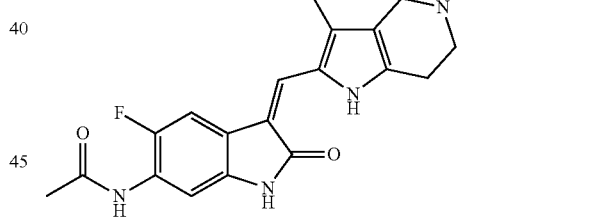

The title compound was prepared under the same conditions as described in Example 15 with 3-methyl-5-(2-morpholin-4-yl-ethyl)-4-oxo-4,5,6,7-tetrahydro-1H-pyrrolo[3,2-c]pyridine-2-carbaldehyde and N-(5-fluoro-2-oxo-2,3-dihydro-1H-indol-6-yl)-acetamide as starting materials to give N-{5-fluoro-3-[3-methyl-5-(2-morpholin-4-yl-ethyl)-4-oxo-4,5,6,7-tetrahydro-1H-pyrrolo[3,2-c]pyridine-2-ylmethylene]-2-oxo-2,3-dihydro-1H-indol-6-yl}-acetamide (35 mg, 39.3%) as a light brown solid.

MS m/z (ESI): 482[M+1]

¹HNMR (400 MHz, DMSO-d6) 7.801~7.773 (d, 1H, —ArH), 7.633 (s, 1H, —CH=C), 7.600~7.584 (d, 1H, —ArH), 3.623~3.498 (m, 8H, 2×-OCH₂; 2×-CONCH₂), 3.005~2.973 (t, 2H, —CH₂), 2.511 (s, 3H, —CH₃), 2.465 (t, 2H, —NCH₂), 2.429 (m, 4H, 2×-NCH₂), 2.100 (s, 3H, —CH₃CO)

Example 20

2-(6-Amino-5-fluoro-2-oxo-1,2-dihydro-indol-3-ylidenemethyl)-3-methyl-5-(2-morpholin-4-yl-ethyl)-1,5,6,7-tetrahydro-pyrrolo[3,2-c]pyridin-4-one

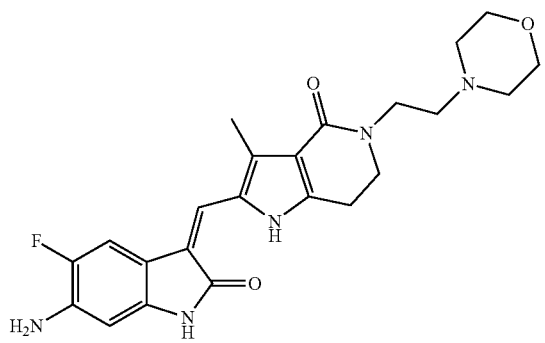 [SMILES: Cc1c(/C=C2\C(=O)Nc3cc(N)c(F)cc32)[nH]c2c1C(=O)N(CCN1CCOCC1)CC2]

The title compound was prepared under the same conditions as described in Example 15 with 3-methyl-5-(2-morpholin-4-yl-ethyl)-4-oxo-4,5,6,7-tetrahydro-1H-pyrrolo[3,2-c]pyridine-2-carbaldehyde and 5-fluoro-6-amino-1,3-dihydro-indol-2-one as starting materials to give 2-(6-amino-5-fluoro-2-oxo-1,2-dihydro-indol-3-ylidenemethyl)-3-methyl-5-(2-morpholin-4-yl-ethyl)-1,5,6,7-tetrahydro-pyrrolo[3,2-c]pyridin-4-one (40 mg, 50%) as a red solid.

MS m/z (ESI): 440[M+1]

$^1$HNMR (MeOH-d6, 400 MHz) 7.500 (s, 1H, —CH═C), 6.786~6.758 (dd, 1H, —ArH), 6.345~6.312 (dd, 1H, —ArH), 3.718~3.630 (m, 8H, 2×-OCH$_2$; 2×-CONCH$_2$), 3.036~3.002 (t, 2H, —CH$_2$), 2.610~2.576 (t, 2H, —NCH$_2$), 2.550 (m, 4H, 2×-NCH$_2$), 2.535 (s, 3H, —CH$_3$)

Example 21

2-(7-Amino-5-fluoro-2-oxo-1,2-dihydro-indol-3-ylidenemethyl)-3-methyl-5-(2-morpholin-4-yl-ethyl)-1,5,6,7-tetrahydro-pyrrolo[3,2-c]pyridin-4-one

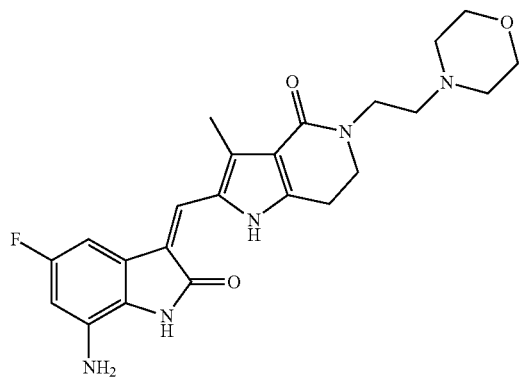 [SMILES: Cc1c(/C=C2\C(=O)Nc3c(N)cc(F)cc32)[nH]c2c1C(=O)N(CCN1CCOCC1)CC2]

The title compound was prepared under the same conditions as described in Example 15 with 3-methyl-5-(2-morpholin-4-yl-ethyl)-4-oxo-4,5,6,7-tetrahydro-1H-pyrrolo[3,2-c]pyridine-2-carbaldehyde and 5-fluoro-7-amino-1,3-dihydro-indol-2-one as starting materials to give 2-(7-amino-5-fluoro-2-oxo-1,2-dihydro-indol-3-ylidenemethyl)-3-methyl-5-(2-morpholin-4-yl-ethyl)-1,5,6,7-tetrahydro-pyrrolo[3,2-c]pyridin-4-one (35 mg, 43.8%) as a red solid.

MS m/z (ESI): 440[M+1]

$^1$HNMR (400 MHz, DMSO-d6) 7.530~7.502 (d, 1H, —ArH), 7.339 (s, 1H, —CH═C), 6.363~6.344 (d, 1H, —ArH), 3.611~3.494 (m, 8H, 2×-OCH$_2$; 2×-CONCH$_2$), 2.970~2.937 (t, 2H, —CH$_2$), 2.482 (t, 2H, —NCH$_2$); 2.461 (s, 3H; —CH$_3$), 2.450 (M, 4H, 2×-NCH$_2$)

Example 22

N-{3-[3-Methyl-5-(2-mopholin-4-yl-ethyl)-4-oxo-4,5,6,7-tetrahydro-1H-pyrrolo[3,2-c]pyridine-2-ylmethylene]-2-oxo-2,3-dihydro-1H-indol-5-yl}-methanesulfonamide

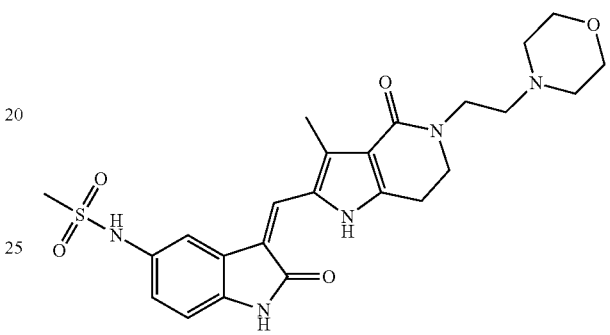

The title compound was prepared under the same conditions as described in Example 15 with 3-methyl-5-(2-morpholin-4-yl-ethyl)-4-oxo-4,5,6,7-tetrahydro-1H-pyrrolo[3,2-c]pyridine-2-carbaldehyde and 5-methanesulfonamino-1,3-dihydro-indol-2-one as starting materials to give N-{3-[3-methyl-5-(2-morpholin-4-yl-ethyl)-4-oxo-4,5,6,7-tetrahydro-1H-pyrrolo[3,2-c]pyridine-2-ylmethylene]-2-oxo-2,3-dihydro-1H-indol-5-yl}-methanesulfonamide (42 mg, 47.8%) as a yellow solid.

MS m/z (ESI): 500[M+1]

H-NMR (400 MHz, DMSO-d6) 7.605 (s, 1H, —CH═C), 7.046~7.027 (d, 1H, —ArH), 6.886~6.866 (d, 1H, —ArH), 6.795~6.775 (d, 1H, —ArH), 3.648~3.485 (m, 8H, 2×-OCH$_2$; 2×-CONCH$_2$), 3.021 (t, 2H, —CH$_2$), 2.955 (s, 3H, —CH$_3$SO$_2$), 2.543 (s, 3H, —CH$_3$), 2.474 (t, 2H, —NCH$_2$), 2.443 (m, 4H, 2×-NCH$_2$)

Example 23

N-{3-[3-Methyl-5-(2-morpholin-4-yl-ethyl)-4-oxo-4,5,6,7-tetrahyrdro-1H-pyrrolo[3,2-c]pyridine-2-ylmethylene]-2-oxo-2,3-dihydro-1H-indol-5-yl}-acetamide

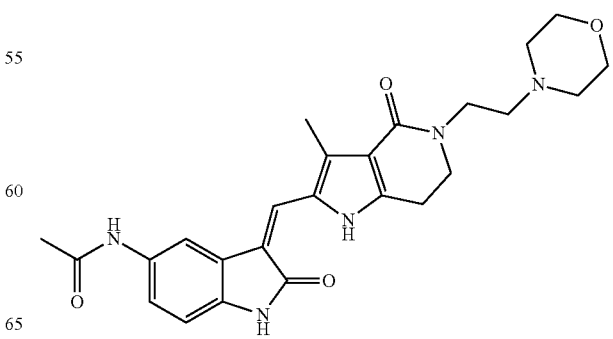

The title compound was prepared under the same conditions as described in Example 15 with 3-methyl-5-(2-morpholin-4-yl-ethyl)-4-oxo-4,5,6,7-tetrahydro-1H-pyrrolo[3,2-c]pyridine-2-carbaldehyde and N-(2-oxo-2,3-dihydro-1H-indol-5-yl)-acetamideas starting materials to give N-{3-[3-methyl-5-(2-morpholin-4-yl-ethyl)-4-oxo-4,5,6,7-tetrahyrdro-1H-pyrrolo[3,2-c]pyridine-2-ylmethylene]-2-oxo-2,3-dihydro-1H-indol-5-yl}-acetamide (60 mg, 71.2%) as a yellow solid.

MS m/z (ESI): 464[M+1]

H-NMR (400 MHz, DMSO-d6). 7.835 (s, 1H, —CH=C), 7.498~7.490 (d, 1H, —ArH), 7.293~7.267 (dd, 1H, —ArH), 6.843~6.822 (d, 1H, —ArH), 3.599~3.507 (m, 8H, 2×-OCH₂; 2×-CONCH₂), 3.017~2.983 (t, 2H, —CH₂), 2.535 (s, 3H, —CH₃), 2.474 (t, 2H, —NCH₂), 2.438 (m, 4H, 2×-NCH₂), 2.033 (s, 3H, —CH₃CO)

Example 24

4-(3-Chloro-4-fluoro-phenylamino)-5-[3-methyl-5-(2-morpholin-4-yl-ethyl)-4-oxo-4,5,6,7-tetrahydro-1H-pyrrolo[3,2-c]pyridine-2-ylmethylenene]-5,7-dihydro-pyrrolo[2,3-d]pyrimidin-6-one

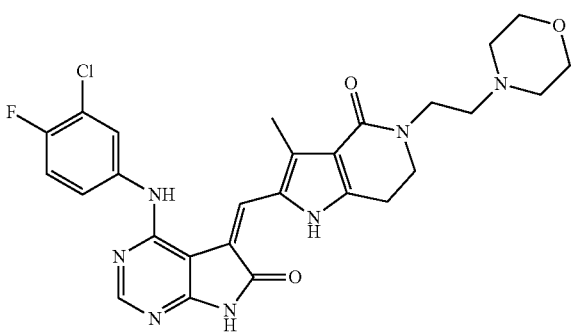 [SMILES: Cc1c(/C=C2\C(=O)Nc3ncnc(Nc4ccc(F)c(Cl)c4)c32)[nH]c2c1C(=O)N(CCN1CCOCC1)CC2]

The title compound was prepared under the same conditions as described in Example 15 with 3-methyl-5-(2-morpholin-4-yl-ethyl)-4-oxo-4,5,6,7-tetrahydro-1H-pyrrolo[3,2-c]pyridine-2-carbaldehyde and 4-(3-chloro-4-fluoro-phenylamino)-5,7-dihydro-pyrrolo[2,3-d]-pyrimidin-6-one as starting materials to give 4-(3-chloro-4-fluoro-phenylamino)-5-[3-methyl-5-(2-morpholin-4-yl-ethyl)-4-oxo-4,5,6,7-tetrahydro-1H-pyrrolo[3,2-c]pyridine-2-ylmethylenene]-5,7-dihydro-pyrrolo[2,3-d]pyrimidin-6-one (33 mg, 37.9%) as a brown solid.

MS m/z (ESI): 553[M+1]

¹HNMR (400 MHz, DMSO-d6) 8.312 (s, 1H, —CH=N), 7.707~7.684 (dd, 1H, —ArH), 7.397~7.333 (m, 3H, —ArH; 3.632~3.497 (m, 8H, 2×-OCH₂; 2×-CONCH₂), 3.041~3.007 (t, 2H, —CH₂), 2.460 (t, 2H, —NCH₂), 2.423 (m, 4H, 2×-NCH₂), 2.376 (s, 3H, —CH₃)

Example 25

2-(5-Fluoro-2-oxo-1,2-dihydro-indol-3-ylidenemethyl)-3-methyl-5-(2-piperidin-1-yl-ethyl)-1,5,6,7-tetrahydro-pyrrolo[3,2-c]pyridin-4-one

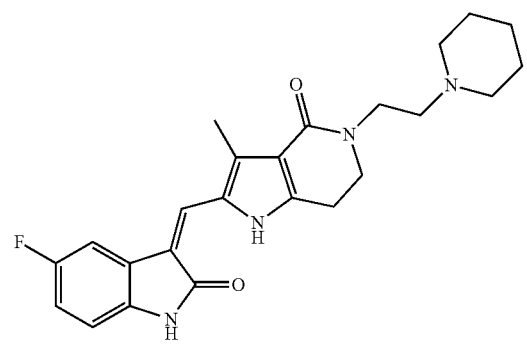

A stirred solution of 2-carboxymethyl-4-methyl-1H-pyrrole-3-carboxylic acid ethyl ester (2.67 g, 12.67 mmol) in N,N-dimethylformamide (6.5 ml) and dichloromethane (65 ml) was added with 2-piperidin-1-yl-ethylamine (1.78 g, 13.9 mmol), N-ethyl-N'-(dimethylaminopropyl)-carbodiimide hydrochloride (4.84 g, 25.34 mmol) and 1-hydroxybenzotriazol (1.71 g, 12.67 mmol) in an ice/water-bath. Upon completion of the addition, the reaction mixture was stirred at room temperature overnight, then added with cold water (50 ml), and extracted with dichloromethane (50 ml×3). The combined organic extracts were washed with saturated sodium bicarbonate (50 ml), water (50 ml), brine (50 ml), dried with anhydrous sodium sulfate, filtered and concentrated under reduced pressure to give 4-methyl-2-[(2-piperidin-1-yl-erhyl carbamoyl)-methyl]-1H-pyrrole-3-carboxylic acid ethyl ester (3.46 g, 85%) as a brown oil which was used as such.

MS m/z (ESI): 322[M+1]

A stirred solution of 4-methyl-2-[(2-piperidin-1-yl-erhyl carbamoyl)-methyl]-1H-pyrrole-3-carboxylic acid ethyl ester (3.46 g, 10.8 mmol) in anhydrous tetrahydrofuran (20 ml) was added dropwise slowly with 1M borane-tetrafuran complex in tetrafuran (32.4 ml, 32.4 mmol) under an argon atmosphere. Upon completion of the addition, the mixture was stirred at room temperature for 1 hour and heated to reflux for another 5 hours. The mixture was added with cold water (5 ml) and 1N hydrochloric acid (15 ml) dropwise and stirred for 5 minutes. The mixture was adjusted to pH 10 with 10% aqueous sodium hydroxide solution and extracted with ethyl acetate (10 ml×5). The combined organic extracts were washed with brine (15 ml), dried with anhydrous sodium sulfate, filtered and concentrated under reduced pressure to give 4-methyl-2-[2-(2-piperidin-1-yl-ethylamino)-ethyl]-1H-pyrrole-3-carboxylic acid ethyl ester (3.07 g) as a brown oil which was used as such.

A stirred solution of 4-methyl-2-[2-(2-piperidin-1-yl-ethylamino)-ethyl]-1H-pyrrole-3-carb oxylic acid ethyl ester (3.07 g, 10 mmol) in toluene (50 ml) was added dropwise slowly with 2M trimethyl aluminum in toluene (10 ml, 20 mmol) under an argon atmosphere. The mixture was stirred for 1 hour at room temperature and heated to reflux for another 4 hours. The reaction mixture was cooled down to 0° C. in ice/water bath, added with cold water (50 ml) and stirred for 5 minutes. The mixture was adjusted to pH12 with 10% aqueous sodium hydroxide solution and extracted with dichloromethane (40 ml×3). The combined organic extracts were washed with brine (15 ml), filtered through a pad of Celite. The filtrate was dried with anhydrous sodium sulfate, filtered and concentrated under reduced pressure to give 3-methyl-5-(2-piperidin-1-yl-ethyl)-1,5,6,7-tetrahydro-pyrrolo[3,2-c]pyridin-4-one (2.29 g) as a red oil which was used as such.

A stirred solution of N,N-dimethylformamide (1.68 ml) was added dropwise slowly with phosphorus oxychloride (0.9 ml, 9.65 mmol) under an argon atmosphere while maintaining the temperature at 0° C. Upon completion of the addition, the mixture was stirred for 15 minutes at room temperature, and cooled down to 0~5° C. in an ice-water bath. A mixture of 3-methyl-5-(2-piperidin-1-yl-ethyl)-1,5,6,7-tetrahydro-pyrrolo[3,2-c]pyridin-4-one (2.29 g, 8.77 mmol) in 10.5 ml of N,N-dimethylformamide was added dropwise to the above solution. Upon completion of the addition, the mixture was stirred for 2 hours at 0° C., added with cold water (5 ml), stirred for 5 minutes. The resulting mixture was adjusted to pH 12 with 10% aqueous sodium hydroxide solution and extracted with dichloromethane (30 ml×3). The combined organic extracts were washed with brine (15 ml), dried with anhydrous sodium sulfate, filtered and concentrated under reduced pressure. The residue was purified by silica gel column chromatography with dichloromethane:methanol (10:1) as eluents to give 3-methyl-4-oxo-5-(2-piperidin-1-yl-ethyl)-4,5,6,7-tetrahydro-1H-pyrrolo[3,2-c]pyridine-2-carbaldehyde (989 mg, 3 steps 31.7%) as a red oil which was used as such.

MS m/z (ESI): 290[M+1]

A stirred solution of 3-methyl-4-oxo-5-(2-piperidin-1-yl-ethyl)-4,5,6,7-tetrahydro-1H-pyrrolo[3,2-c]pyridine-2-carbaldehyde (52 mg, 0.18 mmol), 5-fluoro-1,3-dihydro-indol-2-one (25 mg, 0.4 mmol) in 0.4 ml of ethanol was added dropwise with anhydrous piperidine (0.04 ml). The mixture was stirred at room temperature overnight. The precipitate was filtered under reduced pressure. The resulting solid was washed with anhydrous ethanol (0.2 ml×5), purified by silica gel column chromatography with dichloromethane:methanol (15:1) as eluents to give 2-(5-fluoro-2-oxo-1,2-dihydro-indol-3-ylidenemethyl)-3-methyl-5-(2-piperidin-1-yl-ethyl)-1,5,6,7-tetrahydro-pyrrolo[3,2-c]pyridin-4-one (30 mg, 38%) as a yellow solid MS m/z (ESI): 423[M+1]

$^1$HNMR (400 MHz, DMSO-d6) 7.792~7.786 (d, 1H, —ArH), 6.872~6.839 (dd, 1H, —ArH), 3.633~3.600 (t, 2H, —CONCH$_2$), 3.274 (s, 1H, —CH), 3.027~2.994 (t, 2H, —CH$_2$), 2.543 (s, 3H, —CH$_3$), 1.393 (m, 2H, —CH$_2$)

Example 26

2-(5-Chloro-2-oxo-1,2-dihydro-indol-3-ylidenemethyl)-3-methyl-5-(2-piperidin-1-yl-ethyl)-1,5,6,7-tetrahydro-pyrrolo[3,2-c]pyridin-4-one

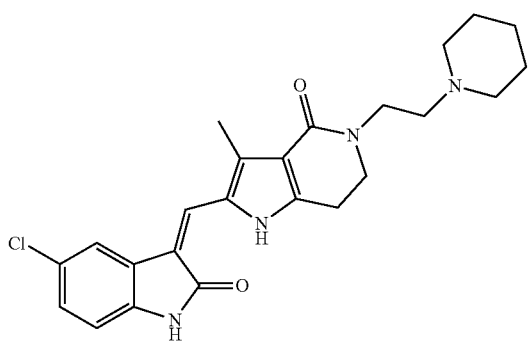

The title compound was prepared under the same conditions as described in Example 25 with 3-methyl-4-oxo-5-(2-piperidin-1-yl-ethyl)-4,5,6,7-etrahydro-1H-pyrrolo[3,2-c]pyridine-2-carbaldehyde and 5-chloro-1,3-dihydro-indol-2-one as starting materials to give 2-(5-chloro-2-oxo-1,2-dihydro-indol-3-ylidenemethyl)-3-methyl-5-(2-piperidin-1-yl-ethyl)-1,5,6,7-tetrahydro-pyrrolo[3,2-c]pyridin-4-one (58 mg, 77.4%) as a yellow solid.

MS m/z (ESI): 439[M+1]

$^1$HNMR (400 MHz, DMSO-d6) 8.000~7.996 (d, 1H, —ArH), 7.807 (s, 1H, —CH═C), 7.167~7.141 (dd, 1H, —ArH), 6.891~6.870 (dd, 1H, —ArH), 3.630~3.492 (m, 4H, 2×-CONCH$_2$), 3.023~2.990 (t, 2H, —CH$_2$), 2.554 (s, 3H, —CH$_3$), 2.405 (m, 6H, 3×-NCH$_2$), 1.393~1.384 (m, 2H, —CH$_2$)

Example 27

2-(5-Bromo-2-oxo-1,2-dihydro-indol-3-ylidenemethyl)-3-methyl-5-(2-piperidin-1-yl-ethyl)-1,5,6,7-tetrahydro-pyrrolo[3,2-c]pyridin-4-one

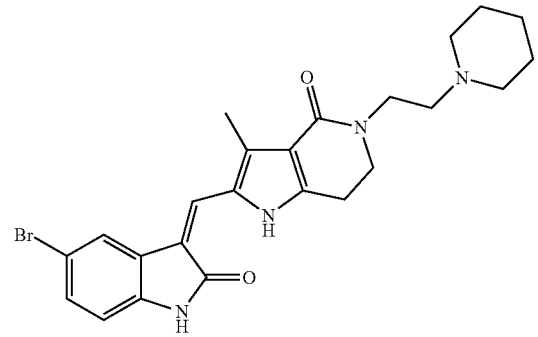

The title compound was prepared under the same conditions as described in Example 25 with 3-methyl-4-oxo-5-(2-piperidin-1-yl-ethyl)-4,5,6,7-etrahydro-1H-pyrrolo[3,2-c]pyridine-2-carbaldehyde and 5-bromo-1,3-dihydro-indol-2-one as starting materials to give 2-(5-bromo-2-oxo-1,2-dihydro-indol-3-ylidenemethyl)-3-methyl-5-(2-piperidin-1-yl-ethyl)-1,5,6,7-tetrahydro-pyrrolo[3,2-c]pyridin-4-one (62 mg, 75.2%) as an orange solid.

MS m/z (ESI): 484[M+1]

$^1$HNMR (400 MHz, DMSO-d6) 8.125~8.121 (d, 1H, —ArH), 7.812 (s, 1H, —CH═C), 7.295~7.270 (dd, 1H, —ArH), 6.848~6.827 (d, 1H, —ArH), 3.630~3.494 (m, 4H, 2×-CONCH$_2$), 3.024~2.990 (t, 2H, —CH$_2$), 2.551 (s, 3H, —CH$_3$), 2.401 (m, 6H, 3×-NCH$_2$), 1.395~1.384 (m, 2H, —CH$_2$)

Example 28

4-(3-Chloro-4-fluoro-phenylamino)-5-[3-methyl-4-oxo-5-(2-piperidin-1-yl-ethyl)-4,5,6,7-tetrahydro-1H-pyrrolo[3,2-c]pyridine-2-ylmethylene]-5,7-dihydro-pyrrolo[2,3-d]pyrimidin-6-one

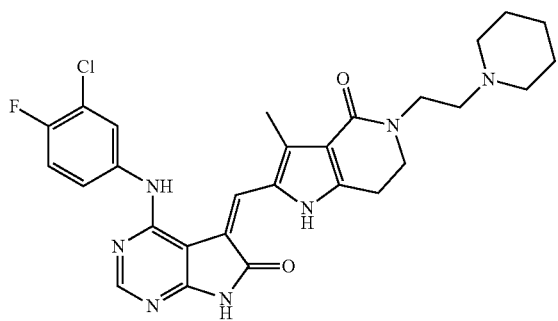

The title compound was prepared under the same conditions as described in Example 25 with 3-Methyl-4-oxo-5-(2-piperidin-1-yl-ethyl)-4,5,6,7-etrahydro-1H-pyrrolo[3,2-c]pyridine-2-carbaldehyde and 4-(3-chloro-4-fluoro-phenylamino)-5,7-dihydro-pyrrolo[2,3-d]-pyrimidin-6-one as starting materials to give 4-(3-chloro-4-fluoro-phenylamino)-5-[3-methyl-4-oxo-5-(2-piperidin-1-yl-ethyl)-4,5,6,7-tetrahydro-1H-pyrrolo[3,2-c]pyridine-2-ylmethylene]-5,7-dihydro-pyrrolo[2,3-d]pyrimidin-6-one (44 mg, 46.8%) as an orange solid.

MS m/z (ESI): 551[M+1]

$^1$HNMR (400 MHz, DMSO-d6) 8.310 (s, 1H, —CH=N), 7.713~7.691 (dd, 1H, —ArH), 7.369~7.354 (m, 3H, —ArH; —CH=C), 3.617~3.584 (t, 2H, —CH$_2$), 3.505~3.472 (t, 2H, —CH$_2$), 3.029~2.996 (t, 2H, —CH$_2$), 1.489~1.464 (t, 4H, 2x-CH$_2$), 1.391~1.369 (dd, 2H, —CH$_2$)

Example 29

N-{3-[3-Methyl-4-oxo-5-(2-piperidin-1-yl-ethyl)-4,5,6,7-tetrahydro-1H-pyrrolo[3,2-c]pyridine-2-ylmethylene]-2-oxo-2,3-dihydro-1H-indol-5-yl}-acetamide

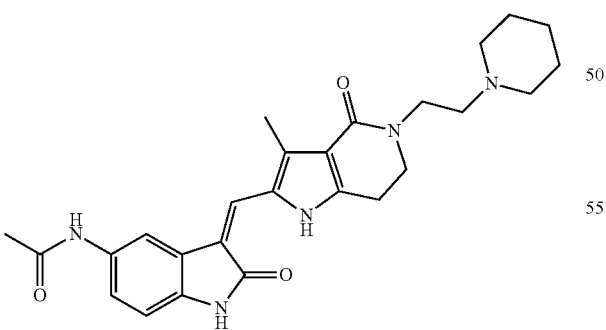

The title compound was prepared under the same conditions as described in Example 25 with 3-methyl-4-oxo-5-(2-piperidin-1-yl-ethyl)-4,5,6,7-etrahydro-1H-pyrrolo[3,2-c]pyridine-2-carbaldehyde and 5-acetamino-1,3-dihydro-indol-2-one as starting materials to give N-{3-[3-methyl-4-oxo-5-(2-piperidin-1-yl-ethyl)-4,5,6,7-tetrahydro-1H-pyrrolo[3,2-c]pyridine-2-ylmethylene]-2-oxo-2,3-dihydro-1H-indol-5-yl}-acetamide (55 mg, 69.7%) as an orange solid.

MS m/z (ESI): 462[M+1]

$^1$HNMR (400 MHz, DMSO-d6) 7.832 (s, 1H, —CH=N), 7.284~7.263 (dd, 1H, —ArH), 6.833~6.812 (d, 1H, —ArH), 3.618~3.584 (t, 2H, —CH$_2$), 3.513~3.479 (t, 2H, —CH$_2$), 3.006~2.971 (t, 2H, —CH$_2$), 2.028 (s, 3H, —CH$_3$), 1.483 (m, 4H, 2x-CH$_2$) 1.377 (m, 2H, —CH$_2$)

Example 30

2-(4-Bromo-2-oxo-1,2-dihydro-indol-3-ylidenemethyl)-5-(2-diethylamino-ethyl)-3-methyl-1,5,6,7-tetrahydro-pyrrolo[3,2-c]pyridin-4-one

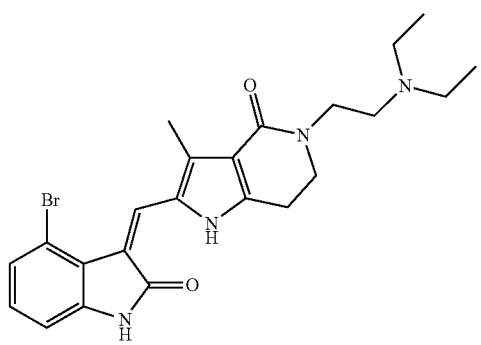 [SMILES: CCN(CC)CCN1CCc2[nH]c(/C=C3\C(=O)Nc4cccc(Br)c43)c(C)c2C1=O]

The title compound was prepared under the same conditions as described in Example 1 with 5-(2-diethylamino-ethyl)-3-methyl-4-oxo-4,5,6,7-tetrahydro-1H-pyrrolo[3,2-c]pyridine-2-carbaldehyde and 4-bromo-1,3-dihydro-indol-2-one (prepared according to US20030225127) as starting materials to give 2-(4-bromo-2-oxo-1,2-dihydro-indol-3-ylidenemethyl)-5-(2-diethylamino-ethyl)-3-methyl-1,5,6,7-tetrahydro-pyrrolo[3,2-c]pyridin-4-one (59 mg, 77.2%) as a bright yellow solid.

MS m/z (ESI): 472[M+1]

$^1$H NMR (400 MHz, DMSO-d6) 8.586 (s, 1H, —CH), 7.242~7.221 (d, 1H, —ArH), 7.099~7.059 (t, 1H, —ArH), 6.952~6.933 (d, 1H, —ArH), 3.646~3.613 (t, 2H, —CH$_2$), 3.456 (t, 2H, —CH$_2$), 3.020 (t, 2H, —CH$_2$), 0.970 (t, 6H, 2xCH$_3$)

Example 31

5-(2-Diethylamino-ethyl)-3-methyl-2-(2-oxo-4-piperidin-4-yl-1,2-dihydro-indol-3-ylidenemethyl)-1,5,6,7-tetrahydro-pyrrolo[3,2-c]pyridin-4-one

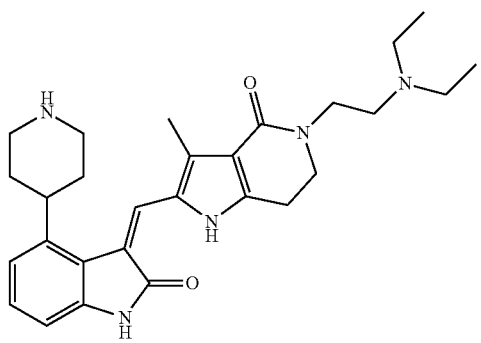 [SMILES: CCN(CC)CCN1CCc2[nH]c(/C=C3\C(=O)Nc4cccc(C5CCNCC5)c43)c(C)c2C1=O]

A suspension of 4-pyridin-4-yl-1,3-dihydro-indol-2-one (4.28 g, 20.4 mmol, prepared according to WO2002055517) in methanol (160 ml), water (70 mL) and acetic acid (30 mL)

was added 37% hydrochloric acid (2 mL) and platinum (IV) oxide (360 mg). The system was hydrogenated for three days. The reaction mixture was filtered through Celite, washed with methanol. The filtrate was evaporated and dried under reduced pressure. The residue was dissolved in methanol (500 mL) and neutralized with hydroxide from resin to pH=9-10. The resin was filtered and washed with methanol, the filtrate was evaporated and concentrated under reduced pressure to give 4-piperidin-4-yl-1,3-dihydro-indol-2-one (4.2 g, 96%) as a white solid.

MS m/z (ESI): 217 [M+1].

The title compound was prepared under the same conditions as described in Example 1 with 5-(2-diethylamino-ethyl)-3-methyl-4-oxo-4,5,6,7-tetrahydro-1H-pyrrolo[3,2-c]pyridine-2-carbaldehyde and 4-piperidin-4-yl-1,3-dihydro-indol-2-one as starting materials to give 5-(2-diethylamino-ethyl)-3-methyl-2-(2-oxo-4-piperidin-4-yl-1,2-dihydro-indol-3-ylidenemethyl)-1,5,6,7-tetrahydro-pyrrolo[3,2-c]pyridin-4-one (20 mg, 26.0%) as a yellow solid.

MS m/z (ESI): 476[M+1]

$^1$HNMR (400 MHz, DMSO-d6), 7.535 (s, 1H, —CH), 7.148~7.109 (d, 1H, —ArH), 6.952~6.932 (d, 1H, —ArH), 6.779~6.760 (d, 1H, —ArH), 3.629~3.595 (t, 2H, —CH$_2$), 3.462~3.427 (t, 2H, —CH$_2$), 2.760~2.703 (t, 2H, —CH$_2$), 1.874~4.844 (d, 2H, —CH$_2$), 0.977~0.942 (t, 6H, 2×-CH$_3$)

Example 32

2-(7-Bromo-5-fluoro-2-oxo-1,2-dihydro-indol-3-ylidenemethyl)-5-(2-diethylamino-ethyl)-3-methyl-1,5,6,7-tetrahydro-pyrrolo[3,2-c]pyridin-4-one

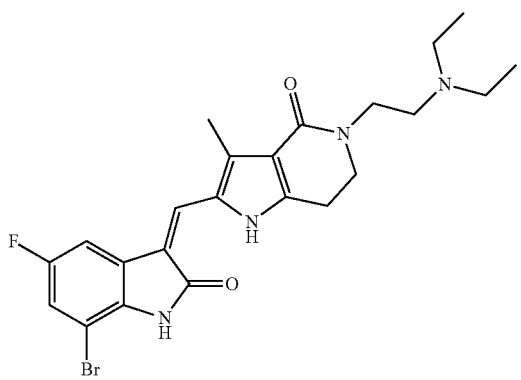 [SMILES: CCN(CC)CCN1CCc2[nH]c(/C=C3\C(=O)Nc4c(Br)cc(F)cc43)c(C)c2C1=O]

A suspension of 5-fluoro-1,3-dihydro-indol-2-one (1.5 g, 10 mmol) in 15 ml of acetonitrile and N-bromosuccinimide (1.8 g, 10 mmol) was stirred at room temperature overnight until the precipitate was formed. The solid was filtered, washed with ethanol (5 ml) and dried in vacuo to give 7-bromo-5-fluoro-1,3-dihydro-indol-2-one (1.6 g, 69.6%) as a white solid.

The title compound was prepared under the same conditions as described in Example 1 with 5-(2-diethylamino-ethyl)-3-methyl-4-oxo-4,5,6,7-tetrahydro-1H-pyrrolo[3,2-c]pyridine-2-carbaldehyde and 5-fluoro-7-bromo-1,3-dihydro-indol-2-one as starting materials to give 2-(7-bromo-5-fluoro-2-oxo-1,2-dihydro-indol-3-ylidenemethyl)-5-(2-diethylamino-ethyl)-3-methyl-1,5,6,7-tetrahydro-pyrrolo[3,2-c]pyridin-4-one (62 mg, 78.2%) as an orange solid.

MS m/z (ESI): 490[M+1]

Example 33

N-{3-[5-(2-Diethylamino-ethyl)-3-methyl-4-oxo-4,5,6,7tetrahydro-1H-pyrrolo[3,2-c]pyridine-2-ylmethylene]-2-oxo-2,3-dihydro-1H-indol-5-yl}-formamide

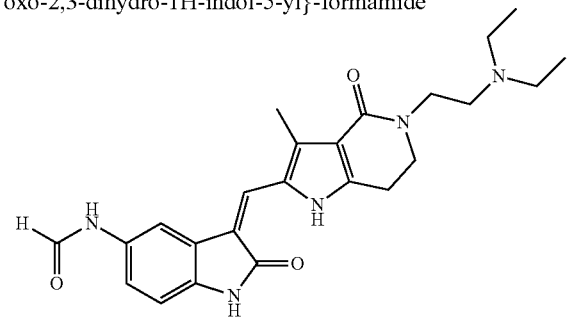

A solution of acetic anhydride (1.6 ml) and formic acid (1.2 ml) was stirred for 1 hour at room temperature, and added with 5-amino-1,3-dihydro-indol-2-one (3.56 g, 24 mmol, prepared according to U.S. Pat. No. 6,114,371) in 60 ml of tetrahydrofuran and piperidine (0.04 ml). The resulting mixture was stirred for 3 hours at room temperature until a precipitate was formed. The solid was filtered and recrystallized from methanol to give N-(2-oxo-2,3-dihydro-1H-indol-5-yl)-formamide (3.6 g, 85%) as a white solid.

MS m/z (ESI): 177[M+1]

The title compound was prepared under the same conditions as described in Example 1 with 5-(2-diethylamino-ethyl)-3-methyl-4-oxo-4,5,6,7-tetrahydro-1H-pyrrolo[3,2-c]pyridine-2-carbaldehyde and N-(2-oxo-2,3-dihydro-1H-indol-5-yl)-formamide as starting materials to give N-{3-[5-(2-diethylamino-ethyl)-3-methyl-4-oxo-4,5,6,7-tetrahydro-1H-pyrrolo[3,2-c]pyridine-2-ylmethylene]-2-oxo-2,3-dihydro-1H-indol-5-yl}-formamide (55 mg, 80.6%) as an orange solid.

MS m/z (ESI): 436[M+1]

$^1$H NMR (400 MHz, DMSO-d6) 9.994~9.966 (d, 1H, —NH), 7.881 (s, 1H, —ArH), 7.322~7.302 (d, 1H, —ArH), 6.874~6.813 (d, 1H, —ArH), 3.633~3.599 (t, 2H, —CH$_2$), 3.447 (t, 2H, —CH$_2$), 3.306 (s, 1H, —CH), 3.007~2.974 (t, 2H, —CH$_2$), 2.518 (s, 3H, —CH$_3$), 0.981~0.947 (t, 6H, 2×-CH$_3$).

Example 34

2-[4-(4-Chloro-2-fluoro-phenyl)-2-oxo-1,2-dihydro-indol-3-ylidenemethyl]-5-(2-diethylamino-ethyl)-3-methyl-1,5,6,7-tetrahydro-pyrrolo[3,2-c]pyridin-4-one

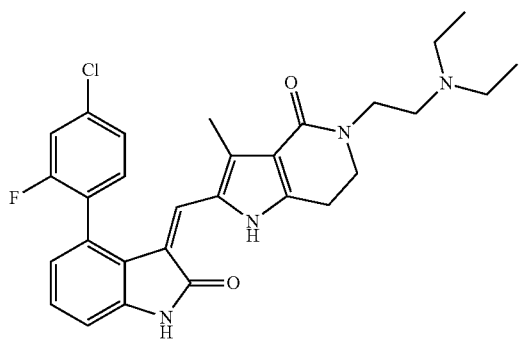 [SMILES: CCN(CC)CCN1CCc2[nH]c(/C=C3\C(=O)Nc4cccc(-c5ccc(Cl)cc5F)c43)c(C)c2C1=O]

The title compound was prepared under the same conditions as described in Example 1 with 5-(2-diethylamino-ethyl)-3-methyl-4-oxo-4,5,6,7-tetrahydro-1H-pyrrolo[3,2-c]pyridine-2-carbaldehyde and 4-(4-chloro-2-fluoro-phenyl)-1,3-dihydro-indol-2-one (prepared according to WO2002055517) as starting materials to give 2-[4-(4-chloro-2-fluoro-phenyl)-2-oxo-1,2-dihydro-indol-3-ylidenemethyl]-5-(2-diethylamino-ethyl)-3-methyl-1,5,6,7-tetrahydro-pyrrolo[3,2-c]pyridin-4-one (35 mg, 38.9%) as a yellow solid.

MS m/z (ESI): 522[M+1]

¹HNMR (400 MHz, DMSO-d6) 7.699~7.674 (d, 1H, —ArH), 7.519 (s, 2H, 2×-ArH), 7.260~7.222 (t, 1H, —ArH), 6.994~6.975 (d, 1H, —ArH), 6.870~6.851 (d, 1H, —ArH), 6.605 (d, 1H, —ArH), 3.590~3.421 (m, 4H, 2×-CONH₂), 3.295 (s, 3H, —CH₃), 2.959 (t, 2H, —CH₂), 1.895 (t, 2H, —CH₂), 1.236 (t, 2H, —CH₂), 0.951 (t, 6H, 2×CH₃)

Example 35

5-(2-Diethylamino-ethyl)-2-(5-methoxy-2-oxo-1,2-dihydro-indol-3-ylidenemethyl)-3-methyl-1,5,6,7-tetrahydro-pyrrolo[3,2-c]pyridin-4-one

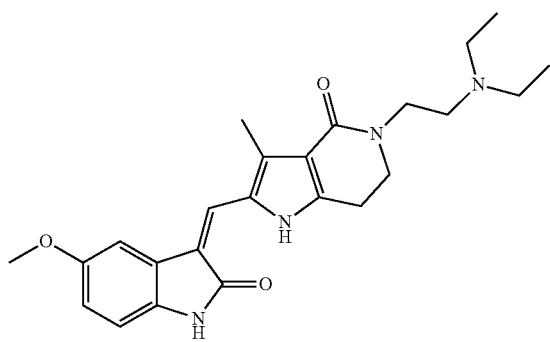 [SMILES: CCN(CC)CCN1CCc2[nH]c(/C=C3\C(=O)Nc4ccc(OC)cc43)c(C)c2C1=O]

The title compound was prepared under the same conditions as described in Example 1 with 5-(2-diethylamino-ethyl)-3-methyl-4-oxo-4,5,6,7-tetrahydro-1H-pyrrolo[3,2-c]pyridine-2-carbaldehyde and 5-methoxy]-1,3-dihydro-indol-2-one (prepared according to U.S. Pat. No. 6,114,371) as starting materials to give 5-(2-diethylamino-ethyl)-2-(5-methoxy-2-oxo-1,2-dihydro-indol-3-ylidenemethyl)-3-methyl-1,5,6,7-tetra hydro-pyrrolo[3,2-c]pyridin-4-one (80 mg, 65.0%) as a yellow solid.

MS m/z (ESI): 423[M+1]

¹H NMR (400 MHz, DMSO-d6) 7.685 (s, 1H, —CH), 7.487~7.481 (d, 1H, —ArH), 6.785~6.764 (d, 1H, —ArH), 6.728~6.701 (d, 1H, —ArH), 3.777 (s, 3H, —CH₃), 3.630~3.596 (t, 2H, —CH₂), 2.998~2.964 (t, 2H, —CH₂), 0.986~0.951 (t, 6H, 2×-CH₃)

Example 36

2-[4-(3-Chloro-2-fluoro-phenyl)-2-oxo-1,2-dihydro-indol-3-ylidenemethyl]-5-(2-diethylamino-ethyl)-3-methyl-1,5,6,7-tetrahydro-pyrrolo[3,2-c]pyridin-4-one

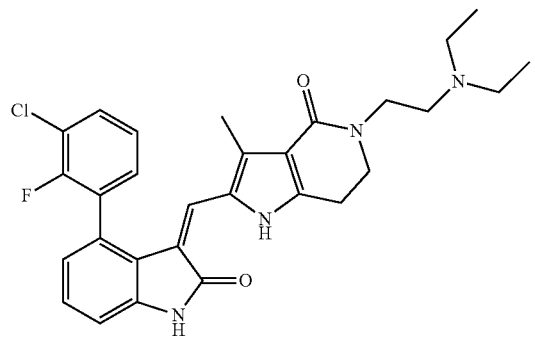 [SMILES: CCN(CC)CCN1CCc2[nH]c(/C=C3\C(=O)Nc4cccc(-c5cccc(Cl)c5F)c43)c(C)c2C1=O]

The title compound was prepared under the same conditions as described in Example 1 with 5-(2-diethylamino-ethyl)-3-methyl-4-oxo-4,5,6,7-tetrahydro-1H-pyrrolo[3,2-c]pyridine-2-carbaldehyde and 4-(3-chloro-2-fluoro-phenyl)-1,3-dihydro-indol-2-one (prepared according to WO2002055517) as starting materials to give 2-[4-(3-chloro-2-fluoro-phenyl)-2-oxo-1,2-dihydro-indol-3-ylidenemethyl]-5-(2-diethylamino-ethyl)-3-methyl-1,5,6,7-tetrahydro-pyrrolo[3,2-c]pyridin-4-one (30 mg, 30.0%) as a light yellow solid.

MS m/z (ESI): 522[M+1]

¹H NMR (400 MHz, DMSO-d6). 7.983 (s, 1H, —CH), 7.585~7.544 (m, 1H, —ArH), 7.345 (m, 2H, 2×-ArH), 7.025~7.005 (d, 1H, —ArH), 6.936~6.917 (d, 1H, —ArH̄), 6.871 (s, 1H, —CH), 3.790 (t, 3H, —CH₃), 2.013 (t, 3H, —CH₃), 1.280 (s, 2H, —CH₂)

Example 37

5-(2-Diethylamino-ethyl)-2-[4-(2-hydroxy-ethyl)-2-oxo-1,2-dihydro-indol-3-ylidenemethyl]-3-methyl-1,5,6,7-tetrahydro-pyrrolo[3,2-c]pyridin-4-one

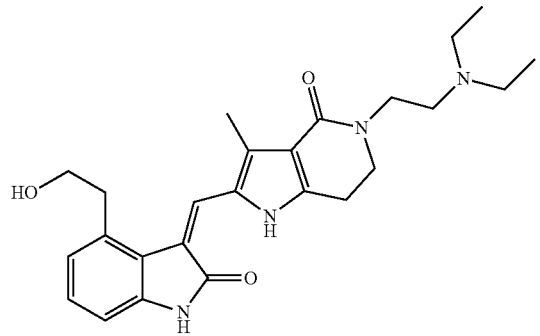 [SMILES: CCN(CC)CCN1CCc2[nH]c(/C=C3\C(=O)Nc4cccc(CCO)c43)c(C)c2C1=O]

135

The title compound was prepared under the same conditions as described in Example 1 with 5-(2-diethylamino-ethyl)-3-methyl-4-oxo-4,5,6,7-tetrahydro-1H-pyrrolo[3,2-c]pyridine-2-carbaldehyde and 4-(2-hydroxy-ethyl)-1,3-dihydro-indol-2-one (prepared according to US2004186160) as starting materials to give 5-(2-diethylamino-ethyl)-2-[4-(2-hydroxy-ethyl)-2-oxo-1,2-dihydro-indol-3-ylidenemethyl]-3-methyl-1,5,6,7-tetrahydro-pyrrolo[3,2-c]pyridin-4-one (30 mg, 35.0%) as a yellow solid.

MS m/z (ESI): 437[M+1]

$^1$H NMR (400 MHz, DMSO-d6) 7.666 (s, 1H, —CH), 7.070~7.031 (s, 1H, —OH), 6.853~6.834 (d, 1H, —ArH), 6.760~6.750 (d, 1H, —ArH), 3.709 (t, 2H, —CH$_2$), 3.209~3.175 (t, 2H, —CH$_2$), 2.503 (s, 3H, —CH$_3$), 0.829~0.799 (t, 2H, —CH$_2$)

Example 38

5-(2-Diethylamino-ethyl)-2-[5-(4-methoxy-phenyl)-2-Oxo-1,2-dihydro-indol-3-ylidenemethyl)-3-methyl-1,5,6,7-tetrahydro-pyrrolo[3,2-c]pyridin-4-one

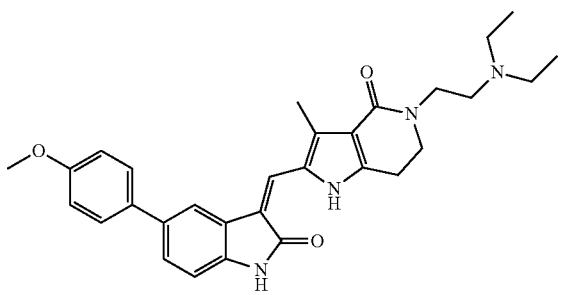 [SMILES: CCN(CC)CCN1CCc2[nH]c(/C=C3\C(=O)Nc4ccc(-c5ccc(OC)cc5)cc43)c(C)c2C1=O]

The title compound was prepared under the same conditions as described in Example 1 with 5-(2-diethylamino-ethyl)-3-methyl-4-oxo-4,5,6,7-tetrahydro-1H-pyrrolo[3,2-c]pyridine-2-carbaldehyde and 5-(4-methoxy-phenyl)-1,3-dihydro-indol-2-one as starting materials to give 5-(2-diethylamino-ethyl)-2-[5-(4-methoxy-phenyl)-2-oxo-1,2-dihydro-indol-3-ylidenemethyl)-3-methyl-1,5,6,7-tetrahydro-pyrrolo[3,2-c]pyridin-4-one (60 mg, 67.0%) as a yellow solid.

MS m/z (ESI): 499[M+1]

$^1$H NMR (400 MHz, DMSO-d6) 7.851~7.831 (d, 1H, —ArH), 7.670 (s, 1H, —ArH), 7.602~7.580 (d, 2H, 2×-ArH), 7.273~7.253 (d, 1H, —ArH), 7.066 (s, 1H, —CH), 7.036~7.014 (d, 2H, 2×-ArH), 3.641~3.607 (t, 2H, —CH$_2$), 3.279 (s, 3H, —CH$_3$), 3.002 (t, 2H, —CH$_2$), 2.535 (s, 3H, —CH$_3$), 2.504~2.496 (m, 4H, 2×-CH$_2$), 0.970 (t, 6H, 2×-CH$_3$)

136

Example 39

5-(2-Diethylamino-ethyl)-2-[4-(2,3-difluoro-phenyl)-2-oxo-1,2-dihydro-indol-3-ylidenemethyl]-3-methyl-1,5,6,7-tetrahydro-pyrrolo[3,2-c]pyridin-4-one

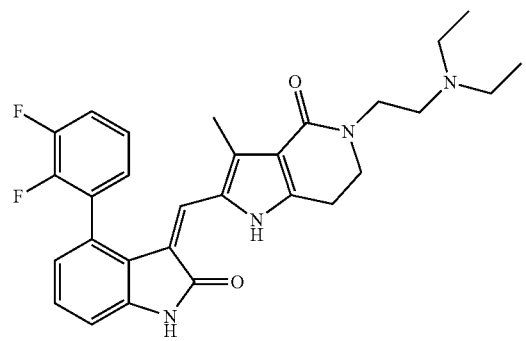 [SMILES: CCN(CC)CCN1CCc2[nH]c(/C=C3\C(=O)Nc4cccc(-c5cccc(F)c5F)c43)c(C)c2C1=O]

The title compound was prepared under the same conditions as described in Example 1 with 5-(2-diethylamino-ethyl)-3-methyl-4-oxo-4,5,6,7-tetrahydro-1H-pyrrolo[3,2-c]pyridine-2-carbaldehyde and 4-(2,3-difluoro-phenyl)-1,3-dihydro-indol-2-one (prepared according to WO2002055517) as starting materials to give 5-(2-diethylamino-ethyl)-2-[4-(2,3-difluoro-phenyl)-2-oxo-1,2-dihydro-indol-3-ylidenemethyl]-3-methyl-1,5,6,7-tetrahydro-pyrrolo[3,2-c]pyridin-4-one (20 mg, 22.0%) as a yellow solid.

MS m/z (ESI): 505[M+1]

$^1$H NMR (400 MHz, DMSO-d6) 7.769 (s, 1H, —CH), 6.926~6.891 (d, 1H, —ArH), 3.614 (t, 4H, 2×-CH$_2$), 2:917~2.884 (t, 3H, —CH$_3$), 1.932 (s, 3H, —CH$_3$), 1.490 (m, 4H, 2×-CH$_2$)

Example 40

2-(5-Bromo-2-oxo-1,2-dihydro-indol-3-ylidenemethyl)-3-methyl-5-(2-pyrrolidin-1-yl-ethyl)-1,5,6,7-tetrahydro-pyrrolo[3,2-c]pyridin-4-one

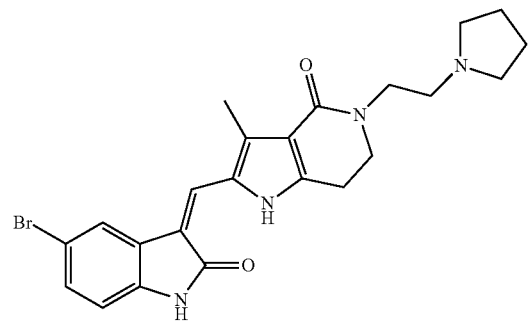 [SMILES: Cc1c(/C=C2\C(=O)Nc3ccc(Br)cc32)[nH]c2c1C(=O)N(CCN1CCCC1)CC2]

The title compound was prepared under the same conditions as described in Example 1 with 5-(2-diethylamino-ethyl)-3-methyl-4-oxo-4,5,6,7-tetrahydro-1H-pyrrolo[3,2-c]

pyridine-2-carbaldehyde and 5-bromo-1,3-dihydro-indol-2-one as starting materials to give 2-(5-bromo-2-oxo-1,2-dihydro-indol-3-ylidenemethyl)-3-methyl-5-(2-pyrrolidin-1-yl-ethyl)-1,5,6,7-tetrahydro-pyrrolo[3,2-c]pyridin-4-one (1.33 g, 94.2%) as an orange solid.

MS m/z (ESI): 470[M+1]

$^1$H NMR (400 MHz, DMSO-d6) 7.53 (d, 1H, ArH, 7.35 (s, 1H, CH), 6.35 (d, 1H, ArH, 5.30 (br s, 1H; NH$_2$), 3.60 (t, 2H, CH$_2$), 3.51 (t, 2H, CH$_2$), 2.96 (t, 2H, CH$_2$), 2.60 (t, 2H, CH$_2$), 2.51 (s, 3H, CH$_3$), 2.47 (q, 4H, 2×NCH$_2$), 1.64~1.69 (m, 4H, 2×CH$_2$)

Example 41

2-(5-Bromo-2-oxo-1,2-dihydro-indol-3-ylidenemethyl)-3-phenyl-1,5,6,7-tetrahydro-pyrrolo[3,2-c]pyridin-4-one

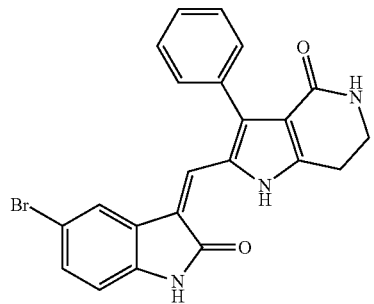

A stirred solution of 2,2-dimethyl-[1,3]dioxane-4,6-dione (7.5 g, 52 mmol), 3-tert-butoxycarbonylamino-propionic acid (9.45 g, 50 mmol), 4-dimethylamino pyridine (9.6 g) in dichloromethane (525 ml) was added dropwise slowly with the solution of N-ethyl-N'-(dimethylaminopropyl)-carbodiimide hydrochloride (11 g, 57.5 mmol) in 352 ml of dichloromethane in an ice-water bath. Upon completion of the addition, the mixture was stirred at room temperature overnight, then washed with 5% aqueous potassium bisulfate solution (300 ml×4), dried with anhydrous sodium sulfate, filtered and concentrated to give [3-(2,2-dimethyl-4,6-dioxo-[1,3]dioxin-5-ylidene)-3-hydroxy-propyl]-carbamic acid tert-butyl ester which was used as such.

MS m/z (ESI): 316[M+1]

A stirred solution of [3-(2,2-dimethyl-4,6-dioxo-[1,3]dioxin-5-ylidene)-3-hydroxy-propyl]-carbamic acid tert-butyl ester in absolute ethanol (112 ml) was heated to reflux at 70° C. overnight, and cooled to room temperature. The mixture was filtered and concentrated under reduced pressure to give 5-tert-butoxycarbonylamino-3-oxo-pentanoic acid ethyl ester (11.22 g, 87%) as a white solid.

MS m/z (ESI): 258[M−1]

A stirred solution of anhydrous sodium acetate (2.66 g, 82 mmol) in 140 ml of water was added with the solution of 5-tert-butoxycarbonylamino-3-oxo-pentanoic acid ethyl ester (4.20 g, 16.2 mmol) in 20 ml of absolute ethanol at room temperature. Upon completion of the addition, the mixture was stirred for 5 minutes, added with 2-amino-1-phenyl-ethanone (2.5 g, 14.6 mmol) and heated to reflux for 3 hours. The resulting mixture was added with water (300 ml), extracted with ethyl acetate (100 ml×3). The organic extracts were washed with brine (50 ml×3), dried with anhydrous sodium sulfate, filtered and concentrated to give 2-(2-tert-butoxycarbonylamino-ethyl)-4-phenyl-1H-pyrrole-3-carboxylic acid ethyl ester (5.0 g, 88.7%).

MS m/z (ESI): 359[M+1]

A stirred solution of dichloromethane (5.5 ml) and N,N-dimethylformamide (0.2 ml) was added dropwise slowly with phosphorus oxychloride (0.184 ml, 2 mmol) under an argon atmosphere while maintaining the temperature at −10° C.~0° C. Upon completion of the addition, the mixture was stirred for 15 minutes at −10° C., added with the solution of 2-(2-tert-butoxycarbonylamino-ethyl)-4-phenyl-1H-pyrrole-3-carboxylic acid ethyl ester (0.36 g, 1 mmol) in dichloromethane (2 ml) while maintaining the temperature at −10° C. ~0° C. for 1 hour. Then the mixture was stirred for another 2.5 hours at room temperature, added with cold water, adjusted to pH 11~12 with 10% aqueous sodium hydroxide solution, extracted with ethyl acetate (50 ml×6), washed with brine, dried with anhydrous sodium sulfate, filtered and concentrated under reduced pressure to give 2-(2-tert-butoxycarbonylamino-ethyl)-5-formyl-4-phenyl-1H-pyrrole-3-carboxylic acid ethyl ester (309 mg, 81.9%) as a red oil.

MS m/z (ESI): 385[M−1]

A stirred solution of 2-(2-tert-butoxycarbonylamino-ethyl)-5-formyl-4-phenyl-1H-pyrrole-3-carboxylic acid ethyl ester (1.120 g, 3 mmol) in dichloromethane (32 ml) was added dropwise slowly with trifluoroacetic acid (3.2 ml) at room temperature. Upon completion of the addition, the mixture was stirred for 3 hours, and concentrated to give 2-(2-amino-ethyl)-4-phenyl-1H-pyrrole-3-carboxylic acid ethyl ester which was used as such.

A stirred solution of 2-(2-amino-ethyl)-4-phenyl-1H-pyrrole-3-carboxylic acid ethyl ester, lithium hydroxide monohydrate (840 mg, 20 mmol) in ethanol (20 ml) was heated to reflux under an argon atmosphere for 3 hours. The mixture was added with cold water (150 ml), stirred for 10 minutes, extracted with dichloromethane:methanol=5:1 (50 ml×7), washed with brine, dried with anhydrous sodium sulfate, filtered and concentrated under reduced pressure. The crude product was recrystallized from dichloromethane and methanol to give 4-oxo-3-phenyl-4,5,6,7-tetrahydro-1H-pyrrolo[3,2-c]pyridine-2-carbaldehyde (280 mg, 38.9%) as a red solid.

MS m/z (ESI): 241[M+1]

$^1$H NMR (400 MHz, DMSO-d6) 9.261 (s, 1H, —NH), 3.418~3.394 (t, 2H, —CH$_2$), 2.882~2.848 (t, 2H, —CH$_2$)

A stirred solution of 4-oxo-3-phenyl-4,5,6,7-tetrahydro-1H-pyrrolo[3,2-c]pyridine-2-carbaldehyde (36 mg, 0.15 mmol), 5-bromo-1,3-dihydro-indol-2-one (33 mg, 0.146 mmol), piperidine (0.05 ml), N,N-dimethylformamide (0.05 ml) in anhydrous ethanol (0.75 ml) was heated to reflux for 2 hours and stirred at room temperature overnight. The resulting mixture was filtered to give (5-bromo-2-oxo-1,2-dihydro-indol-3-ylidenemethyl)-3-phenyl-1,5,6,7-tetrahydro-pyrrolo[3,2-c]pyridin-4-one (61 mg, 88%) as a yellow solid.

MS m/z (ESI): 435[M+1]

$^1$H NMR (400 MHz, DMSO-d6) 7.346~7.341 (d, 1H, —ArH), 7.295~7.270 (dd, 1H, —ArH), 6.857~6.837 (d, 1H, —ArH), 3.033~3.000 (t, 2H, —CH$_2$)

Example 42

2-[4-(2-Hydroxy-ethyl)-2-oxo-1,2-dihydro-indol-3-ylidenemethyl]-3-methyl-5-(2-morpholin-4-yl-ethyl)-1,5,6,7-tetrahydro-pyrrolo[3,2-c]pyridin-4-one

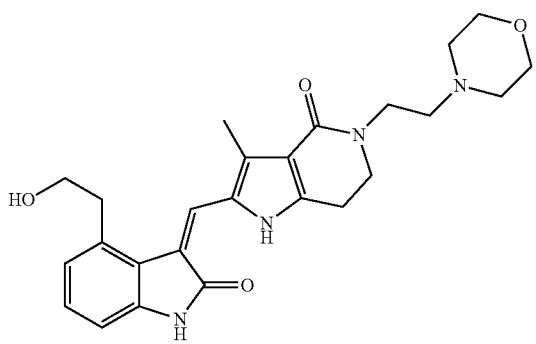 [SMILES: Cc1c(/C=C2\C(=O)Nc3cccc(CCO)c32)[nH]c2c1C(=O)N(CCN1CCOCC1)CC2]

The title compound was prepared under the same conditions as described in Example 13 with 3-methyl-5-(2-morpholin-4-yl-ethyl)-4-oxo-4,5,6,7-tetrahydro-1H-pyrrolo[3,2-c]pyridine-2-carbaldehyde and 4-(2-hydroxy-ethyl)-1,3-dihydro-indol-2-one (prepared according to US2004186160) as starting materials to give 2-[4-(2-hydroxy-ethyl)-2-oxo-1,2-dihydro-indol-3-ylidenemethyl]-3-methyl-5-(2-morpholin-4-yl-ethyl)-1,5,6,7-tetrahydro-pyrrolo[3,2-c]pyridin-4-one (30 mg, 33.3%) as a yellow solid.

MS m/z (ESI): 451[M+1]

$^1$HNMR (400 MHz, DMSO-d6) 7.646 (s, 1H, —CH), 7.084~7.045 (t, 1H, —ArH), 6.845~6.826 (d, 1H, —ArH), 6.784~6.765 (d, 1H, —ArH), 3.752~3.704 (t, 2H, —CH$_2$), 3.628~3.594 (t, 2H, —CH$_2$), 3.108~3.072 (t, 2H, —CH$_2$), 3.020~2.987 (t, 2H, —CH$_2$)

Example 43

2-[4-(4-Chloro-2-fluoro-phenyl)-2-oxo-1,2-dihydro-inol-3-ylidenemethyl]-3-methyl-5-(2-morpholin-4-yl-ethyl)-1,5,6,7-tetrahydro-pyrrolo[3,2-c]pyridin-4-one

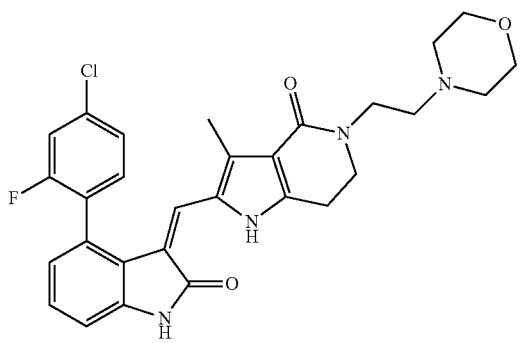

The title compound was prepared under the same conditions as described in Example 13 with 3-methyl-5-(2-morpholin-4-yl-ethyl)-4-oxo-4,5,6,7-tetrahydro-1H-pyrrolo[3,2-c]pyridine-2-carbaldehyde and 4-(4-chloro-2-fluoro-phenyl)-1,3-dihydro-indol-2-one (prepared according to WO2002055517) as starting materials to give 2-[4-(4-chloro-2-fluoro-phenyl)-2-oxo-1,2-dihydro-inol-3-ylidenemethyl]-3-methyl-5-(2-morpholin-4-yl-ethyl)-1,5,6,7-tetrahydro-pyrrolo[3,2-c]pyridin-4-one (30 mg, 33.3%) as a yellow solid.

MS m/z (ESI): 536[M+1]

$^1$HNMR (400 MHz, DMSO-d6) 7.698~7.675 (d, 1H, —ArH), 7.260~7.221 (t, 1H, —ArH), 6.994~6.975 (d, 1H, —ArH), 6.870~6.850 (d, 1H, —ArH), 6.607 (s, 1H, —CH), 3.484~3.444 (t, 2H, —CH$_2$), 2.982~2.948 (t, 2H, —CH$_2$), 1.893 (s, 3H, —CH$_3$)

Example 44

2-[4-(2,3-Difluoro-phenyl)-2-oxo-1,2-dihydro-indol-3-ylidenemethyl]-3-methyl-5-(2-morpholin-4-yl-ethyl)-1,5,6,7-tetrahydro-pyrrolo[3,2-c]pyridin-4-one

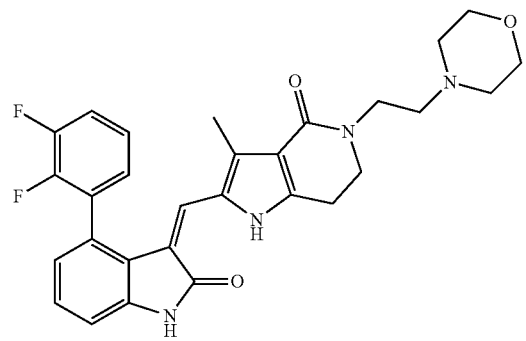

The title compound was prepared under the same conditions as described in Example 13 with 3-methyl-5-(2-morpholin-4-yl-ethyl)-4-oxo-4,5,6,7-tetrahydro-1H-pyrrolo[3,2-c]pyridine-2-carbaldehyde and 4-(2,3-difluoro-phenyl)-1,3-dihydro-indol-2-one (prepared according to WO2002055517) as starting materials to give 2-[4-(2,3-difluoro-phenyl)-2-oxo-1,2-dihydro-indol-3-ylidenemethyl]-3-methyl-5-(2-morpholin-4-yl-ethyl)-1,5,6,7-tetrahydro-pyrrolo[3,2-c]pyridin-4-one (30 mg, 33.3%) as a yellow solid.

MS m/z (ESI): 519[M+1]

$^1$HNMR (400 MHz, DMSO-d6) 7.662~7.596 (q, 1H, —ArH), 7.456~7.404 (q, 1H, —ArH), 7.334~7.300 (t, 1H, —ArH), 7.271~7.233 (s, 1H, —ArH), 7.010~6.990 (d, 1H, —ArH), 6.891~6.872 (d, 1H, —ArH), 6.706 (s, 1H, —CH), 3.495~3.462 (t, 2H, —CH$_2$), 2.982~2.949 (t, 2H, —CH$_2$), 1.877 (s, 3H, —CH$_3$)

Example 45

2-(5-Methoxy-2-oxo-1,2-dihydro-indol-3-ylidenemethyl)-3-methyl-5-(2-morpholin-4-yl-ethyl)-1,5,6,7-tetrahydro-pyrrolo[3,2-c]pyridin-4-one

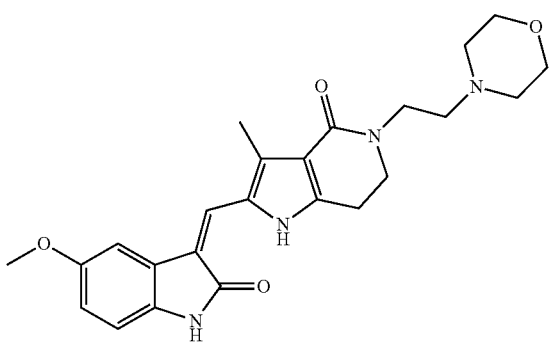

The title compound was prepared under the same conditions as described in Example 13 with 3-methyl-5-(2-morpholin-4-yl-ethyl)-4-oxo-4,5,6,7-tetrahydro-1H-pyrrolo[3,2-c]pyridine-2-carbaldehyde and 5-methoxy-1,3-dihydro-indol-2-one (prepared according to U.S. Pat. No. 6,114,371) as starting materials to give 2-(5-methoxy-2-oxo-1,2-dihydro-indol-3-ylidenemethyl)-3-methyl-5-(2-morpholin-4-yl-ethyl)-1,5,6,7-tetrahydro-pyrrolo[3,2-c]pyridin-4-one (30 mg, 33.3%) as a yellow solid.

MS m/z (ESI): 437[M+1]

$^1$HNMR (400 MHz, DMSO-d6) 7.687 (s, 1H, —CH), 7.488~7.483 (d, 1H, —ArH), 6.786~6.765 (d, 1H, —ArH), 6.729~6.702 (dd, 1H, —ArH), 3.777 (s, 3H, —CH$_3$), 3.627~3.594 (t, 2H, —CH$_2$), 3.569~3.548 (m, 4H, 2×-CH$_2$), 3.534~3.500 (t, 2H, —CH$_2$), 3.006~2.973 (t, 2H, —CH$_2$), 2.536 (s, 3H, —CH$_3$)

Example 46

2-(5-Fluoro-2-oxo-1,2-dihydro-indol-3-ylidenemethyl)-3-(4-fluoro-phenyl)-1,5,6,7-tetrahydro-pyrrolo[3,2-c]pyridin-4-one

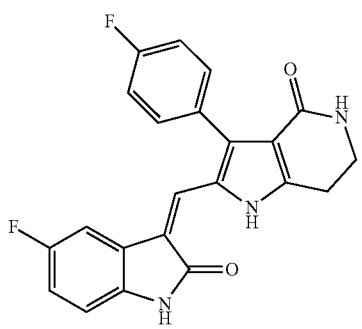 [SMILES: O=C1Nc2ccc(F)cc2/C1=C/c1[nH]c2c(c1-c1ccc(F)cc1)C(=O)NCC2]

A stirred solution of 1,3,5,7-tetraaza-tricyclo[3.3.1.1*3,7*]decane (7.2 g, 51.5 mmol) in chloroform (250 ml) was added with 2-bromo-1-(4-fluoro-phenyl)-ethanone (10.85 g, 50 mmol). Upon completion of the addition, the mixture was heated and maintaining the temperature at 48° C., stirred for 3 hours until a precipitate was formed. The resulting solid was filtered and washed with chloroform to give 1-(4-fluoro-phenyl)-2-(1,3,5,7-tetraaza-tricyclo[3.3.1.1*3,7*]dec-1-yl)-ethanone hydrobromate which was used as such.

A stirred solution of 1-(4-fluoro-phenyl)-2-(1,3,5,7-tetraaza-tricyclo [3.3.1.1*3,7*]dec-1-yl)-ethanone hydrobromate (17.8 g, 50 mmol) in methanol (100 ml) was added dropwise slowly with 12N hydrochloric acid (50 ml) in the ice/water bath. Upon completion of the addition, the mixture was stirred at room temperature overnight until a precipitate formed, then filtered to give 2-amino-1-(4-fluoro-phenyl)-ethanone hydrochloride (8.088 g, 85.36%) as a white solid.

MS m/z (ESI): 154[M+1]

A stirred solution of 2,2-dimethyl-[1,3]dioxane-4,6-dione (7.5 g, 52 mmol), 3-tert-butoxycarbonylamino-propionic acid (9.45 g, 50 mmol), 4-dimethylamino pyridin (9.6 g) in dichloromethane (525 ml) was added dropwise slowly with the solution of N-ethyl-N'-(dimethylaminopropyl)-carbodiimide hydrochloride (11.0 g, 57.5 mmol) in dichloromethane (325 ml). Upon completion of the addition, the mixture was stirred at room temperature overnight, washed with 5% aqueous potassium bisulfate solution (300 ml×4), dried, filtered and concentrated to give [3-(2,2-dimethyl-4,6-dioxo-[1,3]dioxan-5-ylidene)-3-hydroxy-propyl]-carbamic acid tert-butyl ester (18.75 g, 97%) as a light yellow solid.

MS m/z (ESI): 314[M−1]

A stirred solution of [3-(2,2-dimethyl-4,6-dioxo-[1,3]dioxan-5-ylidene)-3-hydroxy-propyl]-carbamic acid tert-butyl ester (18.75 g, 50 mmol) in absolute ethanol (112 ml) was heated overnight at 70° C. The mixture was concentrated under reduced pressure to give 5-tert-butoxycarbonylamino-3-oxo-pentanoic acid ethyl ester (14 g, 98%) as a yellow oil which was used as such.

A stirred solution of anhydrous sodium acetate (2.05 g, 25 mmol) in water (12.5 ml) was added with the solution of 5-tert-butoxycarbonylamino-3-oxo-pentanoic acid ethyl ester (3.23 g, 12.5 mmol) in anhydrous ethanol (2 ml), then the mixture was added with 2-amino-1-(4-fluoro-phenyl)-ethanone hydrochloride (2.37 g, 12.5 mmol), heated to reflux for 3 hours. The resulting mixture was extracted with ethyl acetate (50 ml×3) and the combined extracts were washed with brine (50 ml×3), dried with anhydrous sodium sulfate, filtered and concentrated under reduced pressure to give 2-(2-tert-butoxycarbonylamino-ethyl)-4-(4-fluoro-phenyl)-1H-pyrrole-3-carboxylic acid ethyl ester (4.3 g, 91.7%) as a yellow solid.

MS m/z (ESI): 375[M−1]

A stirred solution of dichloromethane (5 ml) and N,N-dimethylformamide (0.6 ml) was added dropwise slowly with phosphorus oxychloride (0.414 ml, 4.5 mmol) under an argon atmosphere while maintaining the temperature at −10° C.~0° C. Upon completion of the addition, the mixture was stirred for 15 minutes at −10° C., added with the solution of 2-(2-tert-butoxycarbonylamino-ethyl)-4-(4-fluoro-phenyl)-1H-pyrrole-3-carboxylic acid ethyl ester (1.125 g, 3 mmol) in dichloromethane (3 ml) while maintaining the temperature at −10° C.~0° C. for 1 hour. The mixture was stirred for another 2.5 hours at room temperature, added with cold water, adjusted to pH 11~12 with 10% aqueous sodium hydroxide solution, extracted with ethyl acetate (50 ml×6), washed with brine, dried with anhydrous sodium sulfate, filtered and concentrated under reduced pressure to give 2-(2-tert-butoxycarbonylamino-ethyl)-4-(4-fluoro-phenyl)-5-formyl-1H-pyrrole-3-carboxylic acid ethyl ester (1.02 g, 84.37%) as a red oil.

MS m/z (ESI): 403[M+1]

A stirred solution of 2-(2-tert-butoxycarbonylamino-ethyl)-4-(4-fluoro-phenyl)-5-formyl-1H-pyrrole-3-carboxylic acid ethyl ester (1.02 g, 2.5 mmol) in dichloromethane (25 ml) was added dropwise slowly with trifluoroacetic acid (2.5 ml) at room temperature. Upon completion of the addition, the mixture was stirred for 2 hours, and concentrated to give 2-(2-amino-ethyl)-4-(4-fluoro-phenyl)-5-formyl-1H-pyrrole-3-carboxylic acid ethyl ester which was used as such.

MS m/z (ESI): 305[M+1]

A stirred solution of 2-(2-amino-ethyl)-4-(4-fluoro-phenyl)-5-formyl-1H-pyrrole-3-carboxylic acid ethyl ester (257.5 mg, 2.5 mmol), lithium hydroxide monohydrate (840 mg, 20 mmol) in ethanol (95%, 20 ml) was heated to reflux under an argon atmosphere for 3 hours. The mixture was added with cold water (150 ml), stirred for 10 minutes, extracted with a 5 to 1 solvent mixture of dichloromethane and methanol (50 ml×7), washed with brine, dried with anhydrous sodium sulfate and concentrated under reduced pressure. The crude product was recrystallized from dichloromethane and methanol to give 3-(4-fluoro-phenyl)-4-oxo-4,5,6,7-tetrahydro-1H-pyrrolo[3,2-c]pyridine-2-carbaldehyde (170 mg, 26.3%) as a red solid.

MS m/z (ESI): 259[M+1]

A stirred solution of 3-(4-fluoro-phenyl)-4-oxo-4,5,6,7-tetrahydro-1H-pyrrolo[3,2-c]pyridine-2-carbaldehyde (50 mg, 0.194 mmol), 5-fluoro-1,3-dihydro-indol-2-one (28 mg, 0.184 mmol), piperidine (0.05 ml), N,N-dimethylformamide (0.05 ml) in anhydrous ethanol (0.5 ml) was heated to reflux for 2 hours and stirred at room temperature overnight. The resulting mixture was filtered to give 2-(5-fluoro-2-oxo-1,2-dihydro-indol-3-ylidenemethyl)-3-(4-fluoro-phenyl)-1,5,6,7-tetrahydro-pyrrolo[3,2-c]pyridin-4-one (50 mg, 65.92%) as a yellow solid.

MS m/z (ESI): 390[M−1]

¹H NMR (400 MHz, DMSO-d6) 7.509~7.474 (f, 2H, 2×-ArH), 6.984~6.980 (t, 1H, —ArH), 6.879~6.847 (t, 1H, —ArH), 4.332 (s, 1H, —NH), 3.035~3.002 (t, 2H, —CH₂)

Example 47

4-(3-Chloro-4-fluoro-phenylamino)-5-[3-(4-fluoro-phenyl)-4-oxo-4,5,6,7-tetrahydro-1H-pyrrolo[3,2-c]pyridin-2-ylmethylene]-5,7-dihydro-pyrrolo[2,3-d]pyrimidin-6-one

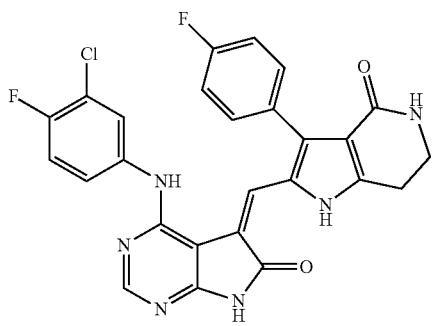 [SMILES: O=C1Nc2ncnc(Nc3ccc(F)c(Cl)c3)c2/C1=C/c1[nH]c2c(c1-c1ccc(F)cc1)C(=O)NCC2]

The title compound was prepared under the same conditions as described in Example 46 with 3-(4-fluoro-phenyl)-4-oxo-4,5,6,7-tetrahydro-1H-pyrrolo[3,2-c]pyridine-2-carbaldehyde and 4-(3-chloro-4-fluoro-phenylamino)-5,7-dihydro-pyrrolo[2,3-d]pyrimidin-6-one as starting materials to give 4-(3-chloro-4-fluoro-phenylamino)-5-[3-(4-fluoro-phenyl)-4-oxo-4,5,6,7-tetrahydro-1H-pyrrolo[3,2-c]pyridin-2-ylmethylene]-5,7-dihydro-pyrrolo[2,3-d]pyrimidin-6-one (80 mg, 77.4%) as a red solid.

MS m/z (ESI): 519[M+1]

¹H NMR (400 MHz, DMSO-d6) 11.896 (s, 1H, —NH), 9.020 (s, 1H, —ArH), 7.220~7.176 (t, 1H, —ArH), 7.141~7.097 (t, 1H, —ArH), 2.863~2.830 (t, 1H, —NH)

Example 48

2-[4-(3-Chloro-2-fluoro-phenyl)-2-oxo-1,2-dihydro-indol-3-ylidenemethyl]-3-methyl-5-(2-morpholin-4-yl-ethyl)-1,5,6,7-tetrahydro-pyrrolo[3,2-c]pyridin-4-one

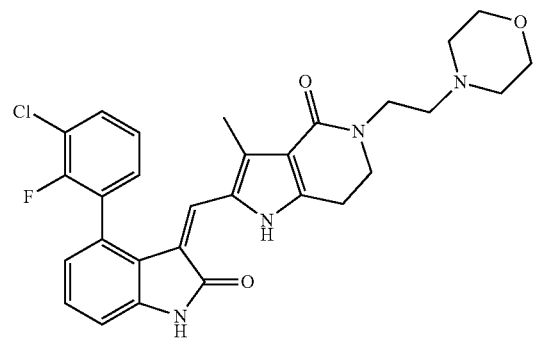

The title compound was prepared under the same conditions as described in Example 13 with 3-methyl-5-(2-morpholin-4-yl-ethyl)-4-oxo-4,5,6,7-tetrahydro-1H-pyrrolo[3,2-c]pyridine-2-carbaldehyde and 4-(3-chloro-2-fluoro-phenyl)-1,3-dihydro-indol-2-one (prepared according to WO2002055517) as starting materials to give 2-[4-(3-chloro-2-fluoro-phenyl)-2-oxo-1,2-dihydro-indol-3-ylidenemethyl]-3-methyl-5-(2-morpholin-4-yl-ethyl)-1,5,6,7-tetrahydro-pyrrolo[3,2-c]pyridin-4-one (54 mg, 62.1%) as a yellow solid.

MS m/z (ESI): 536[M+1]

¹HNMR (400 MHz, DMSO-d6) 7.813~7.771 (m, 1H, —ArH), 7.279~7.241 (t, 1H, —ArH), 7.015~6.996 (d, 1H, —ArH), 6.894~6.875 (d, 1H, —ArH), 6.666 (s, 1H, —CH), 3.502~3.469 (t, 2H, —CH₂), 2.990~2.956 (t, 2H, —CH₂), 1.885 (s, 3H, —CH₃).

Example 49

2-(4-Bromo-2-oxo-1,2-dihydro-indol-3-ylidenemethyl)-3-methyl-5-(2-morpholin-4-yl-ethyl)-1,5,6,7-tetrahydro-pyrrolo[3,2-c]pyridin-4-one

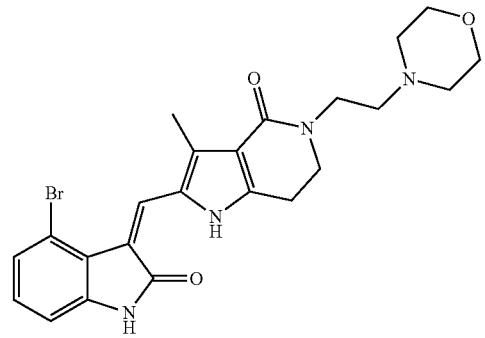

The title compound was prepared under the same conditions as described in Example 13 with 3-methyl-5-(2-morpholin-4-yl-ethyl)-4-oxo-4,5,6,7-tetrahydro-1H-pyrrolo[3, 2-c]pyridine-2-carbaldehyde and 4-bromo-1,3-dihydro-indol-2-one (prepared according to US20030225127) as starting materials to give 2-(4-bromo-2-oxo-1,2-dihydro-indol-3-ylidenemethyl)-3-methyl-5-(2-morpholin-4-yl-ethyl)-1,5,6,7-tetrahydro-pyrrolo[3,2-c]pyridin-4-one (74 mg, 93.6%) as a yellow solid.

MS m/z (ESI): 486[M+1]

¹HNMR (400 MHz, DMSO-d6) 8.587 (s, 1H, —CH), 7.244~7.223 (d, 1H, —ArH), 7.101~7.062 (t, 1H, —ArH), 6.955~6.936 (d, 1H, —ArH), 3.694~3.612 (t, 2H, —CH₂), 3.048~3.015 (t, 2H, —CH₂)

Example 50

2-(5-Bromo-2-oxo-1,2-dihydro-pyrrolo[2,3-b]pyridin-3-ylidenemethyl)-3-methyl-5-(2-morpholin-4-yl-ethyl)-1,5,6,7-tetrahydro-pyrrolo[3,2-c]pyridin-4-one

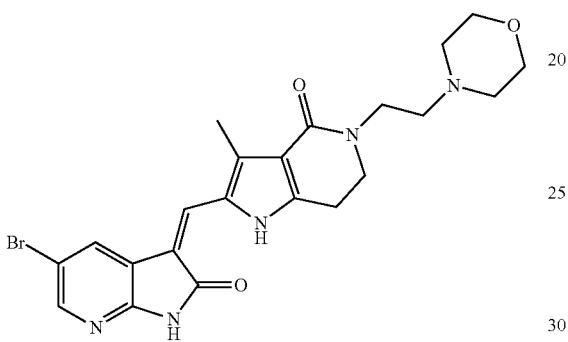

The title compound was prepared under the same conditions as described in Example 13 with 3-methyl-5-(2-morpholin-4-yl-ethyl)-4-oxo-4,5,6,7-tetrahydro-1H-pyrrolo[3,2-c]pyridine-2-carbaldehyde and 5-bromo-1,3-dihydro-pyrrolo[2,3-b]pyridin-2-one (prepared according to Heterocycles, 60 (4), 865-877, 2003) as starting materials to give 2-(5-bromo-2-oxo-1,2-dihydro-pyrrolo[2,3-b]pyridin-3-ylidenemethyl)-3-methyl-5-(2-morpholin-4-yl-ethyl)-1,5,6,7-tetrahydro-pyrrolo[3,2-c]pyridin-4-one (30 mg, 33%) as a yellow solid.

MS m/z (ESI): 487[M+1]

¹HNMR (400 MHz, DMSO-d6) 8.487~8.482 (d, 1H, —ArH), 8.114~8.109 (d, 1H, —ArH), 7.882 (s, 1H, —CH), 3.635~3.601 (t, 2H, —CH₂), 3.046~3.013 (t, 2H, —CH₂), 2.545 (s, 3H, —CH₃)

Example 51

3-Methyl-2-(4-methyl-2-oxo-1,2-dihydro-indol-3-ylidenemethyl)-5-(2-morpholin-4-yl-ethyl)-1,5,6,7-tetrahydro-pyrrolo[3,2-c]pyridin-4-one

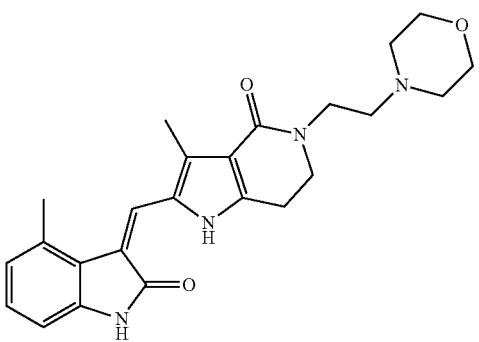

The title compound was prepared under the same conditions as described in Example 13 with 3-methyl-5-(2-morpholin-4-yl-ethyl)-4-oxo-4,5,6,7-tetrahydro-1H-pyrrolo[3,2-c]pyridine-2-carbaldehyde and 4-methyl-1,3-dihydro-indol-2-one (prepared according to U.S. Pat. No. 6,114,371) as starting materials to give 3-methyl-2-(4-methyl-2-oxo-1,2-dihydro-indol-3-ylidenemethyl)-5-(2-morpholin-4-yl-ethyl)-1,5,6,7-tetrahydro-pyrrolo[3,2-c]pyridin-4-one (50 mg, 73.3%) as a yellow solid.

MS m/z (ESI): 421[M+1]

¹HNMR (400 MHz, DMSO-d6) 7.567 (s, 1H, —CH), 7.082~7.043 (t, 1H, —ArH), 6.843~6.824 (d, 1H, —ArH), 6.7896.769 (d, 1H, —ArH), 3.636~3.602 (t, 2H, —CH₂), 3.026~2.993 (1, 2H, —CH₂), 2.595 (s, 3H, —CH₃)

Example 52

3-Methyl-5-(2-morpholin-4-yl-ethyl)-2-(2-oxo-4-piperidin-4-yl-1,2-dihydro-indol-3-ylidenemethyl)-1,5,6,7-tetrahydro-pyrrolo[3,2-c]pyridin-4-one

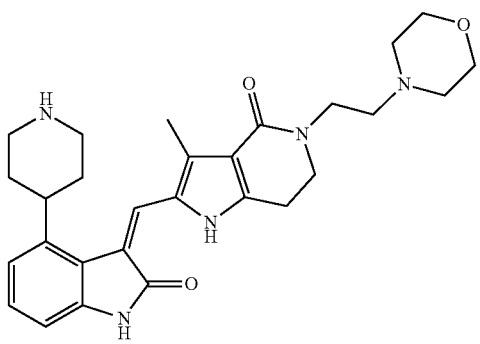

The title compound was prepared under the same conditions as described in Example 13 with 3-methyl-5-(2-morpholin-4-yl-ethyl)-4-oxo-4,5,6,7-tetrahydro-1H-pyrrolo[3,2-c]pyridine-2-carbaldehyde and 4-piperidin-4-yl-1,3-dihydro-indol-2-one as starting materials to give 3-methyl-5-(2-morpholin-4-yl-ethyl)-2-(2-oxo-4-piperidin-4-yl-1,2-dihydro-indol-3-ylidenemethyl)-1,5,6,7-tetrahydro-pyrrolo[3,2-c]pyridin-4-one (34 mg, 42.9%) as a yellow solid.

MS m/z (ESI): 490[M+1]

¹HNMR (400 MHz, DMSO-d6) 7.517 (s, 1H, —CH), 7.171~7.130 (t, 1H, —ArH), 6.945~6.926 (d, 1H, —ArH), 6.803~6.783 (d, 1H, —ArH), 3.633~3.600 (t, 2H, —CH₂), 3.028~2.296 (t, 2H, —CH₂), 1.942~1.916 (m, 2H, —CH₂), 1.754~1.725 (m, 2H, —CH₂)

Example 53

N-{5-Fluoro-3-[3-methyl-5-(2-morpholin-4-yl-ethyl)-4-oxo-4,5,6,7-tetrahydro-1H-pyrrolo[3,2-c]pyridin-2-ylmethylene]-2-oxo-2,3-dihydro-1H-indol-6-yl}-2-methoxy-acetamide

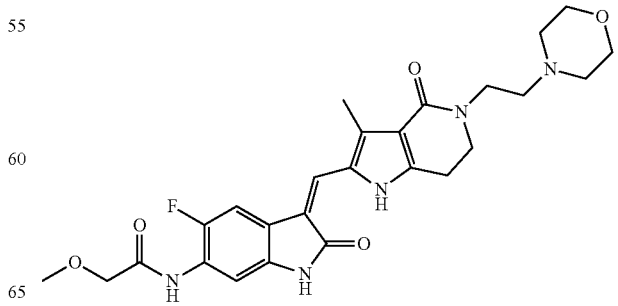

A stirred solution of d 6-amino-5-fluoro-1,3-dihydro-indol-2-one (2.028 g, 12.2 mmol) obtained from Example 7 in 30 ml of tetrahydrofuran was added with piperidine (1.3 ml). The mixture was cooled to −50° C. in an ethanol-dry ice bath and added with methoxyacetyl chloride (1.35 g, 12.5 mmol) in 20 ml of tetrahydrofuran dropwise. Upon the completion of the addition, the resulting mixture was stirred at the room temperature overnight until the precipitate was formed. The solid was filtered, washed with water and recrystallized from methanol to give N-(5-fluoro-2-oxo-2,3-dihydro-1H-indol-6-yl)-2-methoxy-acetamide (2.0 g, 69.2%) as a white solid.

MS m/z (ESI): 237[M−1]

The title compound was prepared under the same conditions as described in Example 13 with 3-methyl-5-(2-morpholin-4-yl-ethyl)-4-oxo-4,5,6,7-tetrahydro-1H-pyrrolo[3,2-c]pyridine-2-carbaldehyde and N-(5-fluoro-2-oxo-2,3-dihydro-1H-indol-6-yl)-2-methoxy-acetamide as starting materials to give N-{5-fluoro-3-[3-methyl-5-(2-morpholin-4-yl-ethyl)-4-oxo-4,5,6,7-tetrahydro-1H-pyrrolo[3,2-c]pyridin-2-ylmethylene]-2-oxo-2,3-dihydro-1H-indol-6-yl}-2-methoxy-acetamide (70 mg, 84.4%) as a brown solid.

MS m/z (ESI): 512[M+1]

¹HNMR (400 MHz, DMSO-d6) 9.325 (s, 1H, —NH), 7.879~7.851 (d, 1H, —ArH), 7.679 (s, 1H, —CH), 7.586~7.548 (d, 1H, —ArH), 4.064 (s, 2H, —CH₂), 3.632~3.599 (t, 2H, —CH₂), 3.021~2.988 (t, 2H, —CH₂)

Example 54

2-(7-Bromo-5-fluoro-2-oxo-1,2-dihydro-indol-3-ylidenemethyl)-3-methyl-5-(2-morpholin-4-yl-ethyl)-1,5,6,7-tetrahydro-pyrrolo[3,2-c]pyridin-4-one

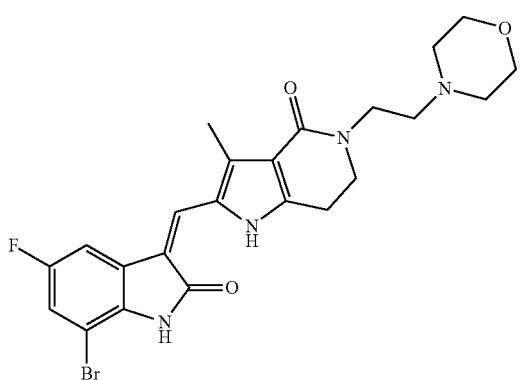

The title compound was prepared under the same conditions as described in Example 13 with 3-methyl-5-(2-morpholin-4-yl-ethyl)-4-oxo-4,5,6,7-tetrahydro-1H-pyrrolo[3,2-c]pyridine-2-carbaldehyde and 5-fluoro-7-bromo-1,3-dihydro-indol-2-one as starting materials to give 2-(7-bromo-5-fluoro-2-oxo-1,2-dihydro-indol-3-ylidenemethyl)-3-methyl-5-(2-morpholin-4-yl-ethyl)-1,5,6,7-tetrahydro-pyrrolo[3,2-c]pyridin-4-one (73 mg, 89.5%) as an orange solid.

MS m/z (ESI): 504[M+1]

¹HNMR (400 MHz, DMSO-d6) 7.892~7.870 (d, 1H, —ArH), 7.809 (s, 1H, —CH), 7.285~7.256 (dd, 1H, —ArH), 3.646~3.612 (t, 2H, —CH₂), 3.061~3.027 (t, 2H, —CH₂), 2.558 (s, 3H, —CH₃)

Example 55

N-{3-[3-Methyl-5-(2-morpholin-4-yl-ethyl)-4-oxo-4,5,6,7-tetrahydro-1H-pyrrolo[3,2-c]pyridin-2-ylmethylene]-2-oxo-2,3-dihydro-1H-indol-5-yl}-formamide

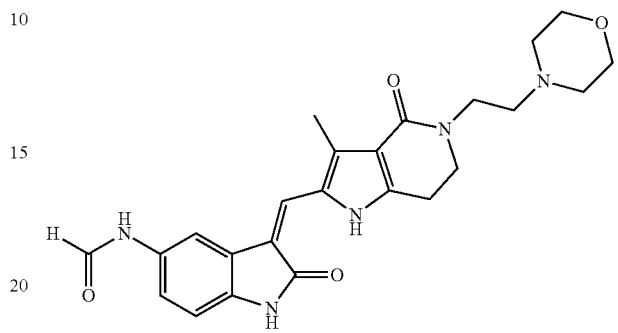

The title compound was prepared under the same conditions as described in Example 13 with 3-methyl-5-(2-morpholin-4-yl-ethyl)-4-oxo-4,5,6,7-tetrahydro-1H-pyrrolo[3,2-c]pyridine-2-carbaldehyde and N-(2-oxo-2,3-dihydro-1H-indol-5-yl)-formamide as starting materials to give N-{3-[3-methyl-5-(2-morpholin-4-yl-ethyl)-4-oxo-4,5,6,7-tetrahydro-1H-pyrrolo[3,2-c]pyridin-2-ylmethylene]-2-oxo-2,3-dihydro-1H-indol-5-yl}-formamide (62 mg, 85.1%) as an orange solid.

MS m/z (ESI): 450[M+1]

¹HNMR (400 MHz, DMSO-d6) 8.248 (s, 1H, —CH), 7.889 (t, 1H, —ArH), 7.515 (s, 1H, —CHO), 7.329~7.308 (m, 1H, —ArH), 3.637~3.603 (t, 2H, —CH₂), 3.025~2.991 (t, 2H, —CH₂).

Example 56

2-(5-Chloro-2-oxo-1,2-dihydro-indol-3-ylidenemethyl)-3-phenyl-1,5,6,7-tetrahydro-pyrrolo[3,2-c]pyridin-4-one

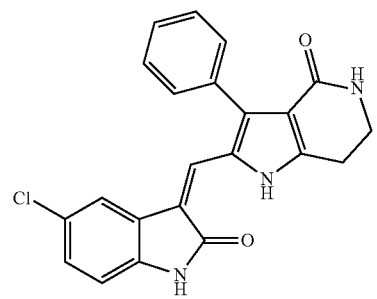 [SMILES: O=C1Nc2ccc(Cl)cc2/C1=C/c1[nH]c2c(c1-c1ccccc1)C(=O)NCC2]

The title compound was prepared under the same conditions as described in Example 41 with 4-oxo-3-phenyl-4,5,6,7-tetrahydro-1H-pyrrolo[3,2-c]pyridine-2-carbaldehyde and 5-chloro-1,3-dihydro-indol-2-one as starting materials to give 2-(5-chloro-2-oxo-1,2-dihydro-indol-3-ylidenemethyl)-3-phenyl-1,5,6,7-tetrahydro-pyrrolo[3,2-c]pyridin-4-one (2.2 mg, 31.9%) as a yellow solid.

MS m/z (ESI): 390[M+1]

¹H NMR (400 MHz, DMSO-d6) 7.428~7.407 (m, 1H, —ArH), 7.174~7.149 (dd, 1H, —ArH), 6.903~6.883 (d, 1H, —ArH), 3.039~3.006 (t, 2H, —CH₂)

Example 57

5-(2-Diethylamino-ethyl)-3-methyl-2-(4-methyl-2-oxo-1,2-dihydro-indol-3-ylidenemethyl)-1,5,6,7-tetrahydro-pyrrolo[3,2-c]pyridin-4-one

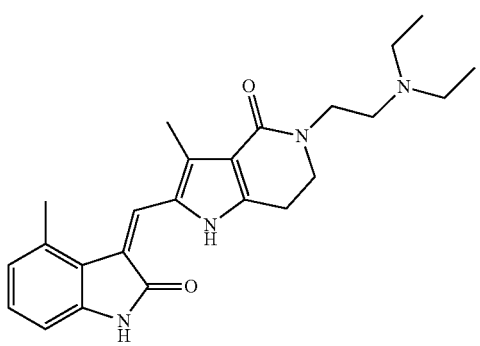 [SMILES: CCN(CC)CCN1CCc2[nH]c(/C=C3\C(=O)Nc4cccc(C)c43)c(C)c2C1=O]

The title compound was prepared under the same conditions as described in Example 1 with 5-(2-diethylamino-ethyl)-3-methyl-4-oxo-4,5,6,7-tetrahydro-1H-pyrrolo[3,2-c]pyridine-2-carbaldehyde and 4-methyl-1,3-dihydro-indole-2-one (prepared according to U.S. Pat. No. 6,114,371) as starting materials to give 5-(2-diethylamino-ethyl)-3-methyl-2-(4-methyl-2-oxo-1,2-dihydro-indol-3-ylidenemethyl)-1,5,6,7-tetrahydro-pyrrolo[3,2-c]pyridin-4-one (40 mg, 52.5%) as a light yellow solid.

MS m/z (ESI): 407[M+1]

¹H NMR (400 MHz, DMSO-d6) 7.697 (s, 1H, —CH), 7.455 (s, 3H, —CH₃), 7.109 (d, 1H, —ArH), 1.060 (s, 2H, —CH₂)

Example 58

2-(5-Chloro-2-oxo-1,2-dihydro-indol-3-ylidenemethyl)-3-(4-fluoro-phenyl)-1,5,6,7-tetrahydro-pyrrolo[3,2-c]pyridin-4-one

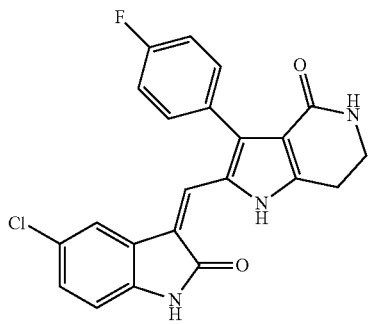 [SMILES: O=C1Nc2ccc(Cl)cc2/C1=C/c1[nH]c2c(c1-c1ccc(F)cc1)C(=O)NCC2]

The title compound was prepared under the same conditions as described in Example 46 with 3-(4-fluoro-phenyl)-4-oxo-4,5,6,7-tetrahydro-1H-pyrrolo[3,2-c]pyridine-2-carbaldehyde and 5-chloro-1,3-dihydro-indol-2-one as starting materials to give 2-(5-chloro-2-oxo-1,2-dihydro-indol-3-ylidenemethyl)-3-(4-fluoro-phenyl)-1,5,6,7-tetrahydro-pyrrolo[3,2-c]pyridin-4-one (32 mg, 34.2%) as a yellow solid.

MS m/z (ESI): 408[M+1]

¹HNMR. (400 MHz, DMSO-d6) 7.426 (s, 1H, —CH), 7.176~7.158 (d, 1H, —ArH), 6.898~6.882 (d, 1H, —ArH), 4.332 (s, 1H, —NH), 3.032~3.006 (t, 2H, —CH₂), 1.066~4.038 (t, 2H, —CH₂)

Example 59

2-[4-(2,3-Difluoro-phenyl)-2-oxo-1,2-dihydro-indol-3-ylidenemethyl]-3-methyl-5-(2-pyrrolidin-1-yl-ethyl)-1,5,6,7-tetrahydro-pyrrolo[3,2-c]pyridin-4-one

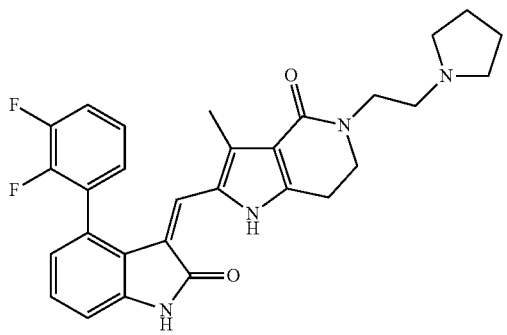 [SMILES: Cc1c(/C=C2\C(=O)Nc3cccc(-c4cccc(F)c4F)c32)[nH]c2c1C(=O)N(CCN1CCCC1)CC2]

The title compound was prepared under the same conditions as described in Example 13 with 3-methyl-4-oxo-5-(2-pyrrolidin-1-yl-ethyl)-4,5,6,7-tetrahydro-1H-pyrrolo[3,2-c]pyridine-2-carbaldehyde and 4-(2,3-difluoro-phenyl)-1,3-dihydro-indol-2-one (prepared according to WO2002055517) as starting materials to give 2-[4-(2,3-difluoro-phenyl)-2-oxo-1,2-dihydro-indol-3-ylidenemethyl]-3-methyl-5-(2-pyrrolidin-1-yl-ethyl)-1,5,6,7-tetrahydro-pyrrolo[3,2-c]pyridin-4-one (30 mg, 33.3%) as a yellow solid.

MS m/z (ESI): 503[M+1]

¹H NMR (400 MHz, DMSO-d6). 7.656~7.604 (dd, 1H, —ArH), 7.450~7.408 (dd, 1H, —ArH), 7.330~7.302 (t, 1H, —ArH), 7.266~7.234 (t, 1H, —ArH), 7.008~6.992 (d, 1H, —ArH), 6.888~6.874 (d, 1H, —ArH), 6.706 (s, 1H, —CH), 3.576~3.550 (t, 2H, —CH₂), 3.484~3.456 (t, 2H, —CH₂), 2.970~2.944 (t, 2H, —CH₂), 2.546 (t, 2H, —CH₂), 1.876 (s, 3H, —CH₃), 1.656 (q, 4H, 2×CH₂)

Example 60

N-{5-Fluoro-3-[3-methyl-4-oxo-5-(2-piperidin-1-yl-ethyl)-4,5,6,7-tetrahydro-1H-pyrrolo[3,2-c]pyridin-2-ylmethylene]-2-oxo-2,3-dihydro-1H-indol-6-yl}-2-methoxy-acetamide

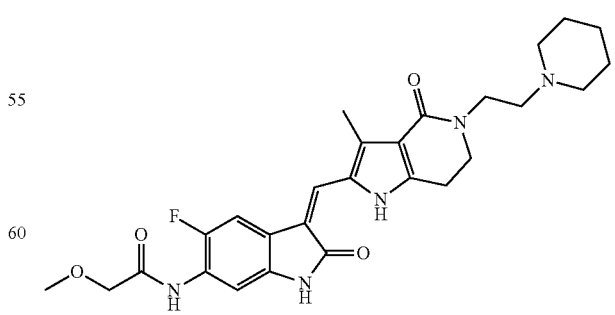

The title compound was prepared under the same conditions as described in Example 25 with 3-methyl-4-oxo-5-(2-piperidin-1-yl-ethyl)-4,5,6,7-tetrahydro-1H-pyrrolo[3,2-c]

pyridine-2-carbaldehyde and N-(5-fluoro-2-oxo-2,3-dihydro-1H-indol-6-yl)-2-methoxy-acetamideas starting materials to give N-{5-fluoro-3-[3-methyl-4-oxo-5-(2-piperidin-1-yl-ethyl)-4,5,6,7-tetrahydro-1H-pyrrolo[3,2-c]pyridin-2-ylmethylene]-2-oxo-2,3-dihydro-1H-indol-6-yl}-2-methoxy-acetamide (55 mg, 55.0%) as a brown solid.

MS m/z (ESI): 510[M+1]

¹HNMR (400 MHz, DMSO-d6) 7.749~7.822 (d, 1H, —ArH), 7.550~7.543 (d, 1H, —ArH), 4.046~4.052 (d, 2H, —OCH₂), 3.613~3.579 (t, 2H, —CH₂), 3.395 (s, 3H, —CH₃), 3.001~3.967 (t, 2H, —CH₂), 2.084 (s, 1H, —NH), 1.480~1.468 (m, 4H, 2×-CH₂), 1.380~4.368 (d, 2H, —CH₂)

Example 61

N-{5-Fluoro-3-[3-methyl-4-oxo-5-(2-piperidin-1-yl-ethyl)-4,5,6,7-tetrahydro-1H-pyrrolo[3,2-c]pyridin-2-ylmethylene]-2-oxo-2,3-dihydro-1H-indol-6-yl}-2-hydroxy-acetamide

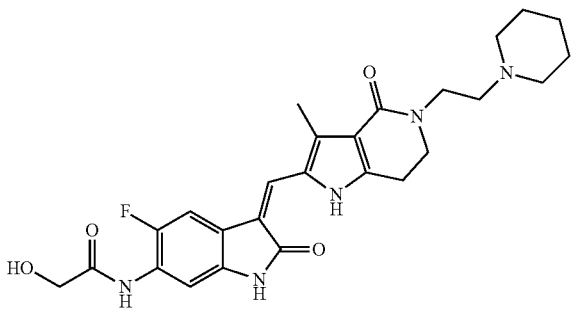 [SMILES: Cc1c(/C=C2\C(=O)Nc3cc(NC(=O)CO)c(F)cc32)[nH]c2c1C(=O)N(CCN1CCCCC1)CC2]

The title compound was prepared under the same conditions as described in Example 25 with 3-methyl-4-oxo-5-(2-piperidin-1-yl-ethyl)-4,5,6,7-tetrahydro-1H-pyrrolo[3,2-c]pyridine-2-carbaldehyde and N-(5-fluoro-2-oxo-2,3-dihydro-1H-indol-6-yl)-2-methoxy-acetamide (prepared according to WO2002055517) as starting materials to give N-{5-fluoro-3-[3-methyl-4-oxo-5-(2-piperidin-1-yl-ethyl)-4,5,6,7-tetrahydro-1H-pyrrolo[3,2-c]pyridin-2-ylmethylene]-2-oxo-2,3-dihydro-1H-indol-6-yl}-2-hydroxy-acetamide (52 mg, 52.7%) as a yellow solid.

MS m/z (ESI): 496[M+1]

¹HNMR. (400 MHz, DMSO-d6) 7.877~7.849 (d, 1H, —ArH), 7.725~7.709 (d, 1H, —ArH), 4.036 (s, 2H, —CH₂), 3.617~3.585 (t, 2H, —CH₂), 3.510~3.477 (t, 2H, —CH₂), 2.086 (s, 4H, 2×-CH₂), 1.482~1.472 (t, 4H, 2×-CH₂), 1.382~1.370 (t, 2H, —CH₂), 1.151 (s, 1H, —OH)

Example 62

2-(6-Methoxy-2-oxo-1,2-dihydro-indol-3-ylidenemethyl)-3-methyl-5-(2-piperidin-1-yl-ethyl)-1,5,6,7-tetrahydro-pyrrolo[3,2-c]pyridin-4-one

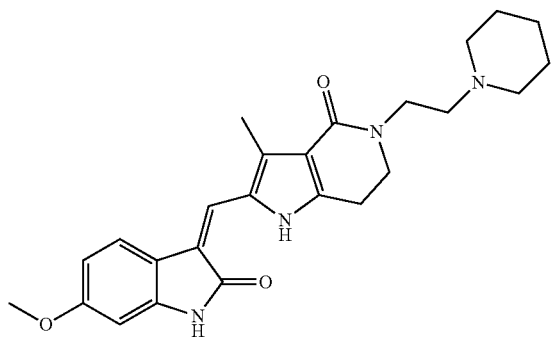 [SMILES: COc1ccc2c(c1)NC(=O)/C2=C\c1[nH]c2c(c1C)C(=O)N(CCN1CCCCC1)CC2]

The title compound was prepared under the same conditions as described in Example with 3-methyl-4-oxo-5-(2-piperidin-1-yl-ethyl)-4,5,6,7-tetrahydro-1H-pyrrolo[3,2-c]pyridine-2-carbaldehyde and 6-methoxy-1,3-dihydro-indol-2-one (prepared according to Journal of Organic Chemistry, 70(5), 1828-1834, 2005) starting materials to give 2-(6-methoxy-2-oxo-1,2-dihydro-indol-3-ylidenemethyl)-3-methyl-5-(2-piperidin-1-yl-ethyl)-1,5,6,7-tetrahydro-pyrrolo[3,2-c]pyridin-4-one (51 mg, 61.8%) as an orange solid.

MS m/z (ESI): 435[M+1]

¹HNMR (400 MHz, DMSO-d6) 7.690~7.669 (d, 1H, —ArH), 6.601~6.574 (dd, 1H, —ArH), 6.477~6.471 (d, 1H, —ArH), 3.763 (s, 3H, —OCH₃), 3.611~3.576 (t, 2H, —CH₂), 2.984~2.951 (t, 2H, —CH₂), 2.087 (s, 3H, —CH₃), 1.492~1.466 (t, 4H, 2×-CH₂), 1.381~1.368 (d, 2H, —CH₂)

Example 63

2-[4-(2,6-Difluoro-phenyl)-2-oxo-1,2-dihydro-indol-3-ylidenemethyl]-3-methyl-5-(2-piperidin-1-yl-ethyl)-1,5,6,7-tetrahydro-pyrrolo[3,2-c]pyridin-4-one

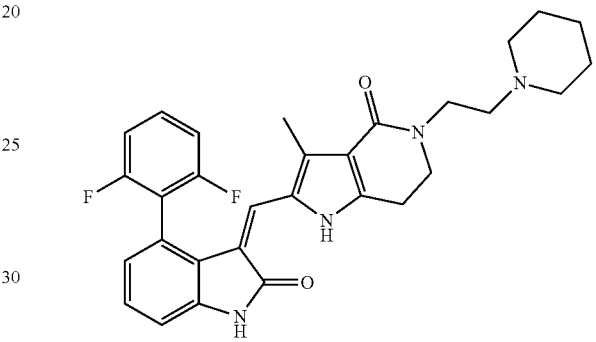

The title compound was prepared under the same conditions as described in Example 25 with 3-methyl-4-oxo-5-(2-piperidin-1-yl-ethyl)-4,5,6,7-tetrahydro-1H-pyrrolo[3,2-c]pyridine-2-carbaldehyde and 4-(2,6-difluoro-phenyl)-1,3-dihydro-indol-2-one (prepared according to WO2002055517) as starting materials to give 2-[4-(2,6-difluoro-phenyl)-2-oxo-1,2-dihydro-indol-3-ylidenemethyl]-3-methyl-5-(2-piperidin-1-yl-ethyl)-1,5,6,7-tetrahydro-pyrrolo[3,2-c]pyridin-4-one (70 mg, 70.7%) as an orange solid.

MS m/z (ESI): 517[M+1]

¹HNMR (400 MHz, DMSO-d6) 7.681~7.639 (t, 1H, —ArH), 7.285~7.247 (t, 1H, —ArH), 7.029~7.009 (d, 1H, —ArH), 6.912~6.894 (t, 1H, —ArH), 6.641 (s, 1H, —CH), 3.572~3.539 (t, 2H, —CH₂), 2.974~2.941 (t, 2H, —CH₂), 1.842 (s, 3H, —CH₃), 1.462~4.365 (t, 4H, 2×-CH₂)

Example 64

2-[4-(3-Fluoro-phenyl)-2-oxo-1,2-dihydro-indol-3-ylidenemethyl]-3-methyl-5-(2-piperidin-1-yl-ethyl)-1,5,6,7-tetrahydro-pyrrolo[3,2-c]pyridin-4-one

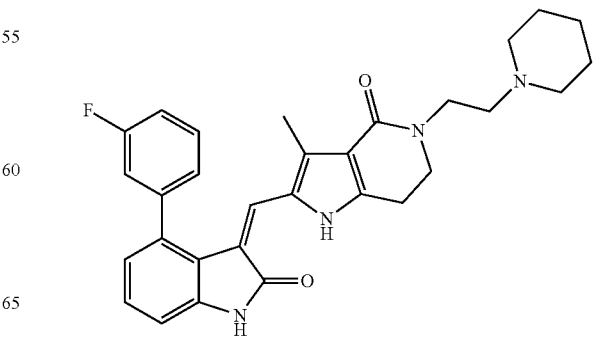

The title compound was prepared under the same conditions as described in Example 25 with 3-methyl-4-oxo-5-(2-piperidin-1-yl-ethyl)-4,5,6,7-tetrahydro-4H-pyrrolo[3,2-c]pyridine-2-carbaldehyde and 4-(3-fluoro-phenyl)-1,3-dihydro-indol-2-one (prepared according to WO2002055517) as starting materials to give 2-[4-(3-fluoro-phenyl)-2-oxo-1,2-dihydro-indol-3-ylidenemethyl]-3-methyl-5-(2-piperidin-1-yl-ethyl)-1,5,6,7-tetrahydro-pyrrolo[3,2-c]pyridin-4-one (63 mg, 60.7%) as an orange solid.

MS m/z (ESI): 499[M+1]

¹HNMR (400 MHz, DMSO-d6) 7.591~7.571 (dd, 1H, —ArH), 7.235~7.197 (t, 1H, —ArH), 6.983~6.945 (d, 1H, —ArH), 3.564~3.531 (t, 2H, —CH₂), 2.957~2.923 (t, 2H, —CH₂), 1.454~4.441 (t, 4H, 2×-CH₂), 1.072~1.037 (t, 2H, —CH₂)

Example 65

N-{5-Fluoro-3-[3-(4-fluoro-phenyl)-4-oxo-4,5,6,7-tetrahydro-1H-pyrrolo[3,2-c]pyridin-2-ylmethylene]-2-oxo-2,3-dihydro-1H-indol-6-yl}-2-hydroxy-acetamide

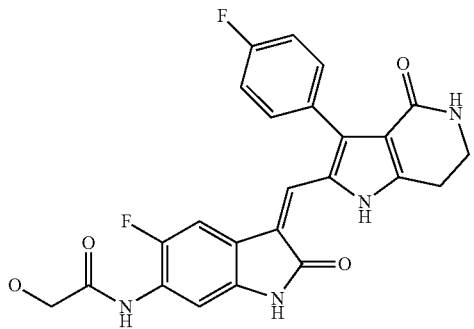 [SMILES: O=C(CO)Nc1cc2c(cc1F)/C(=C/c1[nH]c3c(c1-c1ccc(F)cc1)C(=O)NCC3)C(=O)N2]

The title compound was prepared under the same conditions as described in Example 46 with 3-(4-fluoro-phenyl)-4-oxo-4,5,6,7-tetrahydro-4H-pyrrolo[3,2-c]pyridine-2-carbaldehyde and N-(5-fluoro-2-oxo-2,3-dihydro-1H-indol-6-yl)-2-hydroxy-acetamide as starting materials to give N-{5-fluoro-3-[3-(4-fluoro-phenyl)-4-oxo-4,5,6,7-tetrahydro-1H-pyrrolo[3,2-c]pyridin-2-ylmethylene]-2-oxo-2,3-dihydro-1H-indol-6-yl}-2-hydroxy-acetamide (72 mg, 80.6%), as a red solid.

MS m/z (ESI): 465[M+1]

¹HNMR (400 MHz, DMSO-d6) 9.294 (s, 1H, —NH), 7.944 (s, 1H, —CH), 7.742~7.726 (d, 1H, —ArH), 7.282~7.237 (d, 1H, —ArH), 4.027 (s, 1H, —NH), 3.019~2.985 (t, 2H, —CH₂)

Example 66

N-{3-[3-(4-Fluoro-phenyl)-4-oxo-4,5,6,7-tetrahydro-1H-pyrrolo[3,2-c]pyridin-2-ylmethylene]-2-oxo-2,3-dihydro-1H-indol-5-yl}-2-hydroxy-acetamide

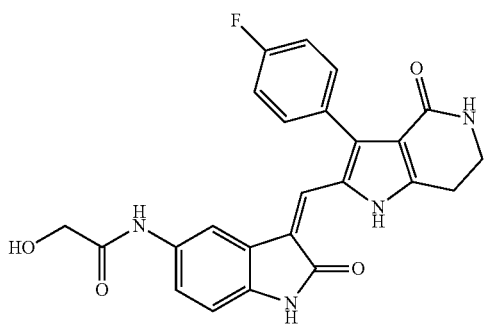 [SMILES: O=C(CO)Nc1ccc2c(c1)/C(=C/c1[nH]c3c(c1-c1ccc(F)cc1)C(=O)NCC3)C(=O)N2]

The title compound was prepared under the same conditions as described in Example 46 with 3-(4-fluoro-phenyl)-4-oxo-4,5,6,7-tetrahydro-1H-pyrrolo[3,2-c]pyridine-2-carbaldehyde and 2-hydroxy-N-(2-oxo-2,3-dihydro-1H-indol-5-yl)-acetamide as starting materials to give N-{3-[3-(4-fluoro-phenyl)-4-oxo-4,5,6,7-tetrahydro-1H-pyrrolo[3,2-c]pyridin-2-ylmethylene]-2-oxo-2,3-dihydro-1H-indol-5-yl}-2-hydroxy-acetamide (50 mg, 47.0%) as a red solid.

MS m/z (ESI): 447[M+1]

¹H NMR (400 MHz, DMSO-d6) 14.052 (s, 1H, —NH), 9.552 (s, 1H, —NH), 7.618 (s, 1H, —NH), 7.420~7.376 (d, 1H, —ArH), 7.110 (s, 1H, —CH), 6.839~6.818 (d, 1H, —ArH), 5.604~5.575 (t, 2H, —CH₂)

Example 67

N-{5-Fluoro-3-[3-(4-fluoro-phenyl)-4-oxo-4,5,6,7-tetrahydro-1H-pyrrolo[3,2-c]pyridin-2-ylmethylene]-2-oxo-2,3-dihydro-1H-indol-6-yl}-2-methoxy-acetamide

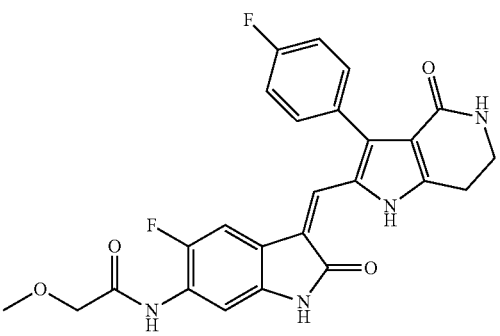 [SMILES: COCC(=O)Nc1cc2c(cc1F)/C(=C/c1[nH]c3c(c1-c1ccc(F)cc1)C(=O)NCC3)C(=O)N2]

The title compound was prepared under the same conditions as described in Example 46 with 3-(4-fluoro-phenyl)-4-oxo-4,5,6,7-tetrahydro-1H-pyrrolo[3,2-c]pyridine-2-carbaldehyde and N-(5-fluoro-2-oxo-2,3-dihydro-1H-indol-6-yl)-2-methoxy-acetamide as starting materials to give N-{5-fluoro-3-[3-(4-fluoro-phenyl)-4-oxo-4,5,6,7-tetrahydro-1H-pyrrolo[3,2-c]pyridin-2-ylmethylene]-2-oxo-2,3-dihydro-1H-indol-6-yl}-2-methoxy-acetamide (50 mg, 54.4%) as a yellow solid.

MS m/z (ESI): 479[M+1]

¹H NMR (400 MHz, DMSO-d6) 9.293 (s, 1H, —NH), 7.594~7.578 (d, 1H, —ArH), 7.167 (s, 1H, —CH), 4.332 (s, 2H, 2×-NH), 3.020~1.987 (t, 2H, —CH₂)

Example 68

2-[4-(3-Chloro-2-fluoro-phenyl)-2-oxo-1,2-dihydro-indol-3-ylidenemethyl]-3-methyl-5-(2-pyrrolidin-1-yl-ethyl)-1,5,6,7-tetrahydro-pyrrolo[3,2-e]pyridin-4-one

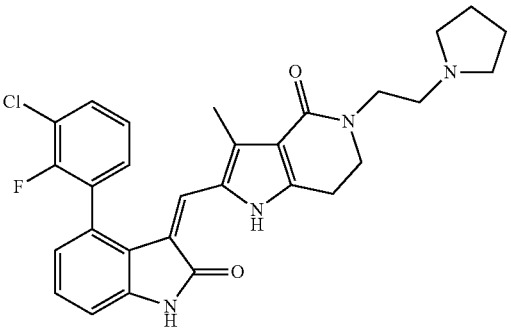 [SMILES: Cc1c(/C=C2\C(=O)Nc3cccc(-c4cccc(Cl)c4F)c32)[nH]c2c1C(=O)N(CCN1CCCC1)CC2]

The title compound was prepared under the same conditions as described in Example 13 with 3-methyl-4-oxo-5-(2-pyrrolidin-1-yl-ethyl)-4,5,6,7-tetrahydro-1H-pyrrolo[3,2-c]pyridine-2-carbaldehyde and 4-(3-chloro-2-fluoro-phenyl)-1,3-dihydro-indol-2-one (prepared according to WO2002055517) as starting materials to give 2-[4-(3-chloro-2-fluoro-phenyl)-2-oxo-1,2-dihydro-indol-3-ylidenemethyl]-3-methyl-5-(2-pyrrolidin-1-yl-ethyl)-1,5,6,7-tetrahydro-pyrrolo[3,2-c]pyridin-4-one (24 mg, 28.5%) as a yellow solid.

MS m/z (ESI): 520[M+1]

¹HNMR (400 MHz, DMSO-d6) 7.278~7.239 (t, 1H, —ArH), 7.016~6.997 (d, 1H, —ArH), 6.885~6.866 (d, 1H, —ArH), 6.656~6.652 (d, 1H, —ArH), 3.579~3.545 (t, 2H, —CH₂), 2.972~2.938 (t, 2H, —CH₂), 1.872 (s, 3H, —CH₃), 1.650 (m, 4H, 2×-CH₂)

Example 69

2-(4-Bromo-2-oxo-1,2-dihydro-indol-3-ylidenemethyl)-3-methyl-5-(2-pyrrolidin-1-yl-ethyl)-1,5,6,7-tetrahydro-pyrrolo[3,2-c]pyridin-4-one

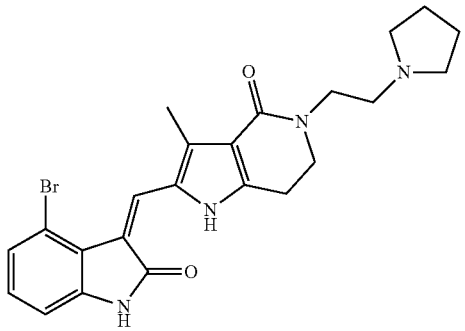 [SMILES: Cc1c(/C=C2\C(=O)Nc3cccc(Br)c32)[nH]c2c1C(=O)N(CCN1CCCC1)CC2]

The title compound was prepared under the same conditions as described in Example 13 with 3-methyl-4-oxo-5-(2-pyrrolidin-1-yl-ethyl)-4,5,6,7-tetrahydro-1H-pyrrolo[3,2-c]pyridine-2-carbaldehyde and 4-bromo-1,3-dihydro-indol-2-one (prepared according to US20030225127) as starting materials to give 2-(4-bromo-2-oxo-1,2-dihydro-indol-3-ylidenemethyl)-3-methyl-5-(2-pyrrolidin-1-yl-ethyl)-1,5,6,7-tetrahydro-pyrrolo[3,2-c]pyridin-4-one (44 mg, 74.4%) as a yellow solid.

MS m/z (ESI): 470[M+1]

¹HNMR (400 MHz, DMSO-d6) 7.238~7.218 (d, 1H, —ArH), 7.101~7.060 (t, 1H, —ArH), 6.959~6.939 (d, 1H, —ArH), 3.631~3.598 (t, 2H, —CH₂), 3.032~3.001 (t, 2H, —CH₂), 2.482 (s, 3H, —CH₃), 1.682 (m, 4H, 2×-CH₂)

Example 70

3-Methyl-2-(4-methyl-2-oxo-1,2-dihydro-indol-3-ylidenemethyl)-5-(2-pyrrolidin-1-yl-ethyl)-1,5,6,7-tetrahydro-pyrrolo[3,2-c]pyridin-4-one

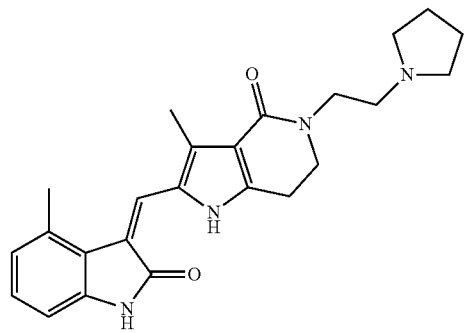 [SMILES: Cc1cccc2c1/C(=C/c1[nH]c3c(c1C)C(=O)N(CCN1CCCC1)CC3)C(=O)N2]

The title compound was prepared under the same conditions as described in Example 13 with 3-methyl-4-oxo-5-(2-pyrrolidin-1-yl-ethyl)-4,5,6,7-tetrahydro-1H-pyrrolo[3,2-c]pyridine-2-carbaldehyde and 4-methyl-1,3-dihydro-indol-2-one (prepared according to U.S. Pat. No. 6,114,371) as starting materials to give 3-methyl-2-(4-methyl-2-oxo-1,2-dihydro-indol-3-ylidenemethyl)-5-(2-pyrrolidin-1-yl-ethyl)-1,5,6,7-tetrahydro-pyrrolo[3,2-c]pyridin-4-one (32 mg, 62.8%) as a yellow solid.

MS m/z (ESI): 405[M+1]

¹HNMR (400 MHz, DMSO-d6) 7.555 (s, 1H, —CH), 7.077~7.039 (t, 1H, —ArH), 6.837~6.818 (d, 1H, —ArH), 6.788~6.769 (d, 1H, —ArH), 3.623~3.588 (t, 2H, —CH₂), 3.523~3.488 (t, 2H, —CH₂), 3.007~2.974 (t, 2H, —CH₂), 1.668 (m, 4H, 2×-CH₂)

Example 71

3-Methyl-2-(2-oxo-4-piperidin-4-yl-1,2-dihydro-indol-3-ylidenemethyl)-5-(2-pyrrolidin-1-yl-ethyl)-1,5,6,7-tetrahydro-pyrrolo[3,2-c]pyridin-4-one

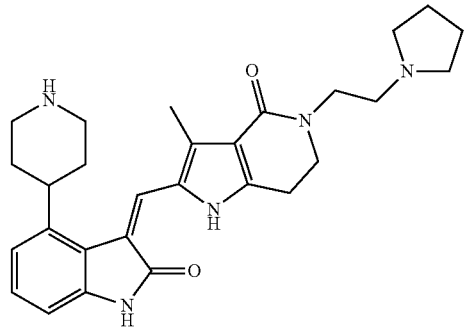 [SMILES: Cc1c(/C=C2\C(=O)Nc3cccc(C4CCNCC4)c32)[nH]c2c1C(=O)N(CCN1CCCC1)CC2]

The title compound was prepared under the same conditions as described in Example 13 with 3-methyl-4-oxo-5-(2-pyrrolidin-1-yl-ethyl)-4,5,6,7-tetrahydro-1H-pyrrolo[3,2-c]pyridine-2-carbaldehyde and 4-piperidin-4-yl-1,3-dihydroindol-2-one as starting materials to give 3-methyl-2-(2-oxo-4-piperidin-4-yl-1,2-dihydro-indol-3-ylidenemethyl)-5-(2-pyrrolidin-1-yl-ethyl)-1,5,6,7-tetrahydro-pyrrolo[3,2-c]pyridin-4-one (18 mg, 30.2%) as a yellow solid.

MS m/z (ESI): 474[M+1]

$^1$H NMR (400 MHz, DMSO-d6) 7.53 (d, 1H, ArH), 7.35 (s, 1H, CH), 6.35 (d, 1H, ArH), 5.30 (br s, 1H, NH2), 3.60 (t, 2H, CH2), 3.51 (t, 2H, CH2), 2.96 (t, 2H, CH2), 2.60 (t, 2H, CH2), 2.51 (s, 3H, CH3), 2.47 (q, 4H, 2×NCH2), 1.64~1.69 (m, 4H, 2×CH2).

Example 72

N-{5-Fluoro-3-[3-methyl-4-oxo-5-(2-pyrrolidin-1-yl-ethyl)-4,5,6,7-tetrahydro-1H-pyrrolo[3,2-c]pyridin-2-ylmethylene]-2-oxo-2,3-dihydro-1H-indol-6-yl}-2-methoxy-acetamide

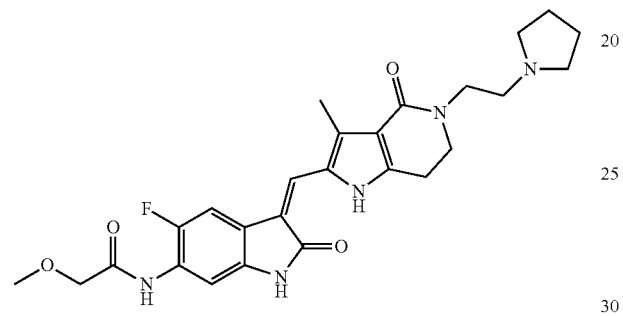

The title compound was prepared under the same conditions as described in Example 13 with 3-methyl-4-oxo-5-(2-pyrrolidin-1-yl-ethyl)-4,5,6,7-tetrahydro-1H-pyrrolo[3,2-c]pyridine-2-carbaldehyde and N-(5-fluoro-2-oxo-2,3-dihydro-1H-indol-6-yl)-2-methoxy-acetamide as starting materials to give N-{5-fluoro-3-[3-methyl-4-oxo-5-(2-pyrrolidin-1-yl-ethyl)-4,5,6,7-tetrahydro-1H-pyrrolo[3,2-c]pyridin-2-ylmethylene]-2-oxo-2,3-dihydro-1H-indol-6-yl}-2-methoxy-acetamide (51 mg, 81.7%) as a brown solid.

MS m/z (ESI): 496[M+1]

$^1$HNMR (400 MHz, DMSO-d6) 7.859~7.831 (d, 1H, —ArH), 7.661 (s, 1H, —CH), 7.558~7.542 (d, 1H, —ArH), 3.621~3.587 (t, 2H, —CH$_2$), 3.520~3.486 (t, 2H, —CH$_2$), 3.391 (s, 3H, —OCH$_3$), 3.004-2.971 (t, 2H, —CH$_2$), 1.669 (m, 4H. 2×-CH$_2$)

Example 73

N-{5-Fluoro-3-[3-methyl-4-oxo-5-(2-pyrrolidin-1-yl-ethyl)-4,5,6,7-tetrahydro-1H-pyrrolo[3,2-c]pyridin-2-ylmethylene]-2-oxo-2,3-dihydro-1H-indol-6-yl}-2-hydroxy-acetamide

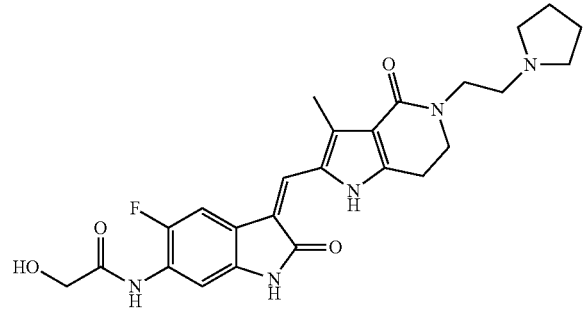 [SMILES: Cc1c(/C=C2\C(=O)Nc3cc(NC(=O)CO)c(F)cc32)[nH]c2c1C(=O)N(CCN1CCCC1)CC2]

The title compound was prepared under the same conditions as described in Example 13 with 3-methyl-4-oxo-5-(2-pyrrolidin-1-yl-ethyl)-4,5,6,7-tetrahydro-1H-pyrrolo[3,2-c]pyridine-2-carbaldehyde and N-(5-fluoro-2-oxo-2,3-dihydro-1H-indol-6-yl)-2-hydroxy-acetamide as starting materials to give N-{5-fluoro-3-[3-methyl-4-oxo-5-(2-pyrrolidin-1-yl-ethyl)-4,5,6,7-tetrahydro-1H-pyrrolo[3,2-c]pyridin-2-ylmethylene]-2-oxo-2,3-dihydro-1H-indol-6-yl}-2-hydroxy-acetamide (40 mg, 43%) as a yellow solid.

MS m/z (ESI): 482[M+1]

$^1$HNMR (400 MHz, DMSO-d6) 7.887~7.859 (d, 1H, —ArH), 7.719~7.703 (d, 1H, —ArH), 7.660 (s, 1H, —CH), 4.046~4.019 (d, 2H, —CH$_2$), 3.621~3.588 (t, 2H, —CH$_2$), 3.527~3.492 (t, 2H, —CH$_2$), 3.008~2.974 (t, 2H, —CH$_2$)

Example 74

2-[4-(4-Chloro-2-fluoro-phenyl)-2-oxo-1,2-dihydro-indol-3-ylidenemethyl]-3-methyl-5-(2-pyrrolidin-1-yl-ethyl)-1,5,6,7-tetrahydro-pyrrolo[3,2-c]pyridin-4-one

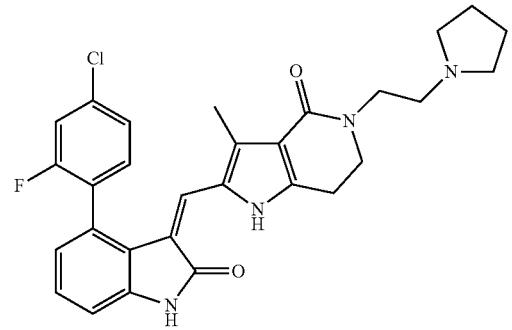 [SMILES: Cc1c(/C=C2\C(=O)Nc3cccc(-c4ccc(Cl)cc4F)c32)[nH]c2c1C(=O)N(CCN1CCCC1)CC2]

The title compound was prepared under the same conditions as described in Example 13 with 3-methyl-4-oxo-5-(2-pyrrolidin-1-yl-ethyl)-4,5,6,7-tetrahydro-1H-pyrrolo[3,2-c]pyridine-2-carbaldehyde and 4-(4-chloro-2-fluoro-phenyl)-1,3-dihydro-indol-2-one (prepared according to WO2002055517) as starting materials to give 2-[4-(4-chloro-2-fluoro-phenyl)-2-oxo-1,2-dihydro-indol-3-ylidenemethyl]-3-methyl-5-(2-pyrrolidin-1-yl-ethyl)-1,5,6,7-tetrahydro-pyrrolo[3,2-c]pyridin-4-one (35 mg, 51.6%) as a yellow solid.

MS m/z (ESI): 520[M+1]

$^1$H NMR (400 MHz, DMSO-d6) 7.694~7.676 (d, 1H, —ArH), 7.530~7.492 (m, 2H, 2×-ArH), 7.254~7.222 (t, 1H, —ArH), 6.990~6.976 (d, 1H, —ArH), 6.866~6.850 (d, 1H, —ArH), 6.606 (s, 1H, —CH), 3.578~3.550 (t, 2H, —CH$_2$), 3.488~3.462 (t, 2H, —CH$_2$), 2.970~2.944 (t, 2H, —CH$_2$), 1.892 (s, 3H, —CH$_3$)

Example 75

2-[4-(2-Hydroxy-ethyl)-2-oxo-1,2-dihydro-indol-3-ylidenemethyl]-3-methyl-5-(2-pyrrolidin-1-yl-ethyl)-1,5,6,7-tetrahydro-pyrrolo[3,2-c]pyridin-4-one

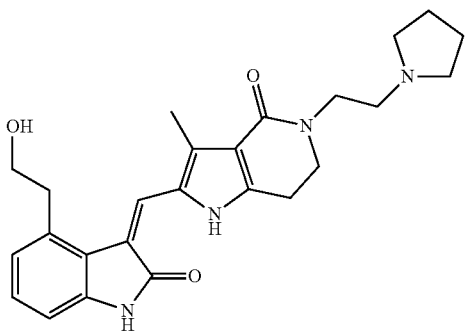 [SMILES: Cc1c(/C=C2\C(=O)Nc3cccc(CCO)c32)[nH]c2c1C(=O)N(CCN1CCCC1)CC2]

The title compound was prepared under the same conditions as described in Example with 3-methyl-4-oxo-5-(2-pyrrolidin-1-yl-ethyl)-4,5,6,7-tetrahydro-1H-pyrrolo[3,2-c]pyridine-2-carbaldehyde and 4-(2-hydroxy-ethyl)-1,3-dihydro-indol-2-one (prepared according to US2004186160) as starting materials to give 2-[4-(2-hydroxy-ethyl)-2-oxo-1,2-dihydro-indol-3-ylidenemethyl]-3-methyl-5-(2-pyrrolidin-1-yl-ethyl)-1,5,6,7-tetrahydro-pyrrolo[3,2-c]pyridin-4-one (30 mg, 30.0%) as a yellow solid.

MS m/z (ESI): 435[M+1]

$^1$H NMR (400 MHz, DMSO-d6) 7.644 (s, 1H, —CH), 7.078~7.046 (t, 1H, —ArH), 6.842~6.826 (t, 1H, —ArH), 6.780~6.764 (t, 1H, —ArH), 4.880~4.862 (t, 1H, —OH), 3.746~3.706 (q, 2H, —CH$_2$), 3.620~3.592 (t, 2H, —CH$_2$), 3.520~3.492 (t, 2H, —CH$_2$), 3.102~3.072 (t, 2H, —CH$_2$), 3.006~2.978 (t, 2H, —CH$_2$), 1.668 (m, 4H, 2×-CH$_2$)

Example 76

2-(5-Bromo-2-oxo-1,2-dihydro-pyrrolo[2,3-b]pyridin-3-ylidenemethyl)-3-methyl-5-(2-pyrrolidin-1-yl-ethyl)-1,5,6,7-tetrahydro-pyrrolo[3,2-c]pyridin-4-one

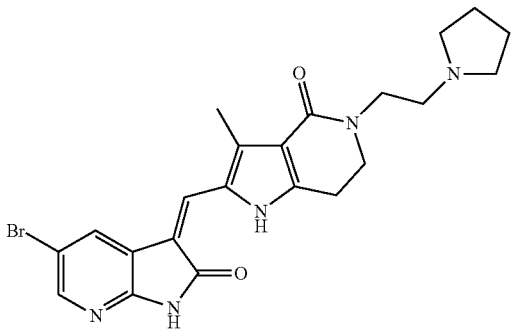 [SMILES: Cc1c(/C=C2\C(=O)Nc3ncc(Br)cc32)[nH]c2c1C(=O)N(CCN1CCCC1)CC2]

The title compound was prepared under the same conditions as described in Example 13 with 3-methyl-4-oxo-5-(2-pyrrolidin-1-yl-ethyl)-4,5,6,7-tetrahydro-1H-pyrrolo[3,2-c]pyridine-2-carbaldehyde and 5-bromo-1,3-dihydro-pyrrolo[2,3-b]pyridin-2-one as starting materials to give 2-(5-bromo-2-oxo-1,2-dihydro-pyrrolo[2,3-b]pyridin-3-ylidenemethyl)-3-methyl-5-(2-pyrrolidin-1-yl-ethyl)-1,5,6,7-tetrahydro-pyrrolo[3,2-c]pyridin-4-one (35 mg, 37.0%) as a yellow solid.

MS m/z (ESI): 471[M+1]

$^1$H NMR (400 MHz, DMSO-d6) 8.116~8.112 (d, 1H, —ArH), 7.886 (s, 1H, —ArH), 3.628~3.602 (t, 2H, —CH$_2$), 3.522~3.494 (t, 2H, —CH$_2$), 3.036~3.008 (t, 2H, —CH$_2$), 2.582~2.534 (m, 4H, 2×-CH$_2$), 2.502~2.482 (m, 4H, 2×-CH$_2$)

Example 77

2-(5-Methoxy-2-oxo-1,2-dihydro-indol-3-ylidenemethyl)-3-methyl-5-(2-pyrrolidin-1-yl-ethyl)-1,5,6,7-tetrahydro-pyrrolo[3,2-c]pyridin-4-one

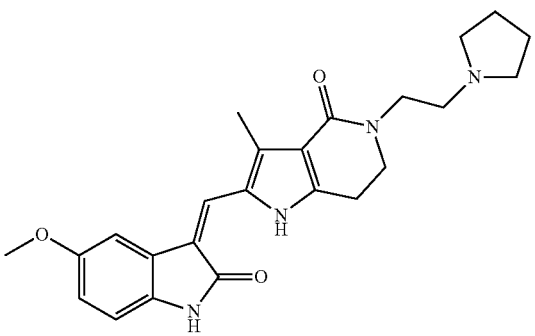 [SMILES: COc1ccc2c(c1)/C(=C/c1[nH]c3c(c1C)C(=O)N(CCN1CCCC1)CC3)C(=O)N2]

The title compound was prepared under the same conditions as described in Example 13 with 3-methyl-4-oxo-5-(2-pyrrolidin-1-yl-ethyl)-4,5,6,7-tetrahydro-1H-pyrrolo[3,2-c]pyridine-2-carbaldehyde and 5-methoxy-1,3-dihydro-indol-2-one (prepared according to U.S. Pat. No. 6,114,371) as starting materials to give 2-(5-methoxy-2-oxo-1,2-dihydro-indol-3-ylidenemethyl)-3-methyl-5-(2-pyrrolidin-1-yl-ethyl)-1,5,6,7-tetra hydro-pyrrolo[3,2-c]pyridin-4-one (30 mg, 33.0%) as a yellow solid.

MS m/z (ESI): 421[M+1]

$^1$HNMR (400 MHz, DMSO-d6) 7.694~7.676 (d, 1H, —ArH), 7.496 (s, 1H, —CH), 6.594~6.572 (d, 1H, —ArH), 6.454~6.450 (d, 1H, —ArH), 3.762 (s, 3H, —CH$_3$), 3.612~3.584 (t, 2H, —CH$_2$), 3.520~3.492 (t, 2H, —CH$_2$), 2.982~2.956 (t, 2H, —CH$_2$), 1.676 (m, 4H, 2×-CH$_2$)

Example 78

N-[5-Fluoro-2-oxo-3-(4-oxo-3-phenyl-4,5,6,7-tetrahydro-1H-pyrrolo[3,2-c]pyridin-2-ylmethylene)-2,3-dihydro-1H-indol-6-yl]-2-hydroxy-acetamide

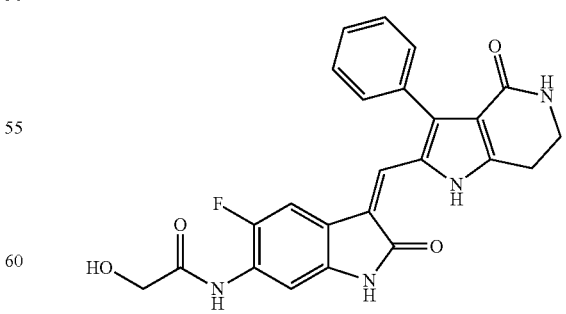

The title compound was prepared under the same conditions as described in Example 41 with 4-oxo-3-phenyl-4,5,6,7-tetrahydro-1H-pyrrolo[3,2-c]pyridine-2-carbaldehyde and N-(5-fluoro-2-oxo-2,3-dihydro-1H-indol-6-yl)-2-hydroxyacetamideas starting materials to give N-[5-fluoro-2-oxo-3-(4-oxo-3-phenyl-4,5,6,7-tetrahydro-1H-pyrrolo[3,2-c]pyridin-2-ylmethylene)-2,3-dihydro-1H-indol-6-yl]-2-hydroxyacetamide (39 mg, 92%) as a red solid.

MS m/z (ESI): 447[M+1]

$^1$H NMR (400 MHz, DMSO-d6) 7.946 (s, 1H, —NH), 7.750~7.733 (d, 1H, —ArH), 7.241~7.214 (d, 1H, —ArH), 7.173 (s, 1H, —ArH), 4.028 (s, 2H, —CH$_2$), 3.027~2.993 (t, 2H, —CH$_2$)

Example 79

2-(7-Bromo-5-fluoro-2-oxo-1,2-dihydro-indol-3-ylidenemethyl)-3-methyl-5-(2-pyrrolidin-1-yl-ethyl)-1,5,6,7-tetrahydro-pyrrolo[3,2-c]pyridin-4-one

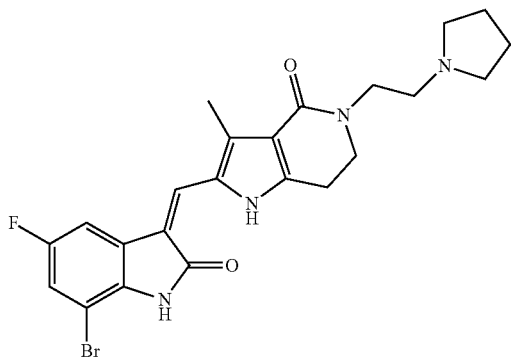 [SMILES: Cc1c(/C=C2\C(=O)Nc3c(Br)cc(F)cc32)[nH]c2c1C(=O)N(CCN1CCCC1)CC2]

The title compound was prepared under the same conditions as described in Example 13 with 3-methyl-4-oxo-5-(2-pyrrolidin-1-yl-ethyl)-4,5,6,7-tetrahydro-1H-pyrrolo[3,2-c]pyridine-2-carbaldehyde and 5-fluoro-7-bromo-1,3-dihydro-pyrrolo[2,3-b]pyridin-2-one as starting materials to give 2-(7-bromo-5-fluoro-2-oxo-1,2-dihydro-indol-3-ylidenemethyl)-3-methyl-5-(2-pyrrolidin-1-yl-ethyl)-1,5,6,7-tetrahydro-pyrrolo[3,2-c]pyridin-4-one (54 mg, 87.9%) as an orange solid.

MS m/z (ESI): 488[M+1]

$^1$H NMR (400 MHz, DMSO-d6) 7.53 (d, 1H, ArH), 7.35 (s, 1H, CH), 6.35 (d, 1H, ArH), 5.30 (br s, 1H, NH$_2$), 3.60 (t, 2H, CH$_2$), 3.51 (t, 2H, CH$_2$), 2.96 (t, 2H, CH$_2$), 2.60 (t, 2H, CH$_2$), 2.51 (s, 3H, CH$_3$), 2.47 (q, 4H, 2×NCH$_2$), 1.64~1.69 (m, 4H, 2×CH$_2$)

Example 80

N-{3-[3-Methyl-4-oxo-5-(2-pyrrolidin-1-yl-ethyl)-4,5,6,7-tetrahydro-1H-pyrrolo[3,2-c]pyridin-2-ylmethylene]-2-oxo-2,3-dihydro-1H-indol-5-yl}-formamide

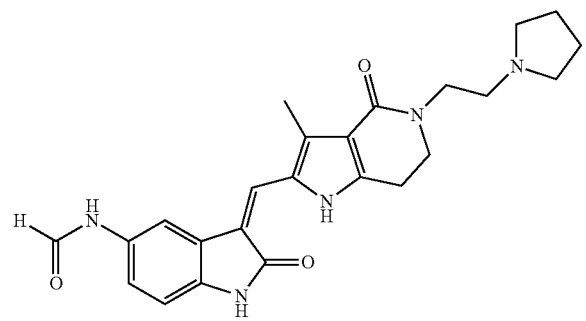 [SMILES: Cc1c(/C=C2\C(=O)Nc3ccc(NC=O)cc32)[nH]c2c1C(=O)N(CCN1CCCC1)CC2]

The title compound was prepared under the same conditions as described in Example 13 with 3-methyl-4-oxo-5-(2-pyrrolidin-1-yl-ethyl)-4,5,6,7-tetrahydro-1H-pyrrolo[3,2-e]pyridine-2-carbaldehyde and N-(2-oxo-2,3-dihydro-1H-indol-5-yl)-formamide as starting materials to give N-{3-[3-methyl-4-oxo-5-(2-pyrrolidin-1-yl-ethyl)-4,5,6,7-tetrahydro-1H-pyrrolo[3,2-c]pyridin-2-ylmethylene]-2-oxo-2,3-dihydro-1H-indol-5-yl}-formamide (48 mg, 87.9%) as an orange solid.

MS m/z (ESI): 434[M+1]

$^1$HNMR (400 MHz, DMSO-d6) 7.874~7.870 (d, 1H, —ArH), 7.508 (s, 1H, —CH), 7.336~7.310 (dd, 1H, —ArH), 1.666~1.659 (m, 6H, 3×-CH$_2$)

Example 81

2-[5-Fluoro-6-(4-fluoro-benzylamino)-2-oxo-1,2-dihydro-indol-3-ylidenemethyl]-3-(4-fluoro-phenyl)-1,5,6,7-tetrahydro-pyrrolo[3,2-c]pyridin-4-one

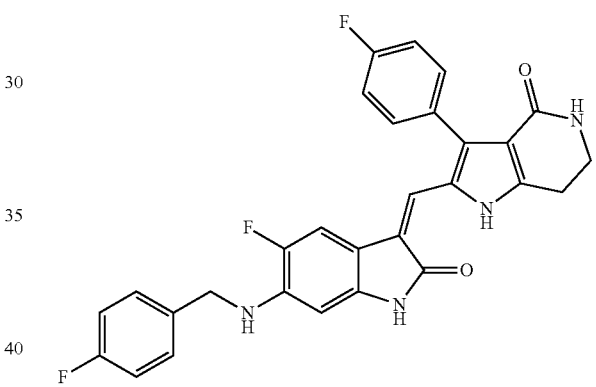

A stirred solution of d 6-amino-5-fluoro-1,3-dihydro-indol-2-one (2.26 g, 13.6 mmol) obtained from Example 6 in 40 ml of ethanol was added with 4-fluoro-benzaldehyde (1.5 ml, 13.6 mmol) at 0° C. in an ice-water bath. The resulting solution was stirred for 1 hour, added with sodium borohydride (1.08 g, 28.5 mmol) and heated to reflux overnight. The resulting mixture was added with water until a precipitate was formed. The solid was filtered and washed with water (50 ml×3). The crude was purified by silica gel column chromatography with dichloromethane and methanol (20:1) as eluents to give 5-fluoro-6-(4-fluoro-benzylamino)-1,3-dihydro-indol-2-one (1.67 g, 45%) as a white solid.

MS m/z (ESI): 275[M+1]

The title compound was prepared under the same conditions as described in Example 46 with 3-(4-fluoro-phenyl)-4-oxo-4,5,6,7-tetrahydro-1H-pyrrolo[3,2-c]pyridine-2-carbaldehyde and 5-fluoro-6-(4-fluoro-benzylamino)-1,3-dihydro-indol-2-one as starting materials to give 2-[5-fluoro-6-(4-fluoro-benzylamino)-2-oxo-1,2-dihydro-indol-3-ylidenemethyl]-3-(4-fluoro-phenyl)-1,5,6,7-tetrahydro-pyrrolo[3,2-c]pyridin-4-one (34 mg, 43.5%) as a red solid.

MS m/z (ESI): 515[M+1] 1H NMR (400 MHz, DMSO-d6) 9.020 (s, 1H, —ArH), 7.220~7.176 (1, 1H, —ArH), 7.141~7.097 (t, 1H, —ArH), 2.863~2.830 (t, 1H, —NH)

Example 82

N-{3-[3-(4-Fluoro-phenyl)-4-oxo-4,5,6,7-tetrahydro-1H-pyrrolo[3,2-c]pyridin-2-ylmethylene]-2-oxo-2,3-dihydro-1H-indol-5-yl}-2-methoxy-acetamide

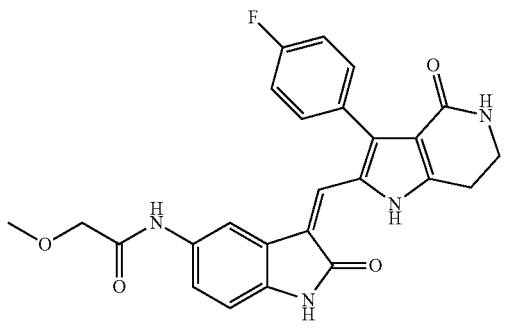 [SMILES: COCC(=O)Nc1ccc2c(c1)/C(=C/c1[nH]c3c(c1-c1ccc(F)cc1)C(=O)NCC3)C(=O)N2]

The title compound was prepared under the same conditions as described in Example 46 with 3-(4-fluoro-phenyl)-4-oxo-4,5,6,7-tetrahydro-1H-pyrrolo[3,2-c]pyridine-2-carbaldehyde and 2-methoxy-N-(2-oxo-2,3-dihydro-1H-indol-5-yl)-acetamide as starting materials to give N-{3-[3-(4-fluoro-phenyl)-4-oxo-4,5,6,7-tetrahydro-1H-pyrrolo[3,2-c]pyridin-2-ylmethylene]-2-oxo-2,3-dihydro-1H-indol-5-yl}-2-methoxy-acetamide (46 mg, 68.7%) as a red solid.

MS m/z (ESI): 461[M+1]
$^1$H NMR (400 MHz, DMSO-d6) 9.020 (s, 1H, —ArH), 7.220~7.176 (t, 1H, —ArH), 7.141~7.097 (t, 1H, —ArH), 2.863~2.830 (t, 1H, —NH)

Example 83

2-[4-(2,3-Difluoro-phenyl)-2-oxo-1,2-dihydro-indol-3-ylidenemethyl]-3-methyl-5-(2-piperidin-1-yl-ethyl)-1,5,6,7-tetrahydro-pyrrolo[3,2-c]pyridin-4-one

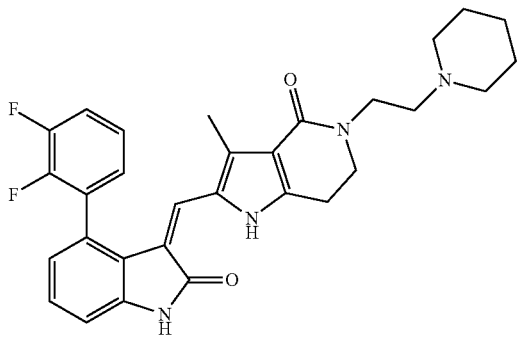 [SMILES: Cc1c(/C=C2\C(=O)Nc3cccc(-c4cccc(F)c4F)c32)[nH]c2c1C(=O)N(CCN1CCCCC1)CC2]

The title compound was prepared under the same conditions as described in Example 25 with 3-methyl-4-oxo-5-(2-piperidin-1-yl-ethyl)-4,5,6,7-tetrahydro-1H-pyrrolo[3,2-c]pyridine-2-carbaldehyde and 4-(2,3-difluoro-phenyl)-1,3-dihydro-indol-2-one (prepared according to WO2002055517) as starting materials to give 2-[4-(2,3-difluoro-phenyl)-2-oxo-1,2-dihydro-indol-3-ylidenemethyl]-3-methyl-5-(2-piperidin-1-yl-ethyl)-1,5,6,7-tetrahydro-pyrrolo[3,2-c]pyridin-4-one (70 mg, 70.7%) as an orange solid.

MS m/z (ESI): 517[M+1]
$^1$HNMR (400 MHz, DMSO-d6) 7.643~7.642 (q, 1H, —ArH), 7.335~7.301 (q, 1H, —ArH), 7.281~7.243 (t, 1H, —ArH), 7.019~6.999 (dd, 1H, —ArH), 6.896~6.877 (d, 1H, —ArH), 3.575~3.541 (t, 2H, —CH$_2$), 2.977~2.944 (t, 2H, —CH$_2$), 2.077~4.969 (t, 2H, —CH$_2$), 1.869 (s, 3H, —CH$_3$)

Example 84

2-[4-(2-Hydroxy-ethyl)-2-oxo-1,2-dihydro-indol-3-ylidenemethyl]-3-methyl-5-(2-piperidin-1-yl-ethyl)-1,5,6,7-tetrahydro-pyrrolo[3,2-c]pyridin-4-one

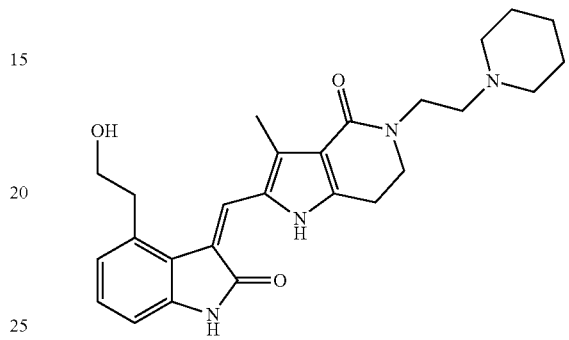

The title compound was prepared under the same conditions as described in Example with 3-methyl-4-oxo-5-(2-piperidin-1-yl-ethyl)-4,5,6,7-tetrahydro-1H-pyrrolo[3,2-c]pyridine-2-carbaldehyde and 4-(2-hydroxy-ethyl)-1,3-dihydro-indol-2-one (prepared according to US2004186160) as starting materials to give 2-[4-(2,3-difluoro-phenyl)-2-oxo-1,2-dihydro-indol-3-ylidenemethyl]-3-methyl-5-(2-piperidin-1-yl-ethyl)-1,5,6,7-tetrahydro-pyrrolo[3,2-c]pyridin-4-one (70 mg, 70.7%) as an orange solid.

MS m/z (ESI): 449[M+1]
$^1$HNMR (400 MHz, DMSO-d6) 7.630 (s, 1H, —CH), 7.091~7.052 (t, 1H, —ArH), 6.846~6.828 (d, 1H, —ArH), 6.795~6.776 (d, 1H, —ArH), 3.732~3.695 (t, 2H, —CH$_2$), 3.614~3.580 (t, 2H, —CH$_2$), 3.105~3.068 (t, 2H, —CH$_2$), 3.007~2.973 (t, 2H, —CH$_2$), 2.469 (s, 3H, —CH$_3$), 1.491~1.466 (q, 4H, 2×-CH$_2$), 1.377~1.366 (t, 2H, —CH$_2$)

Example 85

2-[4-(4-Chloro-2-fluoro-phenyl)-2-oxo-1,2-dihydro-indol-3-ylidenemethyl]-3-methyl-5-(2-piperidin-1-yl-ethyl)-1,5,6,7-tetrahydro-pyrrolo[3,2-c]pyridin-4-one

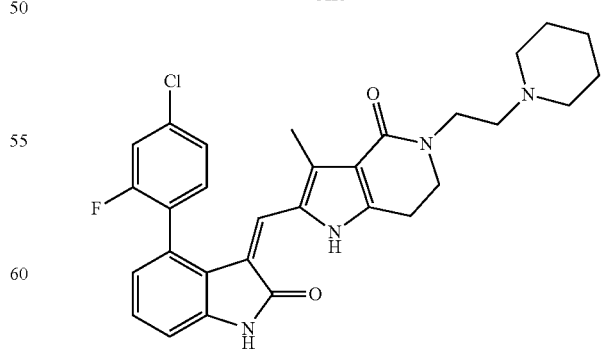

The title compound was prepared under the same conditions as described, in Example 25 with 3-methyl-4-oxo-5-(2-piperidin-1-yl-ethyl)-4,5,6,7-tetrahydro-1H-pyrrolo[3,2-c]

pyridine-2-carbaldehyde and 4-(4-chloro-2-fluoro-phenyl)-1,3-dihydro-indol-2-one (prepared according to WO2002055517) as starting materials to give 2-[4-(4-chloro-2-fluoro-phenyl)-2-oxo-1,2-dihydro-indol-3-ylidenemethyl]-3-methyl-5-(2-piperidin-1-yl-ethyl)-1,5,6,7-tetrahydro-pyrrolo[3,2-c]pyridin-4-one (45 mg, 44.2%) as a yellow solid.

MS m/z (ESI): 534[M+1]

$^1$HNMR (400 MHz, DMSO-d6) 7.690~7.665 (d, 1H, —ArH), 7.248~7.229 (t, 1H, —ArH), 7.004~6.984 (d, 1H, —ArH), 6871~6.852 (d, 1H, —ArH), 6.604 (s, 1H, —NE), 3.574~3.544 (t, 2H, —CH$_2$), 2.955~2.940 (t, 2H, —CH$_2$), 1.887 (s, 3H, —CH$_3$), 1.365 (t, 2H, —CH$_2$)

Example 86

2-[4-(3-Chloro-2-fluoro-phenyl)-2-oxo-1,2-dihydro-indol-3-ylidenemethyl]-3-methyl-5-(2-piperidin-1-yl-ethyl)-1,5,6,7-tetrahydro-pyrrolo[3,2-c]pyridin-4-one

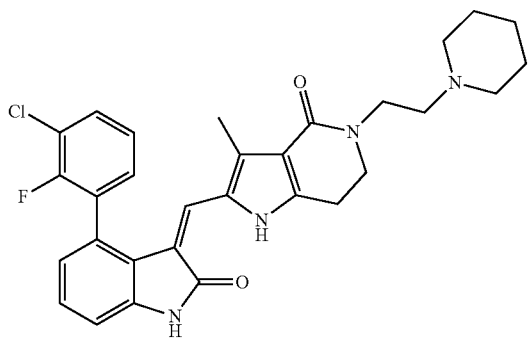 [SMILES: Cc1c(/C=C2\C(=O)Nc3cccc(-c4cccc(Cl)c4F)c32)[nH]c2c1C(=O)N(CCN1CCCCC1)CC2]

The title compound was prepared under the same conditions as described in Example 25 with 3-methyl-4-oxo-5-(2-piperidin-1-yl-ethyl)-4,5,6,7-etrahydro-1H-pyrrolo[3,2-c]pyridine-2-carbaldehyde and 4-(3-chloro-2-fluoro-phenyl)-1,3-dihydro-indol-2-one (prepared according to WO2002055517) as starting materials to give 2-[4-(3-chloro-2-fluoro-phenyl)-2-oxo-1,2-dihydro-indol-3-ylidenemethyl]-3-methyl-5-(2-piperidin-1-yl-ethyl)-1,5,6,7-tetrahydro-pyrrolo[3,2-c]pyridin-4-one (40 mg, 53.1%) as an orange solid.

MS m/z (ESI): 534[M+1]

$^1$HNMR (400 MHz, DMSO-d6) 7.773~7.755 (m, 1H, —ArH), 7.281~7.243 (t, 1H, —ArH), 7.021~7.001 (d, 1H, —ArH), 6.886~6.867 (d, 1H, —ArH), 6.656~6.652 (d, 1H, —ArH), 3.575~3.541 (t, 2H, —CH$_2$), 2.974~2.941 (t, 2H, —CH$_2$), 1.869 (s, 3H, —CH$_3$), 1.470~1.459 (m, 4H, 2x-CH$_2$), 1.373~1.361 (m, 2H, —CH$_2$)

Example 87

2-(4-Bromo-2-oxo-1,2-dihydro-indol-3-ylidenemethyl)-3-methyl-5-(2-piperidin-1-yl-ethyl)-1,5,6,7-tetrahydro-pyrrolo[3,2-c]pyridin-4-one

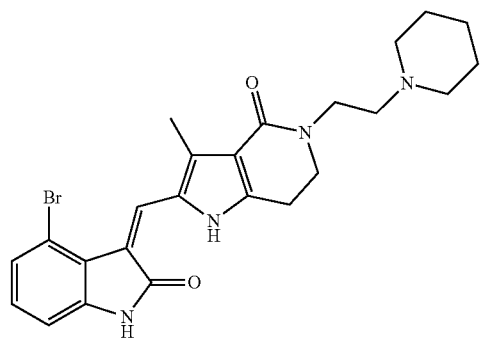 [SMILES: Cc1c(/C=C2\C(=O)Nc3cccc(Br)c32)[nH]c2c1C(=O)N(CCN1CCCCC1)CC2]

The title compound was prepared under the same conditions as described in Example 25 with 3-methyl-4-oxo-5-(2-piperidin-1-yl-ethyl)-4,5,6,7-etrahydro-1H-pyrrolo[3,2-c]pyridine-2-carbaldehyde and 4-bromo-1,3-dihydro-indol-2-one (prepared according to US20030225127) as starting materials to give 2-(4-bromo-2-oxo-1,2-dihydro-indol-3-ylidenemethyl)-3-methyl-5-(2-piperidin-1-yl-ethyl)-1,5,6,7-tetrahydro-pyrrolo[3,2-c]pyridin-4-one (58 mg, 84.9%) as a yellow solid.

MS m/z (ESI): 484[M+1]

$^1$HNMR (400 MHz, DMSO-d6) 8.575 (s, 1H, —CH), 7.239~7.218 (d, 1H, —ArH), 7.099~7.060 (t, 1H, —ArH), 6.957~6.938 (d, 1H, —ArH), 3.629~3.595 (t, 2H, —CH$_2$), 3.029~2.996 (t, 2H, —CH$_2$), 2.483 (s, 3H, —CH$_3$), 1.505~1.452 (m, 4H, 2x-CH$_2$)

Example 88

3-Methyl-2-(4-methyl-2-oxo-1,2-dihydro-indol-3-ylidenemethyl)-5-(2-piperidin-1-yl-ethyl)-1,5,6,7-tetrahydro-pyrrolo[3,2-c]pyridin-4-one

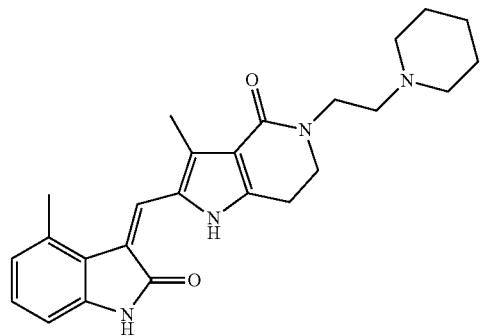

The title compound was prepared under the same conditions as described in Example 25 with 3-methyl-4-oxo-5-(2-piperidin-1-yl-ethyl)-4,5,6,7-etrahydro-1H-pyrrolo[3,2-c]pyridine-2-carbaldehyde and 4-methyl-1,3-dihydro-indol-2- one (prepared according to U.S. Pat. No. 6,114,371) as starting materials to give 3-methyl-2-(4-methyl-2-oxo-1,2-dihydro-indol-3-ylidenemethyl)-5-(2-piperidin-1-yl-ethyl)-1,5,6,7-tetrahydro-pyrrolo[3,2-c]pyridin-4-one (41 mg, 75.9%) as a yellow solid.

MS m/z (ESI): 419[M+1]

¹HNMR (400 MHz, DMSO-d6) 7.558 (s, 1H, —CH), 7.081~7.043 (t, 1H, —ArH), 6.841~6.822 (d, 1H, —ArH), 6.794~6.775 (d, 1H, —ArH), 3.618~3.584 (t, 2H, —CH₂), 3.009~2.975 (t, 2H, —CH₂), 2.585 (s, 3H, —CH₃), 2.461 (s, 3H, —CH₃), 1.486~1.473 (m, 4H, 2×-CH₂), 1.384~1.373 (m, 2H, —CH₂)

Example 89

3-Methyl-2-(2-oxo-4-piperidin-4-yl-1,2-dihydro-indol-3-ylidenemethyl)-5-(2-piperidin-1-yl-ethyl)-1,5,6,7-tetrahydro-pyrrolo[3,2-c]pyridin-4-one

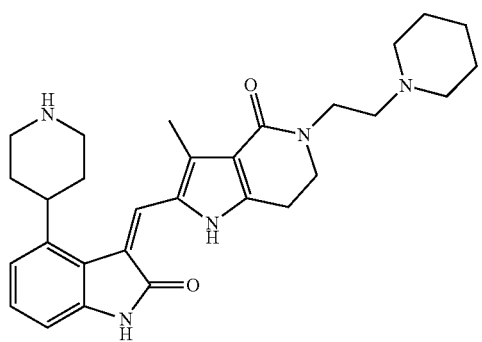

The title compound was prepared under the same conditions as described in Example 25 with 3-methyl-4-oxo-5-(2-piperidin-1-yl-ethyl)-4,5,6,7-etrahydro-1H-pyrrolo[3,2-c]pyridine-2-carbaldehyde and 4-piperidin-4-yl-1,3-dihydro-indol-2-one as starting materials to give 3-methyl-2-(2-oxo-4-piperidin-4-yl-1,2-dihydro-indol-3-ylidenemethyl)-5-(2-piperidin-1-yl-ethyl)-1,5,6,7-tetrahydro-pyrrolo[3,2-c]pyridin-4-one (18 mg, 27.9%) as a yellow solid.

MS m/z (ESI): 488[M+1]

¹HNMR (400 MHz, DMSO-d6) 7.505 (s, 1H, —CH), 7.172~7.133 (t, 1H, —ArH), 6.946~6.926 (d, 1H, —ArH), 6.808~6.789 (d, 1H, —ArH), 3.619~3.585 (t, 2H, —CH₂), 3.013~2.980 (t, 2H, —CH₂), 1.763~1.738 (m, 4H, 2×-CH₂), 1.379~1.369 (m, 2H, —CH₂)

Example 90

2-(7-Bromo-5-fluoro-2-oxo-1,2-dihydro-indol-3-ylidenemethyl)-3-methyl-5-(2-piperidin-1-yl-ethyl)-1,5,6,7-tetrahydro-pyrrolo[3,2-c]pyridin-4-one

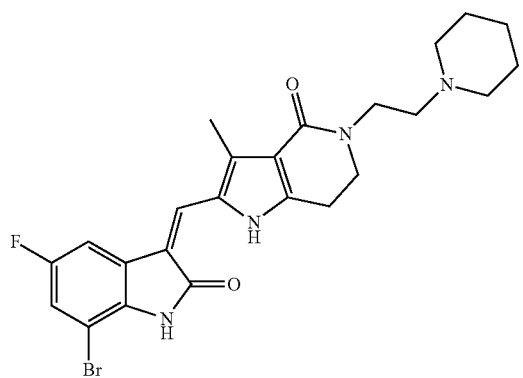

The title compound was prepared under the same conditions as described in Example 25 with 3-methyl-4-oxo-5-(2-piperidin-1-yl-ethyl)-4,5,6,7-etrahydro-1H-pyrrolo[3,2-c]pyridine-2-carbaldehyde and 5-fluoro-7-bromo-1,3-dihydro-indol-2-one as starting materials to give 2-(7-bromo-5-fluoro-2-oxo-1,2-dihydro-indol-3-ylidenemethyl)-3-methyl-5-(2-piperidin-1-yl-ethyl)-1,5,6,7-tetrahydro-pyrrolo[3,2-c]pyridin-4-one (57 mg, 87.0%) as a yellow solid.

MS m/z (ESI): 502[M+1]

¹HNMR (400 MHz, DMSO-d6). 7.891~7.863 (dd, 1H, —ArH), 7.807 (s, 1H, —CH), 7.283~7.255 (dd, 1H, —ArH), 3.638-3.604 (t, 2H, —CH₂), 3.507~3.462 (m, 2H, —CH₂), 3.053~3.022 (t, 2H, —CH₂), 2.557 (s, 3H, —CH₃), 1.487 (m, 4H, 2×-CH₂), 1.384 (m, 2H, —CH₂)

Example 91

N-{3-[3-Methyl-4-oxo-5-(2-piperidin-1-yl-ethyl)-4,5,6,7-tetrahydro-1H-pyrrolo[3,2-c]pyridin-2-ylmethylene]-2-oxo-2,3-dihydro-1H-indol-5-yl}-formamide

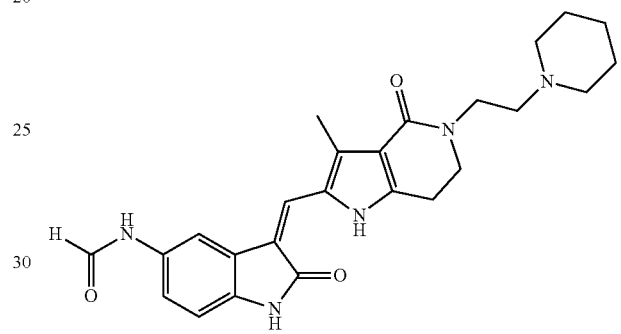

The title compound was prepared under the same conditions as described in Example 25 with 3-methyl-4-oxo-5-(2-piperidin-1-yl-ethyl)-4,5,6,7-etrahydro-1H-pyrrolo[3,2-c]pyridine-2-carbaldehyde and N-(2-oxo-2,3-dihydro-1H-indol-5-yl)-formamide as starting materials to give N-{3-[3-methyl-4-oxo-5-(2-piperidin-1-yl-ethyl)-4,5,6,7-tetrahydro-1H-pyrrolo[3,2-c]pyridin-2-ylmethylene]-2-oxo-2,3-dihydro-1H-indol-5-yl}-formamide (34 mg, 78.7%) as a red solid.

MS m/z (ESI): 448[M+1]

¹HNMR (400 MHz, DMSO-d6) 10.001 (s, 1H, —NH), 8.246~8.242 (d, 1H, —ArH), 7.310~7.306 (d, 1H, —ArH), 3.629~3.595 (t, 2H, —CH₂), 3.017~2.984 (t, 2H, —CH₂), 1.488 (m, 4H, 2×-CH₂)

Example 92

2-(5-Methoxy-2-oxo-1,2-dihydro-indol-3-ylidenemethyl)-3-methyl-5-(2-piperidin-1-yl-ethyl)-1,5,6,7-tetrahydro-pyrrolo[3,2-c]pyridin-4-one

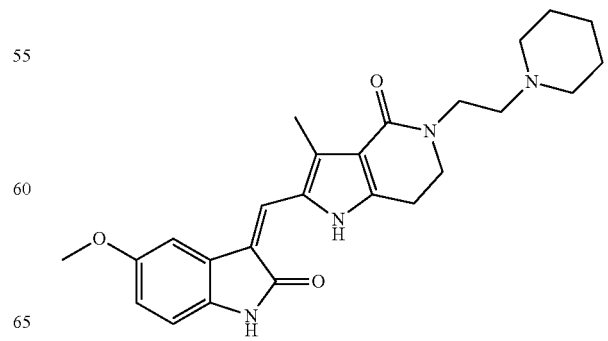

The title compound was prepared under the same conditions as described in Example 25 with 3-methyl-4-oxo-5-(2-piperidin-1-yl-ethyl)-4,5,6,7-etrahydro-1H-pyrrolo[3,2-c]pyridine-2-carbaldehyde and 5-methoxyl-1,3-dihydro-indol-2-one (prepared according to U.S. Pat. No. 6,114,371) as starting materials to give 2-(5-methoxy-2-oxo-1,2-dihydro-indol-3-ylidenemethyl)-3-methyl-5-(2-piperidin-1-yl-ethyl)-1,5,6,7-tetrahydro-pyrrolo[3,2-c]pyridin-4-one (17 mg, 39.9%) as an orange solid.

MS m/z (ESI): 435[M+1]

¹HNMR (400 MHz, DMSO-d6) 7.698 (s, 1H, —CH), 7.499~7.493 (d, 1H, —ArH), 6.795~6.773 (d, 1H, —ArH), 6.739~6.733 (d, 1H, —ArH), 3.784 (s, 31-I, —OCH₃), 3.634~3.600 (t, 2H, —CH₂), 3.012~2.998 (m, 2H, —CH₂), 2.546 (s, 3H, —CH₃)

Example 93

2-(5-Bromo-2-oxo-1,2-dihydro-pyrrolo[2,3-b]pyridin-3-ylidenemethyl)-3-methyl-5-(2-piperidin-1-yl-ethyl)-1,5,6,7-tetrahydro-pyrrolo[3,2-c]pyridin-4-one

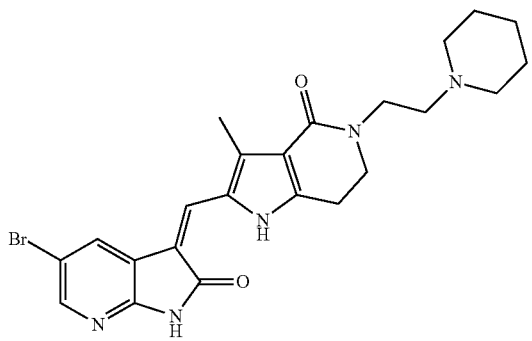

The title compound was prepared under the same conditions as described in Example 25 with 3-methyl-4-oxo-5-(2-piperidin-1-yl-ethyl)-4,5,6,7-tetrahydro-1H-pyrrolo[3,2-c]pyridine-2-carbaldehyde and 5-bromo-1,3-dihydro-pyrrolo[2,3-b]pyridin-2-one as starting materials to give 2-(5-bromo-2-oxo-1,2-dihydro-pyrrolo[2,3-b]pyridin-3-ylidenemethyl)-3-methyl-5-(2-piperidin-1-yl-ethyl)-1,5,6,7-tetrahydro-pyrrolo[3,2-c]pyridin-4-one (32 mg, 65.1%) as an orange solid.

MS m/z (ESI): 485[M+1]

¹HNMR (400 MHz, DMSO-d6) 8.502~8.496 (d, 1H, —ArH), 8.126~8.121 (d, 1H, —ArH), 7.897 (s, 1H, —CH), 3.637~3.603 (t, 2H, —CH₂), 3.050~3.017 (t, 2H, —CH₂), 2.556 (s, 3H, —CH₃), 1.489 (m, 4H, 2×-CH₂), 1.381 (m, 2H, —CH₂)

Example 94

2-[5-Fluoro-6-(4-fluoro-benzylamino)-2-oxo-1,2-dihydro-indol-3-ylidenemethyl]-3-methyl-5-(2-piperidin-1-yl-ethyl)-1,5,6,7-tetrahydro-pyrrolo[3,2-c]pyridin-4-one

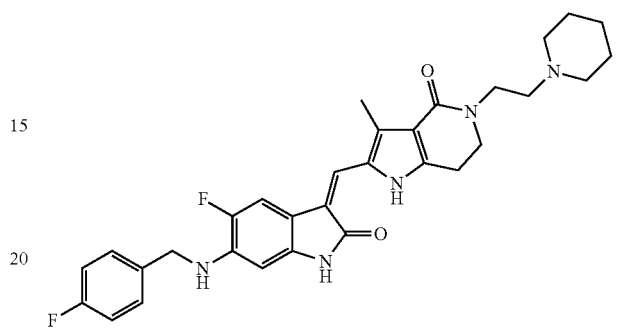

The title compound was prepared under the same conditions as described in Example 25 with 3-methyl-4-oxo-5-(2-piperidin-1-yl-ethyl)-4,5,6,7-tetrahydro-1H-pyrrolo[3,2-c]pyridine-2-carbaldehyde and 5-fluoro-6-(4-fluoro-benzylamino)-1,3-dihydro-indol-2-one as starting materials to give 2-[5-fluoro-6-(4-fluoro-benzylamino)-2-oxo-1,2-dihydro-indol-3-ylidenemethyl]-3-methyl-5-(2-piperidin-1-yl-ethyl)-1,5,6,7-tetrahydro-pyrrolo[3,2-c]pyridin-4-one (44 mg, 65.1%) as a red solid.

MS m/z (ESI): 546[M+1]

¹HNMR (400 MHz, DMSO-d6) 7.614~7.584 (d, 1H, —ArH), 6.431 (t, 1H, —ArH), 6.056~6.038 (d, 1H, —ArH), 4.362~4.347 (d, 2H, —CH₂), 3.600~3.566 (t, 2H, —CH₂), 3.485 (t, 2H, —CH₂), 2.957~2.923 (t, 2H, —CH₂), 2.467 (s, 3H, —CH₃), 1.484 (m, 4H, 2×-CH₂)

Example 95

3-Methyl-2-(2-oxo-4-pyridin-4-yl-1,2-dihydro-indol-3-ylidenemethyl)-5-(2-piperidin-1-yl-ethyl)-1,5,6,7-tetrahydro-pyrrolo[3,2-c]pyridin-4-one

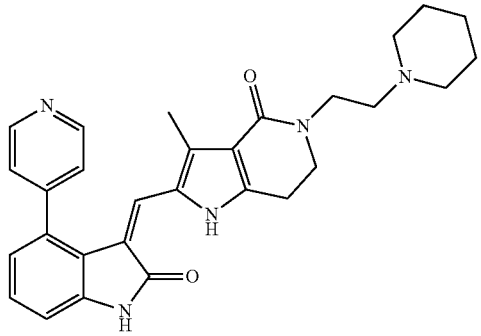

The title compound was prepared under the same conditions as described in Example 25 with 3-methyl-4-oxo-5-(2- piperidin-1-yl-ethyl)-4,5,6,7-tetrahydro-1H-pyrrolo[3,2-c]pyridine-2-carbaldehyde and 4-pyridin-4-yl-1,3-dihydro-indol-2-one (prepared according to WO2002055517) as starting materials to give 3-methyl-2-(2-oxo-4-pyridin-4-yl-1,2-dihydro-indol-3-ylidenemethyl)-5-(2-piperidin-1-yl-ethyl)-1,5,6,7-tetrahydro-pyrrolo[3,2-c]pyridin-4-one (50 mg, 73.1%) as an orange solid.

MS m/z (ESI): 482[M+1]

¹HNMR (400 MHz, DMSO-d6) 6.905~6.883 (dd, 1H, —ArH), 6.733~6.712 (dd, 1H, —ArH), 6.694 (s, 1H, —CH), 2.864~2.830 (t, 2H, —CH$_2$), 1.708 (s, 3H, —CH$_3$)

Example 96

5-(2-Diethylamino-ethyl)-3-methyl-2-(4-methyl-2-oxo-1,2-dihydro-indol-3-ylidenemethyl)-1,5,6,7-tetrahydro-pyrrolo[3,2-c]pyridin-4-one

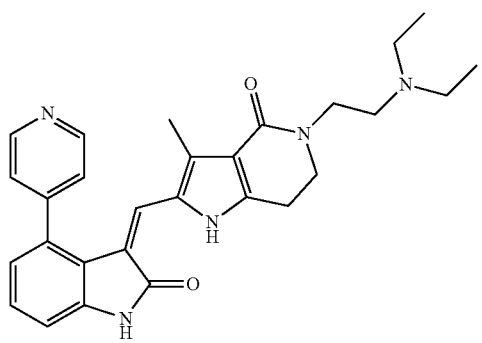 [SMILES: CCN(CC)CCN1CCc2[nH]c(/C=C3\C(=O)Nc4cccc(-c5ccncc5)c43)c(C)c2C1=O]

The title compound was prepared under the same conditions as described in Example 1 with 5-(2-diethylamino-ethyl)-3-methyl-4-oxo-4,5,6,7-tetrahydro-1H-pyrrolo[3,2-c]pyridine-2-carbaldehyde and 4-pyridin-4-yl-1,3-dihydro-indol-2-one (prepared according to WO2002055517) as starting materials to give 542-diethylamino-ethyl)-3-methyl-2-(4-methyl-2-oxo-1,2-dihydro-indol-3-ylidenemethyl)-1,5,6,7-tetrahydro-pyrrolo[3,2-c]pyridin-4-one (48 mg, 64.9%) as an orange solid.

MS m/z (ESI): 470[M+1]

¹H NMR (400 MHz, DMSO-d6) 8.652~8.637 (m, 2H, 2×-CH), 6.902~6.880 (dd, 1H, —ArH), 6.732~6.711 (dd, 1H, —ArH), 6.695 (s, 1H, —CH), 3.482~3.448 (t, 2H, —CH$_2$), 2.864~2.830 (t, 2H, —CH$_2$)

Example 97

3-Methyl-5-(2-morpholin-4-yl-ethyl)-2-(2-oxo-4-pyridin-4-yl-1,2-dihydro-indol-3-ylidenemethyl)-1,5,6,7-tetrahydro-pyrrolo[3,2-c]pyridin-4-one

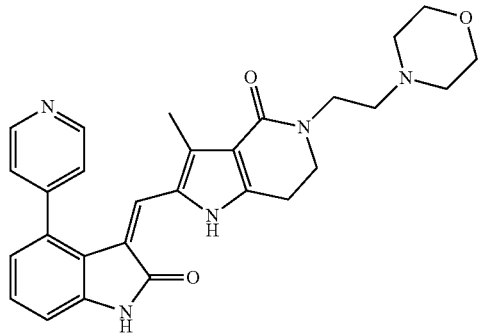

The title compound was prepared under the same conditions as described in Example 15 with 3-methyl-5-(2-morpholin-4-yl-ethyl)-4-oxo-4,5,6,7-tetrahydro-1H-pyrrolo[3,2-c]pyridine-2-carbaldehyde and 4-pyridin-4-yl-1,3-dihydro-indol-2-one (prepared according to WO2002055517) as starting materials to give 3-methyl-5-(2-morpholin-4-yl-ethyl)-2-(2-oxo-4-pyridin-4-yl-1,2-dihydro-indol-3-ylidenemethyl)-1,5,6,7-tetrahydro-pyrrolo[3,2-c]pyridin-4-one (54 mg, 72.0%) as a yellow solid.

MS m/z (ESI): 484[M+1]

¹HNMR (400 MHz, DMSO-d6) 8.649~8.634 (d, 2H, 2×-CH), 6.900~6.881 (dd, 1H, —ArH), 6.730~6.711 (d, 1H, —ArH), 6.689 (s, 1H, —CH), 3.392~3.359 (t, 2H, —CH$_2$), 2.870~2.837 (t, 2H, —CH$_2$), 1.710 (s, 3H, —CH$_3$)

Example 98

(S)—N-{5-Fluoro-3-[3-methyl-5-(2-morpholin-4-yl-ethyl)-4-oxo-4,5,6,7-tetrahydro-1H-pyrrolo[3,2-c]pyridin-2-ylmethylene]-2-oxo-2,3-dihydro-1H-indol-6-yl}-2-hydroxy-propionamide

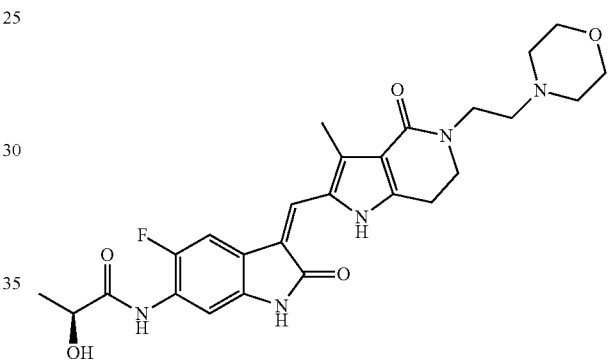

The stirred solution of 5-fluoro-6-amino-1,3-dihydro-indol-2-one (450 mg, 2.71 mmol) in 10 ml of tetrahydrofuran was added with piperidine (0.4 ml). The mixture was cooled to −40° C. in an acetone-dry ice bath and added with (S)-acetic acid 1-chlorocarbonyl-ethyl ester (423 mg, 2.71 mmol) in 10 ml of tetrahydrofuran dropwise. Upon the completion of the addition, the resulting mixture was stirred at the room temperature overnight until the precipitate was formed. The solid was filtered, washed with water and recrystallized from methanol to give acetic acid 1-(5-fluoro-2-oxo-2,3-dihydro-1H-indol-6-ylcarbamoyl)-ethyl ester (750 mg, 99%) as a white solid.

MS m/z (ESI): 279[M−1]

The stirred mixture of acetic acid 1-(5-fluoro-2-oxo-2,3-dihydro-1H-indol-6-ylcarbamoyl)-ethyl ester (750 mg, 2.67 mmol) in methanol (5 ml) and water (5 ml) was added with sodium hydroxide (240 mg, 60 mmol). The resulting mixture was stirred at room temperature overnight and concentrated under reduced pressure. The residue was extracted with ethyl acetate (100×3) and water (100×3). The organic extracts were dried with anhydrous sodium sulfate, filtered and concentrated under reduced pressure to give (S)—N-(5-Fluoro-2-oxo-2,3-dihydro-1H-indol-6-yl)-2-hydroxy-propionamide (270 mg, 42%) as a white solid.

MS m/z (ESI): 237[M−1]

The title compound was prepared under the same conditions as described in Example 15 with 3-methyl-5-(2-morpholin-4-yl-ethyl)-4-oxo-4,5,6,7-tetrahydro-1H-pyrrolo[3, 2-c]pyridine-2-carbaldehyde and (S)—N-(5-fluoro-2-oxo-2,3-dihydro-1H-indol-6-yl)-2-hydroxy-propionamide as starting materials to give (S)—N-{5-fluoro-3-[3-methyl-5-(2-morpholin-4-yl-ethyl)-4-oxo-4,5,6,7-tetrahydro-1H-pyrrolo[3,2-c]pyridin-2-ylmethylene]-2-oxo-2,3-dihydro-1H-indol-6-yl}-2-hydroxy-propionamide (44 mg, 61.3%) as a yellow solid.

MS m/z (ESI): 512[M+1]

¹HNMR (400 MHz, DMSO-d6) 7.773~7.745 (d, 1H, —ArH), 7.638~7.622 (d, 1H, —ArH), 4.142~4.091 (q, 1H, —OH), 3.530~3.496 (t, 2H, —CH₂), 2.915~2.882 (t, 2H, —CH₂), 1.247~1.230 (d, 3H, —CH₃)

Example 99

(S)—N-{3-[5-(2-Diethylamino-ethyl)-3-methyl-4-oxo-4,5,6,7-tetrahydro-1H-pyrrolo[3,2-c]pyridin-2-ylmethylene]-5-fluoro-2-oxo-2,3-dihydro-1H-indol-6-yl}-2-hydroxy-propionamide

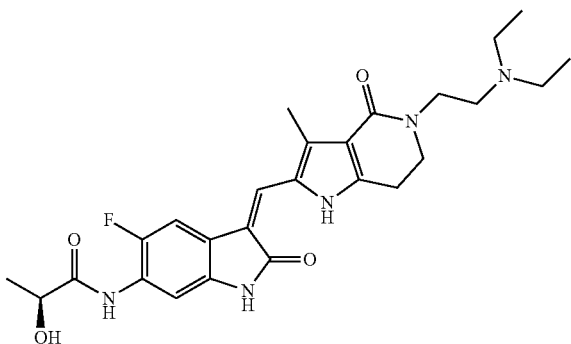 [SMILES: CCN(CC)CCN1CCc2[nH]c(/C=C3\C(=O)Nc4cc(NC(=O)[C@H](C)O)c(F)cc43)c(C)c2C1=O]

The title compound was prepared under the same conditions as described in Example 1 with 5-(2-diethylamino-ethyl)-3-methyl-4-oxo-4,5,6,7-tetrahydro-1H-pyrrolo[3,2-c]pyridine-2-carbaldehyde and (S)—N-(5-fluoro-2-oxo-2,3-dihydro-1H-indol-6-yl)-2-hydroxy-propionamide, as starting materials to give (S)—N-{3-[5-(2-diethylamino-ethyl)-3-methyl-4-oxo-4,5,6,7-tetrahydro-1H-pyrrolo[3,2-c]pyridin-2-yl methylene]-5-fluoro-2-oxo-2,3-dihydro-1H-indol-6-yl}-2-hydroxy-propionamide (37 mg, 50.3%) as an orange solid.

MS m/z (ESI): 498[M+1]

¹H NMR (400 MHz, DMSO-d6) 7.779~7.751 (d, 1H, —ArH), 7.641~7.625 (d, 1H, —ArH), 4.122~4.105 (q, 1H, —OH), 3.532~3.498 (t, 2H, —CH₂), 2.907~2.873 (t, 2H, —CH₂), 1.243~1.226 (d, 3H, —CH₃), 0.887~0.852 (t, 6H, 2×-CH₃)

Example 100

(S)—N-{5-Fluoro-3-[3-methyl-4-oxo-5-(2-piperidin-1-yl-ethyl)-4,5,6,7-tetrahydro-1H-pyrrolo[3,2-c]pyridin-2-ylmethylene]-2-oxo-2,3-dihydro-1H-indol-6-yl}-2-hydroxy-propionamide

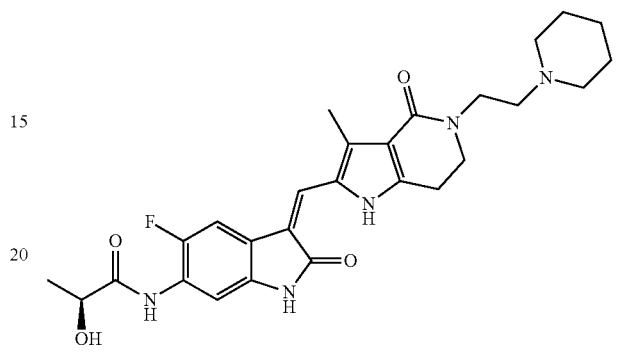

The title compound was prepared under the same conditions as described in Example 25 with 3-methyl-4-oxo-5-(2-piperidin-1-yl-ethyl)-4,5,6,7-tetrahydro-1H-pyrrolo[3,2-c]pyridine-2-carbaldehyde and (S)—N-(5-fluoro-2-oxo-2,3-dihydro-1H-indol-6-yl)-2-hydroxy-propionamide as starting materials to give (S)—N-{5-fluoro-3-[3-methyl-4-oxo-5-(2-piperidin-1-yl-ethyl)-4,5,6,7-tetrahydro-1H-pyrrolo[3,2-c]pyridin-2-ylmethylene]-2-oxo-2,3-dihydro-1H-indol-6-yl}-2-hydroxy-propionamide (44 mg, 58.4%) as an orange solid.

MS m/z (ESI): 510[M+1]

¹HNMR (400 MHz, DMSO-d6) 7.763~7.735 (s, 1H, —ArH), 7.632~7.616 (d, 1H, —ArH), 4.120~4.103 (q, 1H, —OH), 3.514~3.480 (t, 2H, —CH₂), 2.900~2.866 (t, 2H, —CH₂), 1.242~1.225 (d, 3H, —CH₃)

Example 101

(S)—N-{5-Fluoro-3-[3-methyl-4-oxo-5-(2-pyrrolidin-1-yl-ethyl)-4,5,6,7-tetrahydro-1H-pyrrolo[3,2-c]pyridin-2-ylmethylene]-2-oxo-2,3-dihydro-1H-indol-6-yl}-2-hydroxy-propionamide

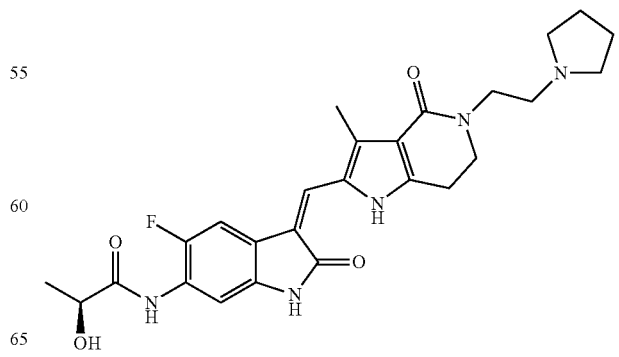

The title compound was prepared under the same conditions as described in Example 13 with 3-methyl-4-oxo-5-(2-pyrrolidin-1-yl-ethyl)-4,5,6,7-tetrahydro-1H-pyrrolo[3,2-c]pyridine-2-carbaldehyde and (S)—N-(5-fluoro-2-oxo-2,3-dihydro-1H-indol-6-yl)-2-hydroxy-propionamide as starting materials to give (S)—N-{5-fluoro-3-[3-methyl-4-oxo-5-(2-pyrrolidin-1-yl-ethyl)-4,5,6,7-tetrahydro-1H-pyrrolo[3,2-c]pyridin-2-ylmethylene]-2-oxo-2,3-dihydro-1H-indol-6-yl}-2-hydroxy-propionamide (48 mg, 67.9%) as a yellow solid.

MS m/z (ESI): 496[M+1]

$^1$HNMR (400 MHz, DMSO-d6) 7.776~7.748 (d, 1H, —ArH), 7.641~7.625 (d, 1H, —ArH), 4.122~4.105 (q, 1H, —OH), 3.524~3.491 (t, 2H, —CH$_2$), 3.426~3.391 (t, 2H, —CH$_2$), 2.908~2.874 (t, 2H, —CH$_2$), 1.244~1.226 (d, 3H, —CH$_3$)

Example 102

3-Methyl-2-(2-oxo-4-pyridin-4-yl-1,2-dihydro-indol-3-ylidenemethyl)-5-(2-pyrrolidin-1-yl-ethyl)-1,5,6,7-tetrahydro-pyrrolo[3,2-c]pyridin-4-one

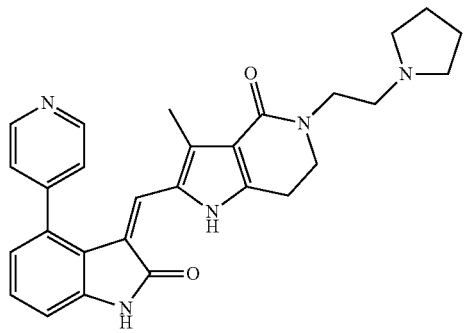 [SMILES: Cc1c(/C=C2\C(=O)Nc3cccc(-c4ccncc4)c32)[nH]c2c1C(=O)N(CCN1CCCC1)CC2]

The title compound was prepared under the same conditions as described in Example 13 with 3-methyl-4-oxo-5-(2-pyrrolidin-1-yl-ethyl)-4,5,6,7-tetrahydro-1H-pyrrolo[3,2-c]pyridine-2-carbaldehyde and 4-pyridin-4-yl-1,3-dihydro-indol-2-one (prepared according to WO2002055517) as starting materials to give 3-methyl-2-(2-oxo-4-pyridin-4-yl-1,2-dihydro-indol-3-ylidenemethyl)-5-(2-pyrrolidin-1-yl-ethyl)-1,5,6,7-tetrahydro-pyrrolo[3,2-c]pyridin-4-one (31 mg, 63.9%) as a yellow solid.

MS m/z (ESI): 468[M+1]

$^1$HNMR (400 MHz, DMSO-d6) 7.156~7.136 (t, 1H, —ArH), 6.906~6.886 (d, 1H, —ArH), 6.739~6.719 (d, 1H, —ArH), 6.704 (s, 1H, —CH), 3.483~3.450 (t, 2H, —CH$_2$), 2.875~2.841 (t, 2H, —CH$_2$), 1.719 (s, 3H, —CH$_3$)

Example 103

N-{5-Fluoro-3-[3-methyl-5-(2-morpholin-4-yl-ethyl)-4-oxo-4,5,6,7-tetrahydro-1H-pyrrolo[3,2-c]pyridin-2-ylmethylene]-2-oxo-2,3-dihydro-1H-indol-6-yl}-2-hydroxy-2-methyl-propionamide

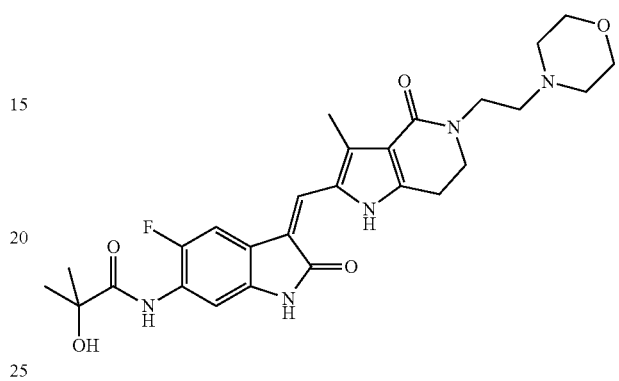

A stirred solution of 5-fluoro-6-amino-1,3-dihydro-indol-2-one (410 mg, 2.46 mmol) in 10 ml of tetrahydrofuran was added with piperidine (0.3 ml). The mixture was cooled to −40° C. in an acetone-dry ice bath and added with acetic acid 1-chlorocarbonyl-1-methyl-ethyl ester (405 mg, 2.46 mmol) in 10 ml of tetrahydrofuran dropwise. Upon the completion of the addition, the resulting mixture was stirred at the room temperature overnight until the precipitate was formed. The solid was filtered, washed with water and recrystallized from methanol to give acetic acid 1-(5-fluoro-2-oxo-2,3-dihydro-1H-indol-6-ylcarbamoyl)-1-methyl-ethyl ester (720 mg, 99.5%) as a white solid.

MS m/z (ESI): 293[M−1]

A stirred mixture of acetic acid 1-(5-fluoro-2-oxo-2,3-dihydro-1H-indol-6-ylcarbamoyl)-ethyl ester (720 mg, 2.45 mmol) in methanol (5 ml) and water (5 ml) was added with sodium hydroxide (200 mg, 50 mmol). The resulting mixture was stirred at room temperature overnight and concentrated under reduced pressure. The residue was extracted with ethyl acetate (100×3) and water (100×3). The organic extracts were dried with anhydrous sodium sulfate, filtered and concentrated under reduced pressure to give N-(5-fluoro-2-oxo-2,3-dihydro-1H-indol-6-yl)-2-hydroxy-2-methyl-propionamide (220 mg, 35.6%) as a white solid.

MS m/z (ESI): 251[M−1]

The title compound was prepared under the same conditions as described in Example 15 with 3-methyl-5-(2-morpholin-4-yl-ethyl)-4-oxo-4,5,6,7-tetrahydro-1H-pyrrolo[3,2-c]pyridine-2-carbaldehyde and N-(5-fluoro-2-oxo-2,3-dihydro-1H-indol-6-yl)-2-hydroxy-2-methyl-propionamide as starting materials to give N-{5-fluoro-3-[3-methyl-5-(2-morpholin-4-yl-ethyl)-4-oxo-4,5,6,7-tetrahydro-1H-pyrrolo[3,2-c]pyridin-2-ylmethylene]-2-oxo-2,3-dihydro-1H-indol-6-yl}-2-hydroxy-2-methyl-propionamide (46 mg, 63.3%) as a yellow solid.

MS m/z (ESI): 526[M+1]

$^1$HNMR (400 MHz, DMSO-d6) 7.903~7.875 (d, 1H, —ArH), 7.795~7.779 (d, 1H, —ArH), 6.055 (s, 1H, —CH), 3.632~3.599 (t, 2H, —CH$_2$), 3.538~3.504 (t, 2H, —CH$_2$), 3.020~2.986 (t, 2H, —CH$_2$), 2.524 (s, 3H, —CH$_3$)

Example 104

N-{5-Fluoro-3-[3-methyl-4-oxo-5-(2-pyrrolidin-1-yl-ethyl)-4,5,6,7-tetrahydro-1H-pyrrolo[3,2-c]pyridin-2-ylmethylene]-2-oxo-2,3-dihydro-1H-indol-6-yl}-2-hydroxy-2-methyl-propionamide

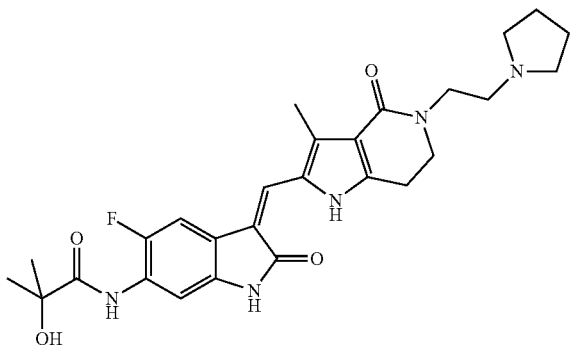 [SMILES: Cc1c(/C=C2\C(=O)Nc3cc(NC(=O)C(C)(C)O)c(F)cc32)[nH]c2c1C(=O)N(CCN1CCCC1)CC2]

The title compound was prepared under the same conditions as described in Example 13 with 3-methyl-4-oxo-5-(2-pyrrolidin-1-yl-ethyl)-4,5,6,7-tetrahydro-1H-pyrrolo[3,2-c]pyridine-2-carbaldehyde and N-(5-fluoro-2-oxo-2,3-dihydro-1H-indol-6-yl)-2-hydroxy-2-methyl-propionamide as starting materials to give N-{5-fluoro-3-[3-methyl-4-oxo-5-(2-pyrrolidin-1-yl-ethyl)-4,5,6,7-tetrahydro-1H-pyrrolo[3,2-c]pyridin-2-ylmethylene]-2-oxo-2,3-dihydro-1H-indol-6-yl}-2-hydroxy-2-methyl-propionamide (40 mg, 43%) as a yellow solid.

MS m/z (ESI): 510[M+1]

$^1$HNMR (400 MHz, DMSO-d6) 7.903~7.875 (t, 1H, —ArH), 7.794~7.778 (d, 1H, —ArH), 6.055 (s, 1H, —CH), 3.630~3.596 (t, 2H, —CH$_2$), 3.531~3.496 (t, 2H, —CH$_2$), 3.013~2.980 (t, 2H, —CH$_2$)

Example 105

N-{3-[5-(2-Diethylamino-ethyl)-3-methyl-4-oxo-4,5,6,7-tetrahydro-1H-pyrrolo[3,2-c]pyridin-2-ylmethylene]-5-fluoro-2-oxo-2,3-dihydro-1H-indol-6-yl}-2-hydroxy-2-methyl-propionamide

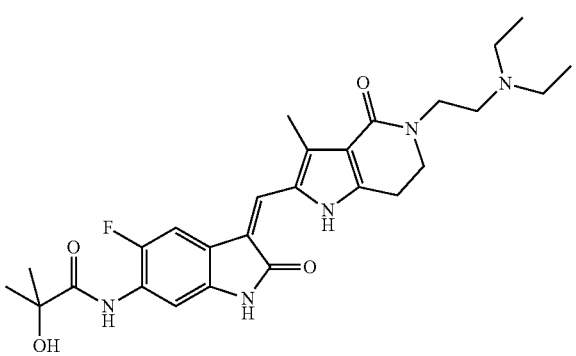 [SMILES: CCN(CC)CCN1CCc2[nH]c(/C=C3\C(=O)Nc4cc(NC(=O)C(C)(C)O)c(F)cc43)c(C)c2C1=O]

The title compound was prepared under the same conditions as described in Example 1 with 5-(2-diethylamino-ethyl)-3-methyl-4-oxo-4,5,6,7-tetrahydro-1H-pyrrolo[3,2-c]pyridine-2-carbaldehyde and N-(5-fluoro-2-oxo-2,3-dihydro-1H-indol-6-yl)-2-hydroxy-2-methyl-propionamide as starting materials to give N-{3-[5-(2-diethylamino-ethyl)-3-methyl-4-oxo-4,5,6,7-tetrahydro-1H-pyrrolo[3,2-c]pyridin-2-ylmethylene]-5-fluoro-2-oxo-2,3-dihydro-1H-indol-6-yl}-2-hydroxy-2-methyl-propionamide (48 mg, 65.7%) as a yellow solid.

MS m/z (ESI): 512[M+1]

$^1$H NMR (400 MHz, DMSO-d6) 7.901~7.873 (d, 1H, —ArH), 7.794~7.778 (d, 1H, —ArH), 6.055 (s, 1H, —CH), 3.635~3.602 (t, 2H, —CH$_2$), 3.467~3.434 (t, 2H, —CH$_2$), 3.011~2.977 (t, 2H, —CH$_2$), 1.377 (s, 6H, 2×-CH$_3$), 0.989~0.954 (t, 6H, 2×-CH$_3$)

Example 106

5-(2-Ethylamino-ethyl)-2-(5-fluoro-2-oxo-1,2-dihydro-indol-3-ylidenemethyl)-3-methyl-1,5,6,7-tetrahydro-pyrrolo[3,2-c]pyridin-4-one

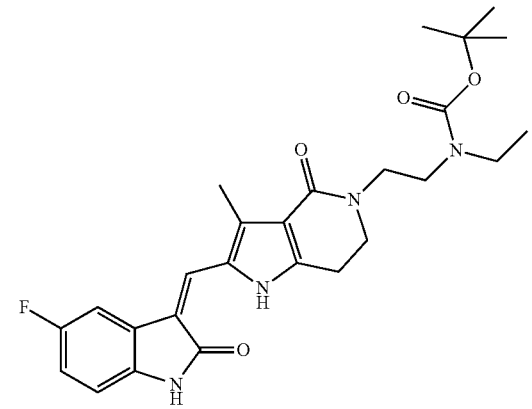 [SMILES: CCN(CCN1CCc2[nH]c(/C=C3\C(=O)Nc4ccc(F)cc43)c(C)c2C1=O)C(=O)OC(C)(C)C]

A solution of ethane-1,2-diamine (200 ml, 3 mol) in ethyl acetate (98 ml, 1 mol) was stirred for 4 days at room temperature. The mixture was concentrated under reduced pressure to give N-(2-amino-ethyl)-acetamide (79 g, 71%) as a white solid.

MS m/z (ESI): 103.0[M+1]

A stirred solution of 2-carboxymethyl-4-methyl-1H-pyrrole-3-carboxylic acid ethyl ester (2.78 g, 13.17 mmol) in dichloromethane (100 ml) was added with N-(2-aminoethyl)-acetamide (1.478 g, 14.5 mmol), N-ethyl-N'-(dimethylaminopropyl)-carbodiimide hydrochloride (6.65 g, 34.25 mmol) and 1-hydroxybenzotriazol (4.6 g, 34.25 mmol) in an ice-water bath. Upon completion of the addition, the reaction mixture was stirred under an argon atmosphere at room temperature overnight. The resulting mixture was added with cold water (100 ml), adjusted to pH 14 with 1M aqueous sodium hydroxide solution and extracted with ethyl acetate (200 ml). The combined organic extracts were washed with brine (200 ml), dried with anhydrous sodium sulfate, filtered and concentrated under reduced pressure to give 2-[(2-acetylamino-ethylcarbamoyl)-methyl]-4-methyl-1H-pyrrole-3-carboxylic acid ethyl ester (3.5 g, 95.7%) as an orange solid.

MS m/z (ESI): 296[M+1]

A stirred solution of 2-[(2-acetylamino-ethylcarbamoyl)-methyl]-4-methyl-1H-pyrrole-3-carboxylic acid ethyl ester (500 mg, 1.695 mmol) in anhydrous tetrahydrofuran (10 ml) was added dropwise slowly with 1M borane-tetrahydrofuran complex in tetrahydrofuran (6.75 ml, 6.75 mmol) under an argon atmosphere. Upon completion of the addition, the mixture Was heated to reflux for 7 hours The mixture was concentrated under reduced pressure. The residue was added with water (10 ml) and adjusted to pH 3 with 2N hydrochloric acid. The resulting mixture: was' adjusted to pH 14 with 2N aqueous sodium hydroxide solution and extracted with ethyl acetate (10 ml×3). The combined organic extracts were washed with brine (20 ml), dried over anhydrous sodium sulfate and concentrated under reduced pressure to, give 2-[2-(2-ethylamino-ethylamino)-ethyl]-4-methyl-1H-pyrrole-3-carboxylic acid ethyl ester (400 mg, 88%) as a brown solid.

MS m/z (ESI): 268[M+1]

A stirred mixture of 2-[2-(2-ethylamino-ethylamino)-ethyl]-4-methyl-1H-pyrrole-3-carboxylic acid ethyl ester (400 mg, 1.498 mmol), lithium hydroxide monohydrate (503 mg, 11.985 mmol) in 25 ml of oxalic acid was heated to reflux at 135° C. The mixture was concentrated under reduced pressure, added with water (10 ml) and extracted with dichloromethane (20 ml×3). The combined extracts Were dried over anhydrous magnesium sulfate, filtered and concentrated wider reduced pressure to give 5-(2-ethylamino-ethyl)-3-methyl-1,5,6,7-tetrahydro-pyrrolo[3,2-c]pyridine-4-one (100 mg, 30.2%) as a brown oil.

MS m/z (ESI): 222[M+1]

A solution of 5-(2-ethylamino-ethyl)-3-methyl-1,5,6,7-tetrahydro-pyrrolo[3,2-c]pyridine-4-one (100 mg, 0.45 mmol), di-tert-butyl dicarbonate (115 mg, 0.54 mmol); potassium carbonate (74.9 mg; 0.54 mmol) in isopropanol (5 ml) and water (6 ml) was stirred for 17 hours at room temperature. The mixture was added with water (10 ml) and extracted with ethyl acetate (20 ml×3). The combined organic extracts were washed with brine (15 ml), dried over anhydrous magnesium sulfate, filtered and concentrated under reduced pressure. The residue was purified by silica gel column chromatography with ethyl acetate: n-hexane (1:3) to give ethyl-[2-(3-methyl-4-oxo-1,4,6,7-tetrahydro-pyrrolo[3,2-c]pyridin-5-yl)-ethyl]-carbamic acid tert-butyl ester (74 mg, 51.37%) as a brown solid.

MS m/z (ESI): 322[M+1]

A stirred solution of dichloromethane (10 ml) and N,N'-dimethyl formamide (0.25 ml) was added slowly with phosphorus oxychloride (269 µl, 1.62 mmol) under a argon atmosphere while maintaining the temperature at −10° C. Upon completion of the addition, the mixture was stirred for 15 minutes at −10° C.~0° C. and cooled down to −10° C. in an ice-water bath with salt. A mixture of ethyl-[2-(3-methyl-4-oxo-1,4,6,7-tetrahydro-pyrrolo[3,2-c]pyridin-5-yl)-ethyl]-carbamic acid tert-butyl ester (400 mg, 1.246 mmol) in 3 ml of dichloromethane was added dropwise to the above solution. Upon completion of the addition, the mixture was stirred for 1 hours at −10° C.~0° C. and another 2.5 hours at room temperature. The mixture was added with cold water (20 ml), adjusted to pH 11~12 with 10% aqueous solution of sodium hydroxide and extracted with ethyl acetate (80 ml×5). The combined organic extracts were washed with brine (50 ml), dried over anhydrous sodium sulfate, filtered and concentrated under reduced pressure. The residue was purified by silica gel column chromatography with saturated ammonia: acetone: methanol: dichloromethane (0.1:1:1:40) as eluents to give ethyl-[2-(2-formyl-3-methyl-4-oxo-1,4,6,7-tetrahydro-pyrrolo[3,2-c]pyridin-5-yl)-ethyl]-carbamic acid tert-butyl ester (160 mg, 37%) as a brown oil.

MS m/z (ESI): 350[M+1]

A stirred solution of ethyl-[2-(2-formyl-3-methyl-4-oxo-1,4,6,7-tetrahydro-pyrrolo[3,2-c]pyridin-5-yl)-ethyl]-carbamic acid tert-butyl ester (160 mg, 0.458 mmol), 5-fluoro-1,3-dihydro-indol-2-one (65.76 mg, 0.435 mmol), in. 0.803, ml of ethanol was added dropwise with anhydrous piperidine (0.022 ml). The mixture was stirred overnight at room temperature until a precipitate was formed. The precipitate was filtered under reduced pressure and washed with ethanol (0.3 ml×3) to give ethyl-{2-[2-(6-fluoro-2-oxo-indan-1-ylidenemethyl)-3-methyl-4-oxo-1,4,6,7-tetrahydro-pyrrolo[3,2-c]pyridin-5-yl]ethyl}-carbamic acid tert-butyl ester (111 mg, 50%) as a yellow solid.

MS m/z (ESI): 483[M+1]

Example 107

2-(5-Fluoro-2-oxo-1,2-dihydro-indol-3-ylidenemethyl)-5-(4-hydroxy-1-methyl-5,6,7-tetrahydro-pyrrolo[3,2-c]pyridine-4-one

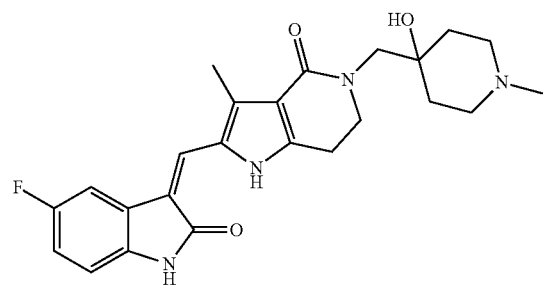 [SMILES: Cc1c(/C=C2\C(=O)Nc3ccc(F)cc32)[nH]c2c1C(=O)N(CC1(O)CCN(C)CC1)CC2]

A stirred solution of 60% aqueous sodium hydroxide solution (117 mg, 2.92 mmol) in dimethyl sulfoxide (2 ml) was added with trimethyl sulfoxinium iodide (627 mg, 2.79 mmol) under a nitrogen atmosphere. The mixture was stirred for 45 minutes in ice-water bath, added slowly with 4-oxo-piperidine-1-carboxylic acid tert-butyl ester (500 mg, 2.5 mmol) while maintaining the temperature below 10° C. Upon completion of the addition, the mixture was stirred for 5 minutes in the ice-water bath and stirred for another 2 hours at 25° C. in an oil bath. The resulting mixture was added with cold water (20 ml) and extracted with ethyl ether (20 ml×3). The combined organic extracts were dried over anhydrous sodium sulfate, filtered and concentrated under reduced pressure to give 1-oxa-6-aza-spiro[2.5]octane-6-carboxylic acid tert-butyl ester (479 mg, 85.5%) as a white solid.

MS m/z (ESI): 213[M+1]

A stirred solution of 1-oxa-6-aza-spiro[2.5]octane-6-carboxylic acid tert-butyl ester (9.0 g, 42.2 mmol) in ethanol (60 ml) was added with ammonia (160 ml). The resulting mixture was stirred under a nitrogen atmosphere overnight. The mixture was concentrated under reduced pressure. The residue was added with Water (50 ml) and extracted with ethyl acetate (150 ml×3). The Combined organic extracts were dried over anhydrous sodium sulfate, filtered and concentrated under reduced pressure. The residue was purified by silica gel column chromatography with dichloromethane:methanol (20:1)

as eluents to give 4-aminomethyl-4-hydroxy-piperidine-1-carboxylic acid tert-butyl ester (5.87 g, 60.5%) as a white solid.

MS m/z (ESI): 231[M+1]

A stirred mixture of 4-aminomethyl-4-hydroxy-piperidine-1-carboxylic acid tert-butyl ester (529 mg, 2.3 mmol) in tetrahydrofuran (15 ml) was added slowly with lithium aluminum hydride (0.88 g, 23 mmol) while maintaining the temperature at 0~5° C. Upon completion of the addition, the mixture was stirred at 80° C. oil bath overnight. The mixture was added with potassium sodium tartrate tetrahydrate (6.3 g, 22.3 mmol) and stirred for 8 hours at room temperature. The mixture was filtered and washed with tetrahydrofuran (10 ml×3). The combined organic extracts were concentrated under reduced pressure to give 4-aminomethyl-1-methyl-piperidin-4-ol (245 mg, 74%) as a white oil which was used as such.

MS m/z (ESI): 145[M+1]

A solution of 2-carboxymethyl-4-methyl-1H-pyrrole-3-carboxylic acid ethyl ester (3.717 g, 17.62 mmol) in dichloromethane (91 ml) in an ice-water bath was added with 4-aminomethyl-1-methyl-piperidin-4-ol (4 g, 19.38 mmol), N,N'-dimethylformamide (9.1 ml), N-ethyl-N'-(dimethylaminopropyl)-carbodiimide hydrochloride (8.751 g, 45.6 mmol) and 1-hydroxybenzotriazol (3.577 g, 26.5 mmol). Upon completion of the addition, the resulting mixture was stirred at room temperature overnight. The mixture was added with ice to quench the reaction, and washed with saturated potassium carbonate solution (10 ml×3) with brine (50 ml×3) The resulting mixture was partitioned and the organic phase was dried over anhydrous sodium sulfate, filtered and concentrated under reduced pressure to give 2-{[(4-hydroxy-1-methyl-piperidin-4-ylmethyl)-carbamoyl]-methyl}-4-methyl-1H-pyrrole-3-carboxylic acid ethyl ester (8.891 g) as a brown oil, which was used as such.

MS m/z (ESI): 338[M+1]

A stirred solution of 2-{[(4-hydroxy-1-methyl-piperidin-4-ylmethyl)-carbamoyl]-methyl}-4-methyl-1H-pyrrole-3-carboxylic acid ethyl ester (5.937 g, 17.62 mmol) in tetrahydrofuran (50 ml) was added slowly with another portion of 1M borane-tetrahydrofuran complex in tetrahydrofuran (52.1 ml, 52.1 mmol) under an argon atmosphere. Upon completion of the addition, the mixture was stirred for 1.5 hours at room temperature, heated to reflux for 1.5 hours and stirred at room temperature overnight. The resulting mixture was added with 1M borane-tetrahydrofuran complex in tetrahydrofuran (36 ml, 36 mmol) and stirred at room temperature for 0.5 hour, heated to reflux for another 5 hours. The mixture was added dropwise with 2 N hydrochloric acid in an ice-water bath. The resulting mixture was adjusted to pH 8 with 2N aqueous sodium hydroxide solution and distilled under reduced pressure. The residue was extracted with ethyl acetate (80 ml×8). The combined extracts were dried with anhydrous sodium sulfate, filtered and concentrated under reduced pressure to give 2-{2-[(4-hydroxy-1-methyl-piperidin-4-ylmethyl)-amino]-ethyl}-4-methyl-1H-pyrrole-3-carboxylic acid ethyl ester (5.931 g) as an orange solid which was used as such.

MS m/z (ESI): 324[M+1]

A stirred mixture of 2-{2-[(4-hydroxy-1-methyl-piperidin-4-ylmethyl)-amino]-ethyl}-4-methyl-1H-pyrrole-3-carboxylic acid ethyl ester (5.931 g, 18.36 mmol) in glycol (257 ml) was added with lithium hydroxide monohydrate (6.169 g, 147 mmol). The resulting mixture was heated to 135° C. for 4 hours. The mixture was added with cold water (250 ml), adjusted to pH from 14 to 12 with 2N hydrochloric acid in an ice-water bath. The mixture was extracted with a 10 to 1 solvent mixture of dichloromethane and methanol (200 ml×8). The combined organic extracts were concentrated under reduced pressure and the residue was purified by silica gel column chromatography with dichloromethane:methanol:ammonia (600:45:2) as eluents to give 5-(4-hydroxy-1-methyl-piperidin-4-ylmethyl)-3-methyl-1,5,6,7-tetrahydro-pyrrolo[3,2-c]pyridin-4-one (11.837 g) as a light brown oil which was used as such.

MS m/z (ESI): 278[M+1]

A stirred solution of N,N'-dimethyl formamide (1.2 ml) in dichloromethane (26 ml) was added dropwise slowly with phosphorus oxychloride (1.4 ml, 15.06 mmol) in an ice-water bath while maintaining the temperature at 0° C. Upon completion of the addition, the mixture was stirred for 10 minutes at room temperature and cooled to 0° C. in an ice-water bath, added with a solution of 5-(4-hydroxy-1-methyl-piperidin-4-ylmethyl)-3-methyl-1,5,6,7-tetrahydro-pyrrolo[3,2-c]pyridin-4-one (1.391 g, 5.02 mmol) in dichloromethane (8 ml) and stirred for 1 hour in an ice-water bath. The resulting mixture was stirred for another 3 hours at room temperature and added with ice to quench the reaction. The mixture was adjusted to pH 11 with 2N aqueous sodium hydroxide solution in an ice-water bath. The resulting mixture was extracted with a 7 to 1 solvent mixture of dichloromethane and methanol (50 ml×4). The combined extracts were dried with anhydrous sodium sulfate, filtered and concentrated to give a brown solid. The solid was purified by silica gel column chromatography with dichloromethane:methanol:ammonia (600:55:2) as eluents to give 5-(4-hydroxy-1-methyl-piperidin-4-ylmethyl)-3-methyl-4-oxo-4,5,6,7-tetrahydro-1H-pyrrolo[3,2-c]pyridine-2-carbaldehyde (147 mg, 9%) as a light brown solid.

MS m/z (ESI): 306[M+1]

The title compound was prepared under the same conditions as described in Example 1 with 5-(4-hydroxy-1-methyl-piperidin-4-ylmethyl)-3-methyl-4-oxo-4,5,6,7-tetrahydro-1H-pyrrolo[3,2-c]pyridine-2-carbaldehyde and 5-fluoro-1,3-dihydro-indol-2-one as starting materials to give 2-(5-fluoro-2-oxo-1,2-dihydro-indol-3-ylidenemethyl)-5-(4-hydroxy-1-methyl-piperidin-4-ylmethyl)-3-methyl-1,5,6,7-tetrahydro-pyrrolo[3,2-c]pyridin-4-one (16 mg, 37.98%) as an orange solid.

MS m/z (ESI): 439[M+1]

¹HNMR (400 MHz, DMSO-d6) 7.671~7.665 (d, 1H, —ArH), 7.638 (s, 1H, —CH), 6.882~6.830 (t, 1H, —ArH), 6.785~6.753 (q, 1H, —ArH), 3.643~3.610 (t, 2H, —NCH₂), 3.291 (s, 2H, —NCH₂), 2.928~2.895 (t, 2H, —CH₂), 2.341~2.314 (t, 2H, —CH₂), 2.165~2.118 (t, 2H, —CH₂), 2.048 (s, 3H, —CH₃)

Example 108

2-[4-(2,3-Difluoro-phenyl)-2-oxo-1,2-dihydro-indol-3-ylidenemethyl]-5-(4-hydroxy-1-methyl-piperidin-4-ylmethyl)-3-methyl-1,5,6,7-tetrahydro-pyrrolo[3,2-c]pyridin-4-one

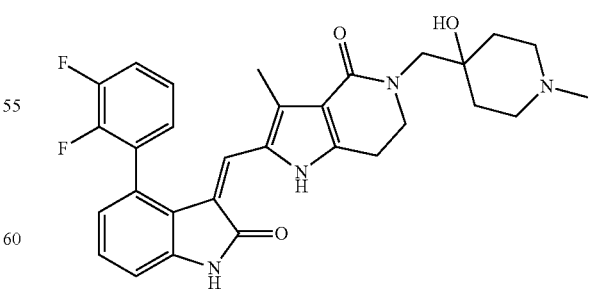

The title compound was prepared under the same conditions as described in Example 1 with 5-(4-hydroxy-1-methyl-piperidin-4-ylmethyl)-3-methyl-4-oxo-4,5,6,7-tetrahydro-1H-pyrrolo[3,2-c]pyridine-2-carbaldehyde and 4-(2,3- difluoro-phenyl)-1,3-dihydro-indol-2-one (prepared according to WO2002055517) as Starting materials to give 2-[4-(2,3-difluoro-phenyl)-2-oxo-1,2-dihydro-indol-3-ylidenemethyl]-5-(4-hydroxy-1-methyl-piperidin-4-ylmethyl)-3-methyl-1,5,6,7-tetrahydro-pyrrolo[3,2-c]pyridin-4-one (67 mg, 74.98%) as an orange solid.

MS m/z (ESI): 533[M+1]

¹HNMR (400 MHz, DMSO-d6) 7.532~7.512 (q, 1H, —ArH), 7.345~7.333 (q, 1H, —ArH), 6.942~6.923 (d, 1H, —ArH)6.806~6.781 (d, 1H, —ArH), 6.615 (s, —ArH), 3.597~3.564 (t, 2H, —CH₂), 3.349 (s, 2H, —NCH₂), 1.780 (s, 3H, —CH₃)

Example 109

2-(5-Chloro-2-oxo-1,2-dihydro-indol-3-ylidenemethyl)-5-(4-hydroxy-1-methyl-piperidin-4-ylmethyl)-3-methyl-1,5,6,7-tetrahydro-pyrrolo[3,2-c]pyridin-4-one

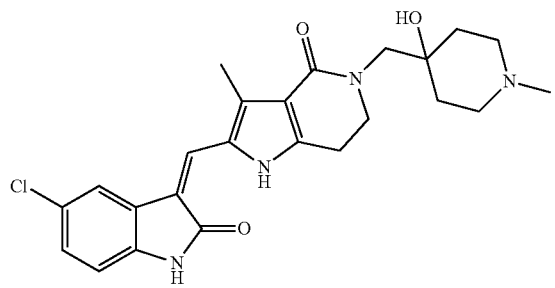 [SMILES: Cc1c(/C=C2\C(=O)Nc3ccc(Cl)cc32)[nH]c2c1C(=O)N(CC1(O)CCN(C)CC1)CC2]

The title compound was prepared under the same conditions as described in Example 1 with 5-(4-hydroxy-1-methyl-piperidin-4-ylmethyl)-3-methyl-4-oxo-4,5,6,7-tetrahydro-1H-pyrrolo[3,2-c]pyridine-2-carbaldehyde and 5-chloro-1,3-dihydro-indol-2-one as starting materials to give 2-(5-chloro-2-oxo-1,2-dihydro-indol-3-ylidenemethyl)-5-(4-hydroxy-1-methyl-piperidin-4-ylmethyl)-3-methyl-1,5,6,7-tetrahydro-pyrrolo[3,2-c]pyridin-4-one (44 mg, 59.14%) as a yellow solid.

MS m/z (ESI): 455[M+1]

¹HNMR (400 MHz, DMSO-d6) 7.894~7.889 (d, 1H, —ArH), 7.700 (s, 1H, —CH), 7.078~7.052 (dd, 1H, —ArH), 6.807~6.787 (d, 1H, —ArH), 3.647~3.614 (t, 2H, —NCH₂), 3.295 (s, 2H, —NCH₂), 2.934~2.902 (t, 2H, —CH₂), 2A45 (s, 3H, —CH₃), 2.051 (s, 3H, —CH₃)

Example 110

2-(5-Bromo-2-oxo-1,2-dihydro-indol-3-ylidenemethyl)-5-(4-hydroxy-1-methyl-piperidin-4-ylmethyl)-3-methyl-1,5,6,7-tetrahydro-pyrrolo[3,2-c]pyridin-4-one

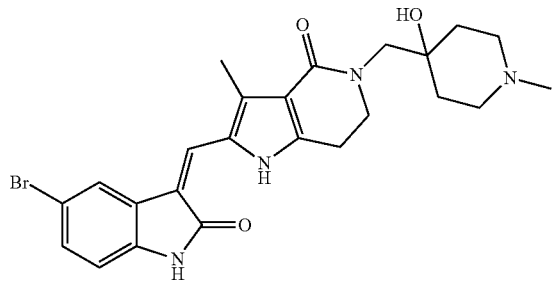

The title compound was prepared under the same conditions as described in Example 1 with 5-(4-hydroxy-1-methyl-piperidin-4-ylmethyl)-3-methyl-4-oxo-4,5,6,7-tetrahydro-1H-pyrrolo[3,2-c]pyridine-2-carbaldehyde and 5-bromo-1,3-dihydro-indol-2-one as starting materials to give 2-(5-bromo-2-oxo-1,2-dihydro-indol-3-ylidenemethyl)-5-(4-hydroxy-1-methyl-piperidin-4-ylmethyl)-3-methyl-1,5,6,7-tetrahydro-pyrrolo[3,2-c]pyridin-4-one (39 mg, 48.05%) as a yellow solid.

MS m/z (ESI): 450[M+1]

1HNMR (400 MHz, DMSO-d6) 8.009~8.005 (d, 1H, —ArH), 7.696 (s, 1H, —CH), 7.204~7.179 (dd, 1H, —ArH), 6.767~6.746 (d, 1H, —ArH), 3.643~3.616 (1, 2H, —NCH₂), 3.294 (s, 2H, —NCH₂), 2.932~2.899 (t, 2H, —CH₂), 2.064 (s, 3H, —CH₃)

Example 111

5-(2-Diethylamino-ethyl)-2-(5-fluoro-2-oxo-1,2-dihydro-indol-3-ylidenemethyl)-3-methyl-1,5-dihydro-pyrrolo[3,2-c]pyridin-4-one

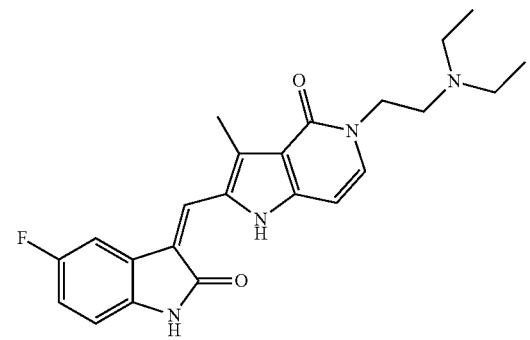 [SMILES: CCN(CC)CCn1ccc2[nH]c(/C=C3\C(=O)Nc4ccc(F)cc43)c(C)c2c1=O]

A stirred solution of 5-(2-diethylamino-ethyl)-2-(5-fluoro-2-oxo-1,2-dihydro-indol-3-ylidenemethyl)-3-methyl-1,5,6,7-tetrahydro-pyrrolo[3,2-c]pyridin-4-one (150 mg, 0.366 mmol) in acetic acid (3.5 ml) was cooled to 1St in an ice-water bath. The mixture was added with lead acetate (130 mg, 0.293 mmol) and stirred for 2.5 hours at room temperature. The mixture was added with 1N aqueous sodium hydroxide solution (60 ml) and extracted with a 5 to 1 solvent mixture of dichloromethane and methanol (40 ml×4). The extracts were combined, washed by brine, dried over anhydrous sodium sulfate, concentrated under reduced pressure and purified by silica gel column chromatography to give 5-(2-diethylamino-ethyl)-2-(5-fluoro-2-oxo-1,2-dihydro-indol-3-ylidenemethyl)-3-methyl-1,5-dihydro-pyrrolo[3,2-c]pyridine-4-one (32 mg) as a yellow solid.

MS m/z (ESI): 409[M+1]

¹HNMR (400 MHz, DMSO-d6) 7.848~7.842 (d, 1H, —ArH), 7.428~7.409 (d, 1H, —ArH), 6.989~6.984 (t, 1H,

—ArH), 6.550~6.531 (d, 1H, —CH), 3.396 (s, 3H, 2×-CH₃), 2.705 (s, 3H, —CH₃), 2.642~2.609 (t, 2H, —CH₂)

Example 112

5-(2-Dimethylamino-ethyl)-2-(5-fluoro-2-oxo-1,2-dihydro-indol-3-ylidenemethyl)-3-methyl-1,5,6,7-tetrahydro-pyrrolo[3,2-c]pyridin-4-one

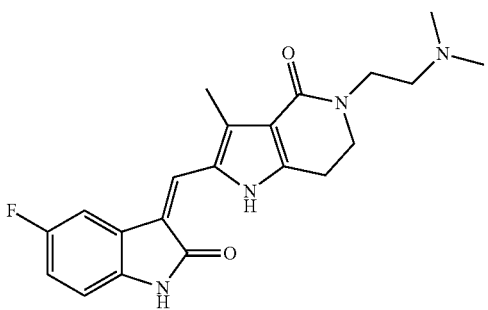 [SMILES: Cc1c(/C=C2\C(=O)Nc3ccc(F)cc32)[nH]c2c1C(=O)N(CCN(C)C)CC2]

A stirred solution of 2-carboxymethyl-4-methyl-1H-pyrrole-3-carboxylic acid ethyl ester (2.11 g, 10 mmol) in N,N-dimethylformamide (5 ml) and dichloromethane (50 ml) was added with N*1*,N*1*-dimethyl-ethane-1,2-diamine (968 mg, 11 mmol), N-ethyl-N'-(dimethylaminopropyl)-carbodiimide hydrochloride (5 g, 26 mmol) and 1-hydroxybenzotriazol (1.5 g, 11 mmol) in an ice-water bath. Upon completion of the addition, the mixture was stirred at room temperature overnight, added with cold water (50 ml) and extracted with dichloromethane (50 ml×3). The combined organic extracts were washed with saturated sodium bicarbonate solution (50 ml), water (50 ml), brine (50 ml), dried over anhydrous sodium sulfate, filtered and concentrated under reduced pressure to give 2-[(2-dimethylamino-ethylcarbamoyl)-methyl]-4-methyl-1H-pyrrole-3-carboxylic acid ethyl ester (28.1 g, 90.9%) as a colorless oil which was used as such.

MS m/z (ESI): 282[M+1]

A stirred solution of 2-[(2-dimethylamino-ethylcarbamoyl)-methyl]-4-methyl-1H-pyrrole-3-carboxylic acid ethyl ester (281 mg, 1 mmol) in anhydrous tetrahydrofuran (2 ml) was added dropwise slowly with 1M borane-tetrahydrofuran complex in tetrahydrofuran (3 ml, 3 mmol) under an argon atmosphere. Upon completion of the addition, the mixture was stirred for 1 hour and heated to reflux for another 5 hours. The mixture was added with cold water (5 ml) and 1N hydrochloric acid (2 ml) and stirred for 5 minutes. The resulting solution was adjusted to pH 10 with 10% aqueous sodium hydroxide solution and extracted with ethyl acetate (10 ml×5). The combined organic extracts were washed with brine (15 ml), dried with anhydrous sodium sulfate, filtered and concentrated under reduced pressure to give 2-[2-(2-dimethylamino-ethylamino)-ethyl]-4-methyl-1H-pyrrole-3-carboxylic acid ethyl ester (300 mg) as a brown oil which was used as such.

MS m/z (ESI): 268[M+1]

A stirred solution of 2-[2-(2-dimethylamino-ethylamino)-ethyl]-4-methyl-1H-pyrrole-3-carboxylic acid ethyl ester (267 mg, 1 mmol) in 5 ml of toluene was added dropwise with 2M trimethyl aluminum in toluene (1 ml, 2 mmol) under an argon atmosphere. The mixture was stirred for 1 hour at room temperature and heated to reflux for another 4 hours. The reaction mixture was cooled down to or in an ice-water bath, added with 1N hydrochloric acid (10 ml) and cold water (10 ml). The mixture was adjusted to pH12 with 10% aqueous sodium hydroxide solution and extracted with dichloromethane (25 ml×5). The combined organic extracts were filtered through a pad of Celite. The filtrate was dried with anhydrous sodium sulfate, filtered and concentrated under reduced pressure to give 5-(2-dimethylamino-ethyl)-3-methyl-1,5,6,7-tetrahydro-pyrrolo[3,2-c]pyridin-4-one (242 mg, 97%) as a brown oil which was used as such.

A stirred solution of N,N-dimethylformamide (2 ml) was added dropwise slowly with phosphorus oxychloride (104 µl, 1.1 mmol) under an argon atmosphere while maintaining the temperature at 0° C. Upon completion of the addition, the mixture was stirred for 15 minutes at room temperature, and cooled down to 0~5° C. in an ice-water bath. A mixture of 5-(2-dimethylamino-ethyl)-3-methyl-1,5,6,7-tetrahydro-pyrrolo[3,2-c]pyridin-4-one (221 mg, 1 mmol) in 1.2 ml of N,N-dimethylformamide was added dropwise to the above solution. Upon completion of the addition, the mixture was stirred for 2 hours at 0° C., added with cold water (15 ml), stirred for 5 minutes. The resulting mixture was adjusted to pH 12 with 10% aqueous sodium hydroxide solution and extracted with dichloromethane (15 ml×6). The combined organic extracts were washed with brine (15 ml), dried with anhydrous sodium sulfate; filtered and concentrated under reduced pressure. The residue was purified by silica gel column chromatography with triethylamine:methanol:dichloromethane (1:20:500) as eluents to give 5-(2-dimethylamino-ethyl)-3-methyl-4-oxo-4,5,6,7-tetrahydro-1H-pyrrolo[3,2-c]pyridine-2-carbaldehyde (105 mg, 38%) as a pink oil which was used as such.

MS m/z (ESI): 248[M−1]

A stirred solution of 5-(2-dimethylamino-ethyl)-3-methyl-4-oxo-4,5,6,7-tetrahydro-1H-pyrrolo[3,2-c]pyridine-2-carbaldehyde (67 mg, 0.267 mmol), 5-fluoro-1,3-dihydro-indol-2-one (40 mg, 0.267 mmol) in 0.66 ml of ethanol was added dropwise with anhydrous piperidine (0.1 ml). The mixture was stirred at room temperature overnight. The resulting solid was filtered under reduced pressure, washed with ethanol (1 ml×3) and purified by silica gel column chromatography with triethylamine:methanol:dichloromethane (1:20:500) as eluents to give 5-(2-dimethylamino-ethyl)-2-(5-fluoro-2-oxo-1,2-dihydro-indol-3-ylidenemethyl)-3-methyl-1,5,6,7-tetrahydro-pyrrolo[3,2-c]pyridin-4-one (60 mg, 54.8%) as a yellow solid.

MS m/z (ESI): 383[M+1]

¹H NMR (400 MHz, DMSO-d6) δ7.76 (d, 1H, ArH), 7.74 (s, 1H, CH), 6.95 (td, 1H, ArH), 6.85~6.88 (m, 1H, ArH), 3.62 (t, 2H, CH2), 3.48 (t, 2H, CH2), 3.45 (t, 2H, CH2), 2.99 (t, 2H, CH2), 2.53 (s, 3H, CH3), 2.49 (q, 4H, 2×NCH2), 0.97 (t, 6H, 2×NCH2 CH3).

Example 113

2-[4-(2,3-Difluoro-phenyl)-2-oxo-1,2-dihydro-indol-3-ylidenemethyl]-5-(2-dimethylamino-ethyl)-3-methyl-1,5,6,7-tetrahydro-pyrrolo[3,2-c]pyridin-4-one

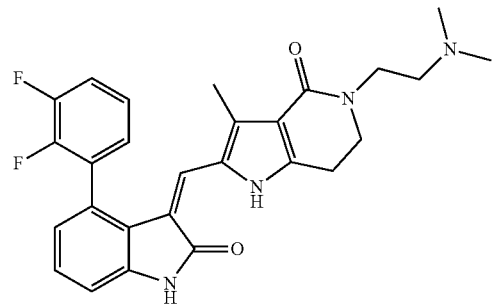 [SMILES: Cc1c(/C=C2\C(=O)Nc3cccc(-c4cccc(F)c4F)c32)[nH]c2c1C(=O)N(CCN(C)C)CC2]

The title compound was prepared under the same conditions as described in Example 112 with 5-(2-dimethylamino-ethyl)-3-methyl-4-oxo-4,5,6,7-tetrahydro-1H-pyrrolo[3,2-c]pyridine-2-carbaldehyde and 4-(2,3-difluoro-phenyl)-1,3-dihydro-indol-2-one (prepared according to WO2002055517) as starting materials to give 2-[4-(2,3-difluoro-phenyl)-2-oxo-1,2-dihydro-indol-3-ylidenemethyl]-5-(2-dimethylamino-ethyl)-3-methyl-1,5,6,7-tetrahydro-pyrrolo[3,2-c]pyridin-4-one (45 mg, 61.6%) as a yellow solid.

MS m/z (ESI): 477[M+1]

¹HNMR (DMSO-D6,400 MHz) 7.279~7.240 (t, 1H, —ArH), 7.017~6.998 (d, 1H, —ArH), 6.900~6.881 (d, 1H, —ArH), 6.715 (s, 1H, —CH), 3.580~3.546 (t, 2H, —CH₂), 3.478~3.444 (t, 2H, —CH₂), 2.981~2.947 (t, 2H, —CH₂), 2.398~2.365 (t, 2H, —CH₂), 2.178 (s, 6H, 2×-CH₃); 1.888 (s, 3H, —CH₃)

Example 114

2-(5-Chloro-2-oxo-1,2-dihydro-indol-3-ylidenemethyl)-5-(2-dimethylamino-ethyl)-3-methyl-1,5,6,7-tetrahydro-pyrrolo[3,2-c]pyridin-4-one

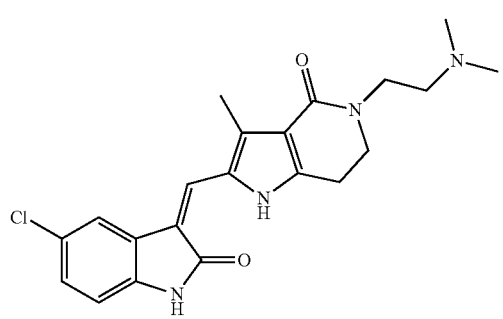 [SMILES: Cc1c(/C=C2\C(=O)Nc3ccc(Cl)cc32)[nH]c2c1C(=O)N(CCN(C)C)CC2]

The title compound was prepared under the same conditions as described in Example 112 with 5-(2-dimethylamino-ethyl)-3-methyl-4-oxo-4,5,6,7-tetrahydro-1H-pyrrolo[3,2-c]pyridine-2-carbaldehyde and 5-chloro-1,3-dihydro-indol-2-one as starting materials to give 2-(5-chloro-2-oxo-1,2-dihydro-indol-3-ylidenemethyl)-5-(2-dimethylamino-ethyl)-3-methyl-1,5,6,7-tetrahydro-pyrrolo[3,2-c]pyridin-4-one (40 mg, 65.5%) as a yellow solid.

MS m/z (ESI): 399[M+1]

¹HNMR (DMSO-D6,400 MHz) 7.167~7.142 (dd, 1H, —ArH), 6.890~6.869 (d, 1H, —ArH), 3.624~3.590 (t, 2H, —CH₂), 3.515~3.481 (t, 2H, —CH₂), 3.019~2.986 (t, 2H, —CH₂), 2.550 (s, 3H, —CH₃), 2.424~2.390 (t, 2H, —CH₂), 2.194 (s, 6H, 2×-CH₂)

Example 115

4-(3-Chloro-4-fluoro-phenylamino)-5-[5-(2-dimethylamino-ethyl)-3-methyl-4-oxo-4,5,6,7-tetrahydro-1H-pyrrolo[3,2-c]pyridin-2-ylmethylene]-5,7-dihydro-pyrrolo[2,3-d]pyrimidin-6-one

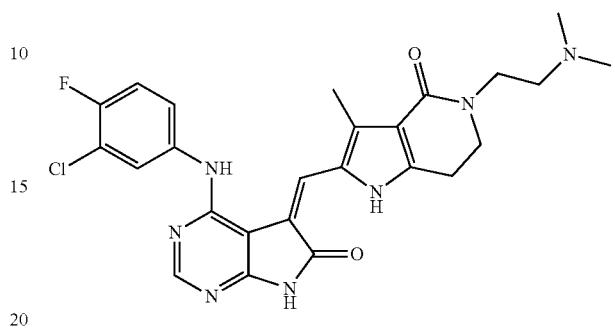

The title compound was prepared under the same conditions as described in Example 102 with 5-(2-dimethylamino-ethyl)-3-methyl-4-oxo-4,5,6,7-tetrahydro-1H-pyrrolo[3,2-c]pyridine-2-carbaldehyde and 4-(3-chloro-4-fluoro-phenylamino)-5,7-dihydro-pyrrolo[2,3-d]pyrimidin-6-one (prepared according to *Bioorganic&Medicinal Chemistry Letters*, 12 (16), 2153-2157, 2002) as starting materials to give 4-(3-chloro-4-fluoro-phenylamino)-5-[5-(2-dimethylamino-ethyl)-3-methyl-4-oxo-4,5,6,7-tetrahydro-1H-pyrrolo[3,2-c]pyridin-2-ylmethylene]-5,7-dihydro-pyrrolo[2,3-d]pyrimidin-6-one (240 mg, 61.5%) as a yellow solid.

MS m/z (ESI): 510[M+1]

¹HNMR (DMSO-D6,400 MHz) 8.322 (s, 1H, —CH), 7.735~7.713 (dd, 1H, —ArH), 3.625~3.591 (t, 2H, —CH₂), 3.508~3.474 (t, 2H, —CH₂), 3.039~3.005 (t, 2H, —CH₂), 2.189 (s, 6H, 2×-CH₃)

Example 116

N-{3-[5-(2-Dimethylamino-ethyl)-3-methyl-4-oxo-4,5,6,7-tetrahydro-1H-pyrrolo[3,2-c]pyridin-2-ylmethylene]-2-oxo-2,3-dihydro-1H-indol-5-yl}-formamide

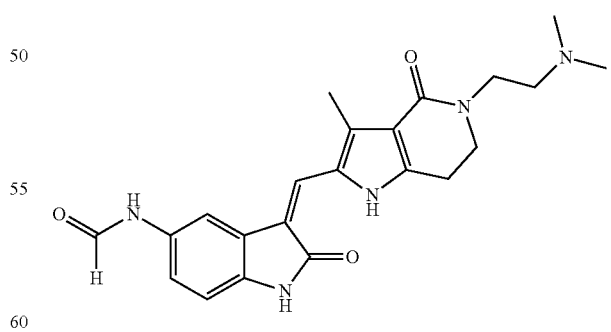

The title compound was prepared under the same conditions as described in Example 112 with 5-(2-dimethylamino-ethyl)-3-methyl-4-oxo-4,5,6,7-tetrahydro-1H-pyrrolo[3,2-c]pyridine-2-carbaldehyde and N-(2-oxo-2,3-dihydro-1H-indol-5-yl)-formamide as starting materials to give N-{3-[5-(2-dimethylamino-ethyl)-3-methyl-4-oxo-4,5,6,7- tetrahydro-1H-pyrrolo[3,2-c]pyridin-2-ylmethylene]-2-oxo-2,3-dihydro-1H-indol-5-yl}-formamide (43 mg, 69.3%) as a yellow solid.

MS m/z (ESI): 408[M+1]

¹HNMR (DMSO-D6,400 MHz) 7.513 (s, 1H, —CH), 7.335~7.310 (d, 1H, —ArH), 3.623~3.590 (t, 2H, —CH₂), 3.513~3.469 (t, 2H, —CH₂), 3.013~2.979 (t, 2H, —CH₂), 2.416~2.382 (t, 2H, —CH₂), 2.189 (s, 6H, 2×-CH₃)

Example 117

N-{3-[5-(2-Dimethylamino-ethyl)-3-methyl-4-oxo-4,5,6,7-tetrahydro-1H-pyrrolo[3,2-c]pyridin-2-ylmethylene]-5-fluoro-2-oxo-2,3-dihydro-1H-indol-6-yl}-2-hydroxy-2-methyl-propionamide

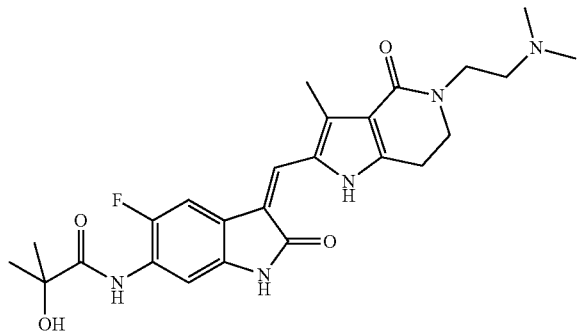 [SMILES: Cc1c(/C=C2\C(=O)Nc3cc(NC(=O)C(C)(C)O)c(F)cc32)[nH]c2c1C(=O)N(CCN(C)C)CC2]

The title compound was prepared under the same conditions as described in Example 112 with 5-(2-dimethylamino-ethyl)-3-methyl-4-oxo-4,5,6,7-tetrahydro-1H-pyrrolo[3,2-c]pyridine-2-carbaldehyde and N-(5-fluoro-2-oxo-2,3-dihydro-1H-indol-6-yl)-2-hydroxy-2-methyl-propionamide as starting materials to give N-{3-[5-(2-dimethylamino-ethyl)-3-methyl-4-oxo-4,5,6,7-tetrahydro-1H-pyrrolo[3,2-c]pyridin-2-ylmethylene]-5-fluoro-2-oxo-2,3-dihydro-1H-indol-6-yl}-2-hydroxy-2-methyl-propionamide (40 mg, 41.8%) as a yellow solid.

MS m/z (ESI): 484[M+1]

¹HNMR (DMSO-D6,400 MHz) 7.903~7.875 (d, 1H, —ArH), 7.795~7.779 (d, 1H, —ArH), 7.669 (s, 1H, —CH), 6.055 (s, 1H, —OH), 3.620~3.587 (t, 2H, —CH₂), 3.514~3.481 (t, 2H, —CH₂), 3.011~2.977 (t, 2H, —CH₂), 2.492~2.396 (t, 2H, —CH₂), 2.199 (s, 6H, 2×-CH₃)

Example 118

5-(2-Ethylamino-ethyl)-2-(5-fluoro-2-oxo-1,2-dihydro-indol-3-ylidenemethyl)-3-methyl-1,5,6,7-tetrahydro-pyrrolo[3,2-c]pyridin-4-one

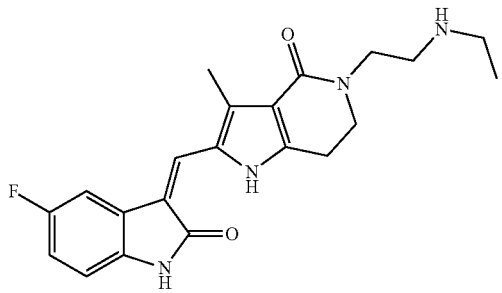 [SMILES: CCNCCN1CCc2[nH]c(/C=C3\C(=O)Nc4ccc(F)cc43)c(C)c2C1=O]

A stirred solution of ethyl-{2-[2-(6-fluoro-2-oxo-indan-1-ylidenemethyl)-3-methyl-4-oxo-1,4,6,7-tetrahydro-pyrrolo[3,2-c]pyridin-5-yl]-ethyl}-carbamic acid tert-butyl ester (1.2 g, 2.5 mmol) obtained from Example 116 in dichloromethane (25 ml) was added dropwise slowly with 2.5 ml of trifluoroacetic acid. Upon the completion of the addition, the mixture was stirred for 2 hours at room temperature. The mixture was concentrated under reduced pressure to give 5-(2-ethylamino-ethyl)-2-(5-fluoro-2-oxo-1,2-dihydro-indol-3-ylidenemethyl)-3-methyl-1,5,6,7-tetrahydro-pyrrolo[3,2-c]pyridin-4-one (0.94 g, 98%) as a yellow solid.

MS m/z (ESI): 383[M+1]

Example 119

5-(2-Diethylamino-ethyl)-2-(5-fluoro-2-oxo-1,2-dihydro-indol-3-ylidenemethyl)-3-hydroxymethyl-1,5,6,7-tetrahydro-pyrrolo[3,2-c]pyridin-4-one

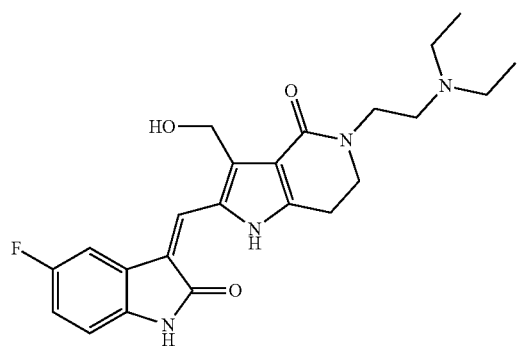 [SMILES: CCN(CC)CCN1CCc2[nH]c(/C=C3\C(=O)Nc4ccc(F)cc43)c(CO)c2C1=O]

A stirred solution of 5-(2-diethylamino-ethyl)-2-(5-fluoro-2-oxo-1,2-dihydro-indol-3-ylidenemethyl)-3-methyl-1,5,6,7-tetrahydro-pyrrolo[3,2-c]pyridin-4-one (82 mg, 0.2 mmol) prepared from Example 1 in 2 ml of tetrachloromethane was added with acetic acid (20 ml), N-bromosuccinimide (43 mg, 0.24 mmol) and azobisisobutyronitrile (2 mg, 0.012 mmol). The mixture was heated to reflux for 45 minutes, cooled down to room temperature filtered and concentrated under reduced pressure. The resulting mixture was purified by silica gel column chromatography to give the mixture (21 mg) of 7-bromo-5-(2-diethylamino-ethyl)-2-(5-fluoro-2-oxo-1,2-dihydro-indol-3-ylidenemethyl)-3-methyl-1,5,6,7-tetrahydro-pyrrolo[3,2-c]pyridin-4-one and 3-bromomethyl-5-(2-diethylamino-ethyl)-2-(5-fluoro-2-oxo-1,2-dihydro-indol-3-ylidenemethyl)-1,5,6,7-tetrahydro-pyrrolo[3,2-c]pyridin-4-one which was used as such.

A solution of 7-bromo-5-(2-diethylamino-ethyl)-2-(5-fluoro-2-oxo-1,2-dihydro-indol-3-ylidenemethyl)-3-methyl-1,5,6,7-tetrahydro-pyrrolo[3,2-c]pyridin-4-one and 3-bromomethyl-5-(2-diethylamino-ethyl)-2-(5-fluoro-2-oxo-1,2-dihydro-indol-3-ylidenemethyl)-1,5,6,7-tetrahydro-pyrrolo[3,2-c]pyridin-4-one in 10 ml of methanol was added with saturated potassium carbonate (2 ml). The mixture was stirred at room temperature overnight, added with water (20 ml) and extracted with the 6 to 1 mixture of dichloromethane and methanol (10 ml×4). The combined extracts were concentrated to give 5-(2-diethylamino-ethyl)-2-(5-fluoro-2-oxo-1,2-dihydro-indol-3-ylidenemethyl)-3-hydroxymethyl-1,5,6,7-tetrahydro-pyrrolo[3,2-c]pyridin-4-one (13 mg, 72%) as a yellow solid.

MS m/z (ESI): 427[M+1]

Example 120

5-(2-Diethylamino-ethyl)-2-(5-fluoro-2-oxo-1,2-dihydro-indol-3-ylidenemethyl)-3-m ethyl-1,5-dihydro-pyrrolo[3,2-c]pyridin-4-one

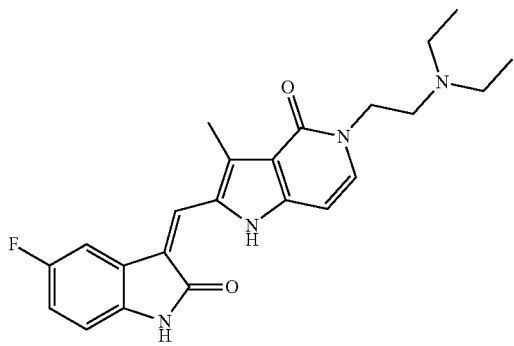 [SMILES: CCN(CC)CCn1ccc2[nH]c(/C=C3\C(=O)Nc4ccc(F)cc43)c(C)c2c1=O]

A stirred solution of 5-(2-diethylamino-ethyl)-2-(5-fluoro-2-oxo-1,2-dihydro-indol-3-ylidenemethyl)-3-methyl-1,5,6,7-tetrahydro-pyrrolo[3,2-c]pyridin-4-one (150 mg, 0.37 mmol) obtained from Example 1 in 4 ml of acetic acid was added with lead acetate (160 mg, 0.37 mmol) in an ice-water bath the control the temperature at 15° C. Upon the completion of the addition, the mixture was stirred at room temperature for 3 hours. The reaction mixture was added with 1N sodium hydroxide (60 ml) and extracted with five to one solvent mixture of dichloromethane, methanol (40 ml×4). The combined organic extracts were washed with brine (50 ml) and water (50 ml), dried with anhydrous sodium sulfate, filtered and concentrated under reduced pressure. The residue was purified by HPLC to give 5-(2-diethylamino-ethyl)-2-(5-fluoro-2-oxo-1,2-dihydro-indol-3-ylidenemethyl)-3-methyl-1,5-dihydro-pyrrolo[3,2-c]pyridin-4-one (64 mg, 42.6%) as a yellow solid.

MS m/z (ESI): 409 [M+1]

Example 121

5-(2-Dimethylamino-ethyl)-2-(5-fluoro-2-oxo-1,2-dihydro-indol-3-ylidenemethyl)-3-methyl-1,5-dihydro-pyrrolo[3,2-c]pyridin-4-one

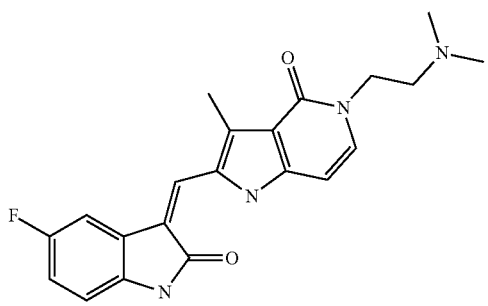 [SMILES: Cc1c(/C=C2\C(=O)Nc3ccc(F)cc32)[nH]c2ccn(CCN(C)C)c(=O)c12]

The title compound was prepared under the same conditions as described in Example 120 with 5-(2-dimethylamino-ethyl)-2-(5-fluoro-2-oxo-1,2-dihydro-indol-3-ylidenemethyl)-3-methyl-1,5,6,7-tetrahydro-pyrrolo[3,2-c]pyridin-4-one obtained from Example 112 as starting materials to give 5-(2-dimethylamino-ethyl)-2-(5-fluoro-2-oxo-1,2-dihydro-indol-3-ylidenemethyl)-3-methyl-1,5-dihydro-pyrrolo[3,2-c]pyridin-4-one (40 mg, 50.8%) as a yellow solid.

MS m/z (ESI): 381[M+1]

Example 122

2-(5-Fluoro-2-oxo-1,2-dihydro-indol-3-ylidenemethyl)-3-methyl-5-(2-morpholin-4-yl-ethyl)-1,5-dihydro-pyrrolo[3,2-c]pyridin-4-one

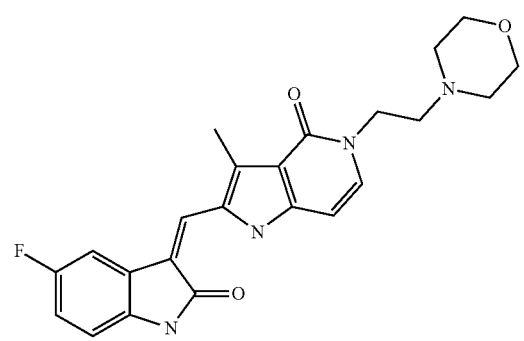 [SMILES: Cc1c(/C=C2\C(=O)Nc3ccc(F)cc32)[nH]c2ccn(CCN3CCOCC3)c(=O)c12]

The title compound was prepared under the same conditions as described in Example 120 with 2-(5-fluoro-2-oxo-1,2-dihydro-indol-3-ylidenemethyl)-3-methyl-5-(2-morpholin-4-yl-ethyl)-1,5,6,7-tetrahydro-pyrrolo[3,2-c]pyridin-4-one obtained from Example 13 as starting materials to give 5-(2-dimethylamino-ethyl)-2-(5-fluoro-2-oxo-1,2-dihydro-indol-3-ylidenemethyl)-3-methyl-1,5-dihydro-pyrrolo[3,2-c]pyridin-4-one (50 mg, 45%) as a yellow solid.

MS m/z (ESI): 423[M+1]

Example 123

5-(2-Diethylamino-ethyl)-2-(5-fluoro-2-oxo-1,2-dihydro-indol-3-ylidenemethyl)-3-tri fluoromethyl-1,5,6,7-tetrahydro-pyrrolo[3,2-c]pyridin-4-one

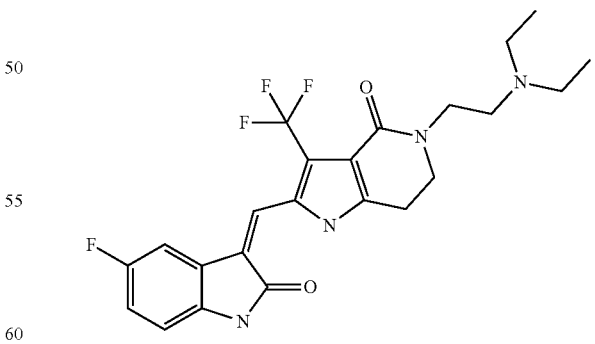

A stirred solution of 4,4,4-trifluoro-3-oxo-butyric acid ethyl ester (3.822 g, 20.75 mmol) in glacial acetic acid was added dropwise with an aqueous solution of sodium nitrite (4 ml, 20.75 mmol) while maintaining the temperature at 0~5° C. Upon completion of the addition, 1 ml of water was added. The reaction mixture was stirred in an ice-water bath for 30 minutes and at room temperature for another 3 hours. The solution of 4,4,4-trifluoro-2-hydroxyimino-3-oxo-butyric acid ethyl ester was obtained which was used as such.

A stirred solution of 4,4,4-trifluoro-2-hydroxyimino-3-oxo-butyric acid ethyl ester (55 g, 0.258 mol) in ethanol (140 ml) was added with palladium on activated carbon and 4N hydrochloric acid (90 ml) accordingly. The reaction mixture was stirred in a Parr shaker under 0.3 MPa of hydrogen at room temperature for 2.5 hours. The reaction mixture was filtered, the filtrate was concentrated to give 2-amino-4,4,4-trifluoro-3-oxo-butyric acid ethyl ester hydrochloride (37.56 g, 61.8%) as a yellow solid.

MS m/z (ESI): 234[M−1]

A stirred solution of [3-(2,2-dimethyl-4,6-dioxo-[1,3]dioxin-5-ylidene)-3-hydroxy-propyl]-carbamic acid tert-butyl ester (9.2 g, 29.2 mmol) obtained from Example 41 in 180 ml of dioxane was heated to reflux for 2 hours. The mixture was evaporated under reduced pressure to give the crude product 2,4-dioxo-piperidine-1-carboxylic acid tert-butyl ester (6.4 g) as a yellow oil which was used as such.

MS m/z (ESI): 212[M−1]

A stirred mixture of 2-amino-4,4,4-trifluoro-3-oxo-butyric acid ethyl ester hydrochloride (7.54 g, 32 mmol), 2,4-dioxo-piperidine-1-carboxylic acid tert-butyl ester (6.2 g, 29.1 mmol) and sodium acetate (2.39 g, 29.1 mmol) in water (35 ml) and dioxane (35 ml) was heated to reflux for 2 hours. The mixture was cooled down to room temperature, and extracted with 15 to 1 solvent mixture of ethyl acetate and methanol (160 ml×3), the combined organic phase was washed with saturated sodium chloride, dried with anhydrous sodium sulfate, filtered and concentrated under reduced pressure, the residue was purified by the silica gel column chromatography with dichloromethane:tetrahydrofuran:methanol (40:5:1) as eluents to give 3-trifluoromethyl-4-oxo-4,5,6,7-tetrahydro-1H-pyrrolo[3,2-c]pyridine-2-carboxylic acid ethyl ester (2.8 g, 35%) as a yellow solid.

MS m/z (ESI): 275[M−1]

A stirred mixture of 3-trifluoromethyl-4-oxo-4,5,6,7-tetrahydro-1H-pyrrolo[3,2-c]pyridine-2-carboxylic acid ethyl ester (2.6 g, 9.4 mmol) in 40 ml of N,N-dimethylformamide was cooled down to 0° C. in an ice-water bath, added with sodium hydride slowly. Upon the completion of the addition, the reaction mixture was cooled down to −30~40° C. and added with (2-bromo-ethyl)-diethyl-amine hydrobromide (2.95 g, 11.3 mmol) in 15 ml of N,N-dimethylformamide. The reaction mixture was stirred at room temperature overnight and extracted with saturated sodium chloride (100 ml) and dichloromethane (100 ml). The combined organic phase was washed with saturated sodium chloride, dried with anhydrous sodium sulfate, filtered and concentrated under reduced pressure. The residue was purified by silica gel column chromatography with dichloromethane:methanol:ammonia (16:1:0.1) as eluents to give 5-(2-diethylamino-ethyl)-3-trifluoromethyl-4-oxo-4,5,6,7-tetrahydro-1H-pyrrolo[3,2-c]pyridine-2-carboxylic acid ethyl ester (1 g, 28.4) as a yellow solid.

MS m/z (ESI): 376[M+1]

A stirred solution of lithium aluminum hydride (396 mg, 10.43 mmol) in 6 ml of anhydrous tetrahydrofuran was cooled down to 0° C. in an ice-water bath, added slowly dropwise with 5-(2-diethylamino-ethyl)-3-trifluoromethyl-4-oxo-4,5,6,7-tetrahydro-1H-pyrrolo[3,2-c]pyridine-2-carboxylic acid ethyl ester (1.63 g, 4.35 mmol) in 10 ml of tetrahydrofuran. Upon the completion of the addition, the reaction mixture was stirred at room temperature for 1 hour and filter through a pad of Celite. The filtrate was evaporated under reduced pressure to give the crude product 5-(2-diethylamino-ethyl)-2-hydroxymethyl-3-trifloromethyl-1,5,6,7-tetrahydro-pyrrolo[3,2-c]pyridin-4-one (1.208 g, 83.4%) as a yellow oil which was used as such.

MS m/z (ESI): 334[M+1]

A stirred solution of 5-(2-diethylamino-ethyl)-2-hydroxymethyl-3-trifloromethyl-1,5,6,7-tetrahydro-pyrrolo[3,2-c]pyridin-4-one (1.208 g, 3.63 mmol) and 4-methylbenzenesulfonic acid monohydrate (690 mg, 3.63 mmol) in 8 ml of N,N-dimethyl sulfoxide was added dropwise with 2-iodoxybenzoic acid (1.63 g, 5.8 mmol) in 8 ml of N,N-dimethyl sulfoxide. Upon the completion of the addition, the mixture was stirred at room temperature for 2.5 hours. The reaction mixture was added with ice to quench the reaction and filtered. The filtrate was added with saturated sodium carbonate to adjust pH9~10, extracted with dichloromethane (50 ml×5). The combined organic phase was washed with saturated sodium carbonate (10 ml), saturated sodium chloride (10 ml), dried with anhydrous sodium sulfate, filtered and concentrated under reduced pressure. The residue was purified by the silica gel column chromatography with dichloromethane:n-hexane:methanol:ammonia (200:20:10:0.5) as eluents to give 5-(2-diethylamino-ethyl)-3-trifluoromethyl-4-oxo-4,5,6,7-tetrahydro-1H-pyrrolo[3,2-c]pyridine-2-carbaldehyde (407 mg, 28%) as a yellow solid.

MS m/z (ESI): 332[M+1]

A stirred solution of 5-(2-diethylamino-ethyl)-3-trifluoromethyl-4-oxo-4,5,6,7-tetrahydro-1H-pyrrolo[3,2-c]pyridine-2-carbaldehyde (40 mg, 0.121 mmol), 5-fluoro-1,3-dihydro-indol-2-one (18 mg, 0.12 mmol) in 0.4 ml of ethanol was added dropwise with anhydrous piperidine (0.1 ml). The mixture was stirred at room temperature overnight. The resulting solid was filtered under reduced pressure, washed with anhydrous ethanol (1 ml×3), purified by silica gel column chromatography with triethylamine:methanol:dichloromethane (1:20:500) as eluents to give 5-(2-diethylamino-ethyl)-2-(5-fluoro-2-oxo-1,2-dihydro-indol-3-ylidenemethyl)-3-trifluoromethyl-1,5,6,7-tetrahydro-pyrrolo[3,2-c]pyridin-4-one (46 mg, 83.6%) as a yellow solid MS m/z (ESI): 465[M+1]

$^1$H NMR (400 MHz, DMSO-d6) 7.75 (d, 1H, ArH, 7.62 (m, 1H, CH), 7.10 (m, 1H, ArH), 6.91 (m, 1H, ArH), $\overline{3.66}$ (t, 2H, CH$_2$), 3.46 (t, 2H, CH$_2$), 3.05 (t, 2H, CH$_2$), 2.54 (t, 2H, CH$_2$), 2.49 (q, 4H, 2×-NCH$_2$), 0.96 (t, 6H, 2×-NCH$_2$CH$_3$).

Example 124

4-(3-Chloro-4-fluoro-phenylamino)-5-[5-(2-diethylamino-ethyl)-4-oxo-3-trifluoromethyl-4,5,6,7-tetrahydro-1H-pyrrolo[3,2-c]pyridin-2-ylmethylene]-5,7-dihydro-pyrrolo[2,3-d]pyrimidin-6-one

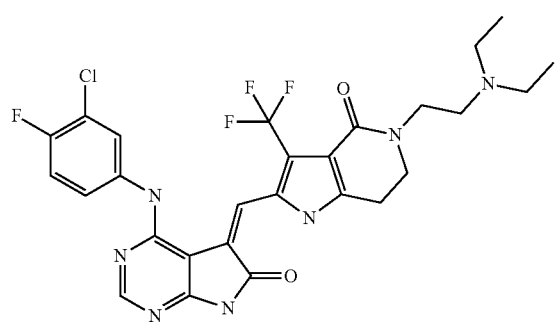 [SMILES: CCN(CC)CCN1CCc2[nH]c(/C=C3\C(=O)Nc4ncnc(Nc5ccc(F)c(Cl)c5)c43)c(C(F)(F)F)c2C1=O]

The title compound was prepared under the same conditions as described in Example 123 with 5-(2-diethylamino-ethyl)-3-trifluoromethyl-4-oxo-4,5,6,7-tetrahydro-1H-pyrrolo[3,2-c]pyridine-2-carbaldehyde and 4-(3-chloro-4-fluoro-phenylamino)-5,7-dihydro-pyrrolo[2,3-d]-pyrimidin-6-one as starting materials to give 4-(3-chloro-4-fluoro-phenylamino)-5-[5-(2-diethylamino-ethyl)-4-oxo-3-trifluoromethyl-4,5,6,7-tetrahydro-1H-pyrrolo[3,2-c]pyridin-2-ylmethylene]-5,7-dihydro-pyrrolo[2,3-d]pyrimidin-6-one (43 mg, 48.5%) as a yellow solid.

MS m/z (ESI): 592[M+1]

$^1$H NMR (400 MHz, DMSO-d6) 8.40 (s, 1H, —CH), 7.69 (dd, 1H, —ArH), 7.32~7.39 (m, 3H, 2×-ArH, —CH), 3.65 (t, 2H, —CH$_2$), 3.46 (t, 2H, —CH$_2$), 3.05 (t, 2H, —CH$_2$), 2.58 (t, 2H, —CH$_2$), 2.51 (q, 4H, 2×-NCH$_2$), 1.00 (t, 6H, 2×-NCH$_2$CH$_3$).

Example 125

5-(2-Diethylamino-ethyl)-2-(5-fluoro-2-oxo-1,2-dihydro-indol-3-ylidenemethyl)-3-methyl-1,5,6,7-tetrahydro-pyrrolo[3,2-c]pyridin-4-one malate

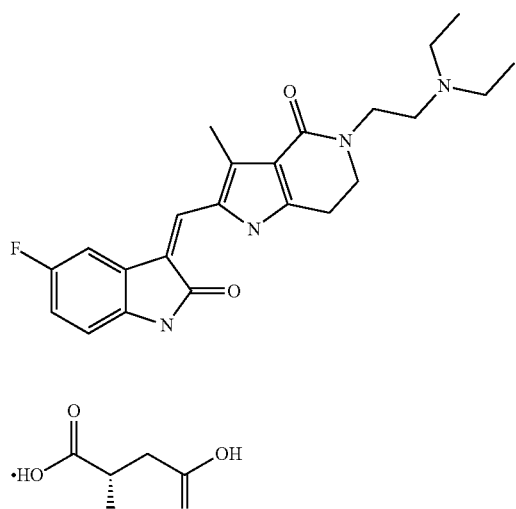

A stirred yellow suspension of 5-(2-diethylamino-ethyl)-2-(5-fluoro-2-oxo-1,2-dihydro-indol-3-ylidenemethyl)-3-methyl-1,5,6,7-tetrahydro-pyrrolo[3,2-c]pyridin-4-one (27 g, 66 mmol) in 600 ml of methanol was added with 2-hydroxyl-succinic acid (9.26 g, 69 mmol). The resulting solution was stirred for 30 minutes. The solvent was evaporated under reduced pressure and the residue was added with 100 ml of acetonitrile. The resulting solution was heated to reflux for 1.5 hours, cooled down to room temperature and filtered. The filter cake was washed with cold acetonitrile (100 ml×3) and ethanol (100 ml×3) and dried in vacuo to give the title compound 5-(2-diethylamino-ethyl)-2-(5-fluoro-2-oxo-1,2-dihydro-indol-3-ylidenemethyl)-3-methyl-1,5,6,7-tetrahydro-pyrrolo[3,2-c]pyridin-4-one malate (35 g, 95%) as a yellow solid.

MS m/z (ESI): 545[M+1]

Example 126

2-(5-Fluoro-2-oxo-1,2-dihydro-indol-3-ylidenemethyl)-3-methyl-5-(2-morpholin-4-yl-ethyl)-1,5,6,7-tetrahydro-pyrrolo[3,2-c]pyridin-4-one malate

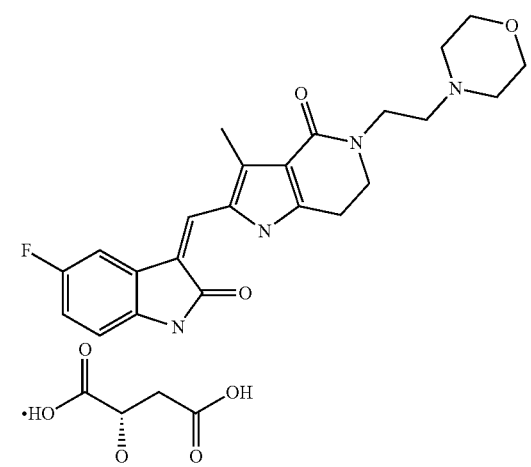

The title compound was prepared under the same conditions described in Example 132 with 2-(5-fluoro-2-oxo-1,2-dihydro-indol-3-ylidenemethyl)-3-methyl-5-(2-morpholin-4-yl-ethyl)-1,5,6,7-tetrahydro-pyrrolo[3,2-c]pyridin-4-one and 2-hydroxyl-succinic acid as starting materials to give 2-(5-fluoro-2-oxo-1,2-dihydro-indol-3-ylidenemethyl)-3-methyl-5-(2-morpholin-4-yl-ethyl)-1,5,6,7-tetrahydro-pyrrolo[3,2-c]pyridin-4-one malate (20 g, 95%) as a yellow solid.

Example 127

5-(2-Diethylamino-ethyl)-2-[4-(2,3-difluoro-phenyl)-2-oxo-1,2-dihydro-indol-3-ylidenemethyl]-3-methyl-1,5,6,7-tetrahydro-pyrrolo[3,2-c]pyridin-4-one malate

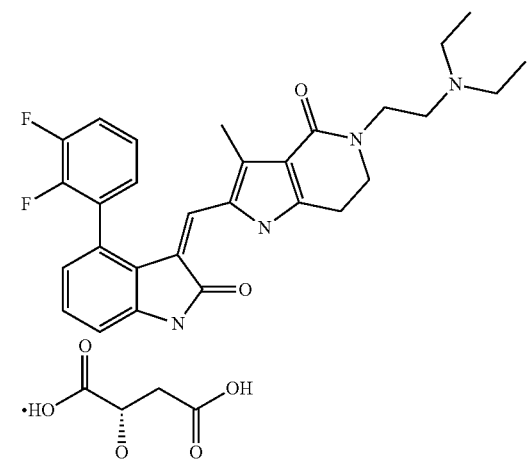

The title compound was prepared under the same conditions described in Example 132 with 5-(2-diethylamino-ethyl)-2-[4-(2,3-difluoro-phenyl)-2-oxo-1,2-dihydro-indol-3-ylidenemethyl]-3-methyl-1,5,6,7-tetrahydro-pyrrolo[3,2-c]pyridin-4-one prepared from Example 39 and 2-hydroxyl-succinic acid as starting materials to give 2-(5-fluoro-2-oxo-1,2-dihydro-5-(2-diethylamino-ethyl)-2-[4-(2,3-difluoro-phenyl)-2-oxo-1,2-dihydro-indol-3-ylidenemethyl]-3-methyl-1,5,6,7-tetrahydro-pyrrolo[3,2-c]pyridin-4-one malate (15 g, 94%) as a yellow solid.

Example 128

5-(2-Diethylamino-ethyl)-2-(5-fluoro-2-oxo-1,2-dihydro-indol-3-ylidenemethyl)-3-methyl-1,5,6,7-tetrahydro-pyrrolo[3,2-c]pyridin-4-one lactate

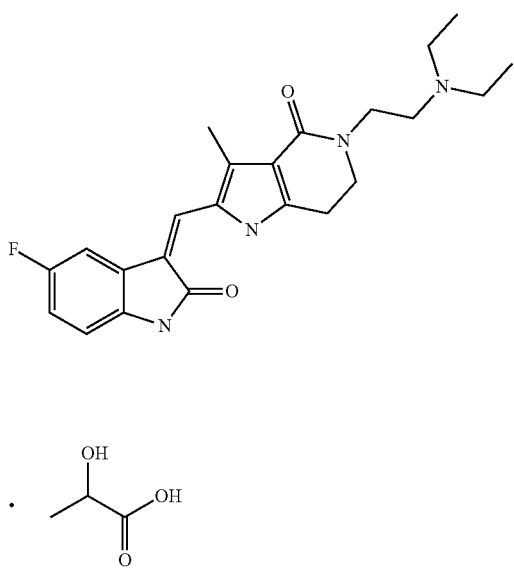

A stirred yellow suspension of 5-(2-diethylamino-ethyl)-2-(5-fluoro-2-oxo-1,2-dihydro-indol-3-ylidenemethyl)-3-methyl-1,5,6,7-tetrahydro-pyrrolo[3,2-c]pyridin-4-one (193 mg, 0.47 mmol) obtained form Example 1 in methanol (8 ml) and dichloromethane (16 ml) was added with lactic acid (40 μl, 0.47 mmol) at room temperature. The resulting solution was stirred for 30 minutes. The solvent was evaporated under reduced pressure and the residue was added with 10 ml of acetonitrile. The resulting solution was heated to reflux for 45 minutes, cooled down to room temperature and filtered. The filter cake was washed with cold acetonitrile (0.5 ml×3) and ethanol (0.5 ml×3) and dried in vacuo to give the title compound 5-(2-diethylamino-ethyl)-2-(5-fluoro-2-oxo-1,2-dihydro-indol-3-ylidenemethyl)-3-methyl-1,5,6,7-tetrahydro-pyrrolo[3,2-c]pyridin-4-one lactate (208 mg, 88.9%) as a yellow solid.

MS m/z (ESI): 501[M+1]

Example 129

5-(2-Diethylamino-ethyl)-2-(5-fluoro-2-oxo-1,2-dihydro-indol-3-ylidenemethyl)-3-methyl-1,5,6,7-tetrahydro-pyrrolo[3,2-c]pyridin-4-one maleate

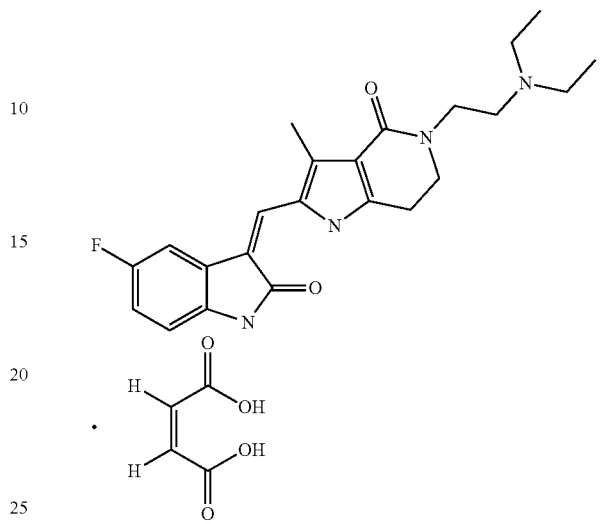

A stirred yellow suspension of 5-(2-diethylamino-ethyl)-2-(5-fluoro-2-oxo-1,2-dihydro-indol-3-ylidenemethyl)-3-methyl-1,5,6,7-tetrahydro-pyrrolo[3,2-c]pyridin-4-one (200 mg, 0.49 mmol) obtained form Example 1 in methanol (4 ml) and dichloromethane (8 ml) was added with maleic acid (57 mg, 0.49 mmol) at room temperature. The resulting solution was stirred for 30 minutes. The solvent was evaporated under reduced pressure and the residue was added with 5 ml of acetonitrile. The resulting solution was heated to reflux for 30 minutes, cooled down to room temperature and filtered. The filter cake was washed with cold acetonitrile (0.5 ml×3) and ethanol (0.5 ml×3) and dried in vacuo to give the title compound 5-(2-diethylamino-ethyl)-2-(5-fluoro-2-oxo-1,2-dihydro-indol-3-ylidenemethyl)-3-methyl-1,5,6,7-tetrahydro-pyrrolo[3,2-c]pyridin-4-one maleate (202 mg, 66.2%) as a yellow solid.

MS m/z (ESI): 527[M+1].

Example 130

5-(2-Diethylamino-ethyl)-2-(5-fluoro-2-oxo-1,2-dihydro-indol-3-ylidenemethyl)-3-methyl-1,5,6,7-tetrahydro-pyrrolo[3,2-c]pyridin-4-one mesylate

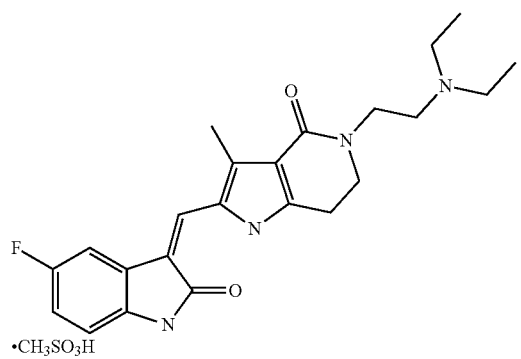

A stirred yellow suspension of 5-(2-diethylamino-ethyl)-2-(5-fluoro-2-oxo-1,2-dihydro-indol-3-ylidenemethyl)-3-methyl-1,5,6,7-tetrahydro-pyrrolo[3,2-c]pyridin-4-one (200 mg, 0.49 mmol) obtained form Example 1 in methanol (4 ml) and dichloromethane (8 ml) was added with methane sulfonic acid (32 μl, 0.49 mmol) at room temperature. The resulting solution was stirred for 30 minutes. The solvent was evaporated under reduced pressure and the residue was added with 5 ml of acetonitrile. The resulting solution was heated to reflux for 30 minutes, cooled down to room temperature and filtered. The filter cake was washed with cold acetonitrile (0.5 ml×3) and ethanol (0.5 ml×3) and dried in vacuo to give the title compound 6-(2-diethylamino-ethyl)-2-(5-fluoro-2-oxo-1,2-dihydro-indol-3-ylidenemethyl)-3-methyl-1,5,6,7-tetrahydro-pyrrolo[3,2-c]pyridin-4-one mesylate (174 mg, 73.1%) as a yellow solid.

MS m/z (ESI): 507[M+1]

The corresponding salts of the title compounds in Example 1-130 can be prepared under the same conditions as described in Example 131, 134, 135 and 136.

Example 131

The compostions of the tablets for oral administration are as follows:

| | |
|---|---|
| Compound of Example 131 (Active ingredient) | 100 g |
| Corn starch | 50 g |
| Sucrose | 20 g |
| Microcrystalline cellulose | 10 g |
| 0.5% CMC | suitable amount |
| Magnesium stearate | 5 g |
| | 1000 pills |

Representative procedure: The ingredients are thoroughly blended, granulated by the conventional wet process, tableted and packaged.

Example 132

Capsules for oral administration are prepared as follows:

| | |
|---|---|
| Compound of Example 132 (Active ingredient) | 100 g |
| Lactose | 40 g |
| Corn starch | 5 g |
| Sucrose | 5 g |
| Microcrystalline cellulose | 10 g |
| 1% HPMC | suitable amount |
| | 1000 pills |

Representative procedure: The ingredients are thoroughly blended, granulated by the conventional wet process, loaded into gelatin capsules and packaged.

Biological Assays

Example 1

Cell Proliferation Inhibition VEGF-R2 Assay

The following in vitro assay may be used to determine the level of activity and effect of different compounds of the present invention on the proliferation inhibition (cell toxic) of endothelium growth factor receptor (VEGFR) high expressing homo sapient cancer cell-HUVEC cell.

The cellular assay described here measure the compounds of their anti-angiogenesis and proliferation inhibition activity and effect through VVEGFR on the cancer cells in vitro. The effect and activity is represented by the $IC_{50}$ value that kills the cancer cell. The general procedures for the assay is as follows: The homo sapient cells highly express VVEGFR are chosen and seeded to 96-well cell culture plate at a suitable concentration (exp 5000 cells/ml medium). The cells then are cultured in carbon dioxide ($CO_2$) incubator till when they confluence to about 85%. Then, the cell culture medium is replaced by fresh one with tested compounds added in it at serial concentrations (general 6 to 7 concentrations). Then the cells are put back to the culture and cultured for continuous 72 hours. 72 hours later, the cell exposed to compounds and control cell are assayed for their proliferation using Sulforhodamine B (SRB) method. Compounds $IC_{50}$ on tested cells are calculated by the data of inhibition rates of serial concentrations of the tested compounds.

Material and Methods:
 a. Dimethyl sulfoxide (Sinophma chemical reagent company, catalog No. T20050806)
 b. HUVEC cells (Purchased from Institute of biochemistry and cell biology)
 c. Falcon 100 mm cell culture plates (Baton Dickison Labware, Baton Dickison and company, Catalog No. 18677)
 d. corning 96-well culture cluster (Corning Incorporated, Catalog No. 3599)
 e. Fisher Pipette (Fisher scientific, Catalog No. 03-692-164)
 f. DMEM/F12 cell medium (Gibco, Catalog No. 12400-024)
 g. Fetal bovine serum, origin from Australia (Gibco, Catalog No. 10099-141)
 h. Phosphate Buffered Saline (Gibco, Catalog No. 10010-072)
 i. 0.25% Trypsin-EDTA (Gibco, Catalog No. 25200-056)
 j. Sulforhodamine B (Sigma, Catalog No. 3520-42-1)
 k. Acetic Acid (Sinophma chemical reagent company, Catalog No. T20060508)
 l. Trichloroacetic Acid (Sinophma chemical reagent company, Catalog No. T20060305)
 m. Tris base (Amresco, Catalog No. 0826)
 n. Class II A/B3 Biological safety cabinet (ThermoForma Catalog No. HB0053-03)
 o. Series II water jacketed $CO_2$ incubator (ThermoForma Model: 3111)
 p. Centrifuge (Fisher Scientific Marathon 8 k, Catalog No. 0027-02)
 q. Novastar Plate reader (BMG Labtech, Catalog No. 700-0081)
 r. Orbital Shaker (Qilinbeier, Catalog No. TS-1)

Protocol:

The following protocol is used to assay the cell toxic activity of $IC_{50}$ value of tested compounds of the invention on HUVEC cell:

1. Growing HUVEC cells in growth media (DMEM/F12, supplemented with 10% FBS) in 100 min corning culture plates till confluence at 37° C., 5% $CO_2$.
2. Wash HUVEC cells in 100 mm plates with PBS, harvest cells by trypsinization and seeded cells to corning 96-well cell culture plates at concentration of 50000 cells/ml, leaving 6 wells/each plate empty as background.
3. Growing seeded 96-well plates at 37° C., 5% $CO_2$, till 85% confluence.
4. Prepare compounds stock solution, using DMSO solve candidate compounds to a concentration of 20 mM. Then use DMSO to dilute the stock solution to a serious concentration of tested compounds solution (namely, 2 mM, 1 mM, 0.2 mM, 20 μM, 2 μM, 0.2 μM).

5. Use cell culture medium (in this case, DMEM/F12+10% FBS) to dilute the compounds solution prepared above. Each DMSO serial concentration compound solution is diluted by 20 times with culture medium by adding 5 μl DMSO compound solution to 95 μl culture medium, then mix well by vortex. This promise that the DMSO concentration at that the HUVEC cell will exposed to will not surpass 0.5%.

6. After HUVEC cell has attached to the dish bottom and confluence about 85%, change the culture medium with fresh DMEM/F12 plus 10% FBS. Each well added 180 μl medium, then add 20 μl medium solution of tested compounds prepared at step 5 to each well. For control group cell, add 20 μl culture medium containing 0.5% pure DMSO. So, now HUVEC cells are exposed to each tested compound at a serial final concentration of 100 μM, 10 μM, 5 μM, 1 μM, 0.1 μM, 0.01 μM, and 0.001 μM. Each 96-well plate, we can test 3 compounds with a control cell group.

7. Put the culture plates back to incubator, culture for 72 hours at 37° C., 5% $CO_2$.

8. 72 hours later, remove cultures from incubator into sterile work area.

9. Prepare fixative (50% Trichloroacetic Acid-TCA) by adding reagent grade water to the TCA, fix the cells by gently layering 50 μl of cold TCA solution on top of the growth medium.

10. Incubate plates for 1 hour at 4° C. and then rinse with water several times to remove TCA, serum proteins, etc. Plates are air dried and stored until use. Bland background optical density is measured in wells incubated with growth medium without cells.

11. Use 10% acetic acid solution to prepare 0.4% Sulforhodamine B solution. Add 50 μl sulforhodamine B solution to each well of 96-well plates.

12. Allow cells to stain for 30 minutes.

13. Prepared the wash solution of 10% acetic acid. At the end of the staining period, the stain is removed and the cells rinsed quickly with 1% acetic acid. Repeat until unincorporated dye is removed. Keep wash times to a minimum to reduce desorption of protein-bound dye. After being rinsed, the cultures are air dried until no moisture is visible.

14. The incorporated dye is then solubilized in a volume of Sulforhodamine B assay Solubilization solution (10 mM Tris) equal to the original volume of culture medium. Allow cultures to stand for 5 minutes at room temperature. Gentle stirring in a gyratory shaker to enhance mixing of the dye.

15. Spectrophotometrically measure absorbance at a wavelength of 565 nm using a plate reader (BMG). Measure the background absorbance of 96-well plates at 690 nm and subtract from the measurement at 565 nm.

16. Calculate the inhibition rate (IR) as follows: IR=100× (Absorbance of control cells−Absorbance of cells exposed to tested compounds at each concentration)/Absorbance of control cells %. The $IC_{50}$ value can be derived from the IRs of compounds at different concentration gradients.

The Activity of the Compounds of the Invention

The biological activity of the compounds of the invention is tested using the assay described above. The $IC_{50}$ values are measured and showed in table below:

| Example | $IC_{50}$ (VEGFR/HUVEC)(μM) |
|---|---|
| 1 | 0.002 |
| 2 | 0.41 |
| 3 | 0.15 |
| 4 | 3.6 |
| 5 | 10.53 |
| 7 | 1.38 |
| 8 | 3.14 |
| 9 | 5.8 |
| 10 | 0.36 |
| 11 | 0.17 |
| 12 | 3.0 |
| 13 | 0.41 |
| 14 | 1.05 |
| 15 | 5.64 |
| 16 | 0.58 |
| 17 | 2.26 |
| 19 | 2.56 |
| 20 | 15.3 |
| 21 | 2.1 |
| 24 | 2.42 |
| 30 | 0.22 |
| 31 | 0.19 |
| 33 | 0.67 |
| 34 | 0.12 |
| 35 | 0.13 |
| 36 | 0.11 |
| 37 | 0.11 |
| 38 | 1.28 |
| 39 | 0.05 |
| 40 | 0.13 |
| 41 | 0.22 |
| 42 | 0.28 |
| 44 | 1.32 |
| 45 | 1.15 |
| 46 | 10.5 |
| 50 | 1.16 |
| 51 | 0.78 |
| 52 | 0.26 |
| 55 | 3.72 |
| 58 | 3.99 |
| 59 | 0.30 |

Example 2

VEGF-R2 Kinase Assay

This assay is used to measure the in vitro kinase activity of recombinant human VEGF-R2 in an ELISA assay.

Materials and Reagents:

a. Wash Buffer (PBS-T Buffer): 1×PBS (137 mM NaCl, 2.7 mM KCl, 4.3 mM $Na_2HPO_4$, 1.4 mM $KH_2PO_4$, adjust the pH to 7.2) and 0.05% Tween-20.

b. 1% Bovine Serum Albumin (BSA, Calbiochem #136593) in PBS-T.

c. Stop Buffer: 50 mM EDTA, pH 8.0.

d. DELFIA® Europium-labeled Anti-mouse IgG (PerkinElmer Life Sciences #AD0124).

e. DELFIA® Enhancement Solution (PerkinElmer Life Sciences #1244-105).

f. DELFIA® Streptavidin coated, 96-well, yellow plate (PerkinElmer Life Sciences #AAAND-0005).

g. recombinant human VEGF-R2 kinase (supplied in 50 mM Tris-HCl (pH 8.0), 100 mM NaCl, 5 mM DTT, 15 mM reduced glutathione and 20% glycerol. Cell signaling technology #7787).

h. 10 mM ATP solution (Cell signaling technology #9804).

i. Biotin-Gastrin Precursor (Tyr87) Peptide (Cell signaling technology #1310).

j. Phospho-Tyrosine Mouse mAb (P-Tyr-100) (Cell signaling technology #9411).

k. HTScan™Tyrosine Kinase Buffer (4×)
1× Kinase Buffer:
60 mM HEPES
5 mM $MgCl_2$
5 mM $MnCl_2$
3 μM $Na_3VO_4$
(Cell signaling technology #9805).
l. 1.25 M DTT (1000×) (Cell signaling technology).
Procedure:
The following protocol was used:
1. Dilute test compound with DMSO to the desired final assay concentration. Add 1 μl test compound for every assay, to the negative control (sample which do not receive any test compound), add 1 μl DMSO.
2. Dilute 6 μM substrate peptide (Tyr87) 1:1 with $dH_2O$, add 15 μl to every assay.
3. Immediately transfer VEGF-R2 enzyme from −80° C. to ice. Allow enzyme to thaw on ice.
4. Take 2.2 μg VEGF-R2 enzyme to the enzyme tube.
5. Add 10 μl of DTT (1.25 M) to 2.5 ml of 4×HTScan™ Tyrosine Kinase Buffer (240 mM HEPES pH 7.5, 20 mM $MgCl_2$, 20 mM $MnCl_2$, 12 μM $Na_3VO_4$) to make DTT/Kinase buffer.
6. Transfer 0.75 ml of DTT/Kinase buffer to each enzyme tube to make 4× reaction cocktail. Add 7.5 μl 4× reaction cocktail to every assay.
7. Add 2 μl ATP (10 mM) to 498 μl $dH_2O$, take 7.5 μl for every assay.
Final Assay Conditions for a 30 μl Reaction
    60 mM HEPES pH 7.5
    5 mM $MgCl_2$
    5 mM $MnCl_2$
      3 μM $Na_3VO_4$
      1.25 mM DTT
    10 μM ATP
    1.5 μM substrate peptide
      22 ng VEGF-R2 Kinase
8. Incubate reaction tube at 25° C. for 30 minutes.
9. Add 30 μl/assay stop buffer (50 mM EDTA, pH 8.0) to stop the reaction.
10. Transfer 25 μl of each reaction and 75 μl $dH_2O$/well to a 96-well streptavidin coated plate and incubate, with shaking at room temperature for 60 minutes.
11. Wash three times with 200 μl/well PBS-T buffer. Pat plate on paper towel to remove excess liquid.
12. Dilute primary antibody, Phospho-Tyrosine mAb (P-Tyr-100), 1:1000 in PBS-T buffer with 1% BSA. Add 100 μl diluted primary antibody to each well.
13. Incubate, with shaking at room temperature for 60 minutes.
14. Wash as described above in step 11.
15. Dilute Europium labeled anti-mouse IgG 1:500 in PBS-T buffer with 1% BSA. Add 100 μl diluted antibody to each well.
16. Incubate, with shaking at room temperature for 30 minutes.
17. Wash five times with 200 μDwell PBS-T buffer. Pat plate on paper towel to remove excess liquid.
18. Add 100 μl/well DELFIA® Enhancement Solution.
19. Incubate, with shaking at room temperature for 5 minutes.
20. Detect 615 nm fluorescence emission with appropriate Time-Resolved Plate Reader.
Calculate the inhibition rate: IR (%)=100−100*(X−B)/(N−B)
X=the fluorescence value of the well contained test compound
N=negative control
B=blank The $IC_{50}$ value can be derived from the IRs of compounds at different concentration gradients.
The Activity of the Compounds of the Invention
The biochemical activity of the compounds of the invention is tested using the assay described above. The $IC_{50}$ values are measured and showed in table below:

| Example | $IC_{50}$ (VEGFR/bio)(μM) |
|---|---|
| 1 | 0.03 |
| 2 | <0.01 |
| 3 | 0.016 |
| 12 | 1.89 |
| 15 | 0.025 |
| 16 | 0.044 |
| 24 | 0.68 |
| 30 | 0.094 |
| 31 | 0.035 |
| 34 | 0.011 |
| 36 | 0.01 |
| 37 | 0.07 |
| 39 | 0.0071 |
| 40 | 0.047 |
| 52 | 1.27 |

Example 3

Cell Proliferation Inhibition EGFR Assay

The following in vitro assay may be used to determine the level of activity and effect of different compounds of the present invention on the proliferation inhibition (cell toxic) of endothelium growth factor receptor (EGFR) high expressing homo sapient cancer cell-A431 cell.

The cellular assay described here measure the compounds of their anti-angiogenesis and proliferation inhibition activity and effect through EGFR on the cancer cells in vitro. The effect and activity is represented by the $IC_{50}$ value that kills the cancer cell. The general procedures for the assay is as follows: The homo sapient cells highly express EGFR are chosen and seeded to 96-well cell culture plate at a suitable concentration (exp 5000 cells/ml medium). The cells then are cultured in carbon dioxide ($CO_2$) incubator till when they confluence to about 85%. Then, the cell culture medium is replaced by fresh one with tested compounds added in it at serial concentrations (general 6 to 7 concentrations). Then the cells are put back to the culture and cultured for continuous 72 hours. 72 hours later, the cell exposed to compounds and control cell are assayed for their proliferation using Sulforhodamine B (SRB) method. Compounds $IC_{50}$ on tested cells are calculated by the data of inhibition rates of serial concentrations of the tested compounds.
Material and Methods:
a. Dimethyl sulfoxide (Sinophma chemical reagent company, catalog No. T20050806)
b. A431 cells (Purchased from Institute of biochemistry and cell biology)
c. Falcon 100 mm cell culture plates (Baton Dickison Labware, Baton Dickison and company, Catalog No. 18677)
d. coming 96-well culture cluster (Corning Incorporated, Catalog No. 3599)
e. Fisher Pipette (Fisher scientific, Catalog No. 03-692-164)
f. DMEM/F12 cell medium (Gibco, Catalog No. 12400-024)
g. Fetal bovine serum, origin from Australia (Gibco, Catalog No. 10099-141)

h. Phosphate Buffered Saline (Gibco, Catalog No. 10010-072)
i. 0.25% Trypsin-EDTA (Gibco, Catalog No. 25200-056)
j. Sulforhodamine B (Sigma, Catalog No. 3520-42-1)
k. Acetic Acid (Sinophma chemical reagent company, Catalog No. T20060508)
l. Trichloroacetic Acid (Sinophma chemical reagent company, Catalog No. T20060305)
m. Tris base (Amresco, Catalog No. 0826)
n. Class II A/B3 Biological safety cabinet (ThermoForma Catalog No. HB0053-03)
o. Series II water jacketed $CO_2$ incubator (ThermoForma Model: 3111)
p. Centrifuge (Fisher Scientific Marathon 8 k, Catalog No. 0027-02)
q. Novastar Plate reader (BMG Labtech, Catalog No. 700-0081)
r. Orbital Shaker (Qilinbeier, Catalog No. TS-1)

Protocol:

The following protocol is used to assay the cell toxic activity of $IC_{50}$ value of tested compounds of the invention on A431 cell:

1. Growing A431 cells in growth media (DMEM/F12, supplemented with 10% FBS) in 100 mm corning culture plates till confluence at 37° C., 5% $CO_2$.
2. Wash A431 cells in 100 mm plates with PBS, harvest cells by trypsinization and seeded cells to coming 96-well cell culture plates at concentration of 50000 cells/ml, leaving 6 wells/each plate empty as background.
3. Growing seeded 96-well plates at 37° C., 5% $CO_2$, till 85% confluence.
4. Prepare compounds stock solution, using DMSO solve candidate compounds to a concentration of 20 mM. Then use DMSO to dilute the stock solution to a serious concentration of tested compounds solution (namely, 2 mM, 1 mM, 0.2 mM, 20 µM, 2 µM, 0.2 µM).
5. Use cell culture medium (in this case, DMEM/F12+10% FBS) to dilute the compounds solution prepared above. Each DMSO serial concentration compound solution is diluted by 20 times with culture medium by adding 5 µl DMSO compound solution to 95 µl culture medium, then mix well by vortex. This promise that the DMSO concentration at that the A431 cell will exposed to will not surpass 0.5%.
6. After A431 cell has attached to the dish bottom and confluence about 85%, change the culture medium with fresh DMEM/F12 plus 10% FBS. Each well added 180 µl medium, then add 20 µl medium solution of tested compounds prepared at step 5 to each well. For control group cell, add 20 µl culture medium containing 0.5% pure DMSO. So, now A431 cells are exposed to each tested compound at a serial final concentration of 100 µM, 10 µM, 5 µM, 1 µM, 0.1 µM, 0.01 µM, and 0.001 µM. Each 96-well plate, we can test 3 compounds with a control cell group.
7. Put the culture plates back to incubator, culture for 72 hours at 37° C., 5% $CO_2$.
8. 72 hours later, remove cultures from incubator into sterile work area.
9. Prepare fixative (50% Trichloroacetic Acid-TCA) by adding reagent grade water to the TCA, fix the cells by gently layering 50 µA of cold TCA solution on top of the growth medium.
10. Incubate plates for 1 hour at 4° C. and then rinse with water several times to remove TCA, serum proteins, etc. Plates are air dried and stored until use. Bland background optical density is measured in wells incubated with growth medium without cells.
11. Use 10% acetic acid solution to prepare 0.4% Sulforhodamine B solution. Add 50 µl sulforhodamine B solution to each well of 96-well plates.
12. Allow cells to stain for 30 minutes.
13. Prepared the wash solution of 10% acetic acid. At the end of the staining period, the stain is removed and the cells rinsed quickly with 1% acetic acid. Repeat until unincorporated dye is removed. Keep wash times to a minimum to reduce desorption of protein-bound dye. After being rinsed, the cultures are air dried until no moisture is visible.
14. The incorporated dye is then solubilized in a volume of Sulforhodamine B assay Solubilization solution (10 mM Tris) equal to the original volume of culture medium. Allow cultures to stand for 5 minutes at room temperature. Gentle stirring in a gyratory shaker to enhance mixing of the dye.
15. Spectrophotometrically measure absorbance at a wavelength of 565 nm using a plate reader (BMG). Measure the background absorbance of 96-well plates at 690 nm and subtract from the measurement at 565 nm.
16. Calculate the inhibition rate (IR) as follows: IR=100× (Absorbance of control cells−Absorbance of cells exposed to tested compounds at each concentration)/Absorbance of control cells %. The $IC_{50}$ value can be derived from the IRs of compounds at different concentration gradients.

The Activity of the Compounds of the Invention

The biological activity of the compounds of the invention is tested using the assay described above. The $IC_{50}$ values are measured and showed in table below:

| Compound | $IC_{50}$ (A431)(µM) |
|---|---|
| 1 | 1.09 |
| 2 | 1.04 |
| 3 | 1.26 |
| 4 | 12.6 |
| 5 | 1.38 |
| 6 | 1.38 |
| 7 | 10.5 |
| 8 | 0.37 |
| 9 | 9.29 |
| 12 | 0.067 |
| 13 | 1.31 |
| 14 | 10.7 |
| 15 | 1.35 |
| 16 | 10.2 |
| 22 | 2.85 |
| 24 | 0.33 |
| 30 | 0.33 |
| 31 | 0.35 |
| 33 | 0.84 |
| 34 | 3.23 |
| 35 | 4.35 |
| 36 | 7.32 |
| 37 | 3.85 |
| 38 | 3.89 |
| 39 | 0.38 |
| 42 | 16.5 |
| 48 | 6.11 |
| 50 | 15.9 |
| 52 | 1.9 |
| 59 | 2.19 |
| 61 | 1.25 |
| 63 | 0.53 |
| 64 | 0.18 |
| 65 | 3.06 |
| 67 | 2.03 |
| 68 | 13.82 |
| 69 | 0.2 |
| 71 | 0.59 |
| 75 | 1.68 |
| 90 | 0.27 |

| Compound | IC$_{50}$ (A431)(μM) |
|---|---|
| 91 | 0.12 |
| 93 | 1.66 |
| 94 | 0.34 |

Example 4

EGFR Kinase Assay

EGFR kinase activity in vitro was measured as described below:

Materials and Reagents:
a. Wash Buffer (PBS-T Buffer): 1×PBS (137 mM NaCl, 2.7 mM KCl, 4.3 mM Na$_2$HPO$_4$, 1.4 mM KH$_2$PO$_4$, adjust the pH to 7.2) and 0.05% Tween-20.
b. 1% Bovine Serum Albumin (BSA, Calbiochem #136593) in PBS-T.
c. Stop Buffer: 50 mM EDTA, pH 8.0
d. DELFIA® Europium-labeled Anti-mouse IgG (PerkinElmer Life Sciences #AD0124)
e. DELFIA® Enhancement Solution (PerkinElmer Life Sciences #1244-105)
f. DELFIA® Streptavidin coated, 96-well, yellow plate (PerkinElmer Life Sciences #AAAND-0005)
g. EGFR kinase (supplied in 50 mM Tris-HCl (pH 8.0), 100 mM NaCl, 5 mM DTT, 15 mM reduced glutathione and 20% glycerol. Cell signaling technology #7908).
h. 10 mM ATP solution (Cell signaling technology #9804).
i. PTP1B (Tyr66) Biotinylated Peptide (Cell signaling technology #1325).
j. Phospho-Tyrosine Mouse mAb (P-Tyr-100) (Cell signaling technology #9411).
k. HTScan™Tyrosine Kinase Buffer (4×)
1× Kinase Buffer:
60 mM HEPES
5 mM MgCl$_2$
5 mM MnCl$_2$
3 μM Na$_3$VO$_4$
    (Cell signaling technology #9805).
l. 1.25 M DTT (1000×) (Cell signaling technology).

Procedure:

The following protocol was used:
1. Dilute test compound with DMSO to the desired final assay concentration. Add 1 μl test compound for every assay, to the negative control (sample which do not receive any test compound), add 1 μl DMSO.
2. Dilute 6 μM substrate peptide (Tyr66) 1:1 with dH$_2$O, add 15 μl to every assay.
3. Immediately transfer EGFR enzyme from −80° C. to ice. Allow enzyme to thaw on ice.
4. Take 3 μg EGFR enzyme to the enzyme tube.
5. Add 10 μl of DTT (1.25 M) to 2.5 ml of 4×HTScan™ Tyrosine Kinase Buffer (240 mM HEPES pH 7.5, 20 mM MgCl$_2$, 20 mM MnCl$_2$, 12 μM Na$_3$VO$_4$) to make DTT/Kinase buffer.
6. Transfer 0.75 ml of DTT/Kinase buffer to each enzyme tube to make 4× reaction cocktail. Add 7.5 μl 14× reaction cocktail to every assay.
7. Add 4 μl ATP (10 mM) to 496 μl dH$_2$O, take 7.5 μl for every assay.
Final Assay Conditions for a 30 μl Reaction
    60 mM HEPES pH 7.5
    5 mM MgCl$_2$
    5 mM MnCl$_2$
    3 μM Na$_3$VO$_4$
    1.25 mM DTT
    20 μM ATP
    1.5 μM substrate peptide
        30 ng EGFR Kinase
8. Incubate reaction tube at 25° C. for 45 minutes.
9. Add 30 μl/assay stop buffer (50 mM EDTA, pH 8.0) to stop the reaction.
10. Transfer 25 μl of each reaction and 75 μl dH$_2$O/well to a 96-well streptavidin coated plate and incubate, with shaking at room temperature for 60 minutes.
11. Wash three times with 200 μl/well PBS-T buffer. Pat plate on paper towel to remove excess liquid.
12. Dilute primary antibody, Phospho-Tyrosine mAb (P-Tyr-100), 1:1000 in PBS-T buffer with 1% BSA. Add 100 μl diluted primary antibody to each well.
13. Incubate, with shaking at room temperature for 60 minutes.
14. Wash as described above in step 11.
15. Dilute Europium labeled anti-mouse IgG 1:500 in PBS-T buffer with 1% BSA. Add 100 μl diluted antibody to each well.
16. Incubate, with shaking at room temperature for 30 minutes.
17. Wash five times with 200 μl/well PBS-T buffer. Pat plate on paper towel to remove excess liquid.
18. Add 100 μl/well DELFIA® Enhancement Solution.
19. Incubate, with shaking at room temperature for 5 minutes.
20. Detect 615 nm fluorescence emission with appropriate Time-Resolved Plate Reader.

Calculate the inhibition rate: IR (%)=100−100*(X−B)/(N−B)
X=the fluorescence value of the well contained test compound
N=negative control
B=blank
The IC$_{50}$, value can be derived from the IRs of compounds at different concentration gradients.

The Activity of the Compounds of the Invention

The biochemical activity of the compounds of the invention is tested using the assay described above. The IC$_{50}$ values are measured and showed in table below:

| Example | IC$_{50}$ (EGFR)(μM) |
|---|---|
| 1 | 0.28 |
| 2 | 0.29 |
| 3 | 0.49 |
| 12 | 0.06 |
| 13 | 0.19 |
| 24 | 0.31 |
| 30 | 4.95 |
| 31 | 0.21 |
| 34 | 0.94 |
| 35 | 3.32 |
| 36 | 0.18 |
| 37 | 2.89 |
| 39 | 0.34 |
| 40 | 0.76 |
| 41 | 6.01 |
| 50 | 0.51 |

Example 5

HER-2 Kinase Assay

An enzyme linked immunosorbent assays (ELISA) was conducted to measure the kinase activity of HER-2 in vitro.

Materials and Reagents:
a. Wash Buffer (PBS-T Buffer): 1×PBS (137 mM NaCl, 2.7 mM KCl, 4.3 mM $Na_2HPO_4$, 1.4 mM $KH_2PO_4$, adjust the pH to 7.2) and 0.05% Tween-20.
b. 1% Bovine Serum Albumin (BSA, Calbiochem #136593) in PBS-T.
c. Stop Buffer: 50 mM EDTA, pH 8.0.
d. DELFIA® Europium-labeled Anti-mouse IgG (PerkinElmer Life Sciences #AD0124).
e. DELFIA® Enhancement Solution (PerkinElmer Life Sciences #1244-105).
f. DELFIA® Streptavidin coated, 96-well, yellow plate (PerkinElmer Life Sciences #AAAND-0005).
g. HER-2/ErbB2 kinase (Invitrogen corporation #PV3366).
h. 10 mM ATP solution (Cell signaling technology #9804).
i. FLT3 (Tyr589) Biotinylated Peptide (Cell signaling technology #1305).
j. Phospho-Tyrosine Mouse mAb (P-Tyr-100) (Cell signaling technology #9411).
k. HTScan™Tyrosine Kinase Buffer (4×)
1× Kinase Buffer:
60 mM HEPES
5 mM $MgCl_2$
5 mM $MnCl_2$
3 μM $Na_3VO_4$
  (Cell signaling technology #9805).
l. 1.25 M DTT (1000×) (Cell signaling technology).
Procedure:
The following protocol was used:
1. Dilute test compound with DMSO to the desired final assay concentration. Add 1 μl test compound for every assay, to the negative control. (sample which do not receive any test compound), add 1 μl DMSO.
2. Dilute 6 μM substrate peptide (Tyr589) 1:1 with $dH_2O$, add 15 μl to every assay.
3. Immediately transfer HER-2 enzyme from −80° C. to ice. Allow enzyme to thaw on ice.
4. Take 4.5 μg HER-2 enzyme to the enzyme tube.
5. Add 10 μl of DTT (1.25 M) to 2.5 ml of 4×HTScan™ Tyrosine Kinase Buffer (240 mM HEPES pH 7.5, 20 mM $MgCl_2$, 20 mM $MnCl_2$, 12 μM $Na_3VO_4$) to make DTT/Kinase buffer.
6. Transfer 0.75 ml of DTT/Kinase buffer to each enzyme tube to make 4× reaction cocktail. Add 7.5 μl 14× reaction cocktail to every assay.
7. Add 4 μl ATP (10 mM) to 496 μl $dH_2O$, take 7.5 μl for every assay.
Final Assay Conditions for a 30 μl Reaction
  60 mM HEPES pH 7.5
  5 mM $MgCl_2$
  5 mM $MnCl_2$
    3 μM $Na_3VO_4$
    1.25 mM DTT
  20 μM ATP
  1.5 μM substrate peptide
    45 ng HER-2 Kinase
8. Incubate reaction tube at 25° C. for 60 minutes.
9. Add 30 μl/assay stop buffer (50 mM EDTA, pH 8.0) to stop the reaction.
10. Transfer 25 μl of each reaction and 75 μl $dH_2O$/well to a 96-well streptavidin coated plate and incubate, with shaking at room temperature for 60 minutes.
11. Wash three times with 200 μl/well PBS-T buffer. Pat plate on paper towel to remove excess liquid.
12. Dilute primary antibody, Phospho-Tyrosine mAb (P-Tyr-100), 1:1000 in PBS-T buffer with 1% BSA. Add 100 μl diluted primary antibody to each well.
13. Incubate, with shaking at room temperature for 60 minutes.
14. Wash as described above in step 11.
15. Dilute Europium labeled anti-mouse IgG 1:500 in PBS-T buffer with 1% BSA. Add 100 μl diluted antibody to each well.
16. Incubate, with shaking at room temperature for 30 minutes.
17. Wash five times with 200 μl/well PBS-T buffer. Pat plate on paper towel to remove excess liquid.
18. Add 100 μl/well DELFIA® Enhancement Solution.
19. Incubate, with shaking at room temperature for 5 minutes.
20. Detect 615 nm fluorescence emission with appropriate Time-Resolved Plate Reader.

Calculate the inhibition rate: IR (%)=100−100*(X−B)/(N−B)

X=the fluorescence value of the well contained test compound

N=negative control

B=blank

The $IC_{50}$ value can be derived from the IRs of compounds at different concentration gradients.

The Activity of the Compounds of the Invention

The biochemical activity of the compounds of the invention is tested using the assay described above. The $IC_{50}$ values are measured and showed in table below:

| Compound | $IC_{50}$ (Her-2)(μM) |
|---|---|
| 12 | 0.09 |
| 24 | 0.83 |
| 31 | 0.98 |
| 39 | 0.27 |
| 42 | 41.1 |
| 49 | 36.1 |
| 52 | 8.32 |
| 59 | 0.72 |
| 64 | 0.68 |
| 68 | 0.53 |
| 69 | 0.91 |
| 71 | 1.09 |

We claim:

1. A compound having the following Formula (II) or pharmaceutically acceptable salts thereof:

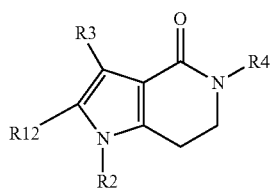

II which is an intermediate in the synthesis of the following compound:

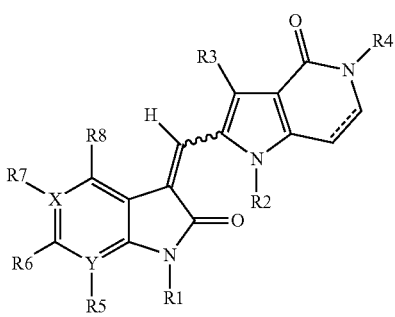

wherein:
- ⋯ is a single bond or a double bond;
- X and Y are each independently selected from C or N;
- X and Y are N, wherein R5 and R7 are absent;
- $R_1$ is selected from H, alkyl, cycloalkyl, hetereocyclo alkyl, aryl, heteroaryl, alkoxyl, aryoxyl, —$COOR_9$, —$CONR_9R_{10}$, —$C(=S)NR_9R_{10}$, —$COR_9$, —$SOR_9$, —$SO_2R_9$, —$SO_2NR_9R_{10}$ and —$P(=O)(OR_9)(OR_{10})$;
- $R_2$ is H;
- $R_3$ is selected from alkyl, trifluoromethyl, aryl and aralkyl; wherein said alkyl, aryl and aralkyl are each optionally substituted by one or more halogen and hydroxyl;
- $R_4$ is selected from alkyl, cycloalkyl, hetereocyclo alkyl, aryl, heteroaryl, —$(CH_2)_n(OCH_2CH_2)_rR_{11}$, —$[CH_2CH(OH)]_rCH_2NR_9R_{10}$ and —$(CH_2)_nNR_9R_{10}$; wherein said alkyl, cycloalkyl, aryl, heteroaryl and heterocyclo alkyl are each optionally substituted by one more groups selected from the group consisting of aryl, hydroxyl, amino, amide group, aminocarbonyl, alkoxyl, aryoxyl, aminoalkyl, hydroxyalkyl, heterocyclo alkyl, carboxylic acid, carboxylic ester and —$NR_9R_{10}$;
- X and Y are C, wherein $R_5$, $R_6$, $R_7$, $R_8$ are each independently selected from hydrogen, halo, haloalkoxyl, alkyl, cycloalkyl, heterocyclo alkyl, alkenyl, alkynyl, aryl, heteroaryl, hydroxyl, —$OR_9$, —$O[CH_2CH_2O]_rR_{11}$, —$SR_9$, —$NR_9R_{10}$, —$SOR_9$, —$SO_2R_9$, —$NHSO_2R_9$, —$SO_2NR_9R_{10}$, —$(CH_2)_nCO_2R_9$, —$(CH_2)_nCONR_9R_{10}$, —$C(=S)NR_9R_{10}$, —$COR_9$, —$NR_9COR_{10}$, —$NHCO_2R_{10}$, —$OCO_2R_9$, —$OCO_2NR_9R_{10}$, —CN and —$NO_2$, wherein said aryl, heteroaryl, cycloalkyl, heterocyclo alkyl are substituted by one more groups consisting of alkyl, alkoxyl and halogen;
- $R_9$ and $R_{10}$ are each independently selected from hydrogen, alkyl, cycloalkyl, aryl, heteroaryl and heterocyclo alkyl, wherein said alkyl, cycloalkyl, aryl, heteroaryl and heterocyclo alkyl are each substituted by one more groups consisting of alkyl, aryl, hydroxyl, amino, amide group, aminocarbonyl, cyano, alkoxyl, aryoxyl, aminoalkyl, hydroxyalkyl, heterocyclo alkyl, carboxylic acid and carboxylic ester;
- $R_9$ and $R_{10}$ are taken together with the atom to which they are attached to form 4 and 8 membered rings, wherein the 5 to 8 membered rings further optionally contain one to three heteroatoms selected from the group consisting of N, O and S, and the 4 to 8 membered rings so formed are optionally substituted by one more groups consisting of alkyl, aryl, heteroaryl, haloalkyl, haloalkoxyl, hydroxyl, amino, amide group, cyano, alkoxyl, aryoxyl, aminoalkyl, hydroxyalkyl, heterocyclo alkyl, carboxylic acid, carboxylic ester, halogen and —$NR_9R_{10}$;

- $R_{11}$ is hydrogen or alkyl;
- $R_{12}$ is hydrogen or aldehyde;
- n is 2-6; and
- r is 1-6.

2. A method for making a compound of formula (II) of claim 1, comprising: selectively hydrolyzing pyrrole triester IIa by a first base at a certain temperature to give pyrrole acid diester IIb;

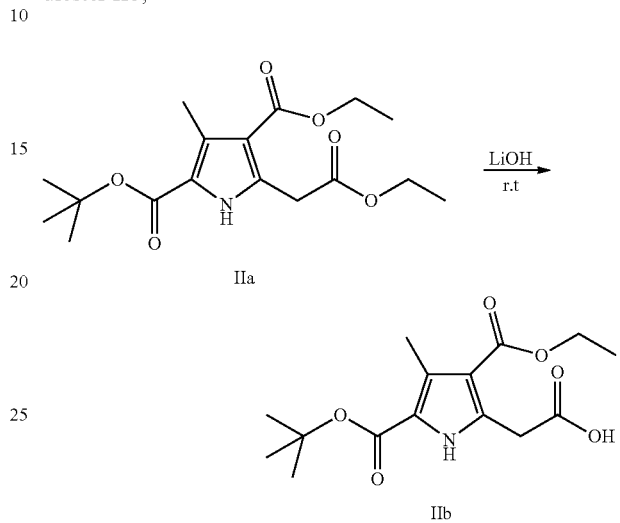

decarboxylating pyrrole acid diester IIb with trifluoroacetic acid, then amidating the decarboxylated product with various amine, selectively reducing the amidated product with borane to obtain pyrrole amine ester IIc;

and heating pyrrole amine ester IIc with a second base in solvent to give the cyclized product of pyrrolofused lactam IId,

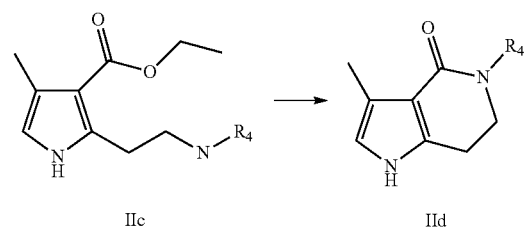

formulating pyrrolofused lactam IId with phosphorus oxychloride to obtain compound (II); wherein said first base is selected from aqueous lithium hydroxide, sodium hydroxide or potassium hydroxide; and said second base is selected from lithium hydroxide, triethylamine, t-BuOK or trimethyl aluminum; and $R_4$ is defined as that in claim 1.

3. The method of claim 2, wherein the solvent is toluene or glycol.

4. The method of claim 2, wherein the temperature of selective hydrolyzation of Pyrrole trimester IIa is from about 10° C. to about 50° C.

5. A method for making a compound of formula (II) of claim 1, comprising: heating pyrrole amine ester IIe with a base in 95% ethanol to a reaction temperature to give the cyclized product of pyrrolo lactam II;

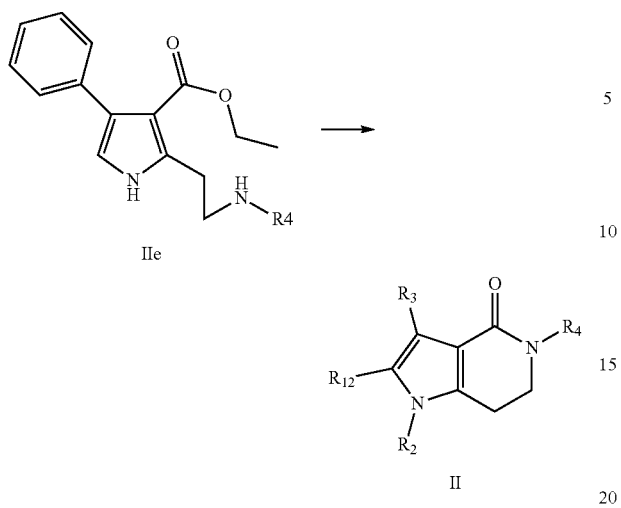

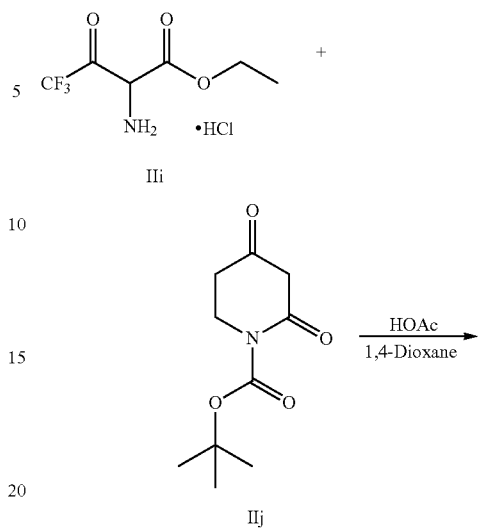

wherein said base is selected from lithium hydroxide or potassium carbonate;

wherein $R_2$ is H; $R_3$ is phenyl; $R_{12}$ is aldehyde group; and $R_4$ is defined as that in claim 1.

6. The method of claim 5, wherein the reaction temperature is from about 35° C. to about 80° C.

7. A method for making a compound of formula (II) of claim 1, comprising: heating pyrrole amine ester IIg with a base in 95% ethanol to a reaction temperature to give the cyclized product of pyrrolo lactam II;

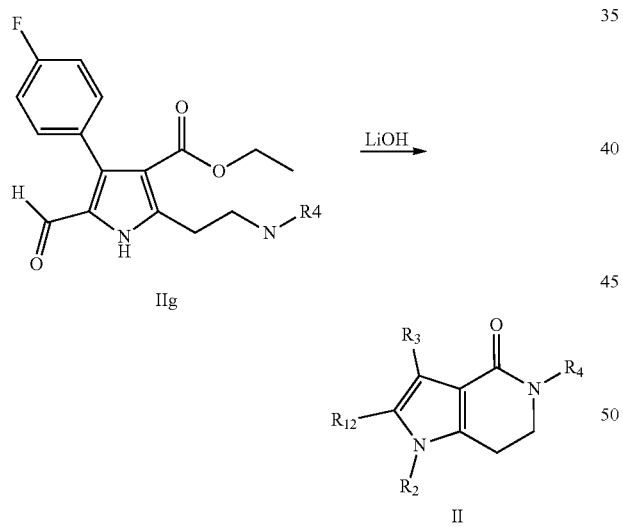

wherein said base is selected from lithium hydroxide or potassium carbonate;

wherein $R_2$ is H; $R_3$ is 4-fluorophenyl; $R_{12}$ is aldehyde group; and $R_4$ is defined as that in claim 1.

8. The method of claim 7, wherein the reaction temperature is from about 35° C. to about 80° C.

9. A method for making a compound of formula (II) of claim 1, comprising: reacting trifluoromethyl amine ester IIi and lactam keton IIj in acetic acid by knorr cyclization to afford trifluoromethyl pyrrolo lactam IIk;

selectively alkylating trifluoromethyl pyrrolo lactam IIk by sodium hydride and $R_4$Br in dimethyl formamide to give compound IIL;

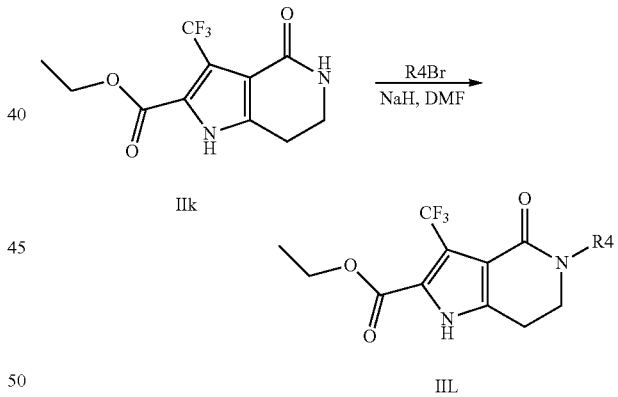

reacting the compound IIL; with a reducing agent such as lithium aluminum hydride or DIBAL H in tetrahydrofuran or dichloromethane at a certain temperature to obtain hydroxyl pyrrolo lactam IIm;

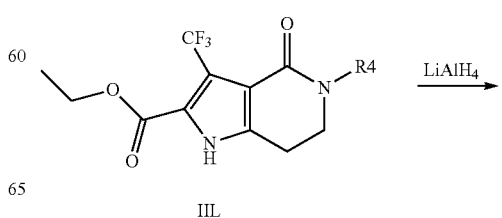

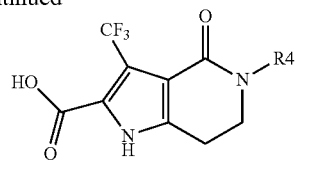

IIm oxidating hydroxyl pyrrolo lactam IIm with 2-iodoxybenzoic acid as oxidant and paratoluenesulfonic acid in DMSO to give aldehyde pyrrolo lactam II;

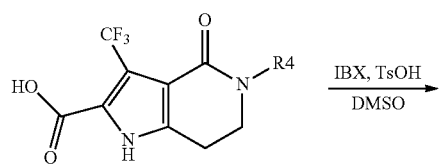

IIm

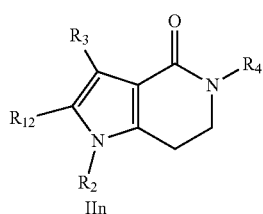

IIn wherein $R_2$ is H; $R_3$ is trifluoromethyl; $R_{12}$ is aldehyde group; and $R_4$ is defined as that in claim 1.

10. The method of claim 9, wherein the temperature of knorr cyclization is from about 100° C. to about 140° C.

11. The method of claim 10, wherein the certain temperature of reduction is from about −5° C. to about 25° C.

* * * * *